(12) United States Patent
Kosak et al.

(10) Patent No.: US 10,905,173 B1
(45) Date of Patent: Feb. 2, 2021

(54) PUMPING/NURSING GARMENT

(71) Applicant: Simple Wishes LLC, Dallas, TX (US)

(72) Inventors: Joy Kosak, Moraga, CA (US); Debra Abbaszadeh, San Francisco, CA (US)

(*) Notice: Subject to any disclaimer, the term of this patent is extended or adjusted under 35 U.S.C. 154(b) by 0 days.

(21) Appl. No.: 16/909,882

(22) Filed: Jun. 23, 2020

Related U.S. Application Data

(60) Provisional application No. 62/967,474, filed on Jan. 29, 2020.

(51) Int. Cl.
*A41C 3/04* (2006.01)
*A41C 3/12* (2006.01)
*A41C 3/00* (2006.01)

(52) U.S. Cl.
CPC .............. *A41C 3/04* (2013.01); *A41C 3/0007* (2013.01); *A41C 3/0028* (2013.01); *A41C 3/0035* (2013.01); *A41C 3/12* (2013.01)

(58) Field of Classification Search
CPC ....... A41C 3/04; A41C 3/0007; A41C 3/0028; A41C 3/0035; A41C 31/12
See application file for complete search history.

(56) References Cited

U.S. PATENT DOCUMENTS

| | | |
|---|---|---|
| 623,413 A | 4/1899 | Murray |
| 949,414 A | 2/1910 | Cunningham |
| 2,305,051 A | 11/1940 | Witkower |
| 2,436,430 A | 2/1948 | Hart |
| 2,492,862 A | 12/1949 | Harvey |
| 2,522,010 A | 9/1950 | Woodruff |
| 2,585,338 A | 2/1952 | Meares |
| 2,613,355 A | 10/1952 | Coleman |
| 2,679,048 A | 5/1954 | Alberts |

(Continued)

FOREIGN PATENT DOCUMENTS

| | | |
|---|---|---|
| AU | 2011100851 A4 | 7/2011 |
| AU | 2013203882 | 10/2014 |

(Continued)

OTHER PUBLICATIONS

Office Action for U.S. Appl. No. 12/453,073, dated Sep. 23, 2011, 11 pages.

(Continued)

*Primary Examiner* — Gloria M Hale
(74) *Attorney, Agent, or Firm* — Cooley LLP

(57) ABSTRACT

Apparatus are described herein for providing a garment (e.g. a bra) that can be used by a wearer during extraction of breast milk using a breast pump, and/or during breast feeding. In some embodiments, a garment can include a support strap having an adjustable portion, a shoulder strap, and a back panel. The support strap can be coupled to the shoulder strap via an engagement mechanism. The adjustable portion of the support strap can be configured to be adjusted relative to the engagement mechanism to change a length of the support strap between the engagement mechanism and the back panel so that the support strap can be disposed over a flange of a breast pump to hold the flange against the breast of a user. An outer panel can be coupled to the back panel and the engagement mechanism. In another embodiment, an inner panel can be removably coupled to the inner panel and the engagement mechanism.

30 Claims, 60 Drawing Sheets

(56) References Cited

U.S. PATENT DOCUMENTS

| | | | |
|---|---|---|---|
| 2,738,509 A | 3/1956 | Bauder | |
| 3,002,515 A | 10/1961 | Glogover | |
| 4,335,728 A | 6/1982 | Fildan | |
| 4,640,287 A | 2/1987 | Anderson et al. | |
| 4,648,404 A | 3/1987 | Clark | |
| 4,878,879 A | 11/1989 | Kunstadter | |
| 4,911,677 A | 3/1990 | White | |
| 5,098,330 A | 3/1992 | Greenberg | |
| 5,334,082 A | 8/1994 | Barker | |
| 5,341,514 A | 8/1994 | Dale | |
| 5,380,238 A | 1/1995 | Crew-Gee | |
| 5,395,280 A | 3/1995 | Greenberg | |
| 5,514,166 A | 5/1996 | Silver et al. | |
| 5,575,768 A | 11/1996 | Lockridge et al. | |
| 5,616,125 A | 4/1997 | Jelks | |
| 5,624,296 A * | 4/1997 | Weber-Unger | A41C 3/04 2/101 |
| 5,690,537 A | 11/1997 | Kalmus | |
| 6,004,186 A | 12/1999 | Penny | |
| 6,027,396 A | 2/2000 | Yonchar | |
| 6,086,451 A | 7/2000 | Fernandes | |
| 6,227,936 B1 | 5/2001 | Mendoza | |
| 6,247,996 B1 | 6/2001 | Fields | |
| 6,319,092 B1 | 11/2001 | Leyhe et al. | |
| 6,438,758 B1 | 8/2002 | Burkard et al. | |
| 6,440,100 B1 | 8/2002 | Prentiss | |
| 6,705,910 B2 | 3/2004 | Engel | |
| 6,854,132 B1 | 2/2005 | Polzin | |
| 6,866,558 B2 | 3/2005 | Luciano et al. | |
| 6,887,217 B1 | 5/2005 | Logan | |
| 6,974,361 B2 | 12/2005 | Cravaack et al. | |
| 7,232,359 B1 | 6/2007 | Richardson | |
| 7,306,505 B2 | 12/2007 | Barbour et al. | |
| 7,507,141 B2 | 3/2009 | Ward et al. | |
| 7,591,706 B2 | 9/2009 | Barbour et al. | |
| 8,192,247 B2 | 6/2012 | Abbaszadeh | |
| 8,323,070 B2 | 12/2012 | Abbaszadeh | |
| 8,523,629 B2 | 9/2013 | Pundyk | |
| 9,167,855 B2 | 10/2015 | Abbaszadeh | |
| 9,498,005 B2 | 11/2016 | Abbaszadeh | |
| 9,872,524 B2 | 1/2018 | Abbaszadeh | |
| 9,894,942 B2 | 2/2018 | Burrell | |
| 10,212,972 B2 | 2/2019 | Abbaszadeh | |
| 10,420,377 B2 * | 9/2019 | Abbaszadeh | A61M 1/062 |
| 10,420,378 B2 * | 9/2019 | Kosak | A41C 3/04 |
| 10,426,203 B2 * | 10/2019 | Kosak | A41C 3/04 |
| 10,772,361 B2 | 9/2020 | Abbaszadeh | |
| 2002/0062512 A1 | 5/2002 | Gustafson et al. | |
| 2003/0027491 A1 | 2/2003 | Cravaack et al. | |
| 2003/0167037 A1 | 9/2003 | Fialkoff | |
| 2003/0191433 A1 | 10/2003 | Prentiss | |
| 2003/0232573 A1 | 12/2003 | Plew | |
| 2004/0016039 A1 | 1/2004 | Caprin | |
| 2006/0025039 A1 | 2/2006 | Barbour et al. | |
| 2006/0211336 A1 | 9/2006 | Brigham | |
| 2007/0161330 A1 | 7/2007 | Whitehead et al. | |
| 2008/0022434 A1 | 1/2008 | Adelman | |
| 2008/0039781 A1 | 2/2008 | Bjorge | |
| 2008/0146118 A1 | 6/2008 | Solberg et al. | |
| 2008/0262420 A1 | 10/2008 | Dao et al. | |
| 2009/0286452 A1 | 11/2009 | Grayson | |
| 2010/0031418 A1 | 2/2010 | Op't Hof | |
| 2010/0068971 A1 * | 3/2010 | Hendrickson | A41C 3/04 450/31 |
| 2010/0159801 A1 | 6/2010 | Abbaszadeh | |
| 2010/0159802 A1 | 6/2010 | Abbaszadeh | |
| 2010/0261410 A1 * | 10/2010 | Hirtz | A41C 3/04 450/36 |
| 2011/0081826 A1 * | 4/2011 | Hendrickson | A41C 3/0028 450/36 |
| 2011/0092134 A1 | 4/2011 | Alva | |
| 2011/0237156 A1 | 9/2011 | Boonen et al. | |
| 2011/0314587 A1 * | 12/2011 | Ritchie | A41C 3/04 2/104 |
| 2012/0129427 A1 * | 5/2012 | Perez | A41C 3/04 450/36 |
| 2012/0184179 A1 | 7/2012 | Blitz | |
| 2013/0095727 A1 | 4/2013 | Abbaszadeh | |
| 2014/0087625 A1 | 3/2014 | Ironi | |
| 2014/0220860 A1 | 8/2014 | Alva | |
| 2014/0273737 A1 | 9/2014 | Cortese et al. | |
| 2014/0364035 A1 * | 12/2014 | Abbaszadeh | A41C 3/04 450/36 |
| 2014/0364036 A1 * | 12/2014 | Abbaszadeh | A61M 1/06 450/36 |
| 2016/0015092 A1 | 1/2016 | Abbaszadeh | |
| 2016/0095967 A1 | 4/2016 | Weston | |
| 2016/0150834 A1 | 6/2016 | Boele et al. | |
| 2017/0172502 A1 * | 6/2017 | Rofe | G01L 1/2256 |
| 2017/0265530 A1 | 9/2017 | Donlon et al. | |
| 2017/0280786 A1 | 10/2017 | Abbaszadeh | |
| 2017/0280787 A1 | 10/2017 | Burrell | |
| 2018/0064177 A1 | 3/2018 | Akerson et al. | |
| 2018/0064178 A1 * | 3/2018 | Akerson | A61B 5/4288 |
| 2018/0132542 A1 * | 5/2018 | Abbaszadeh | A41C 3/04 |
| 2018/0206559 A1 * | 7/2018 | Kosak | A41F 1/006 |
| 2018/0255840 A1 | 9/2018 | Abbaszadeh | |
| 2018/0352884 A1 * | 12/2018 | Vanos | A41C 3/0028 |
| 2019/0014829 A1 * | 1/2019 | Kim | A41C 3/0007 |
| 2019/0142078 A1 | 5/2019 | Kosak | |
| 2019/0208839 A1 * | 7/2019 | Amos | A41D 1/215 |
| 2019/0261698 A1 * | 8/2019 | Akerson | A41C 3/0014 |
| 2019/0289926 A1 | 9/2019 | Abbaszadeh | |
| 2020/0154792 A1 | 5/2020 | Abbaszadeh | |
| 2020/0154793 A1 | 5/2020 | Kosak | |

FOREIGN PATENT DOCUMENTS

| | | |
|---|---|---|
| CN | 201479956 U | 5/2010 |
| CN | 104223390 A | 12/2014 |
| CN | 204907978 U | 12/2015 |
| EP | 2810573 | 8/2016 |
| FR | 881406 A | 4/1943 |
| FR | 919893 A | 3/1947 |
| GB | 2536541 A | 9/2016 |
| KR | 2011-0001216 | 2/2011 |
| WO | WO 2007/053073 | 5/2007 |
| WO | WO 2008/005713 | 1/2008 |
| WO | WO 2010/080122 | 7/2010 |
| WO | WO 2011/135092 | 11/2011 |

OTHER PUBLICATIONS

International Search Report and Written Opinion for International Application No. PCT/US2009/006618, dated Mar. 8, 2010, 9 pages.
Office Action for U.S. Appl. No. 12/585,829, dated Aug. 24, 2011, 10 pages.
Office Action for U.S. Appl. No. 13/692,204, dated Oct. 1, 2014, 9 pages.
Office Action for U.S. Appl. No. 13/692,204, dated Jul. 3, 2013, 6 pages.
Office Action for U.S. Appl. No. 13/692,204, dated Apr. 8, 2014, 6 pages.
Office Action for U.S. Appl. No. 14/867,979, dated Nov. 5, 2015, 8 pages.
Office Action for U.S. Appl. No. 14/867,979, dated Apr. 4, 2016, 6 pages.
Office Action for U.S. Appl. No. 15/357,596, dated Dec. 31, 2018, 12 pages.
Extended European Search Report for European Application No. 14171552.4, dated Sep. 9, 2014, 6 pages.
Office Action for European Application No. 14171552.4, dated Dec. 3, 2015, 4 pages.
Office Action for U.S. Appl. No. 14/172,812, dated Jun. 16, 2016, 7 pages.
First Office Action for Chinese Application No. 201410077245.4, dated Dec. 7, 2016, 31 pages.
Second Office Action for Chinese Application No. 201410077245.4, dated Oct. 30, 2017, 29 pages.

(56) References Cited

OTHER PUBLICATIONS

Third Office Action for Chinese Application No. 201410077245.4, dated Jul. 9, 2018, 34 pages.
Fourth Office Action for Chinese Application No. 201410077245.4, dated Mar. 21, 2019, 27 pages.
Decision on Rejection for Chinese Application No. 201410077245.4, dated Aug. 5, 2019, 26 pages.
Extended European Search Report for European Application No. 14171556.5, dated Sep. 10, 2014, 5 pages.
Office Action for U.S. Appl. No. 14/172,826, dated May 20, 2016, 8 pages.
Office Action for U.S. Appl. No. 14/172,826, dated Dec. 29, 2016, 5 pages.
Office Action for U.S. Appl. No. 14/172,826, dated Apr. 10, 2017, 15 pages.
Extended European Search Report for European Application No. 16179769.1, dated Feb. 10, 2017, 8 pages.
Office Action for U.S. Appl. No. 15/873,317, dated Jun. 29, 2018, 9 pages.
Office Action for U.S. Appl. No. 15/872,360, dated Dec. 30, 2019, 14 pages.
International Search Report and Written Opinion for International Application No. PCT/US2016/043326, dated Nov. 28, 2016, 19 pages.
First Office Action for Chinese Application No. 201880007431.7, dated Jul. 3, 2020, 29 pages.
Office Action for U.S. Appl. No. 15/873,456, dated Mar. 21, 2019, 14 pages.
International Search Report and Written Opinion for International Application No. PCT/US2018/014245, dated Jun. 12, 2018, 15 pages.
Office Action for U.S. Appl. No. 16/201,718, dated Mar. 21, 2019, 11 pages.
LactaMed, "EverBeautyBra™ Hands Free Pumping and Nursing Bra in One," 2020, [Online], [Retrieved on Sep. 4, 2020], Retrieved from the Internet: URL: <https://lactamed.com/products/everbeautybra-all-in-one?_pos=5&_sid=3f52c4eee&_ss=r>, 8 pages.
Screen captures from YouTube video clip entitled "EverBeautyBra™ by LactaMed™," 2 Pages, uploaded Apr. 23, 2018 by user "LactaMed Inc". Retrieved from the Internet: <URL: https://www.youtube.com/watch?v=-KUuqkxejIM>.
Nursing Bra Express, "Pump Up the Band Hands Free Nursing Bra," [online], [Retrieved on Mar. 2, 2013], Retrieved from the Internet: URL: http://www.nursingbraexpress.com/nursing-bras/pump-band-hands-free-nursing-bra, 1 page.
Office Action for U.S. Appl. No. 16/550,902, dated Sep. 17, 2020, 12 pages.
Third Party Submission for U.S. Appl. No. 16/551,295, dated Sep. 17, 2020, 23 pages.

\* cited by examiner

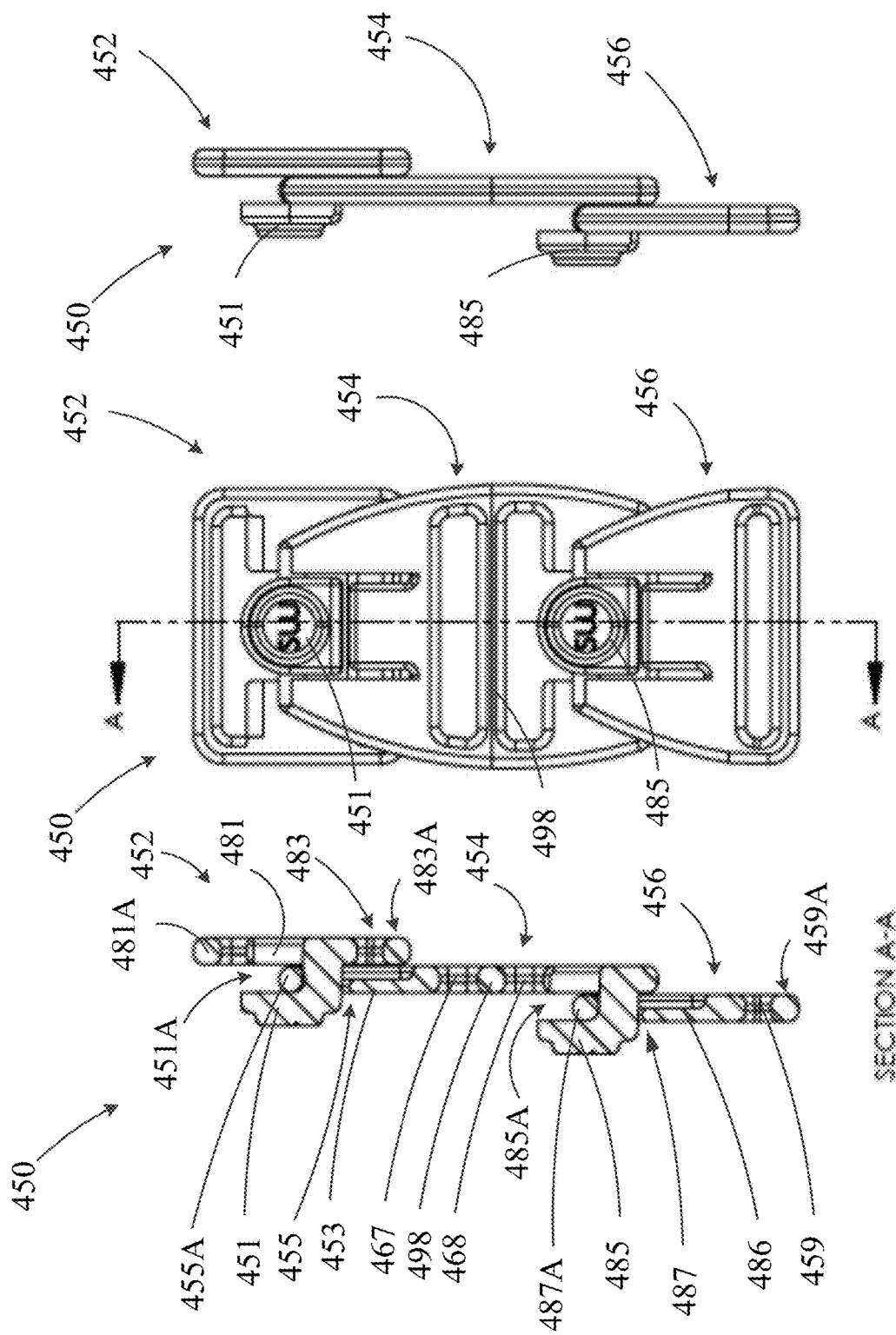

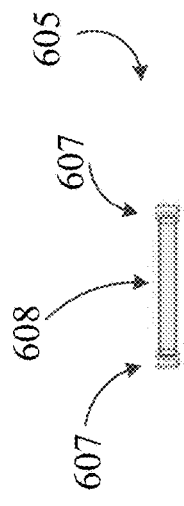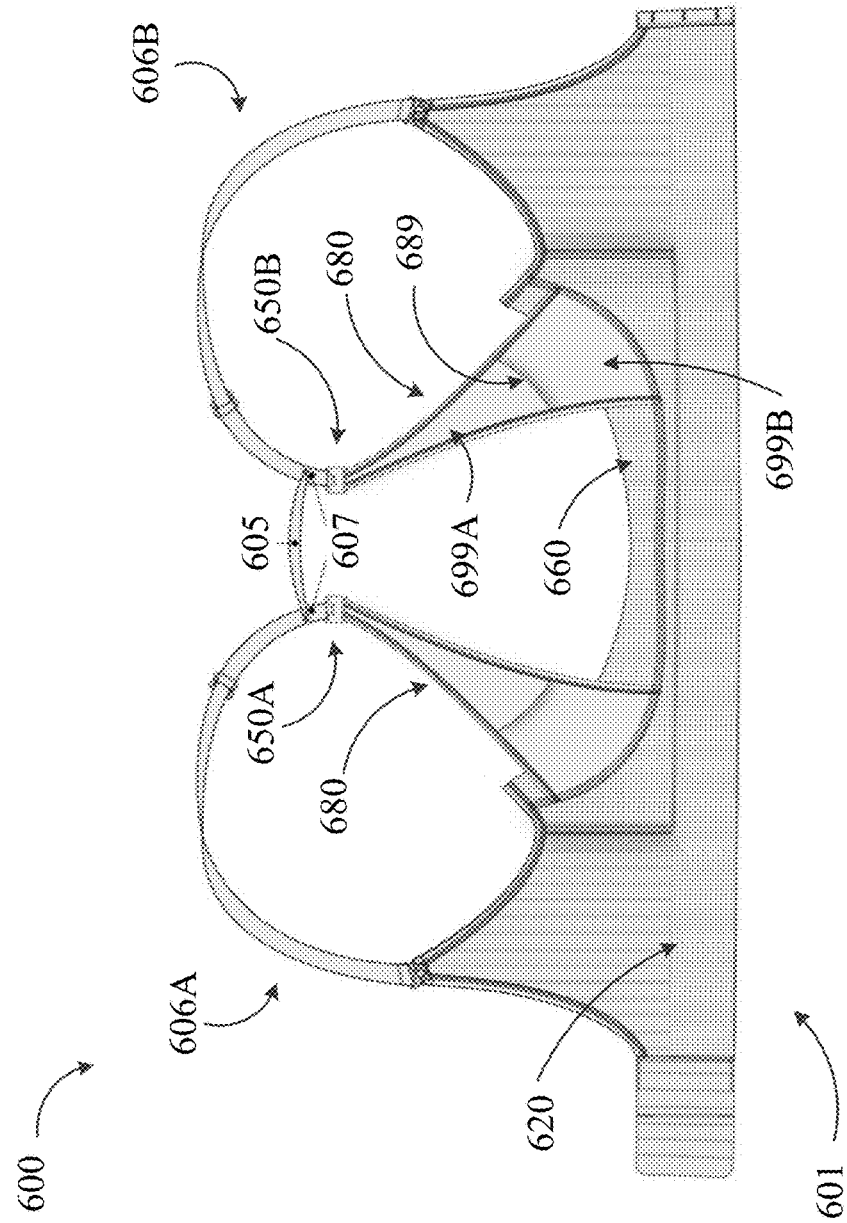

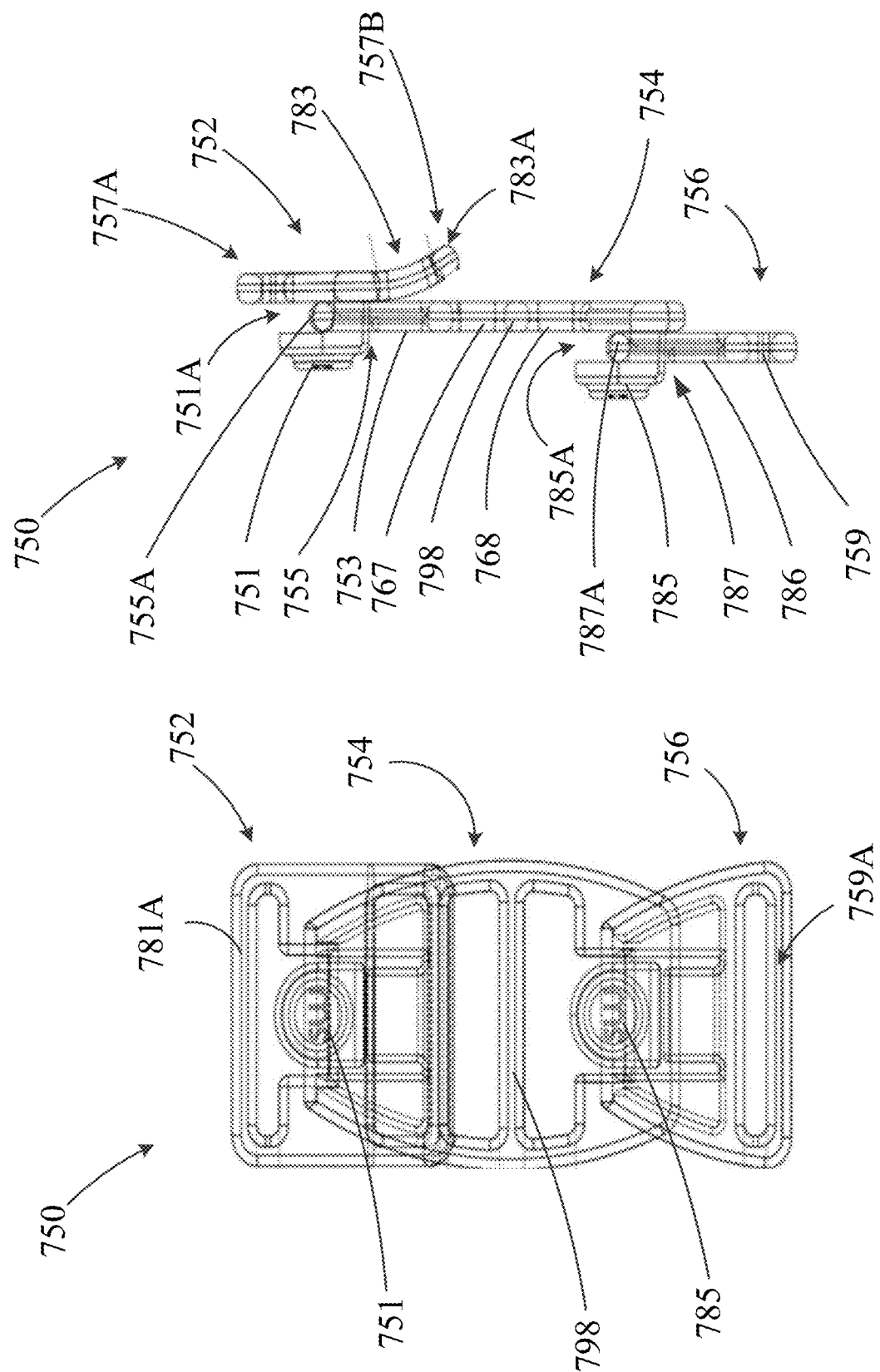

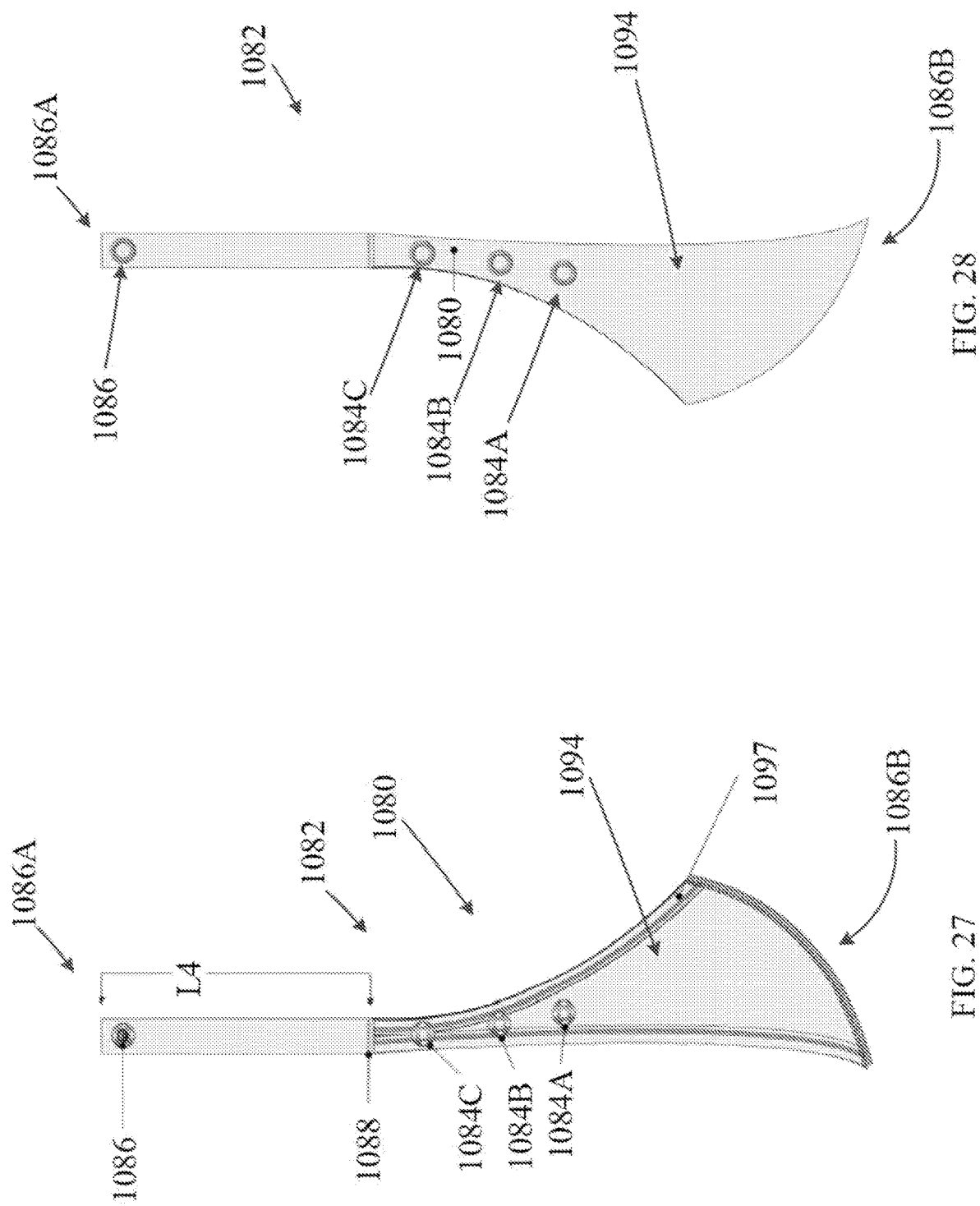

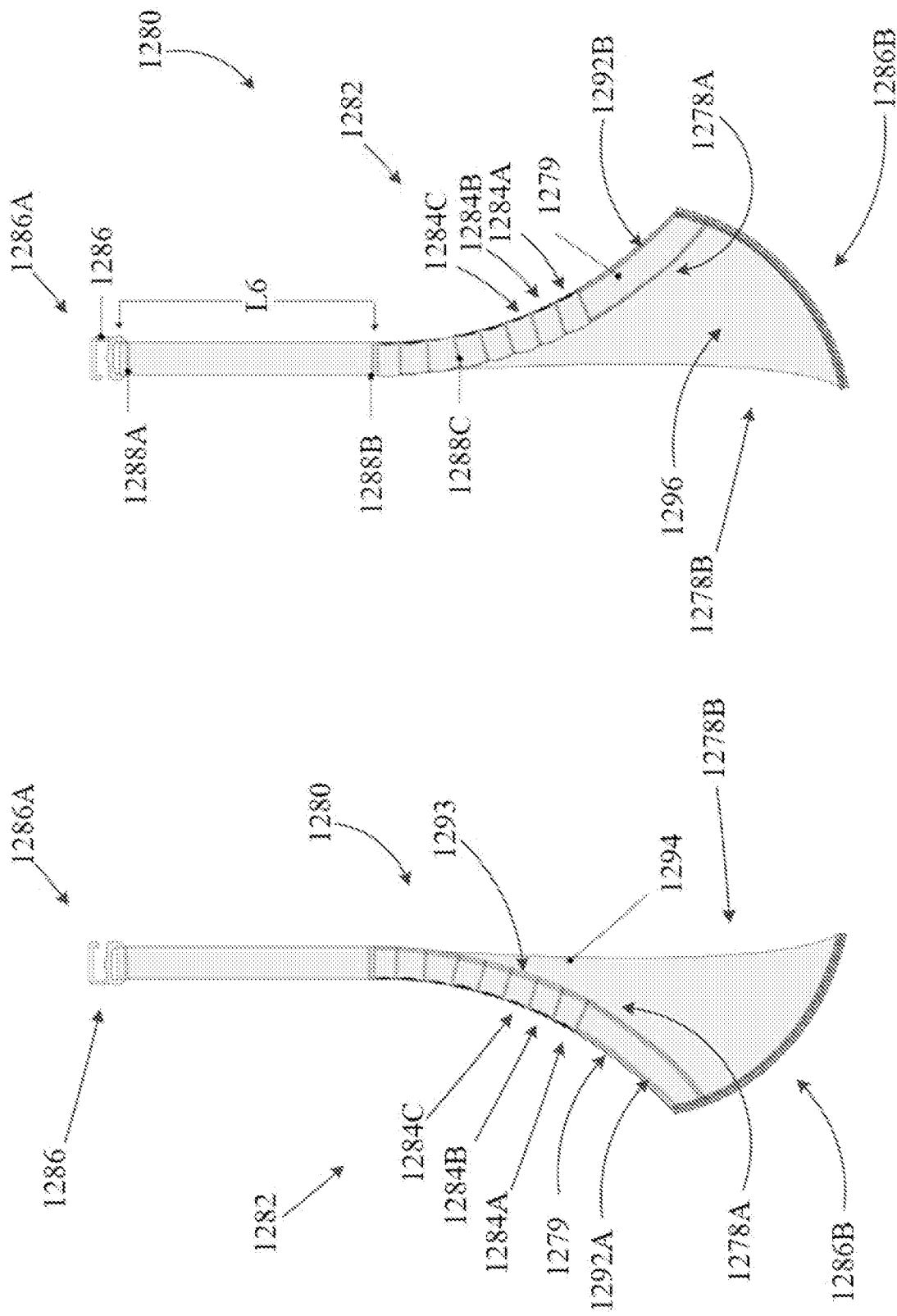

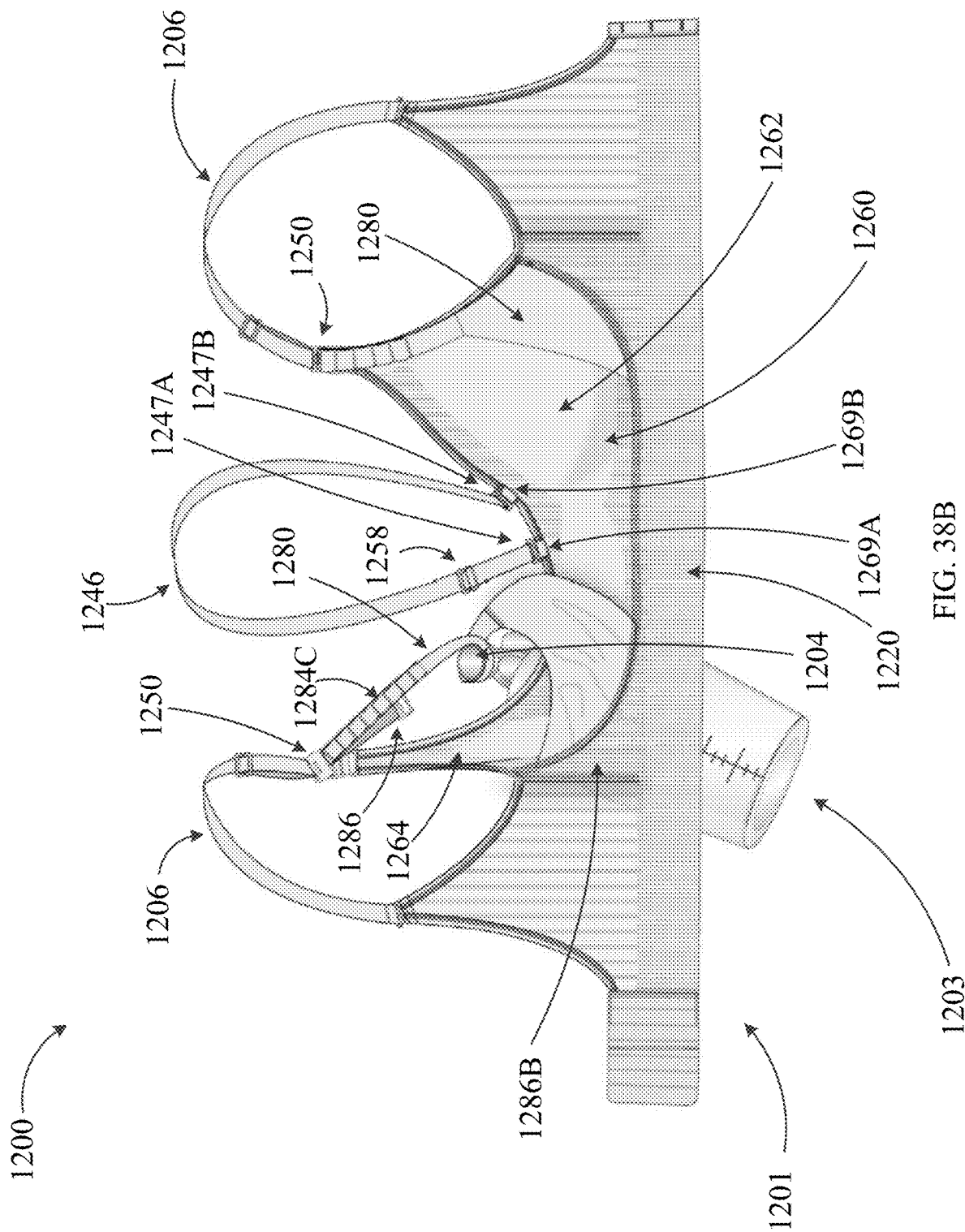

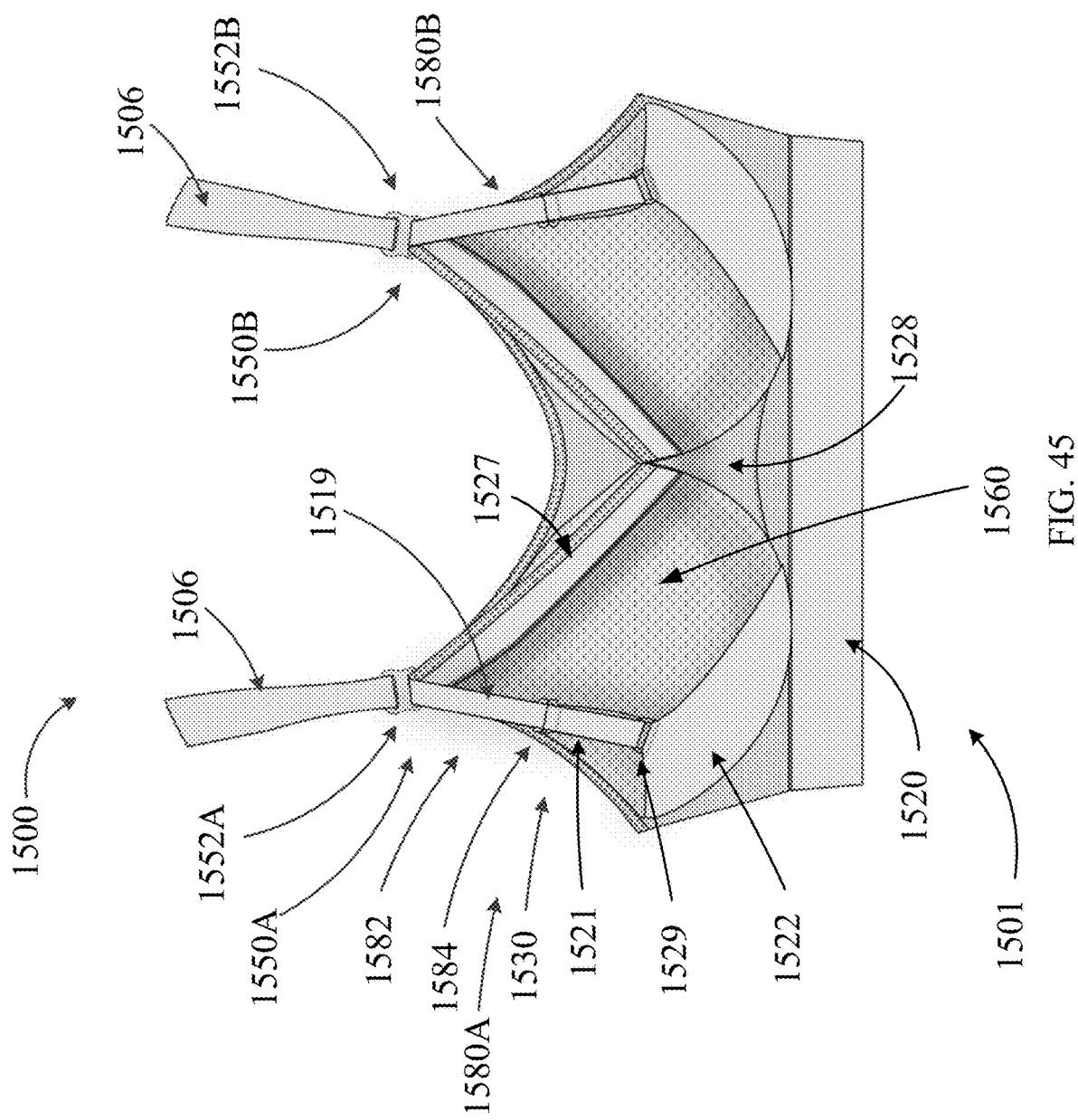

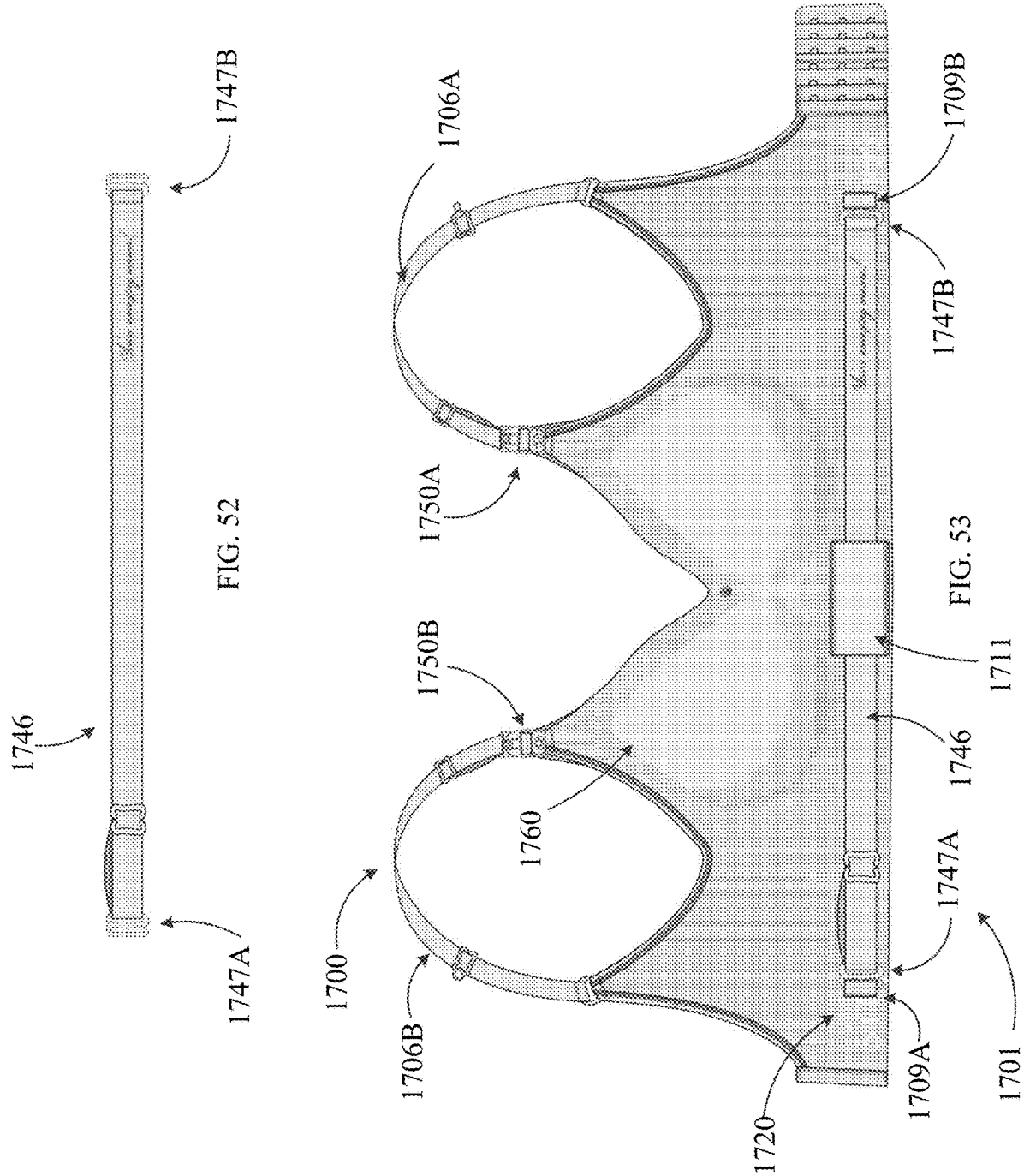

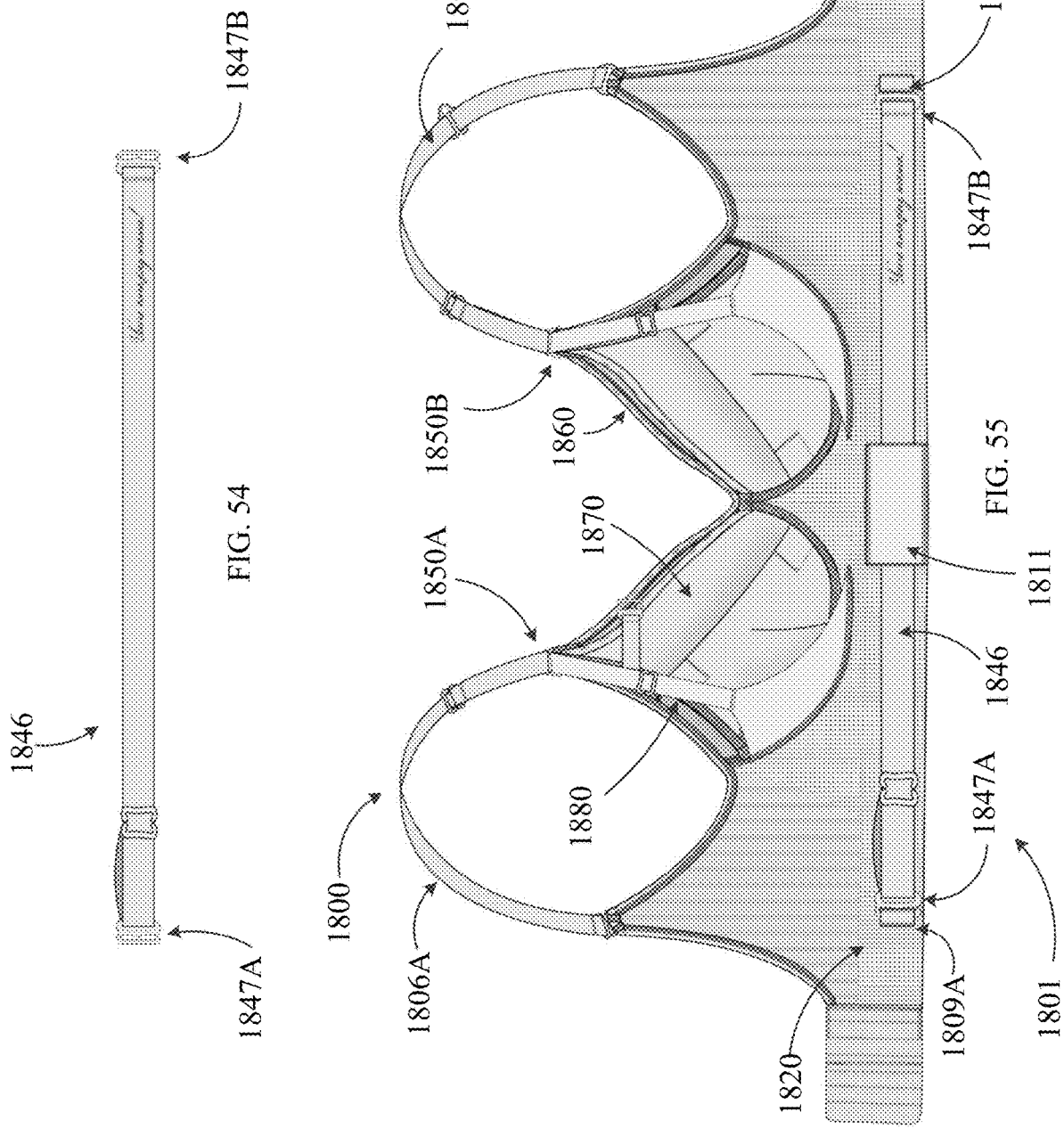

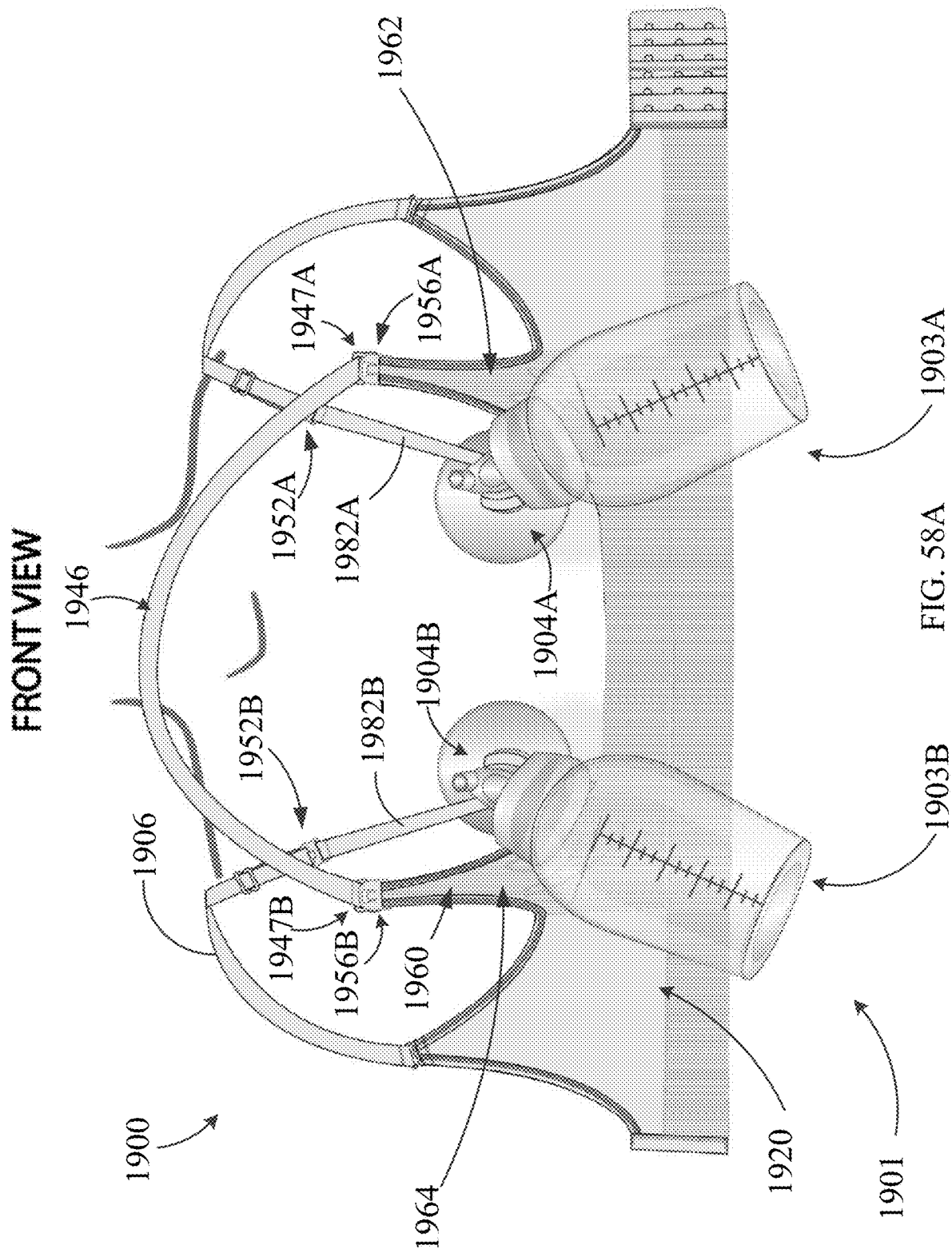

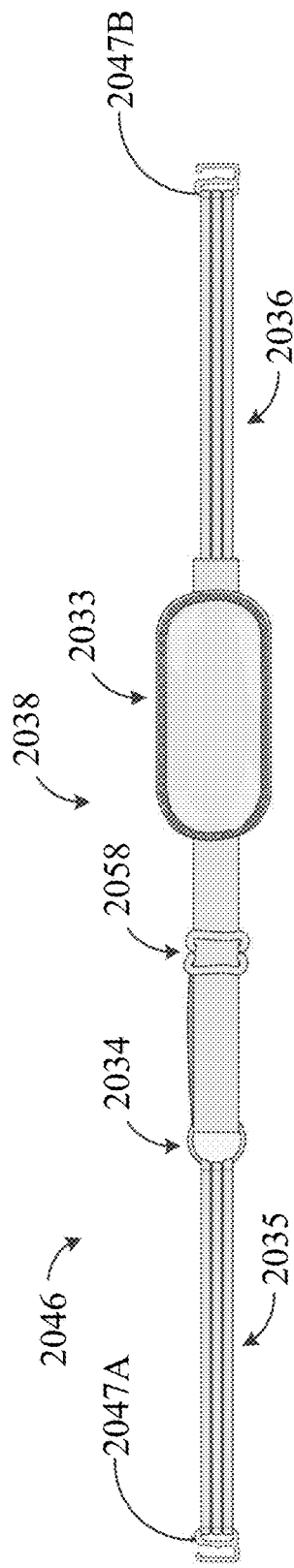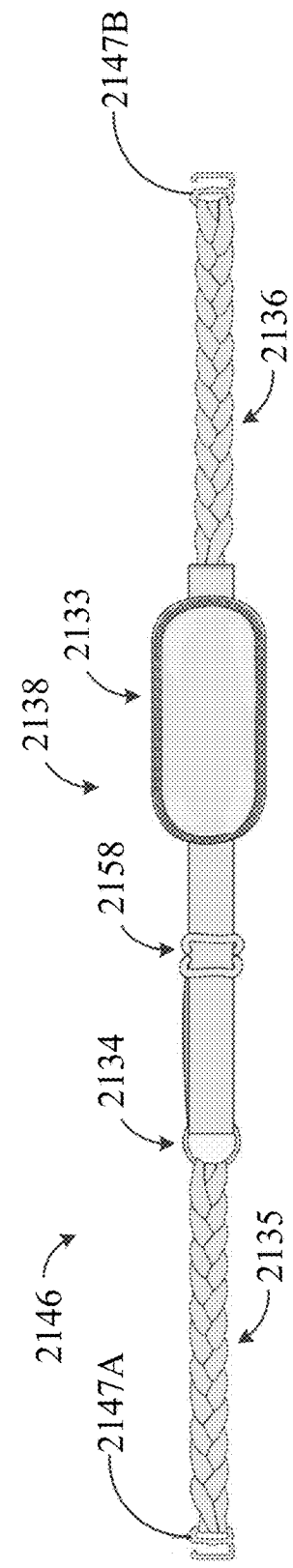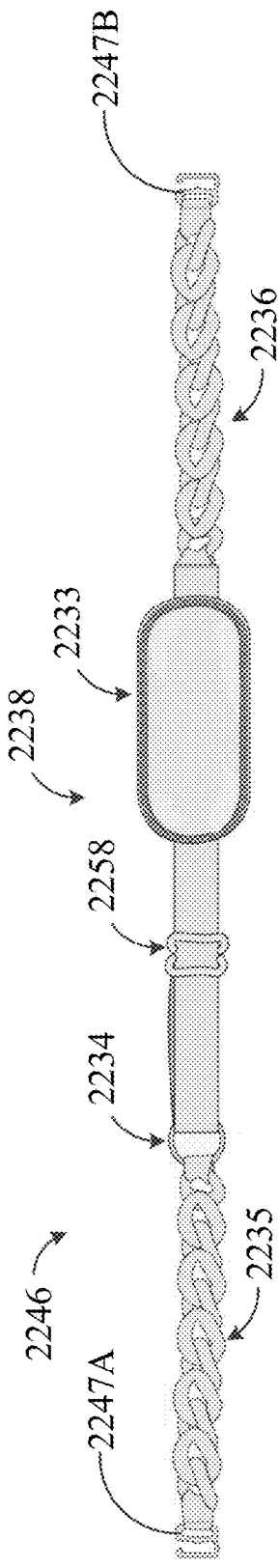

PUMPING/NURSING GARMENT

CROSS-REFERENCE TO RELATED APPLICATIONS

This application claims priority to and the benefit of U.S. Provisional Patent Application No. 62/967,474, filed Jan. 29, 2020, entitled "Pumping/Nursing Garment," the entire disclosure of which is incorporated by reference herein.

BACKGROUND

Embodiments described herein relate to a bra that can provide support to a breast pumping device while the wearer of the bra is pumping breast milk using the breast pumping device.

A breast pump may be used to express milk from a breast. Implementations of breast pumps have a pump body to express the milk and a milk container to receive the milk. The pump body of a breast pump may have a breast shield or a flange having a funnel shape with a cup portion that fits over at least a portion of a breast.

A let-down cushion or let-down massage cushion of a breast pump may fit between a breast shield or a flange of a pump body of the breast pump and a breast. The let-down cushion may fit within the breast shield or flange and have an edge that folds over an edge of the breast shield or the flange of the pump body. The let-down cushion may flex in and out to massage the areola of a breast to help stimulate milk flow. A seal may be formed between the let-down cushion and a breast to create suction and encourage breast milk expression.

To use a breast pump, a user manually holds the breast flange, shield, or pump body over a breast. While using the breast pump, the wearer is not able to use their hands for other tasks. Additionally, it may be desirable to express milk from both breasts simultaneously, but doing so, requires the user to hold both breast pump bodies against oneself and is both awkward and does not allow the user to do other tasks. As such, garments that assist in supporting the breast pump body for milk expression are needed to allow a wearer to use their hands for other tasks during milk expression with a breast pump.

SUMMARY

Apparatus are described herein for providing a garment (e.g. a bra, tank top, or dress) that can be used by a wearer during extraction of breast milk using a breast pump, and/or during breast feeding. In some embodiments, a garment can include a support strap having an adjustable portion, a shoulder strap, and a back panel. The support strap can be coupled to the shoulder strap via an engagement mechanism. The adjustable portion of the support strap can be configured to be adjusted relative to the engagement mechanism to change a length of the support strap between the engagement mechanism and the back panel so that the support strap can be disposed over a flange of a breast pump to hold the flange against the breast of a user. An outer panel can be coupled to the back panel and the engagement mechanism. In another embodiment, an inner panel can be removably coupled to the inner panel and the engagement mechanism.

BRIEF DESCRIPTION OF THE DRAWINGS

FIG. 8 is a front view of the engagement mechanism of FIG. 7.

FIG. 9 is a cross-sectional view of the engagement mechanism of FIG. 7 taken along line A-A in FIG. 8.

FIG. 10 is a side view of the engagement mechanism of FIG. 7.

FIG. 13 is a back view of a garment, according to an embodiment.

FIG. 14 is a front view of a strap connector of the garment of FIG. 13.

FIG. 16 is a front view of the engagement mechanism of FIG. 15.

FIG. 17 is a side view of the engagement mechanism of FIG. 15.

FIG. 27 is a front view of the support strap of the garment of FIG. 22.

FIG. 28 is a back view of the support strap of FIG. 27.

FIG. 33 is a front view of a support strap of a garment, according to an embodiment.

FIG. 34 is a back view of the support strap of FIG. 33.

FIG. 38B is a back view of the garment of FIG. 37 shown without the flange of the breast shield in an alternative support strap configuration.

FIG. 45 is a back view of a garment, according to an embodiment.

FIG. 52 is a front view of a neck strap, according to an embodiment.

FIG. 53 is a front view of a garment including the neck strap of FIG. 52 in a storage configuration, according to an embodiment.

FIG. 54 is a front view of a neck strap, according to an embodiment.

FIG. 55 is a back view of a garment including the neck strap of FIG. 54 in a storage configuration, according to an embodiment.

FIG. 58A is a front view of the garment of FIG. 57 in the configuration in which the garment includes the neck strap and is supporting the first breast pump and the second breast pump.

FIG. 59 is a top view of a neck strap, according to an embodiment.

FIG. 60 is a top view of a neck strap, according to an embodiment.

FIG. 61 is a top view of a neck strap, according to an embodiment.

DETAILED DESCRIPTION

Figure 1:
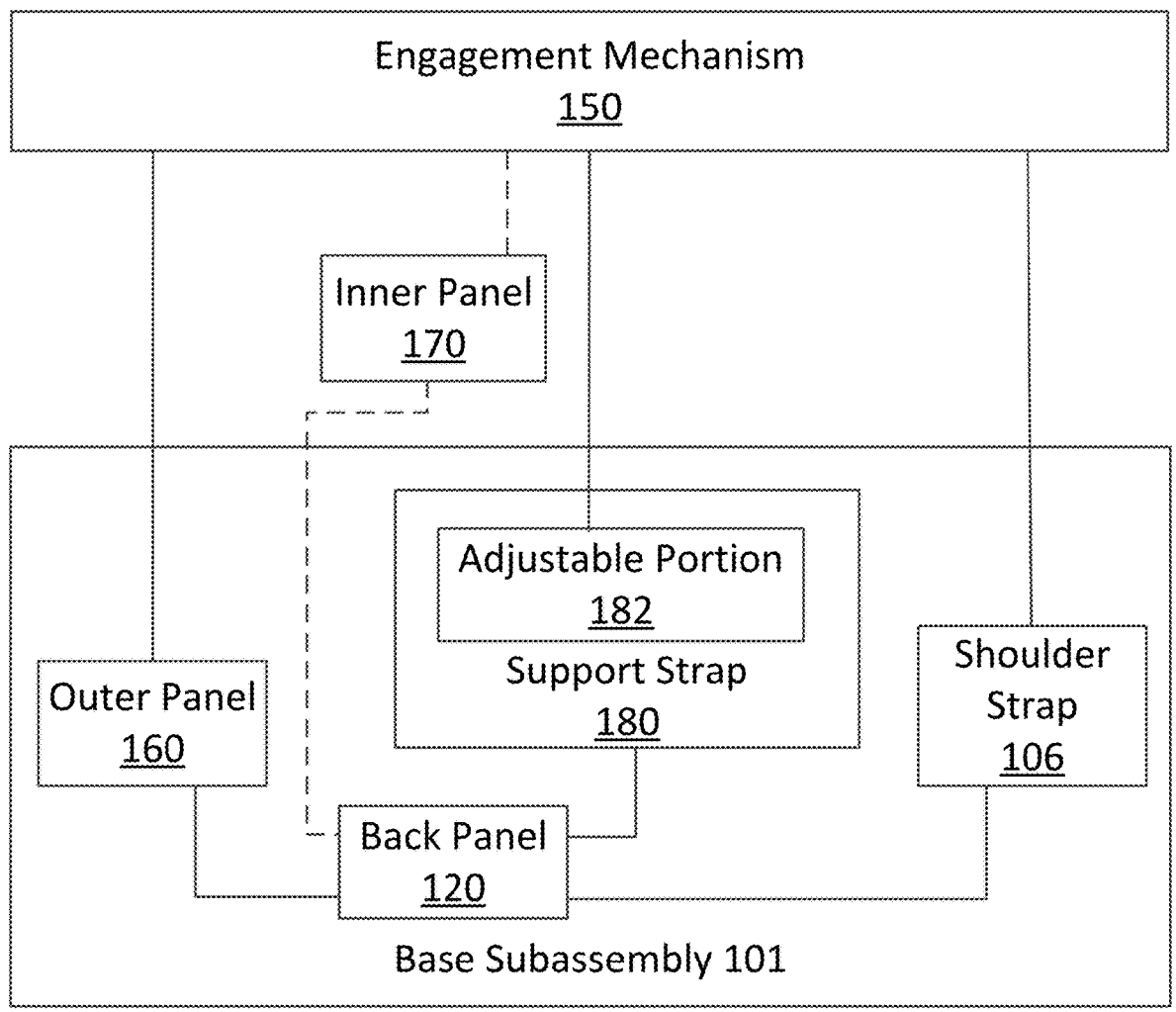
FIG. 1 is a schematic illustration of a garment, according to an embodiment.

Apparatuses, articles, processes for manufacture, garments, bustiers, breast pumping bras, and nursing bras that provide support to a wearer and/or at least a portion of a breast pump to aid with milk expression using a breast pump are described herein. For example, a garment, such as a bra, a tank top, a nightgown, or a bustier, may provide support for the weight of a breast pump body, milk container, and/or a wearer's breast, help secure the breast pump body in place, and/or stabilize the breast pump body for milk expression. Various embodiments may provide support to aid with creation of a tight seal between the wearer's breast and at least a portion of a breast pump body for milk expression (e.g., a breast shield and/or a let-down cushion of a breast pump body). The wearer of the garment may be able to pump breast milk without having to manually hold the breast pump body against themselves.

Garments in accordance with some embodiments may have openings formed/defined between layers of material that are fastened together and/or to panels of the garment to provide openings for access to a wearer's breasts. In particular, the garment may have an inner panel (e.g., a pumping panel) having two openings providing access to the wearer's breasts that are formed between respective sets of layers of material. The layers of material can be coupled together such that at least a portion of the layers of material overlap each other, or alternatively can be coupled together in an abutting or edge-to-edge relationship. In some embodiments, the layers of material can be coupled together such that a portion of the layers overlap each other and a portion of the layers are coupled together in an abutting or edge-to-edge manner. Each opening is between the corresponding set of layers of material and the layers of material are fastened together in such a manner to define/provide the respective opening.

In some embodiments, the garment may have an exterior surface of one or more panels of material that cover the inner panel. When the panels of material and the layers of material that cover an opening are moved, the wearer can insert a portion of the breast pump body through the opening, and the layers of material and/or the panels of material of the garment can aid in supporting the breast pump body and/or the wearer's breast. In some embodiments, the materials used for the inner and the exterior panels may be a fabric capable of being stretched to allow for pushing the material out of the way to insert the pump body portion. The fabric may also have some elasticity to fit snugly under and/or around the pump body portion for support and be capable of returning to the panel's original shape. In some embodiments, the garment may have elastic edges to prevent the garment from slipping down as well as providing additional support for the wearer's breasts.

In some embodiments, a garment (e.g., a bra) described herein can include an inner pumping panel with layers of material and an outer panel that can at least partially cover the inner pumping panel. A first portion of the layers of material of the inner pumping panel may be disposed on a left side of the bra to cover a portion of the wearer's left breast and can be fastened together such that at least a portion of the layers of material overlap and define a first opening. A second portion of the layers of material of the inner pumping panel may be disposed on a right side of the bra to cover a portion of the wearer's right breast, and can be fastened together such that at least a portion of the layers of material overlap and define a second opening. The first and second openings are each optionally disposed at an oblique angle relative to a bottom edge of the bra and are sized and positioned to help support at least a portion of a breast pump disposable through the first and/or second opening.

Some embodiments may have one or more loops of a material (e.g., elastic, fabric, etc.) attached to the garment. Each loop may be designed to secure a portion of a breast pump in place (e.g., a loop to hook or fit around a breast shield to aid in the support of the breast pump body and milk container for pumping milk).

Some embodiments may have support straps including an adjustable portion. Each support strap can be fixedly coupled to a back panel of the garment and can be coupled to a shoulder strap of the garment via an engagement mechanism. The adjustable portion of the support strap can be configured to be adjusted relative to the engagement mechanism to change a length of the support strap between the engagement mechanism and the back panel so that the support strap can be disposed over (e.g., wrapped at least partially around) a flange of a breast pump to hold the flange against the breast of a user (e.g., sealed against the breast). Thus, in some embodiments (e.g., any of the embodiments described herein including a support strap having an adjustable portion), the support strap can have a first configuration in which the support strap is not used to support a breast pump but is used to maintain the engagement mechanism and end of the shoulder strap a particular distance from the back panel (e.g., during a period of time when the user is not pumping or nursing and/or while the user is nursing). The support strap can have a second configuration in which the support strap is disposed over a flange of a breast pump to hold the flange against a user's breast. The support strap can couple an end of the shoulder strap to the back panel of the garment in both the first configuration and the second configuration. Additionally, the support strap can couple an end of the shoulder strap to the back panel of the garment regardless of whether an outer panel or an inner panel is coupled to the end of the shoulder strap via a portion of the engagement mechanism. Since the support strap includes an adjustable portion that allows the user to adjust the length of the support strap extending from the engagement mechanism to the back panel, the length of the support strap can be adjusted depending which of the first or the second configuration is desired, thus avoiding overstretching the support strap in the second configuration such that the support strap is too long to return to the first configuration. In some embodiments, the adjustable portion is configured such that the support strap can have multiple additional configurations (e.g., associated with various lengths between the engagement mechanism and the back panel) such that the user can adjust the support strap for improved fit.

Some embodiments may have adjustable straps that may be selectively attached to the garment. For example, the garment can have a top line on the garment with corresponding attachment mechanisms to those found on the strap thereby allowing the strap to be attached thereto. For example, the top line may be a piece of material (e.g., an elastic band) attached to an edge of a panel (e.g., an inner panel) and the corresponding attachment mechanisms may be sewn to the garment with stitching between the elastic band and the fabric of the garment. The one or more attachment mechanisms (e.g., corresponding attachment mechanisms to the attachment mechanisms found on the strap) may be sewn in to the garment for selectively attaching a strap in one of a multiple different positions to support a breast pump body.

By way of further example, a neck strap can optionally be used and may extend around the back of the wearer's neck and be attached to the top line of the garment. The garment (e.g., a top line of a pumping/nursing bra) may have one or more selective attachment mechanisms (e.g., loops or hooks allowing for attachment of the strap to the garment). Multiple selective attachment mechanisms may be provided on the garment to provide multiple different positions for the strap. Attachment mechanisms may include, for example, hooks that may be selectively attached to a loop (e.g., a fabric, metal, or plastic loop), snaps, buttons and button holes, ribbon ties, lace ties, string ties, and/or any other attachment mechanism that can be selectively attached or detached. For example, a wearer could use a ribbon, lace, heavy string, etc. that could be threaded through a loop on the topline and tied where the two ends join. There may be a single strap and/or multiple straps that extend from one area of the bra to another as opposed to fitting around the neck. For example, a single strap could attach at the front topline, extend over the shoulder and hook at the topline below the underarm or back.

In some embodiments, the neck strap may have a single hook that can be attached to the garment or multiple hooks that can be attached to the garment. The neck strap may be used, for example, to ensure that the garment remains in place during breast pumping, particularly when the breast pump bottle becomes heavier as the container, which is used with the breast pump to collect milk, fills with milk. For example, a neck strap may encircle the neck of the wearer and have at least one hook attached to the top line of the garment to ensure that the garment remains in place during the use of a breast pump with at least one of the wearer's breasts. The neck strap may be used with or without shoulder straps of the garment. In some embodiments, a neck strap can include a comfort strap portion that has a width that is greater than a width of a typical strap to provide further comfort to the user. For example, the comfort strap portion can extend around the user's neck. In some embodiments, the comfort strap portion of the neck strap can be padded and/or can be formed with a material to provide softer comfort to the user's neck. In some embodiments, the width of the comfort portion can var. For example, the width can be tapered or narrower at the ends of the comfort portion than at a center of the comfort portion. In some embodiments, the neck strap can include a first coupling member at a first end of the neck strap and a second coupling member at a second end of the neck strap. A portion of the first coupling member can be configured to be engaged with a complementary portion of an engagement mechanism of the garment and a portion of the second coupling member can be configured to be engaged with the first coupling member, another complementary portion of the engagement mechanism, and/or a complementary portion of a second engagement mechanism of the garment.

In some embodiments, a pocket or a channel may be provided on a shoulder strap that contains and/or houses a cord or a strap with a hook or an attachment piece to connect to another area of the garment, as shown and described for example in International Application No. PCT/US16/43326 incorporated by reference above. The cord may be elastic to allow for the cord to be stretched and/or the cord may be stored within the pocket or channel rolled up into a coil, so that the cord can be extended and retracted. The cord may also have a slider to lengthen and shorten the strap as needed.

In some embodiments, the garment can include openings or holes along a perimeter top edge of the garment and the fastening mechanisms of the straps can be received therein to couple the straps to the garment. Such an embodiment is described in more detail below with reference to specific embodiments.

In some embodiments, a garment as described herein can be used in conjunction with a wearable breast pump and/or a wearable milk collection device. In such a garment, the garment can include an extender in place of the inner panel and the extender can be used to selectively adjust the position of the outer panel (e.g., the bra cup) to accommodate the wearable breast pump. The wearable breast pump or collection device can be positioned between the user's breast and the outer panel of the garment. The extenders can be attached to a portion of the engagement mechanism (e.g., engagement mechanism 150) on both the right side and left side of the garment. The outer panel of the garment (e.g., the right outer panel and the left outer panel) can be removably and selectively coupled to the extender to adjust the position and size of the outer panel in relation to the user's breast and the wearable breast pump or collection device.

Such adjustment of the size and position of the outer panel (e.g., the bra cup) may be desirable, for example, to prevent stretching of the cup portion (e.g., outer panel) of the garment during use of the wearable breast pump or milk collection device. Because such devices are disposed between the breast and the cup portion of the garment, and due to the size of some such devices, the cup portion of the garment may stretch or lose its form or shape during use of such devices and may then provide reduced support to the user's breast.

Other objects and advantages of the disclosed embodiments will become apparent from the following detailed description when viewed in conjunction with the accompanying drawings, which disclose numerous embodiments. It should be understood, however, that the disclosed embodiments are merely exemplary, and may be embodied in various forms. Therefore, the details disclosed herein are not to be interpreted as limiting.

FIG. 1 is a schematic illustration of a garment 100. The garment 100 can be, for example, in the form of a bra, to be worn around a chest or upper torso of a wearer, typically a woman, who may desire to express milk from one or both breasts using a breast pump. The garment 10 can include a base subassembly 101 that includes an outer panel 160, one or more support straps 180, one or more shoulder straps 106 and a back panel 120. The garment 100 can include an inner panel 170. The support straps 180 can each include an adjustable portion 182. In some embodiments, each shoulder strap 106 can be coupled to the outer panel 160, the inner panel 170, and the support straps 180 via an engagement mechanism 150 (also referred to herein as a "clasp"). The support straps 180 can be coupled on a first end to the back panel 120, and on a second end to one of the shoulder straps 106 via the engagement mechanism 150. In alternative embodiments, the support straps 180 can be attached to a lower band of the garment (not shown) rather than to the back panel 120. In some embodiments, the back panel 120 and a lower band can be formed integrally. Each of the shoulder straps 106 can have a first end coupled to the support strap 180 (via the engagement mechanism 150) and a second end coupled to the back panel 120 and/or a lower band or other portion of the garment 100, via, for example, stitching. The outer panel 160 can be attached to the back panel 120 and/or along a bottom band of the garment 100, for example, along a bottom edge of the outer panel 160, via, for example, sewing/stitching. The inner panel 170 can optionally be coupled to the back panel 120 and/or along a bottom band of the garment 100, for example, along a bottom edge of the outer panel 160 and/or along a bottom edge of the inner panel 170, via, for example, coupling mechanisms such as mating snap mechanisms. The inner panel 170 can optionally be directly coupled to the outer panel 160, back panel 120, and/or support strap 180 via coupling mechanisms such as, for example, mating snap mechanisms.

The adjustable portion 182 of the support strap 180 can be configured such that a length of the support strap 180 between the engagement mechanism 150 and the back panel 120 can be adjusted. For example, the length of the support strap 180 between the engagement mechanism 150 and the back panel 120 can have a first length associated with the support strap 180 not being used to support a breast pump but being used to couple an end of the shoulder strap 206 to the back panel 220. The length of the support strap 180 between the engagement mechanism 150 and the back panel 120 can have a second length associated with the support strap 180 supporting a portion of a breast pump body (e.g., a flange and/or stem of a breast shield) to aid with creation of a tight seal between the wearer's breast and at least a portion of a breast pump body for milk expression (e.g., a breast shield and/or a let-down cushion of a breast pump body) while still being used to couple an end of the shoulder strap 106 to the back panel 120. For example, the second length of the support strap 180 can be sufficiently long such that the support strap 180 can extend from the back panel 120, wrap around a flange and/or stem of a breast shield disposed on the wearer's breast to support the breast shield against the wearer's breast, and be coupled to the shoulder strap 106 via the engagement mechanism 150. In some embodiments, the support strap 180 can have additional lengths (e.g., a third length and/or a fourth length) associated with various incremental sizes of an adjustable loop portion of the support strap 180. In some embodiments, such as when the support strap 180 includes one coupling mechanism that includes a slider component (also referred to herein as a "slider") configured to translate along a strap portion of the support strap 180 forming a loop, the support strap 180 can have an infinite number of additional lengths depending on the location that the slider component is secured along the strap portion of the support strap 180. The support strap 180 can be transitioned between the first length, the second length, and any additional lengths by the user (e.g., for adjustability of use of the support strap 180 and/or comfort).

In some embodiments, the adjustable portion 182 can include a first coupling mechanism (also referred to as a first coupling member) disposed proximate a second end of the support strap 180 and a set of second coupling mechanisms (also referred to as a set of second coupling members) disposed along the adjustable portion (e.g., closer to the first end than the first coupling mechanism). For example, a first coupling mechanism can be disposed closer to the second end of the support strap 180 than a second coupling mechanism and a third coupling mechanism (also referred to as a second coupling member and a third coupling member, respectively). The second coupling mechanism and the third coupling mechanism can be included in the set of second coupling mechanisms, and can each be configured to be releasably engaged with the first coupling mechanism. For example, the first coupling mechanism can include a male or female portion of a snap component, and the second coupling mechanism and the third coupling mechanism, can each include the other of the male or female portion of the snap component. As another example, one of the second coupling mechanisms of the set of second coupling mechanisms can be disposed proximate the second end of the support strap 180 and the first coupling mechanism and the remainder of the second coupling mechanisms of the set of second coupling mechanisms can be disposed along the adjustable portion (e.g., closer to the second end than the second coupling mechanism disposed proximate the second end).

The adjustable portion 182 can be configured such that the second end can be looped through an opening of the engagement mechanism 150 and the first coupling mechanism is engaged with a second coupling mechanism of the set of second coupling mechanisms. Each of the coupling mechanisms of the set of second coupling mechanisms can be disposed a different distance from the first end of the support strap 180 (e.g., in a different location along a length from the first end of the support strap 180 to the second end of the support strap 180). Thus, the length of the support strap 180 between the engagement mechanism 150 and the back panel 120 can be adjusted depending on which coupling mechanism of the set of second coupling mechanisms the first coupling mechanism is engaged with. Each of the coupling mechanisms of the set of second coupling mechanisms can be disposed any suitable distance from the second end of the support strap 180. The adjustable portion 182 can include any suitable number of second coupling mechanisms (e.g., two, three, four, or more coupling mechanisms) configured to alternatively releasably engage with the first coupling mechanism.

In some embodiments, rather than including a set of second coupling mechanisms, the first coupling mechanism can selectively engaged with the material of the support strap 180 directly. For example, the first coupling mechanism can include a buckle or slider component configured to maintain a position of the second end of the support strap 180 relative to a portion of the support strap 180 that is threaded through the buckle or slider component. In some embodiments, rather than including a first coupling mechanism and a set of second coupling mechanisms, the support strap 180 can be formed of or include a material that is sufficiently elastic such that at least the adjustable portion 182 of the support strap 180 can be stretched to be disposed over a flange of a breast pump and accommodate the flange to hold the flange against the breast of a user (e.g., pulled by the wearer toward a center of the user's chest and released to engage a portion of the breast pump on an opposite side of the breast pump than the support strap 180 was disposed in the first configuration).

The first coupling mechanism and the set of second coupling mechanisms can include any suitable coupling or mating components such that the first coupling mechanism can be releasably and selectively coupled to (e.g., selectively attached and detached) each of the coupling mechanisms of the set of second coupling mechanisms. Each of the coupling mechanisms of the set of second coupling mechanisms can include a substantially identical coupling or mating component to each of the other second coupling mechanisms. For example, the first coupling mechanism can include a male snap connector and the second coupling mechanisms of the set of second coupling mechanisms can each include a female snap connector, or vice versa. As another example, the first coupling mechanism can include a button and the second coupling mechanisms of the set of second coupling mechanisms can each include or define a button hole configured to receive the button or can include a string configured to be tied to the button, or vice versa. As another example, the first coupling mechanism can include a first portion of a hook and loop fastener (e.g., a hook portion) and the second coupling mechanisms of the set of second coupling mechanisms can each include a second portion of hook and loop fastener (e.g., a loop portion), or vice versa. As another example, the first coupling mechanism can include a hook (e.g., a swan hook) and the second coupling mechanisms of the set of second coupling mechanisms can each include a loop (e.g., a fabric, metal, or plastic loop) or define a discrete opening that the hook can be selectively attached to, or vice versa.

The inner panel 170 and the outer panel 160 can each include one or more panels each formed with one or more layers of material. For example, the outer panel 160 can include a right outer panel (not shown in FIG. 1) and a left outer panel (not shown in FIG. 1). The right outer panel and the left outer panel can be shaped and sized for coverage of a wearer's right breast and left breast, respectively. The inner panel 170 can include a right inner panel (not shown in FIG. 1) and a left inner panel (not shown in FIG. 1). The right inner panel and the left inner panel can be shaped and sized for coverage of a wearer's right breast and left breast, respectively. Each of the right inner panel and the left inner panel can include a first portion and a second portion that are coupled together such that a portion of a border of each of the first portion and the second portion is unattached and can define an opening between the first portion and the second portion. In some embodiments, the first portion and the second portion can include an overlapping portion, which can define the opening. The first portion and the second portion can be separated by, for example, moving the first portion and the second portion away from each other, thereby creating the opening and providing access to the user's breast. A breast pump can then be inserted through the opening and the inner panel 170 can help support the breast pump during milk extraction.

The inner panel 170, the outer panel 170, the back panel 120, the shoulder strap 106, and/or the engagement mechanism 150 can be the same or similar in structure and/or function to any of the inner panels or pumping panels, outer panels, back panels shoulder straps, and engagement mechanisms, respectively, described in U.S. Pat. No. 10,426,203, filed on Jan. 17, 2018, issued Oct. 1, 2019, entitled "Pumping/Nursing Garment," which is incorporated by reference herein in its entirety.

The engagement mechanism 150 can be used to releasably couple the outer panel 160, the inner panel 170, the shoulder strap 106 and the support strap 180 to one another in various configurations. For example, in some embodiments, at least a portion of the outer panel 160 can be releasably coupled to and decoupled from the inner panel 170, and at least a portion of the inner panel 170 can be releasably coupled to and decoupled from the support strap 180 and the shoulder strap 106. When the outer panel 160 is coupled to the inner panel 170, the inner panel 170 and the outer panel 16 can collectively be coupled to and decoupled from the support strap 180 and shoulder strap 106. In some embodiments, when the inner panel 170 is not included or is separated from the base subassembly 101, the outer panel 160 can be releasably coupled to and decoupled from the support strap 180 and the shoulder strap 106 via the engagement mechanism 150 or a portion of the engagement mechanism 150.

Figure 2:
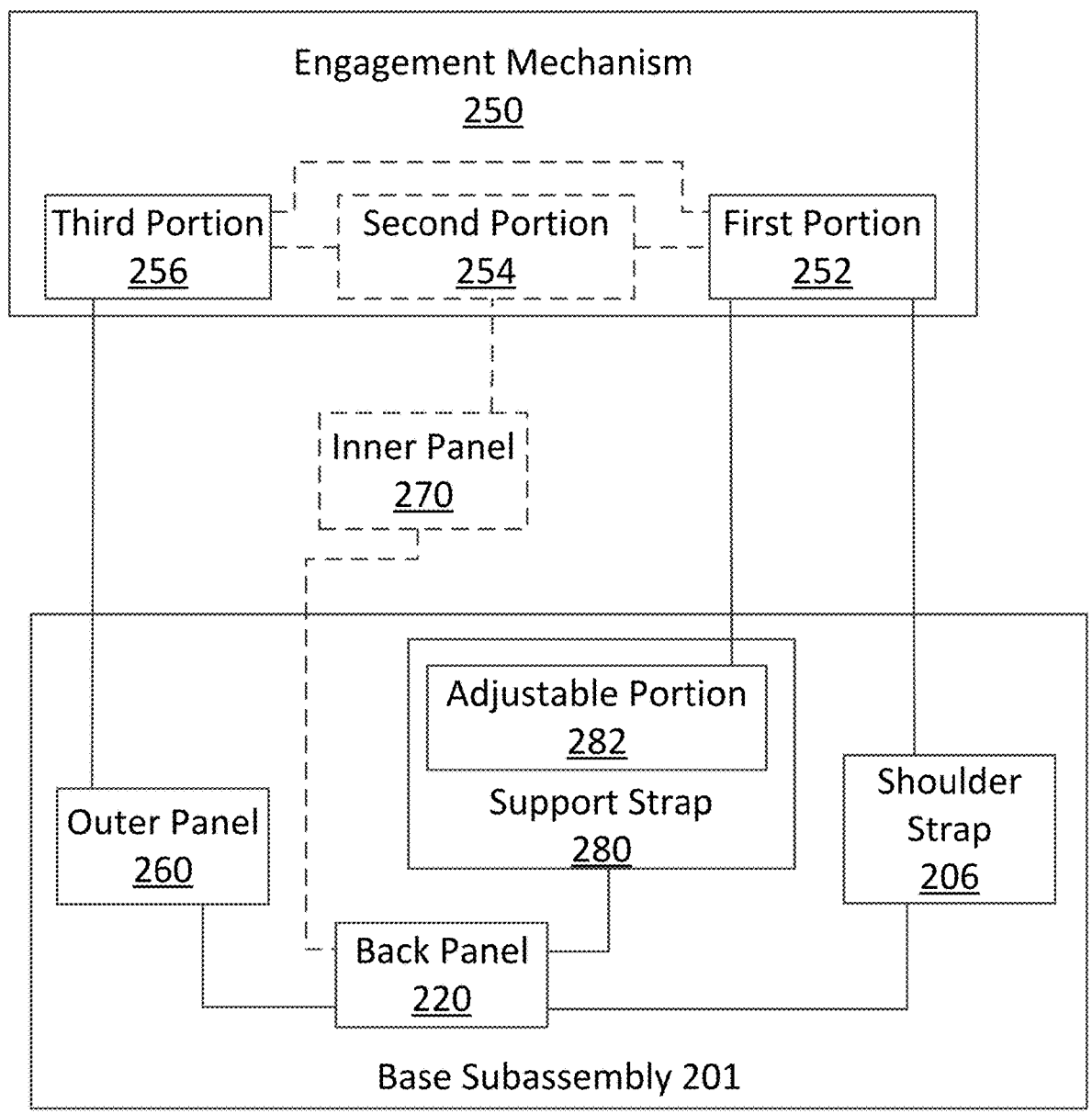
FIG. 2 is a schematic illustration of a garment, according to an embodiment.

In some embodiments, an engagement mechanism can include two or more portions. For example, FIG. 2 is a schematic illustration of a garment 200. The garment 200 can be the same or similar in structure and/or function to the garment 100. For example, the garment 200 can include an engagement mechanism 250 and a base subassembly 201 that is the same or similar in structure and/or function to the base subassembly 101. The base subassembly 201 includes a shoulder strap 206, a back panel 220, an outer panel 260, and a support strap 280 that can be the same or similar in structure and/or function to the shoulder strap 106, the back panel 120, the outer panel 160, and the support strap 180, respectively. For example, the support strap 280 can include an adjustable portion 282. The system can also include an optional inner panel 270 that is the same or similar in structure and/or function to the inner panel 170.

As shown in FIG. 2, the engagement mechanism 250 can include a first portion 252, a second portion 254, and a third portion 256. The first portion 252 can be coupled to the support strap 280 and the shoulder strap 206. The second portion 254 can be coupled to the inner panel 270. A third portion 256 can be coupled to the outer panel 260. The first portion 252 can be releasably coupled to the second portion 254 and the second portion 254 can be releasably coupled to the third portion 256. Thus, the first portion 252 can be coupled to the third portion 256 via the second portion 254. The first portion 252 can also be directly coupled to the third portion 256 (e.g., if the inner panel 270 and second portion 254 are not used or included in the system 200). Furthermore, the support strap 280 can be coupled to the first portion 252 via the adjustable portion 282 of the support strap 280. Thus, the outer panel 260, the inner panel 270, the support strap 280, and the shoulder strap 206 can be coupleable to and decoupleable from one another via the first portion 252, the second portion 254, and the third portion of the engagement mechanism 250. For example, the second portion 254 of the engagement mechanism 250 can be releasably coupled to the first portion 252 to couple the inner panel 270 to the support strap 280 and the shoulder strap 206. The third portion 256 of the engagement mechanism 250 can be releasably coupled to the second portion 254 to releasably couple the outer panel 260 to the inner panel 270. The third portion 256 of the engagement mechanism 250 can be releasably coupled to the first portion 252 to releasably coupled the outer panel 260 to the inner panel 270 (e.g., if the inner panel 270 and the second portion 254 are not being used).

In some embodiments, the first portion 252 can be releasably coupled to the support strap 280. For example, the adjustable portion 282 of the support strap 280 can be configured such that a length of the support strap 280 between the engagement mechanism 250 and the back panel 220 can be adjusted. The adjustable portion 282 can be the same or similar in structure and/or function to the adjustable portion 182 described above. For example, in some embodiments, the adjustable portion 282 can include a first coupling mechanism (also referred to as a first coupling member) disposed proximate a second end of the support strap 180. The second end can be an end of the support strap 180 opposite a first end fixedly coupled to the back panel 220. The adjustable portion 282 can also include a set of second coupling mechanisms (also referred to as a set of second coupling members) disposed along the adjustable portion (e.g., closer to the first end than the first coupling mechanism). The adjustable portion 282 can be configured such that the second end of the support strap 282 can be looped through a first opening in the first portion 252 such that the first coupling mechanism is on a first side of the first portion 252 and can be engaged with a second coupling mechanism from the set of second coupling mechanisms on a second side of the first portion 252 to form a loop.

In some embodiments, one of the coupling mechanisms of the set of second coupling mechanisms can be disposed proximate the second end of the support strap 280 and the first coupling mechanism and the remainder of the coupling mechanisms of the set of second coupling mechanisms can be disposed along the adjustable portion (e.g., closer to the second end than the second coupling mechanism disposed proximate the second end). The adjustable portion 282 can be configured such that the second end of the support strap 282 and a sufficient length of the support strap 282 can be looped through a first opening in the first portion 252 (e.g., looped around a second securement bar of the first portion 252) such that the first coupling mechanism can be disposed on a first side of the first portion 252 and can be engaged with a coupling mechanism from the set of second coupling mechanisms disposed on a second side of the first portion 252 to form a loop. Additionally, the second end of the support strap 282 and a sufficient length of the support strap can be looped through a first opening in the first portion 252 such that a second coupling mechanism of the set of second coupling mechanisms is on a first side of the first portion 252 and can be engaged with the first coupling mechanism that remains on a second side of the first portion 252 to form a loop.

In some embodiments, the first portion 252 can be fixedly coupled to the shoulder strap 106 via, for example, an end of the shoulder strap 106 being looped through a second opening of the first portion 252 (e.g., looped around a first securement bar of the first portion 252) and being secured (e.g., stitched) to a portion of the shoulder strap 106 to form a loop. In some embodiments, the first portion 252 can be coupled to an adjustable portion of the shoulder strap 106 such that a length of the shoulder strap 106 between the first portion 252 and the back panel 220 can be adjusted (e.g., via adjusting the length of a loop extending through the second opening by moving a buckle attached to an end of the shoulder strap 106 along a portion of the shoulder strap).

The second portion 254 can be fixedly coupled to the inner panel 270 via, for example, a first portion of the inner panel 270 being looped through an opening of the second portion 254 (e.g., looped around a securement bar of the second portion 254) and being secured (e.g., via stitching or any suitable coupling mechanism) to a second portion of the inner panel 270 to form a loop. In some embodiments, the inner panel 270 can be coupleable to and decouplable from the second portion 254 via any suitable coupling mechanism. Additionally the inner panel 270 can be directly coupleable to and decoupleable from the outer panel 260, the back panel 220, and/or the support strap 280 via any suitable coupling mechanisms (e.g., mating snap mechanisms).

The third portion 256 can be fixedly coupled to the outer panel 260 via, for example, a first portion of the outer panel 260 being looped through an opening of the third portion 256 (e.g., looped around a securement bar of the third portion 256) and being secured (e.g., via stitching or any suitable coupling mechanism) to a second portion of the outer panel 260 to form a loop. In some embodiments, the outer panel 260 can be coupleable to and decouplable from the third portion 256 via any suitable coupling mechanism.

In some embodiments, the first portion 252, the second portion 254, and the third portion 256 can include complementary mating features or any other suitable coupling mechanisms such that the first portion 252, the second portion 254, and the third portion 256 are releasably coupleable to and decoupleable from one another. For example, the first portion 252, the second portion 254, and the third portion 256 can include complementary mating features such that the second portion 254 or the third portion 256 can be releasably coupleable to and decoupleable from the first portion 252 and so that the third portion 256 can be releasably coupleable to and decoupleable from the second portion 254. For example, the first portion 252 can include an extension portion (e.g., a hook) that forms a slot and the second portion 254 can define an engagement aperture (also referred to as an opening) configured to receive the extension portion such that a portion of the second portion 254 is disposed within the slot of the first portion 252. The second portion 254 can also include an extension portion (e.g., a hook) that forms a slot that is the same or similar in shape and size to the extension portion of the first portion 252. The third portion 256 can define an engagement aperture (also referred to as an opening) that is the same or similar in shape and size to the engagement aperture of the second portion 254 such that the engagement aperture of the third portion 256 is configured to receive the extension portion of the second portion 254 such that a portion of the third portion 256 is disposed within the slot of the second portion 252. Since the extension portions of the first portion 252 and the second portion 254 are similarly shaped and sized and the engagement apertures of the second portion 254 and the third portion 256 are similarly shaped and sized, the extension aperture of the first portion 252 can be received within the engagement aperture of the third portion 256 such that a portion of the third portion 256 is in the slot of the first portion 252, and thus coupling the third portion 256 directly to the first portion 252.

In use, the garment 200 can be worn around a chest or upper torso of a wearer with the first portion 252 coupled to the second portion 254 and the second portion 254 coupled to the third portion 256 such that the inner panel 270 and the outer panel 260 cover one or both breasts of the wearer. If access to a breast of the wearer is desired, such as for breast pumping, the outer panel 260 (e.g., the right outer panel and/or the left outer panel) can be detached from the inner panel 270 (e.g., the right inner panel and/or the left inner panel) by detaching or uncoupling the third portion 256 from the second portion 254 of the engagement mechanism 250. The outer panel 260 can then be moved (e.g., folded down) such that the inner panel 270 is accessible. The outer panel 260 can remain attached to the back panel 220 via, for example, stitching at a base of the outer panel 260. The first portion and the second portion of the inner panel (e.g., the right inner panel and/or the left inner panel) can be separated (e.g., stretched or folded) to create an opening through which the wearer's breast is accessible and a portion of a breast pump can be inserted. If further access to the breast of the wearer is desired, for example, for nursing, the inner panel 270 can be detached from the support strap 280 and shoulder strap 206 by removing/detaching the second portion 254 of the engagement mechanism 250 from the first portion 252 of the engagement mechanism 250. Because the support strap 280 and the shoulder strap 206 remain coupled to the back panel 220, the garment 200 can still be held in place on the body of the wearer via the shoulder straps 206 and the support straps 280. In some embodiments, the outer panel 260 and the inner panel 270 can be detached from the shoulder strap 206 and the support strap 280 simultaneously without decoupling the outer panel 260 from the inner panel 270. When desired, the inner panel 270 and the outer panel 260 can be reattached to the shoulder strap 206 and the support strap 280 by recoupling the second portion 254 to the first portion 252 of the clasp 250, and the outer panel 260 can be recoupled to the inner panel 270.

In some embodiments, if the inner panel 270 is not desired to be used, the inner panel 270 can be removed from the garment 200 and the outer panel 260 can be reattached to the shoulder strap 206 by attaching the third portion 256 directly to the first portion 252. If the garment 200 is desired to be used for breast pumping, the wearer can adjust the length of the support strap 280 from a first length to second length greater than the first length. For example, in embodiments including a first coupling mechanism and a set of second coupling mechanisms, the wearer can uncouple the first coupling mechanism of the adjustable portion 282 of the support strap 280 from a coupling mechanism of the set of second coupling mechanisms (e.g., a second coupling mechanism) of the adjustable portion 282. The support strap 280 can then be separated from the first portion 252. A portion of a breast pump (e.g., a flange of a shield of a breast pump) can be applied to a breast of the wearer. The support strap 280 can then be wrapped fully or partially around the portion of the breast pump (e.g., a flange and/or a stem of a shield of the breast pump) and the adjustable portion 282 can be inserted into and/or threaded through an opening of the first portion 252 until the length of the support strap 280 between the first portion 252 and the back panel 220 is sufficient to support the breast pump against the breast of the wearer. The first coupling mechanism of the adjustable portion 282 can then be coupled to another coupling mechanism of the set of second coupling mechanisms (e.g., a third coupling mechanism) that can be the same or different from the coupling mechanism of the set of second coupling mechanisms (e.g., the second coupling mechanism) that the first coupling mechanism was coupled to before wrapping the support strap 280 around the portion of the breast pump. The support strap 280 can then support the portion of the breast pump against the breast of the wearer for a pumping procedure such that the support strap 280 is in supportive contact with the breast pump and the pumping procedure can be performed hands-free. In some embodiments, rather than fully separating the support strap 280 from the first portion 252, the first coupling mechanism of the adjustable portion 282 can be decoupled from a second coupling mechanism from the set of second coupling mechanisms, the length of the support strap 280 between the first portion and the back panel 220 can be adjusted by pulling a portion of the support strap 280 through the opening of the first portion 252, and then the first coupling mechanism can be coupled to another coupling mechanism for the set of second coupling mechanisms.

In embodiments in which the first coupling mechanism of the adjustable portion 282 includes a slider component configured to maintain a position of the second end of the support strap 280 relative to a portion of the support strap 280 that is threaded through the slider, for example, the wearer can pull the slider component from a first location to which the slider component was secured along the support strap 280 to a second location to which the slider component was secured such that a loop of the adjustable portion 282 coupled to the slider component is decreased and the overall length of the support strap 280 is increased. The support strap 280 can then be pulled toward a center of the wearer's chest (e.g., laterally inwardly) such that the support strap 280 is moved from being on an outer side of the wearer's breast on a first side of the areola and/or nipple of the wearer to an inner side of the wearer's breast on a second side of the areola and/or nipple of the wearer. A portion of a breast pump (e.g., a flange of a shield of a breast pump) can be applied to a breast of the wearer (e.g., aligned with the wearer's areola and/or nipple). The support strap 280 can then be disposed against a portion of the breast pump in supportive contact with the breast pump. In some embodiments, the support strap 280 can then be adjusted (e.g., tightened against the breast pump by shortening the support strap 280) if needed (e.g., the slider component can be translated to reduce the overall length of the support strap 280 such that the breast pump is sealed and/or secured against the wearer's breast) top properly align the breast pump with the breast and/or to properly seal a breast shield of the breast pump against the breast.

When in the second configuration, the support strap 280 (and any of the support straps described herein) can be disposed against a neck portion and/or a flange of a breast shield of a breast pump to apply a force against the breast shield (e.g., a laterally outward and/or upward force) to create and/or maintain a seal between the breast shield and the breast of the wearer. Additionally, as described above, the support strap 280 can provide supportive contact to the neck portion and/or the flange of the breast shield to support the weight of the breast pump as the pump operates to extract fluid from the breast (e.g., and as a container such as a bottle coupled to the pump fills), while maintaining the seal between the breast shield and the breast. In some embodiments, a first portion of the support strap 280 can apply a force to a lower portion of the flange (e.g., below the neck and the nipple) and a second portion of the support strap 280 can apply a force to an upper portion of the flange (e.g., above the neck and the nipple) to maintain the seal between the breast shield and the breast. In some embodiments, such as any of the embodiments described herein, the outer panel 260 can be used in combination with the support strap 280 to apply supportive contact to the neck portion and/or the flange of the breast shield to assist in supporting the weight of the breast pump and maintaining the seal of the breast shield against the user's breast while the pump operates to extract fluid. For example, the outer panel 260 (e.g., when supported by the shoulder strap 206 or a separate neck strap) can apply a force against the neck and/or flange of the breast shield that is laterally inward to counterbalance a force applied to the neck and/or flange of the breast shield applied by the support strap 280 that is laterally outward. The outer panel 260 can also apply a force to the flange of the breast shield that pushes the breast shield against the breast of the wearer to create and/or maintain a seal between the breast shield and the skin of the wearer.

In some embodiments, the inner panel 270 may not be included in the garment 200 (e.g., due to being available as a separate unpurchased component or due to being temporarily unused), and the outer panel 260 can be detached from the shoulder strap 206 and reattached to the shoulder strap 206 via uncoupling the third portion 256 from the first portion 252 and reattaching the third portion to the first portion 252. The inner panel 270 could be added to the garment 200 at a later time, via uncoupling the third portion 256 from the first portion 252, disposing the inner panel 270 between the support strap 280 and the outer panel 260 coupling the second portion 254 to the first portion 252, and coupling the third portion 256 to the second portion 254 (along with coupling the inner panel 270 to the back panel 220, the support strap 180, and/or the outer panel 260 directly via coupling mechanisms such as snap coupling mechanisms).

Although the garment 200 is described with respect to being used to support a breast pump against one breast of a wearer, in some configurations the garment 20 can be used to simultaneously support a first breast pump against a first breast of a wearer and a second breast pump against a second breast pump of the wearer. For example, the garment 200 can include a first support strap and a second support strap, each of the first support strap and the second support strap configured to support a first breast pump and a second breast pump for a pumping procedure, respectively. For such an embodiments, each of the components described with respect to FIG. 2 can be duplicated to be associated with the second breast of the wearer, such that the garment 200 includes a second engagement mechanism 250, a second shoulder strap 206, and a second support strap 280, each having the same structure and/or function as the engagement mechanism 250, shoulder strap 206, and support strap 280 described above.

FIGS. 3-11 illustrate various views and components of a garment 400 that can be used with a wearable breast pump or wearable milk collection device. Such wearable breast pumps or milk collection devices can be placed in contact with a user's breast and maintained in place by a portion of the garment 400.

Figure 3:
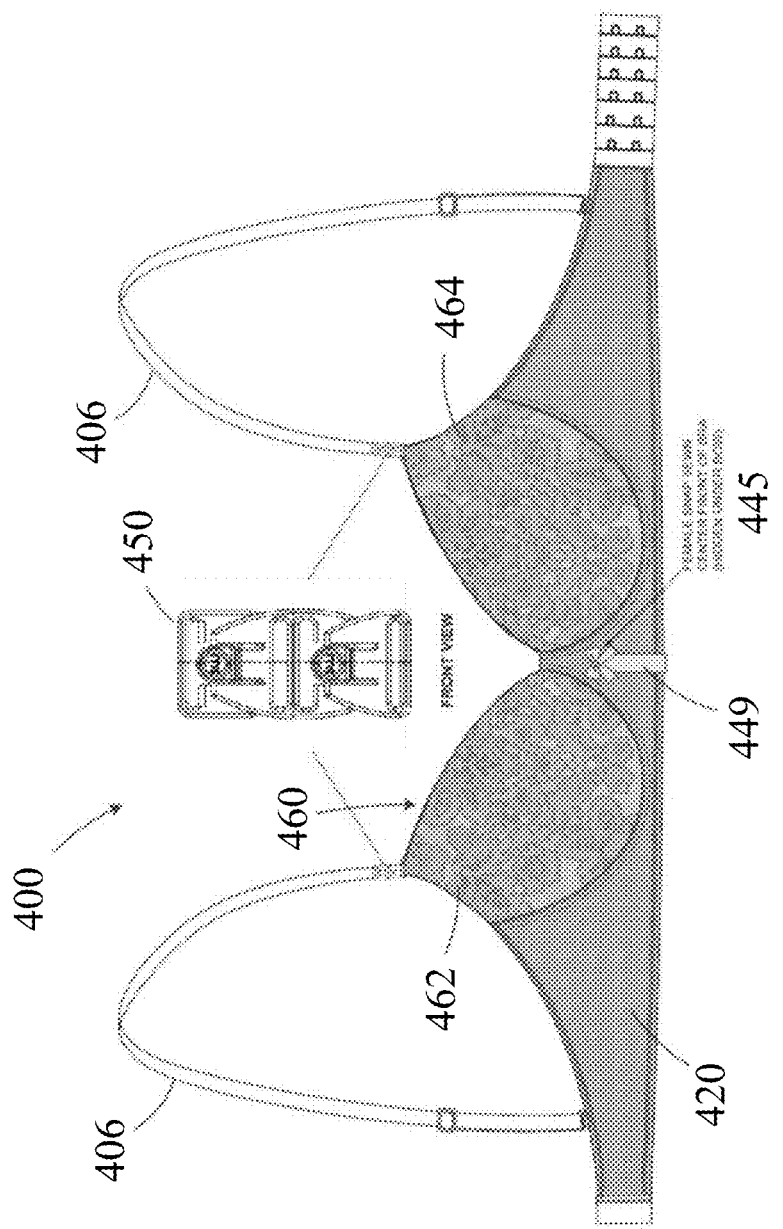
FIG. 3 is a front view of a garment, according to an embodiment.
Figure 4:
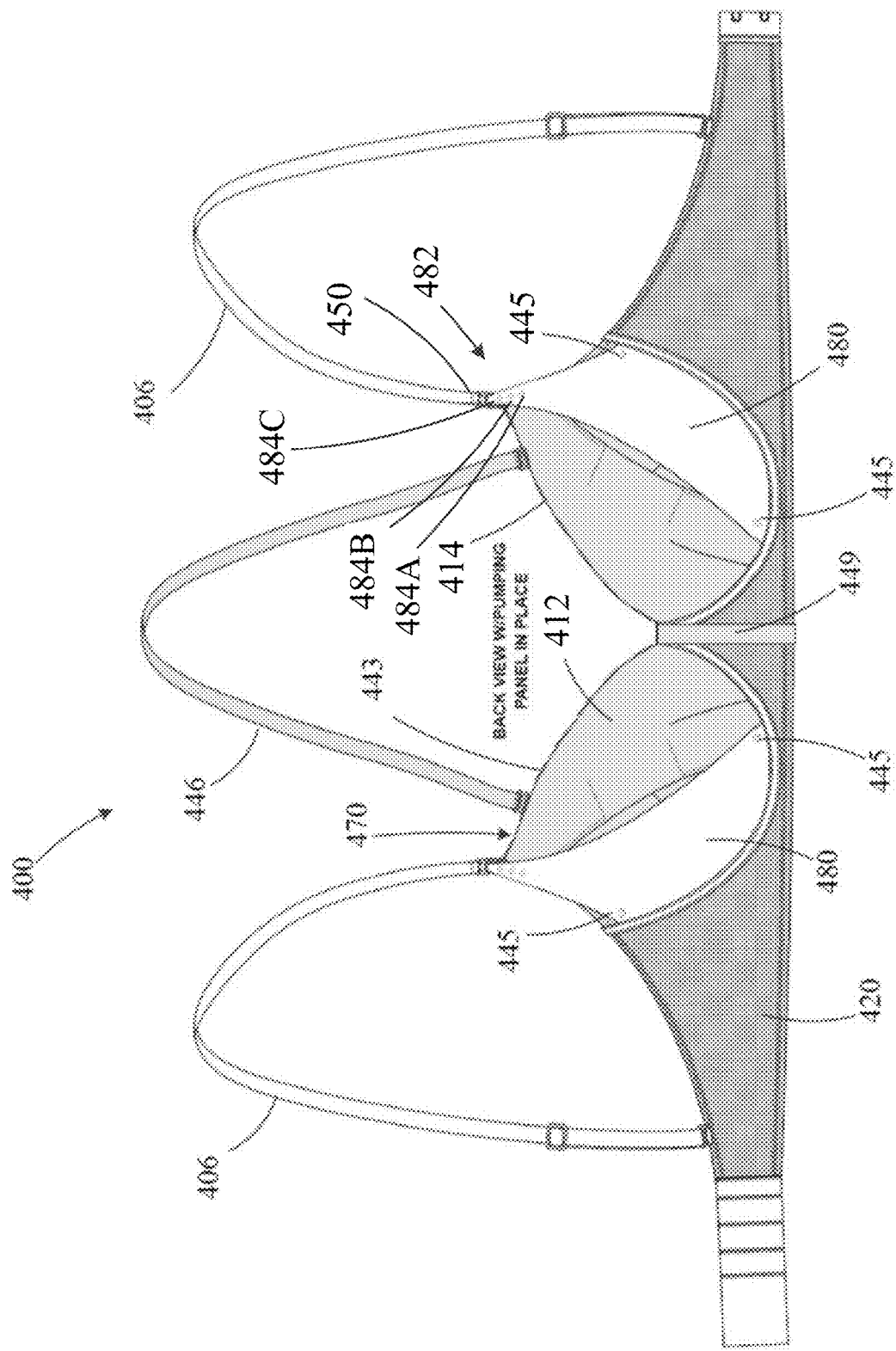
FIG. 4 is a back view of the garment of FIG. 3.
Figure 5:
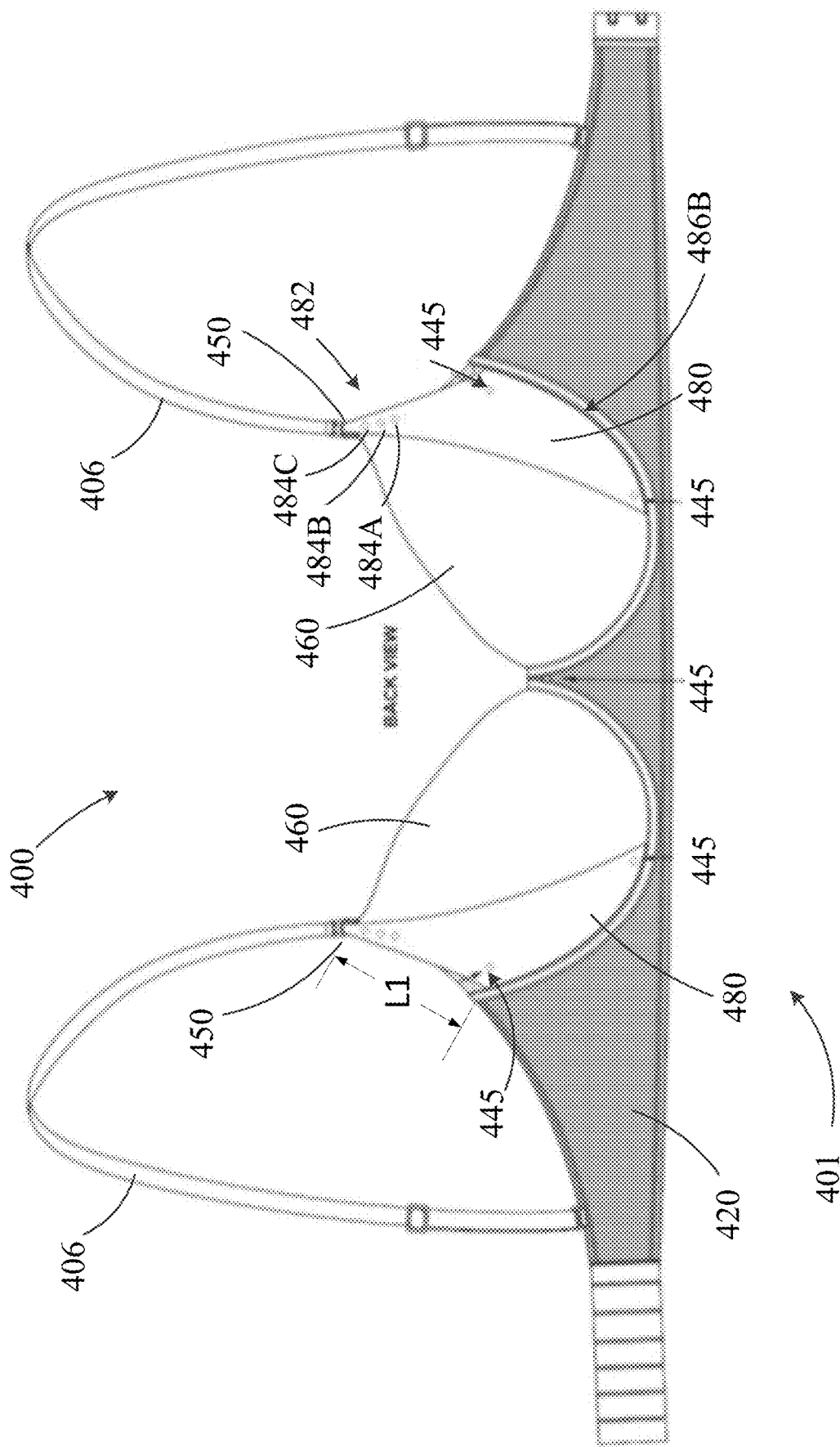
FIG. 5 is a back view of the garment of FIG. 3 with the inner pumping panel removed.

FIG. 3 is a front view of the garment 400. FIG. 4 is a back view of the garment 400 with an optional pumping panel 470 attached. FIG. 5 is a back view of the garment 400 with the optional pumping panel 470 removed. The garment 400 can include the same or similar components and/or functions as any of the garments described herein. For example, the garment 400 includes an outer panel 460, the inner pumping panel 470 (shown in FIG. 4) (also referred to as an "inner panel" or a "pumping panel"), a back panel 420, two support straps 480 (shown in FIG. 4) and two shoulder straps 406. The garment 40 can also include a center or neck strap 446 that can be removably coupled to the inner pumping panel 470 as shown in FIG. 4. Each shoulder strap 406 can be coupled to the outer panel 460, the inner panel 470, and a support strap 480 via an engagement mechanism 450 (also referred to herein as a "clasp"). The engagement mechanism 450 can be the same or similar as any of the engagement mechanisms described herein, such as the engagement mechanism 250. The inner panel 470 can be the same or similar in structure and/or function to any of the inner panels or pumping panels described herein. The outer panel 460, support straps 480, shoulder straps 406 and back panel 420 can be the same or similar in construction and function as, for example, the outer panel 260, support straps 280, shoulder straps 206 and back panel 220, respectively, and therefore, some features and details are not described with reference to this embodiment. For example, the various components can be coupled together in the same manner as described above for previous embodiments. In some embodiments, the various components are coupled together via stitching.

The inner panel 470 and the outer panel 460 can each include one or more panels each formed with one or more layers of material. As shown, for example, in FIG. 3, the outer panel 460 includes a right outer panel 462 and a left outer panel 464. As shown, for example, in FIG. 4, the inner panel 470 includes a right inner panel 412 and a left inner panel 414. The right inner panel 412 and the left inner panel 414 can be shaped and sized for coverage of a wearer's right breast and left breast, respectively. Each of the right inner panel 412 and the left inner panel 414 can include a first portion and a second portion that are coupled together such that a portion is unattached and can define an opening between the first portion and the second portion. In some embodiments, the first portion and the second portion can include an overlapping portion which can define the opening. The first portion and the second portion can be separated by, for example, moving the first portion and the second portion away from each other, thereby creating the opening and providing access to the user's breast. A breast pump can then be inserted through the opening and the inner pumping panel 470 can help support the breast pump during milk extraction.

Additionally, as shown in FIG. 4, the inner panel 470 can include one or more holes 443 defined in an upper edge of the inner panel 470. For example, the inner panel 470 can define the holes 443 and/or the holes 443 can be defined by a separate component (e.g., loops) coupled to the inner panel 470. A center strap 446 can be attached to the inner panel 470 via selective releasable engagement with any of the holes 443.

The support straps 480 can be coupled on a first end to the back panel 420 and on a second end to one of the shoulder straps 406 via the engagement mechanism 450. In alternative embodiments, the support straps 480 can be attached to a lower band of the garment 400 rather than to the back panel 420. Each of the shoulder straps 406 can have a first end coupled to a support strap 480 of the support straps 480 (via the engagement mechanism 450) and a second end coupled to the back panel 420, with for example, sewing/stitching. The outer panel 46 can be attached to the back panel 420, for example, along a bottom edge of the outer panel 460, via, for example, sewing/stitching. The optional inner pumping panel 470 can be removably coupled to the shoulder straps 406.

Figure 6:
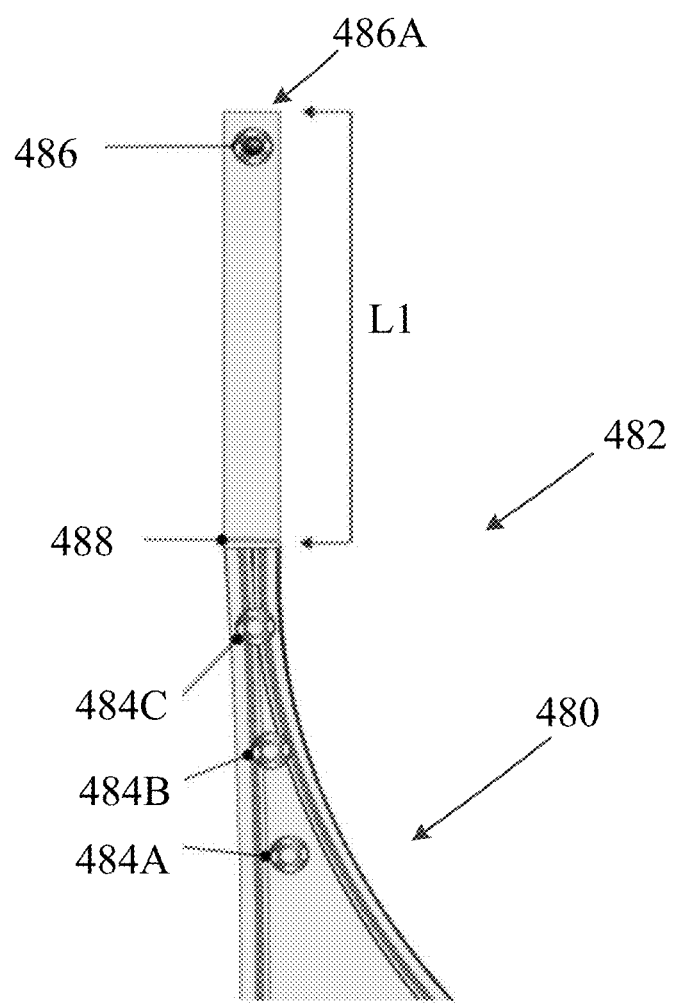
FIG. 6 is an enlarged view of a portion of a support strap of the garment of FIG. 3.

As shown in FIGS. 4 and 5, each support strap 480 can include an adjustable portion 482. FIG. 6 is an enlarged view of a portion of a support strap 480 of the support straps 480 including the adjustable portion 482. The adjustable portion 482 can be the same or similar in structure and/or function to any of the adjustable portion described herein, such as the adjustable portion 282. For example, the adjustable portion 482 can include a first coupling mechanism 486 (also referred to as a first coupling member) disposed proximate a second end 486A of the support strap 480. The second end 486A can be an end of the support strap 480 opposite a first end 486B. The first end 486B can be fixedly coupled to the back panel 420 (e.g., via sewing/stitching). The adjustable portion 482 can also include a set of second coupling mechanisms disposed along the adjustable portion 482 (e.g., closer to the first end 486B than the first coupling mechanism 486). The set of second coupling mechanisms can include, for example, a second coupling mechanism 484A, a third coupling mechanism 484B, and a fourth coupling mechanism 484C (also referred to as a second coupling member 484A, a third coupling member 484B, and a fourth coupling member 484C, respectively). The adjustable portion 482 can be configured such that the second end 486A of the support strap 482 can be looped through a first opening 483 and around a securement bar 483A (shown, for example, in FIG. 9) in a first portion 452 of the engagement portion 450 and the first coupling mechanism 486 can be engaged with any of the second coupling mechanism 484A, the third coupling mechanism 484B, and the fourth coupling mechanism 484C. Thus, the wearer can adjust the length of the support strap 480 between the engagement portion 450 and the first end 486B based on which of the second coupling mechanism 484A, the third coupling mechanism 484B, and the fourth coupling mechanism 484C the first coupling mechanism 486 is engaged with. For example, the first coupling mechanism 486 can be engaged with the second coupling mechanism 484A closest to the first end 486B in a first configuration in which the support strap 480 is not being used to support a portion of a breast pump against a breast, but is being used to maintain a distance between an end of the shoulder strap 406 coupled to the first portion 452 and the first end 486B and/or the base panel 420. When the support strap 480 is being used to support a portion of a breast pump (e.g., a flange of a shield of a breast pump) against the breast (e.g., by being wrapped fully or partially around a flange and/or a stem of a shield of the breast pump and then being attached to the first portion 452), the support strap 480 can be transitioned to a second configuration in which the first coupling mechanism 486 can be attached to one of the third coupling mechanism 484B or the fourth coupling mechanism 484C, such that the length of the support strap 480 between the first portion 452 and the first end 486B is longer than in the first configuration and can comfortably maintain the flange of the breast pump against the breast.

In some embodiments, the first coupling mechanism 486 can be disposed on a length of the support strap 480 that can be separated from a remainder of the support strap 480 via, for example, bar tack 488. Such a length can be, for example, reinforced and/or non-elastic. In some embodiments, the length can have a length L1 of, for example, about 6.5 inches. In some embodiments, the length can have a length L1 of, for example, between about 6 inches and about 7 inches. In some embodiments, the length can have a length L1 of, for example, between about 5 inches and about 8 inches.

Figure 7:
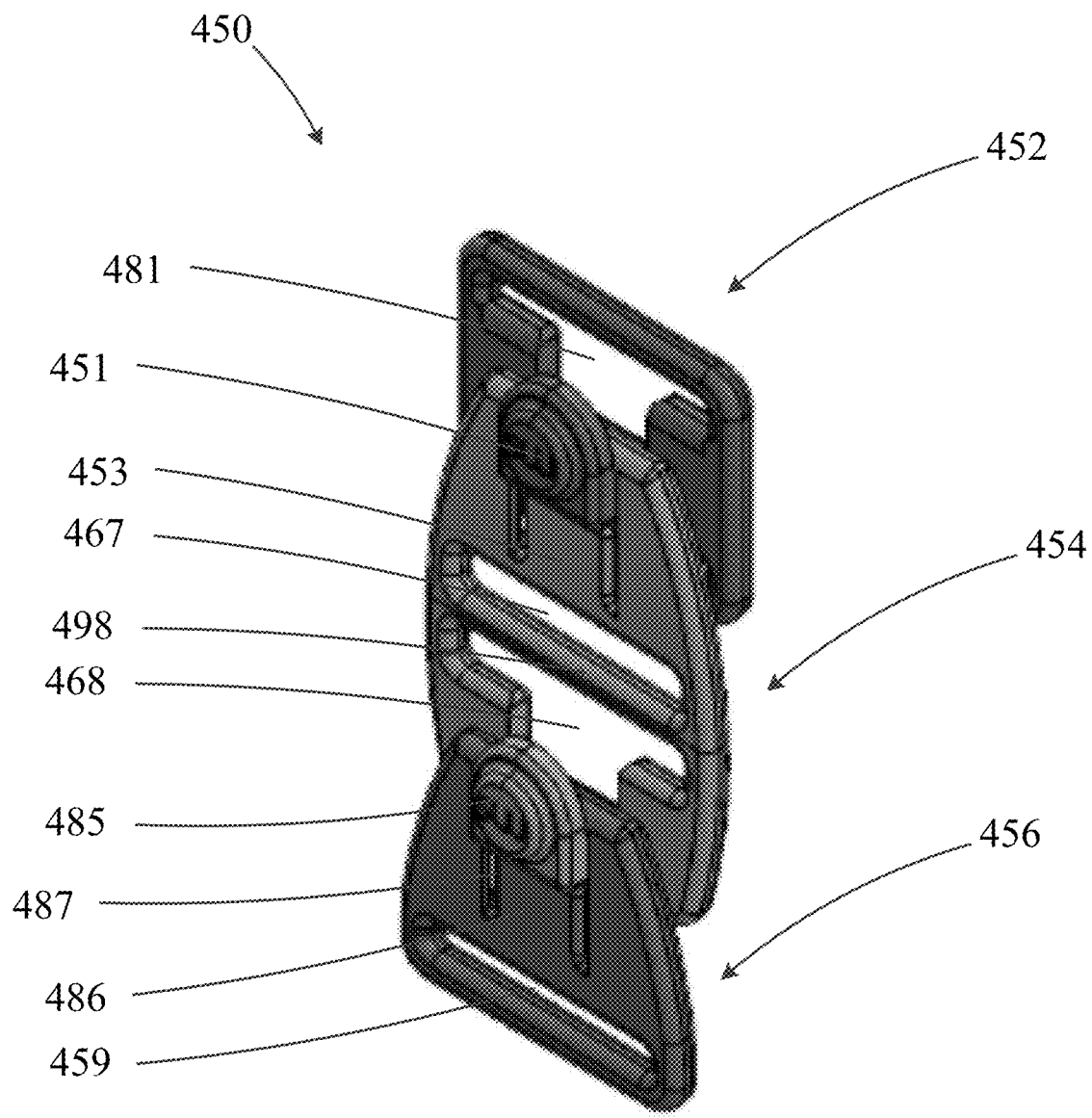
FIG. 7 is a perspective view of an engagement mechanism of the garment of FIG. 3.

FIG. 7 is a perspective view of the engagement mechanism 450. FIGS. 8-10 are a front view, a cross-sectional view taken along line A-A in FIG. 9, and a side view, respectively, of the clasp 450. The engagement mechanism 450 can include a first portion 452 (also referred to as a top portion), a second portion 454 (also referred to as an intermediate portion), and a third portion 456 (also referred to as a bottom portion). As shown in FIGS. 7-10, the first portion 452 can be configured to be releasably engageable with the second portion 454. The second portion 454 can be configured to be releasably engageable with the third portion 456. Thus, the first portion 452 can be releasably coupled to the third portion 456 via the second portion 454. Additionally, the first portion 452 can be configured to be releasably coupled to the third portion 456 (e.g., when the second portion 454 is not used or included).

The first portion 452 can include an extension portion 451, a first opening 481, and a second opening 483. As shown in FIG. 9, the second opening 483 can be on an opposite side of the extension portion 451 than the first opening 481. The extension portion 451 can be formed as a hook that forms a slot 451A (best shown in FIG. 9). The second portion 454 can include a tab portion 453, a first opening 455 (also referred to as an engagement aperture), a securement bar 498, a second opening 467, a third opening 468, and an extension portion 485. The extension portion 485 can be formed as a hook that forms a slot 485A (best shown in FIG. 9). The extension portion 485 can be disposed opposite the securement bar 498 from the first opening 455. The third portion 456 can include a tab portion 486, a first opening 487 (also referred to as an engagement aperture), and a second opening 459. The extension portion 451 of the first portion 452 and the extension portion 485 of the second portion 454 can be the same or similar in shape and size. The first opening 455 of the second portion 454 and the first opening 487 of the third portion 456 can be the same or similar in shape and size. The tab portion 453 of the second portion 454 and the tab portion 486 of the third portion 456 can be the same or similar in shape and size. Thus, the first portion 452, the second portion 454, and the third portion 456 can include complementary mating features such that the second portion 454 and the third portion 456 can be releasably coupleable to and decoupleable from the first portion 452 and the third portion 456 can be releasably coupleable to and decoupleable from the second portion 454.

The first opening 455 of the second portion 454 can be shaped and sized such that the first opening 455 can receive the extension portion 451 of the first portion 452 and a portion of the second portion 454 partially defining the first opening 455 (e.g., a securement portion 455A) can be received in the slot 451A of the first portion 452. The tab portion 453 of the second portion 454 can be shaped and sized such that when the extension portion 451 of the first portion 452 is received through the first opening 455 of the second portion 454, the tab portion 453 contacts or engages the extension portion 451 and is flexed or clicked into locking engagement with the first portion 452 (e.g., with an underside of the extension portion 451). In some embodiments, the tab portion 453 can be sufficiently elastic such that as the second portion 454 is moved into engagement with the first portion 452, the tab portion 453 can bend slightly and then snap into locking engagement. The securement bar 498 of the second portion 454 is configured for attachment to the inner panel 470 of the garment 400. For example, a loop portion of the inner panel 470 can be secured around the securement bar 498.

The first opening 487 of the third portion 456 can be shaped and sized such that the first opening 487 can receive the extension portion 485 of the second portion 454 and a portion of the third portion 456 partially defining the first opening 487 (e.g., a securement portion 487A) can be received in the slot 485A of the second portion 454. The tab portion 486 of the third portion 456 can be shaped and sized such that when the extension portion 485 of the second portion 454 is received through the first opening 487 of the third portion 456, the tab portion 486 contacts or engages the extension portion 485 and is flexed or clicked into locking engagement with the second portion 454 (e.g., with an underside of the extension portion 485). In some embodiments, the tab portion 486 can be sufficiently elastic such that as the third portion 456 is moved into engagement with the second portion 454, the tab portion 486 can bend slightly and then snap into locking engagement.

Furthermore, the first opening 487 of the third portion 456 can be shaped and sized such that the first opening 487 can receive the extension portion 451 of the first portion 452 and a portion of the third portion 456 partially defining the first opening 487 (e.g., the securement portion 487A) can be received in the slot 451A of the first portion 452. The tab portion 486 of the third portion 456 can be shaped and sized such that when the extension portion 451 of the first portion 452 is received through the first opening 487 of the third portion 456, the tab portion 486 contacts or engages the extension portion 451 and is flexed or clicked into locking engagement with the first portion 452 (e.g., with an underside of the extension portion 451). In some embodiments, the tab portion 486 can be sufficiently elastic such that as the third portion 456 is moved into engagement with the first portion 452, the tab portion 486 can bend slightly and then snap into locking engagement.

The first portion 452 of the engagement mechanism 450 can be coupled to a shoulder strap 406 of the garment 400 with, for example, stitching. For example, an end portion of the shoulder strap 406 can be looped through the first opening 481 and around a securement bar 481A and attached to itself such that a top portion of the first portion 452 is secured within the loop of the shoulder strap. Additionally, the first portion 452 can receive a portion of a support strap 480 of the garment 400 through the second opening 483 such that the support strap 480 can be secured to the first portion 452 of the engagement mechanism 450. For example, the adjustable portion 482 of the support strap 480 can be looped through the second opening 483 of the first portion 452 and around a securement bar 483A and attached to itself (e.g., via engaging the first coupling mechanism 486 with one of the second coupling mechanism 484A, the third coupling mechanism 484B, or the fourth coupling mechanism 484C) such that a bottom portion of the first portion 452 is secured within the loop of the adjustable portion 482.

The second portion 454 of the engagement mechanism 450 can be coupled to the inner pumping panel 470 with, for example, stitching. For example, a portion of the inner pumping panel 470 can be looped through the second opening 467, around the securement bar 498, back through the third opening 468, and attached to itself such that the securement bar 498 is secured within the loop of the inner pumping panel 470. Additionally, when the second portion 454 is coupled to the inner panel 470, the inner panel 470 can be disposed on an opposite side of the second portion 454 than the extension portion 485 is disposed.

Additionally, the inner pumping panel 470 can be removably coupled to the support straps 480 via coupling members (not shown) disposed on a back side of the panels 412 and 414 that can be removably coupled to complementary coupling members 445 disposed on a front side of the support panels 480. FIGS. 4 and 5 show the back side of the support straps 480 and indicate where the coupling members 445 are disposed thereon. In addition, the inner panel 470 can include a coupling strap 449 that extends from a center portion of the inner panel 470 and has a coupling member (not shown) disposed thereon. The coupling strap 449 can wrap around the back panel 420 (as shown in FIG. 4) and the coupling member disposed thereon can be coupled to a complementary coupling member 445 disposed on a front side of the back panel 1420. FIG. 3 indicates where the coupling member of the coupling strap 449 is hidden underneath a bow on the coupling strap 449.

In some embodiments, the coupling members 445 and the coupling members of the inner panel 470 can be, for example, a female and male snap connector, respectively. It should be understood that in alternative embodiments, the coupling members 445 can be a female snap connector and the coupling member of the inner panel 470 can be a male snap connector, and vice versa. In addition, other types of coupling members can alternatively be used such as, for example, hook and loop fasteners such as VELCRO, or buttons, hooks, etc. The coupling members 445 and the coupling members of the inner panel 470 can be attached to the inner panel 470, back panel 420 and support straps 480 by, for example, sewing or stitching.

More specifically, a portion of the outer panel 460 can be attached to the third portion 456 of the engagement portion 450 via passing the portion through the opening 459 of the third portion 456, looping the portion over a bottom portion of the third portion 456 of the engagement mechanism 450 (e.g., a securement bar 459A), and then attaching the portion to itself (e.g., sewn or stitched) in a similar manner as how the inner layer 470 is attached to the third portion 456.

As shown in FIGS. 3-5, the garment 400 includes two shoulder straps 406, two engagement mechanisms 450, two support straps 480, optional inner panel 470 including a right inner panel 414 and a left inner panel 412, and an outer panel 460 including a left outer panel 464 and a right outer panel 462. Each shoulder strap 406, engagement mechanism, support strap 480, right inner panel 414, left inner panel 412, right outer panel 462, and/or left outer panel 464, respectively, can be the same or similar in structure and/or function to the shoulder strap 406, engagement mechanism 450, support strap 480, the inner panel 470 and outer panel 460 described above. Thus, the garment 400 can be used to support two breast pumps simultaneously for a hands free pumping procedure.

Figure 11:
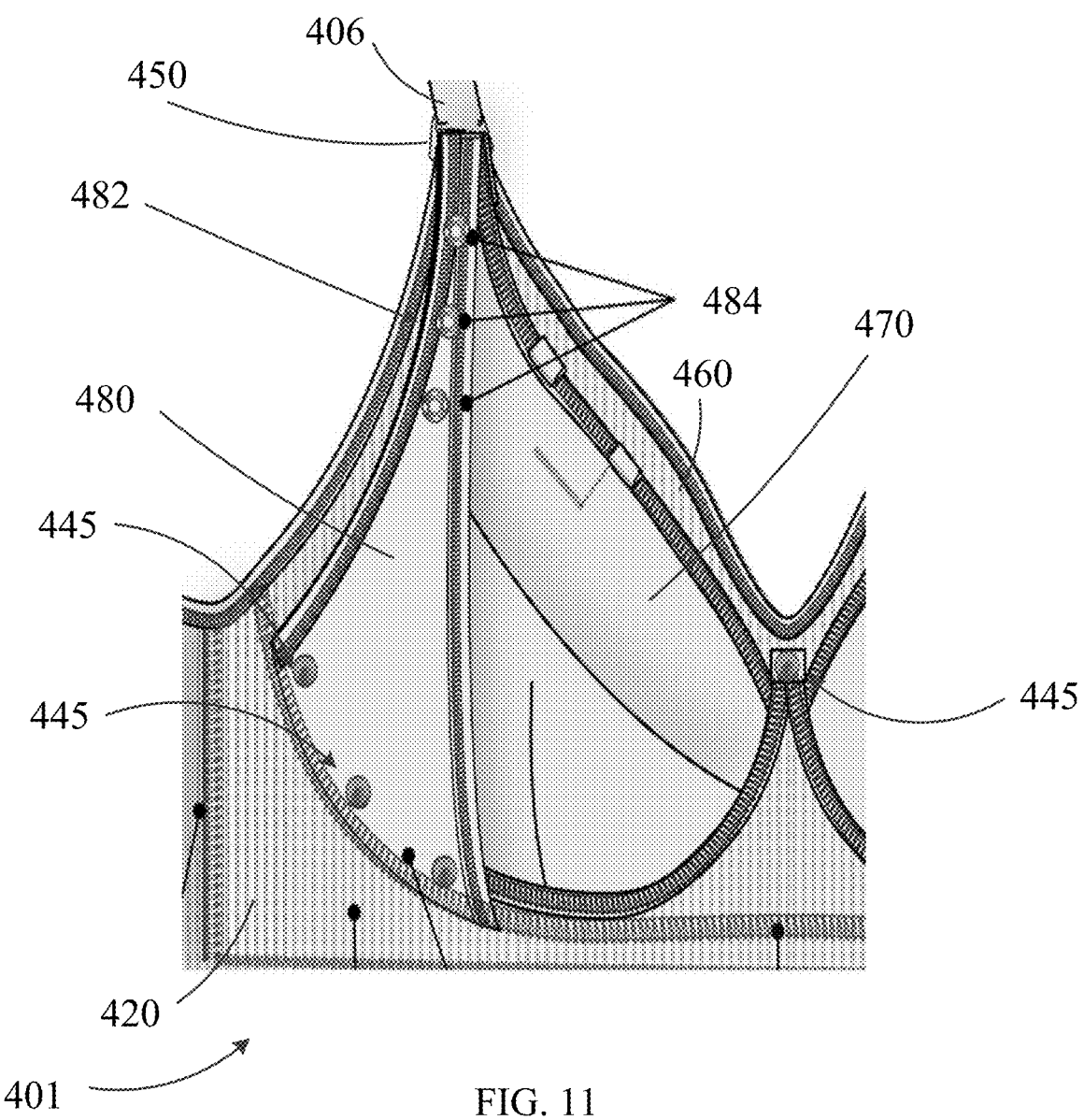
FIG. 11 is a back view of a portion of the garment of FIG. 3.

FIG. 11 is a back view of a portion the garment 400 in a configuration in which the support strap 480 is in the first configuration and the inner panel 470 is coupled to the support strap 480 and the engagement mechanism 450.

In use, the garment 400 can be worn by a wearer and if access to a breast of the wearer is desired, such as for breast pumping, the outer panel 460 (e.g., the right outer panel 462 and/or the left outer panel 464) can be detached from the inner panel 470 (e.g., the right inner panel 412 and/or the left inner panel 414) by detaching or uncoupling the third portion 456 from the second portion 454 of the engagement mechanism 450 and moving the outer panel 460 (e.g., folding the outer panel 460 down) such that the inner panel 470 is accessible. The first portion and the second portion of the inner panel 470 (e.g., of the right inner panel 412 and/or the left inner panel 414) can be separated (e.g., stretched or folded) to create an opening through which the wearer's breast is accessible and a portion of a breast pump can be inserted. If further access to the breast of the wearer is desired, the inner panel 470 can be detached from the shoulder straps 406 by removing/detaching the second portion 454 of the engagement mechanism 450 from the first portion 452 of the engagement mechanism 450. The inner panel 470 can also optionally be decoupled from the support straps 480 by decoupling the coupling members 445 and the coupling members of the inner panel 470. When desired, the inner panel 470 and the outer panel 460 can be reattached to shoulder strap 406 by recoupling the second portion 454 to the first portion 452 of the engagement mechanism 450 and optionally recoupling the coupling members 445 to the coupling members of the inner panel 470. The third portion 456 of the engagement mechanism 450 can be recoupled to the second portion 454 of the engagement mechanism 450. In some embodiments, the outer panel 460 and the inner panel 470 can be detached from the shoulder straps 406 simultaneously by detaching the second portion 454 from the first portion 452 but not detaching the third portion 456 from the second portion 454.

In some embodiments, if the inner panel 470 is no longer desired to be used, the inner panel 470 can be removed from the garment 400 as described above and the outer panel 460 can be reattached to the shoulder strap 406 by attaching the third portion 456 to the first portion 452. To use one of the support straps 480 as a support for a portion of a breast pump, the user can transition the support strap 480 from a first configuration to a second configuration. For example, the wearer can uncouple the first coupling mechanism 486 of the adjustable portion 482 of the support strap 480 from a second coupling mechanism (e.g., coupling mechanism 484A) of the set of second coupling mechanisms of the adjustable portion 482. The support strap 480 can then be translated through the opening 483 and/or separated from the first portion 452 by pulling the adjustable portion 482 through the second opening 483 of the first portion 452. A portion of a breast pump (e.g., a flange of a breast shield) can be applied to a breast of the wearer. The support strap 480 can then be wrapped fully or partially around a portion of the breast pump (e.g., the flange and/or a stem of the breast pump) and the adjustable portion 482 can be threaded and/or translated through the second opening 483 of the first portion 452 and folded onto itself to form a loop. The first coupling mechanism 486 of the adjustable portion 482 can then be coupled to a second coupling mechanism (e.g., coupling mechanism 484C or 484B) of the set of second coupling mechanisms that can be the same or different from the second coupling mechanism the first coupling mechanism 486 was coupled to before wrapping the support strap 480 around the flange and/or stem of the breast pump. In the second configuration, the support strap 480 can then support the flange against the breast of the wearer for a pumping procedure such that the pumping procedure can be performed hands-free. When desired (e.g., after removing the breast pump from a breast of the user), the first coupling mechanism 486 can be decoupled from the second coupling mechanism, separated from the first portion 452 as described above, and then recoupled to the first portion 452 as described above (e.g., by coupling the first coupling mechanism 486 to a second coupling mechanism such as coupling mechanism 484A) such that the length of the support strap 480 between the first portion 452 and the second end 486B of the support strap 480 is shorter than when the support strap 480 is used to support the flange of the breast pump. In some embodiments, in the first configuration, the support strap 480 is entirely disposed on a first side of an areola and/or a nipple of a wearer. In the first configuration, the support strap 480 maintains a distance between the end of the shoulder strap 406 coupled to the first portion 452 of the engagement mechanism 450 and the base panel 420 or first end 486B of the support strap 480, regardless of whether the inner panel 470 or the outer panel 460 are coupled to the shoulder strap 406 via the first portion 452. In the second configuration, a portion of the support strap 480 is disposed on a second side of the areola and/or nipple of the wearer and in supportive contact with the breast pump such that the breast pump can be maintained against the breast of the wearer for a hands free pumping procedure.

The garment 400 can also be used with the inner panel 470 completely removed from the garment 400. In such a use, the third portion 456 can be coupled to the first portion 452 such that the outer panel 460 covers the breasts of a user and the support straps 480. The outer panel 460 can be detached from the shoulder straps 406 and folded or moved downward to expose and gain access to one or both breast. For example, the third portion 456 of the engagement mechanism 450 can be detached from the first portion 452 of the engagement mechanism 450. One of the support straps 480 can then be transitioned from a first configuration to a second configuration as described above to support a flange of a breast pump against the breast of a user. When desired, the support strap 480 can be transitioned from the second configuration to the first configuration as described above, and the third portion 456 can be recoupled to the first portion 452 such that the outer panel 460 covers the breasts of the user and the support straps 480.

In some embodiments, an outer panel, such as any of the outer panels described herein, can be used to provide additional support for a portion of the breast pump supported by a support strap, such as any of the support straps described herein. For example, when the support strap 480 is disposed in the second configuration described above such that the support strap 480 is wrapped fully or partially around a flange and stem of a breast pump, the outer panel 460 can be recoupled to the support strap 480 (e.g., via coupling the third portion 456 to the first portion 452). The outer panel 460 can be disposed in supportive contact with a portion of the breast pump to provide additional support to the breast pump (e.g., to the same portion as the support strap 480, an adjacent or overlapping portion, or another portion) for the hands free pumping procedure.

Figure 12:
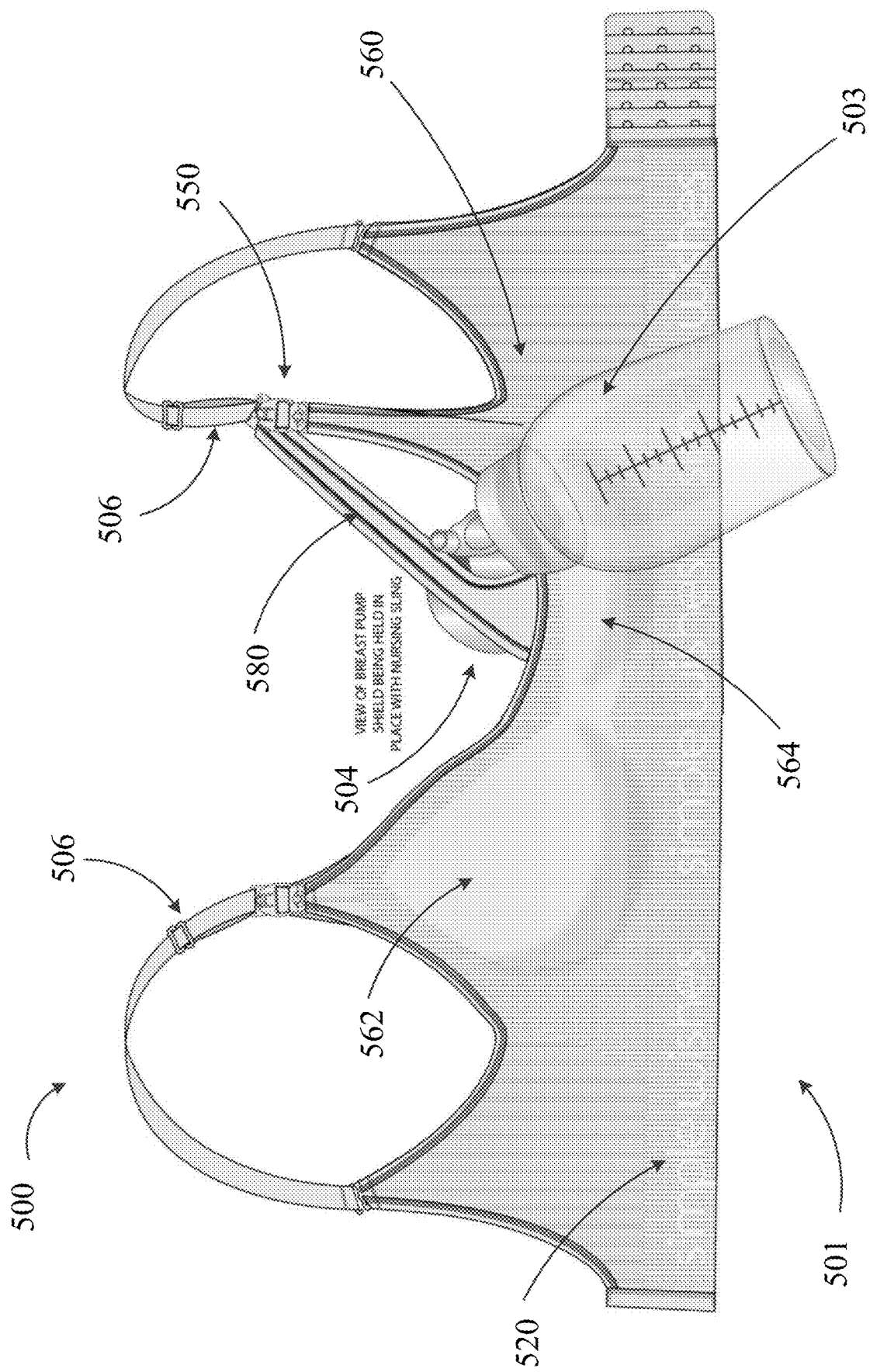
FIG. 12 is a front view of a garment in a configuration in which the garment is supporting a breast pump, according to an embodiment.

As another example, FIG. 12 is a front view of a garment 500 in a configuration in which the garment 500 is supporting a breast pump 503 (e.g., the breast pump 503 is coupled to a user (not shown)). The garment 500 can be the same or similar in structure and/or function to any of the garments described herein. For example, the garment 500 includes a base subassembly 501 including a back panel 520, an outer panel 560, shoulder straps 506, and support straps 580. The outer panel 560 can have a first portion 562 and a second portion 564. The garment 500 also includes engagement mechanisms 550 that can be the same or similar in structure and/or function to any of the engagement mechanisms described herein. As shown in FIG. 12, the support strap 580 can be arranged in a configuration in which the support strap 580 has a first end coupled to the back panel 520, an adjustable portion 582 coupled to the engagement mechanism 550, and is disposed around a portion 504 (e.g., flange and stem) of a breast pump 503 that is coupled to a wearer's breast to support the breast pump 503 against the wearer's breast for a pumping operation (e.g., a hands free pumping operation). As shown in FIG. 12, the outer panel 560 can also support the breast pump 503 against the wearer's breast in combination with the support strap 580. For example, the second portion 564 can be coupled to the engagement mechanism 550 and disposed around the portion 504 (e.g., a different portion of the flange and stem) in supportive contact with the breast pump 503 to support the breast pump 503 against the wearer's breast for a pumping operation (e.g., a hands free pumping operation). Thus, the breast pump 503 (e.g., the stem of a breast shield of the breast pump 503) can be disposed between the support strap 580 and the portion 564 of the outer panel 560 (e.g., in an opening defined between the support strap 580 and the portion 564 of the outer panel 560) during the pumping operation.

FIG. 13 is a back view of a garment 600 in a configuration in which an outer panel 660 of the garment 600 is folded down relative to support strap 680 of the garment. The garment 600 can be the same or similar in structure and/or function to any of the other garments described herein. For example, the garment 600 can include a base subassembly 601 including a back panel 620, the outer panel 660, the support straps 680, a first shoulder strap 606A, and a second shoulder strap 606B. The garment 600 also includes a first engagement mechanism 650A and a second engagement mechanism 650B that can each be the same or similar in structure and/or function to any of the engagement mechanisms described herein.

Each support strap 680 can be configured to define an opening 689. For example, each support strap 680 can include a first portion 699A and a second portion 699B that are coupled together such that a portion of each of the first portion 699A and the second portion 699B is unattached and can define the opening 689 between the first portion and the second portion. In some embodiments, the first portion 699A and the second portion 699B can include an overlapping portion which can define the opening 689. The first portion 699A and the second portion 699B can be separated by, for example, moving the first portion 699A and the second portion 699B away from each other, thereby creating the opening 689 and providing access to the user's breast. A breast pump (e.g., a breast shield having a flange) can then be inserted through the opening 689 and the support strap 680 can help support the breast pump against the wearer during milk extraction.

As shown in FIG. 13, the garment can include a strap connector 605 configured to be coupled to the first shoulder strap 606A and the second shoulder strap 606B to retain the support straps 680 in a configuration in which one or both of the support straps 680 can each support a breast pump against a breast of the wearer for a pumping procedure. For example, the strap connector 605 can have a sufficient length and elasticity such that the strap connector 605 can be coupled to the first shoulder strap 606A and the second shoulder strap 606B to pull the support straps 680 toward each other such that the openings 689 of the support straps are properly aligned with the wearer's breasts (e.g., aligned with the wearer's nipples) to support a breast pump within at least one of the openings 689 against at least one of the wearer's breasts for a pumping procedure.

FIG. 14 is a front view of the strap connector 605 in an unattached configuration. The strap connector 605 can include a strap member 608 having a first end and a second end. The strap connector 605 can also include coupling members 607 disposed at the first end and the second end and configured to be coupled to the first shoulder strap 606A and the second shoulder strap 606B. The coupling members 607 can be, for example, S-hooks. In some embodiments, the strap member 608 can be elastic. In some embodiments, the strap member 608 can be inelastic.

In use, the garment 600 can be worn by a wearer and if access to a breast of the wearer is desired, such as for breast pumping, the outer panel 660 (or one side of the outer panel 660) can be detached from the support straps 680 by detaching or uncoupling a portion of the engagement mechanism(s) 650 from another portion of the engagement mechanism(s) 650. The strap connector 605 can then be coupled to the first shoulder strap 606A and the second shoulder strap 606B such that the support straps 680 are drawn toward each other (e.g., across a chest of the wearer). For example, the strap connector 605 can be centered on a user's chest and maintain the openings 689 of each of the support straps 680 such that they are properly aligned with each of the wearer's breasts (e.g., with a nipple of the wearer). A portion of a breast pump (e.g., a breast shield) can then be inserted through the opening 689 of one of the support straps 680. The support strap 680 can support the breast pump against the wearer's breast during a pumping procedure. If desired, a second breast pump can be simultaneously supported by the other of the two support straps 680 by inserting a portion of the second breast pump through the opening 689 of the other of the support straps 680.

In some embodiments, the first engagement mechanism 650A and the second engagement mechanism 650B can be a first distance apart in a first configuration of the garment 600 in which the strap connector 605 is not coupled to the first shoulder strap 606A and the second shoulder strap 606B. Additionally, in the first configuration, the openings 689 of each support strap 680 can be not aligned with a nipple of the wearer such that any breast pumps inserted through the openings 689 would not be properly aligned for a pumping procedure. In the second configuration of the garment 600 in which the strap connector 605 coupled the first shoulder strap 606A to the second shoulder strap 606B, the first engagement mechanism 650A and the second engagement mechanism 650B can be a second distance apart that is smaller than the first distance. Additionally, in the second configuration, the openings 689 of each support strap 680 can be properly aligned with the nipples of the wearer such that a breast pump inserted through each opening would be properly aligned with the nipples for a pumping procedure.

In some embodiments, rather than coupling the strap connector 605 to the first shoulder strap 606A and the second shoulder strap 606B, the strap connector 605 can be coupled to the first shoulder strap 680 and the second shoulder strap 680 to maintain the first shoulder strap 680 and the second shoulder strap 680 in the second configuration.

Figure 15:
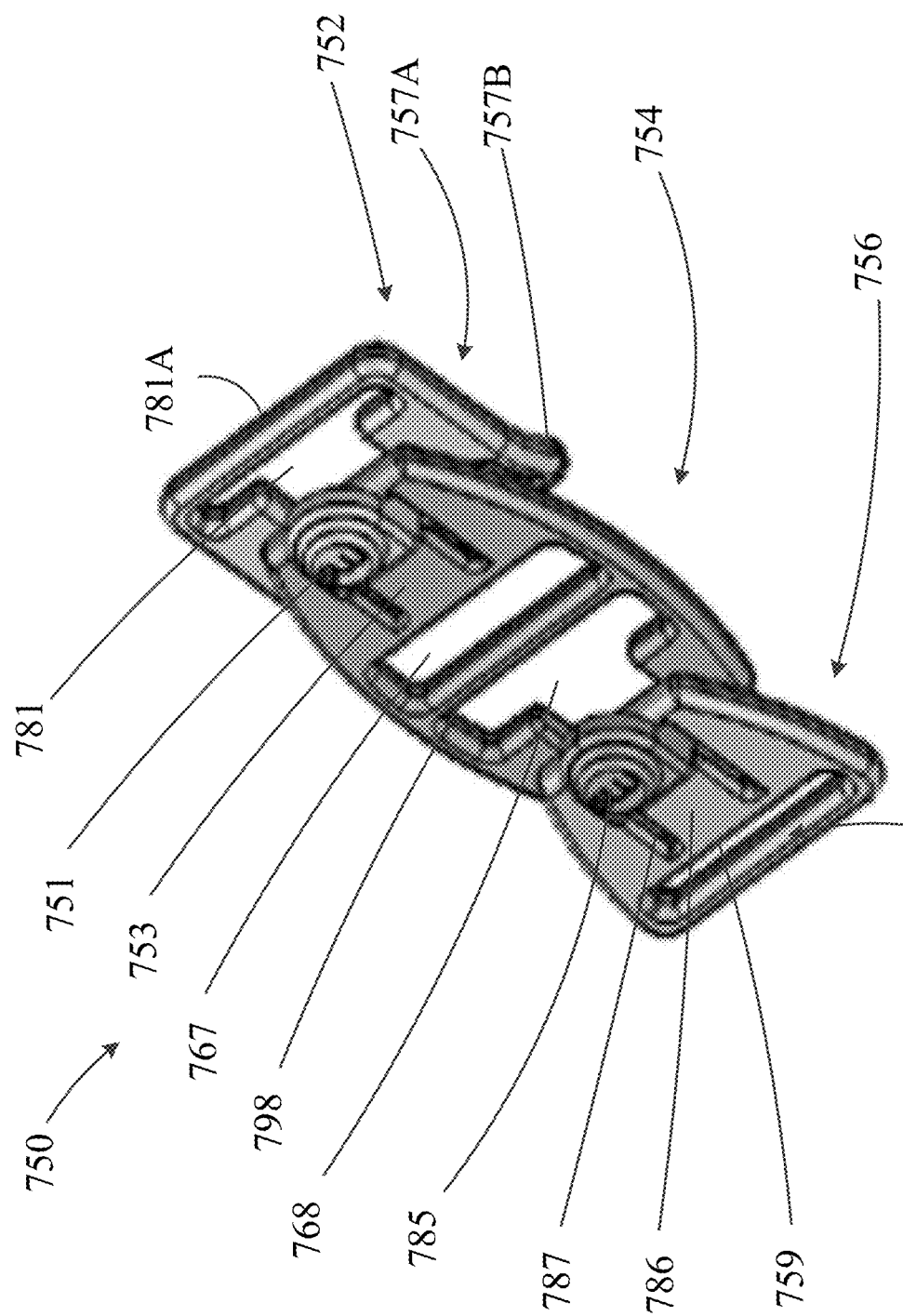
FIG. 15 is a perspective view of an engagement mechanism, according to an embodiment.

FIG. 15 is a perspective view of an engagement mechanism 750. FIGS. 16 and 17 are a front view and a side view, respectively, of the clasp 750. The engagement mechanism 750 can be similar in structure and function to any of the engagement mechanisms described herein, such as the engagement mechanism 450. For example, the engagement mechanism 750 can include a first portion 752 (also referred to as a top portion), a second portion 754 (also referred to as an intermediate portion), and a third portion 756 (also referred to as a bottom portion). As shown in FIGS. 15-17, the first portion 752 can be configured to be releasably engageable with the second portion 754. The second portion 754 can be configured to be releasably engageable with the third portion 756. Thus, the first portion 752 can be releasably coupled to the third portion 756 via the second portion 754. Additionally, the first portion 752 can be configured to be releasably coupled to the third portion 756 (e.g., when the second portion 754 is not used or included).

The first portion 752 can include an extension portion 751, a base portion 757A, and an angled portion 757B. The base portion 757A can define a first opening 781 and the angled portion 757B can define a second opening 783. The second opening 783 can be on an opposite side of the extension portion 751 than the first opening 781. The angled portion 757B can be disposed at any suitable non-zero angle relative to the base portion 757A such a gap exists between the portion of the angled portion 757B defining the second opening 783 and the second portion 754 when the first portion 752 is engaged with the second portion 754. For example, as shown in FIG. 17, when the first portion 752 is engaged with the second portion 754, a surface of the base portion 757A can be coupled to a surface of the second portion 754 (e.g., the surfaces can be disposed in parallel planes) and the angled portion 757B can be disposed at an angle relative to both the surface of the base portion 757A and the surface of the second portion 754.

The extension portion 751 can be formed as a hook that forms a slot 751A (shown in FIG. 17). The second portion 754 can include a tab portion 753, a first opening 755 (also referred to as an engagement aperture), a securement bar 798, a second opening 767, a third opening 768, and an extension portion 785. The extension portion 785 can be formed as a hook that forms a slot 785A (shown in FIG. 17). The extension portion 785 can be disposed opposite the securement bar 798 from the first opening 755. The third portion 756 can include a tab portion 786, a first opening 787 (also referred to as an engagement aperture), and a second opening 759. The extension portion 751 of the first portion 752 and the extension portion 785 of the second portion 754 can be the same or similar in shape and size. The first opening 755 of the second portion 754 and the first opening 787 of the third portion 756 can be the same or similar in shape and size. The tab portion 753 of the second portion 754 and the tab portion 786 of the third portion 756 can be the same or similar in shape and size. Thus, the first portion 752, the second portion 754, and the third portion 756 can include complementary mating features such that the second portion 754 and the third portion 756 can be releasably coupleable to and decoupleable from the first portion 752 and the third portion 756 can be releasably coupleable to and decoupleable from the second portion 754.

The first opening 755 of the second portion 754 can be shaped and sized such that the first opening 755 can receive the extension portion 751 of the first portion 752 and a portion of the second portion 754 partially defining the first opening 755 (e.g., a securement portion 755A) can be received in the slot 751A of the first portion 752. The tab portion 753 of the second portion 754 can be shaped and sized such that when the extension portion 751 of the first portion 752 is received through the first opening 755 of the second portion 754, the tab portion 753 contacts or engages the extension portion 751 and is flexed or clicked into locking engagement with the first portion 752 (e.g., with an underside of the extension portion 751). In some embodiments, the tab portion 753 can be sufficiently elastic such that as the second portion 754 is moved into engagement with the first portion 752, the tab portion 753 can bend slightly and then snap into locking engagement. The securement bar 798 of the second portion 754 is configured for attachment to the inner panel 770 of the garment 700. For example, a loop portion of the inner panel 770 can be secured around the securement bar 798.

The first opening 787 of the third portion 756 can be shaped and sized such that the first opening 787 can receive the extension portion 785 of the second portion 754 and a portion of the third portion 756 partially defining the first opening 787 (e.g., a securement portion 787A) can be received in the slot 785A of the second portion 754. The tab portion 786 of the third portion 756 can be shaped and sized such that when the extension portion 785 of the second portion 754 is received through the first opening 787 of the third portion 756, the tab portion 786 contacts or engages the extension portion 785 and is flexed or clicked into locking engagement with the second portion 754 (e.g., with an underside of the extension portion 785). In some embodiments, the tab portion 786 can be sufficiently elastic such that as the third portion 756 is moved into engagement with the second portion 754, the tab portion 786 can bend slightly and then snap into locking engagement.

Furthermore, the first opening 787 of the third portion 756 can be shaped and sized such that the first opening 787 can receive the extension portion 751 of the first portion 752 and a portion of the third portion 756 partially defining the first opening 787 (e.g., the securement portion 787A) can be received in the slot 751A of the first portion 752. The tab portion 786 of the third portion 756 can be shaped and sized such that when the extension portion 751 of the first portion 752 is received through the first opening 787 of the third portion 756, the tab portion 786 contacts or engages the extension portion 751 and is flexed or clicked into locking engagement with the first portion 752 (e.g., with an underside of the extension portion 751). In some embodiments, the tab portion 786 can be sufficiently elastic such that as the third portion 756 is moved into engagement with the first portion 752, the tab portion 786 can bend slightly and then snap into locking engagement. Thus, the angled portion 757B can be disposed at any suitable non-zero angle relative to the base portion 757A such a gap exists between the portion of the angled portion 757B defining the second opening 783 and the third portion 756 when the first portion 752 is engaged with the third portion 756. For example, when the first portion 752 is engaged with the third portion 756, a surface of the base portion 757A can be coupled to a surface of the third portion 756 (e.g., the surfaces can be disposed in parallel planes) and the angled portion 757B can be disposed at an angle relative to both the surface of the base portion 757A and the surface of the third portion 756.

The first portion 752 of the engagement mechanism 750 can be coupled to a shoulder strap of a garment such as, for example, any of the shoulder straps described herein (e.g., the shoulder strap 406 of the garment 400), with, for example, stitching. For example, an end portion of a shoulder strap can be looped through the first opening 781 and around a securement bar 781A and attached to itself such that a top portion of the first portion 752 is secured within the loop of the shoulder strap. Additionally, the first portion 752 can receive a portion of a support strap such as any of the support straps described herein (e.g., the support strap 480 of the garment 400) through the second opening 783 such that the support strap can be secured to the first portion 752 of the engagement mechanism 750. For example, an adjustable portion of the support strap can be looped through the second opening 783 of the first portion 752 and around a securement bar 783A and attached to itself (e.g., via engaging a first coupling mechanism with a coupling mechanism of a set of second coupling mechanisms) such that a bottom portion of the first portion 752 (e.g., a securement bar 783A of the first portion 752) is secured within the loop of the adjustable portion. Since the angled portion 757B of the first portion 752 extends away from the second portion 754, when the support strap is attached to the angled portion 757B (via being looped through the opening 783), the support strap can be partially disposed in the gap between the angled portion 757B and the back surface of the second portion 754. Thus, due to the gap between the angled portion 757B and the back surface of the second portion 754, the first portion 752 and the second portion 754 can be engaged without the support strap attached to the first portion 752 interfering with the coupling between the first portion 752 and the second portion 754. The support strap can be disposed to lie flat against the back of the second portion 754 or the third portion 756 (depending which is engaged with the first portion 752) in a first configuration of the support strap.

The second portion 754 of the engagement mechanism 750 can be coupled to an inner pumping panel such as any of the inner pumping panels described herein (e.g., the inner pumping panel 470) with, for example, stitching. For example, a portion of an inner pumping panel can be looped through the second opening 767, around the securement bar 798, back through the third opening 768, and attached to itself such that the securement bar 798 is secured within the loop of the inner pumping panel. Additionally, when the second portion 754 is coupled to the inner pumping panel, the inner pumping panel can be disposed on an opposite side of the second portion 754 than the extension portion 785 is disposed (e.g., contacting a back surface of the second portion 754).

Additionally, an outer panel such as any of the outer panels described herein (e.g., the panel 1462 or the panel 1464 of the outer panel 1460) can be attached to the third portion 756 of an engagement portion 750 via passing a portion of the outer panel through the opening 759 of the third portion 756, looping the portion over a bottom portion of the second portion 756 of the engagement mechanism 750 (e.g., a securement bar 759A), and then attaching the portion to itself (e.g., sewn or stitched) in a similar manner as how the inner layer 770 is attached to the third portion 756.

Figure 19:
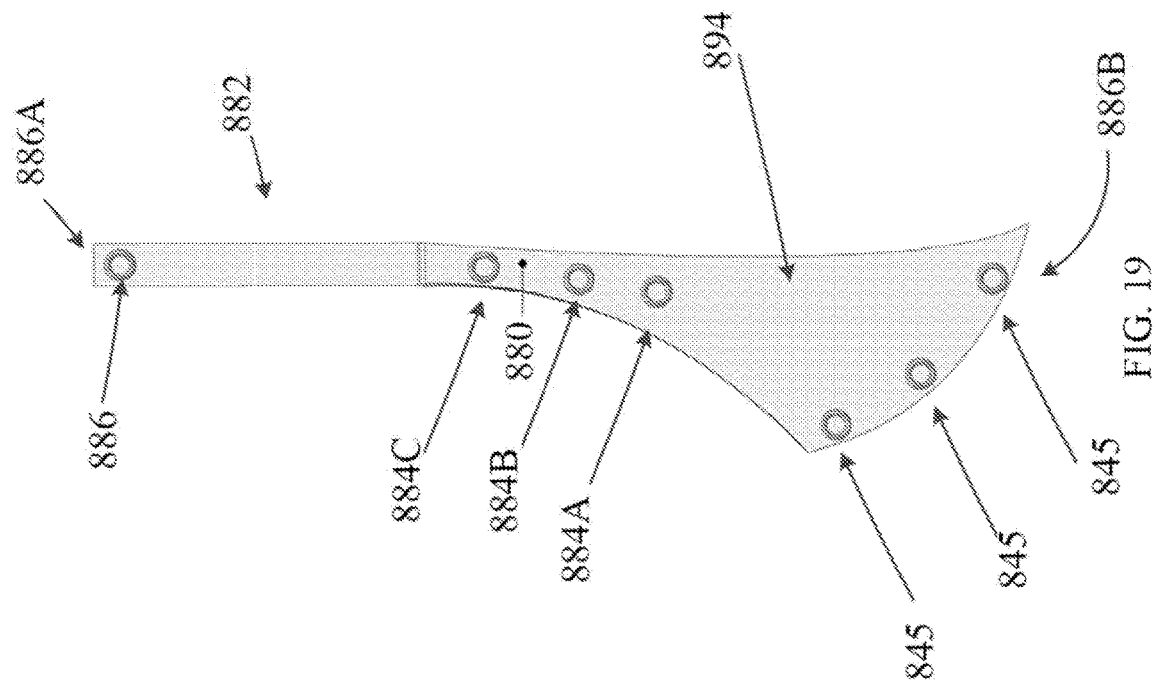
FIG. 19 is a back view of a first layer of the support strap of FIG. 18.
Figure 18:
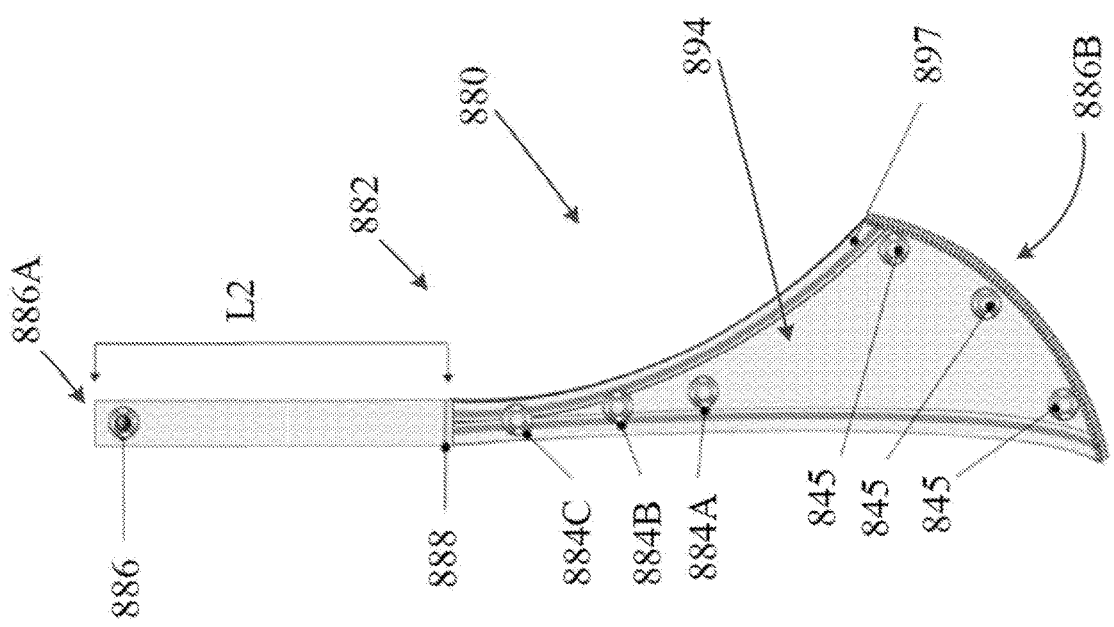
FIG. 18 is a front view of a support strap, according to an embodiment.

In some embodiments, a support strap can include multiple layers such that one or more coupling mechanisms and/or one or more coupling members of the support strap (e.g., the backs of the coupling mechanisms or coupling members) are isolated from contacting the skin of the wearer and/or prevented from causing discomfort to the wearer. For example, FIG. 18 is a front view of a support strap 880 and FIG. 19 is a back view of a first layer 894 of the support strap 880. The support strap 880 can be the same or similar in structure and/or function to any of the support straps described herein, such as the support strap 480 of the garment 400. For example, the support strap 880 includes an adjustable portion 882 that can be the same or similar to any of the adjustable portions described herein, such as the adjustable portion 482. The adjustable portion 882 can include a first coupling mechanism 886 (also referred to as a first coupling member) disposed proximate a second end 886A of the support strap 880. The second end 886A can be an end of the support strap 880 opposite a first end 886B. The first end 886B can be fixedly coupled to a back panel, such as any of the back panels described herein (e.g., the back panel 420) (e.g., via sewing/stitching). The adjustable portion 882 can also include a set of second coupling mechanisms disposed along the adjustable portion 882 (e.g., closer to the first end 886B than the first coupling mechanism 886). The set of second coupling mechanisms can include, for example, a second coupling mechanism 884A, a third coupling mechanism 884B, and a fourth coupling mechanism 884C (also referred to as a second coupling member, a third coupling member, and a fourth coupling member, respectively). The adjustable portion 882 can be configured such that the second end 886A of the support strap 882 can be looped through a first opening in a first portion of an engagement portion (e.g., the first opening 483 in the first portion 452 of the engagement portion 450) and the first coupling mechanism 886 can be engaged with any of the coupling mechanism 884A, the coupling mechanism 884B, and the coupling mechanism 884C. Thus, the wearer can adjust the length of the support strap 880 between the engagement portion and the first end 886B based on which of the coupling mechanism 884A, the coupling mechanism 884B, and the coupling mechanism 884C the first coupling mechanism 886 is engaged with. The support strap 880 can also include coupling members 845 such that the support strap 880 can be coupled to a pumping panel such as any of the pumping panels described herein via the coupling members 845. The coupling members 845 can be the same or similar in structure and/or function to any of the coupling members described herein such as the coupling members 445 described above. Additionally, as shown in FIG. 18, in some embodiments, one or more edges 897 of the first layer 894 of the support strap 880 (e.g., all edges except the edge coupled to the back panel) can include fold-over elastic secured to another portion of the first layer 894 via a coverstitch.

In some embodiments, the first coupling mechanism 886 can be disposed on a length of the support strap 880 that can be separated from a remainder of the support strap 880 via, for example, bar tack 888. Such a length can be, for example, reinforced and/or non-elastic. In some embodiments, the length can have a length L2 of, for example, about 6.5 inches. In some embodiments, the length can have a length L2 of, for example, between about 6 inches and about 7 inches. In some embodiments, the length can have a length L2 of, for example, between about 5 inches and about 8 inches.

Figure 20:
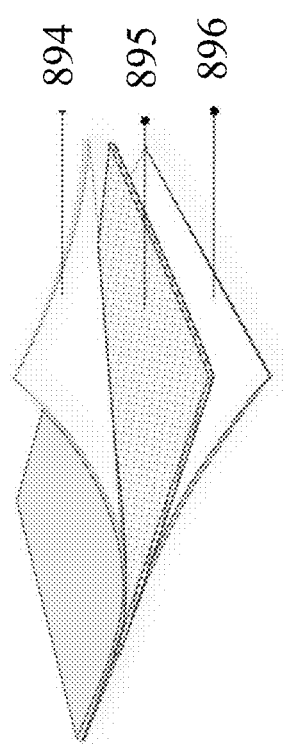
FIG. 20 is a perspective view of a portion of the support strap of FIG. 18.

In some embodiments, the support strap 880 can include a second layer 896 coupled to the first layer 894 such that, when in use, the backs of the coupling mechanisms 884A, 884B, and 884C and the backs of the coupling members 845 are covered by the second layer 896 and the second layer 896 is disposed between the backs of the coupling mechanisms 884A, 884B, and 884C and the coupling members 845 and the skin of the wearer. In some embodiments, a cushion layer 895 (e.g., a foam layer) can be disposed between the first layer 894 and the second layer 896 (e.g., at least between the portions including the coupling mechanisms 884A, 884B, and 884C and the coupling members 845 and the second layer 896). For example, the cushion layer 895 can be disposed between the coupling mechanisms 884A, 884B, and 884C and/or the coupling members 845 and the skin of the wearer when the wearer is wearing a garment including the support strap 880 in the first configuration of the support strap 880. FIG. 20, for example, shows is a perspective view of a portion of the support strap 880 with portions peeled away for illustrative purposes. As shown in FIG. 20, the cushion layer 895 can be disposed between the first layer 894 and the second layer 896. The support strap 880 can be bound along all of the edges (e.g., via stitching and/or adhesive) such that the first layer 894 and the second layer 896 are bound together and the cushion layer 895 is secured between the first layer 894 and the second layer 896. Thus, the backs of the coupling mechanisms 884A, 884B, and 884C and the coupling member 845 shown in FIG. 19 will be covered by the cushion layer 895 and the second layer 896 and not visible when the support strap 880 is assembled. In some embodiments, the support strap 880 can include the first layer 894 and the second layer 896 and not include the cushion layer 895.

Figure 21:
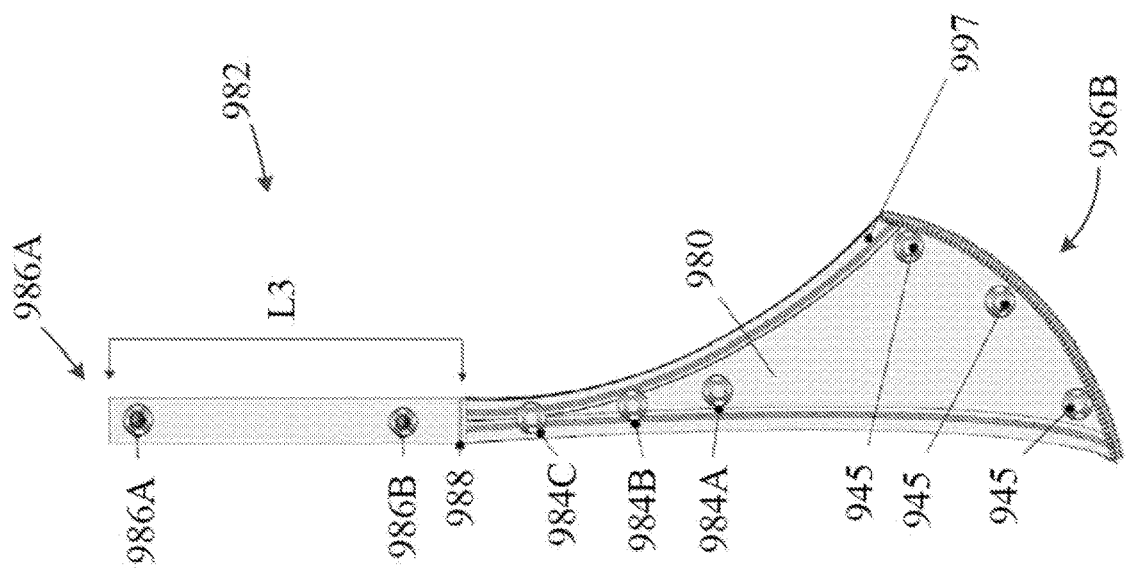
FIG. 21 is a front view of a support strap, according to an embodiment.

In some embodiments, a support strap, such as any of the support straps described herein, can include a set of first coupling mechanisms configured to releasably engage with a set of second coupling mechanisms. For example FIG. 21 is a front view of a support strap 980. The support strap 980 can be the same or similar in structure and/or function to any of the support straps described herein, such as the support strap 480 of the garment 400. For example, the support strap 980 includes an adjustable portion 982 that can be similar to any of the adjustable portions described herein, such as the adjustable portion 482. The adjustable portion 982 can include a set of first coupling mechanisms including a first coupling mechanism 986A and a first coupling mechanism 986B. The first coupling mechanism 986A (also referred to as a first coupling member) can be disposed proximate a second end 986A of the support strap 980 and the first coupling mechanism 986B can be disposed closer to the first end 986B than the first coupling mechanism 986A. The second end 986A can be an end of the support strap 980 opposite a first end 986B. The first end 986B can be fixedly coupled to a back panel, such as any of the back panels described herein (e.g., the back panel 420) (e.g., via sewing/stitching). The adjustable portion 982 can also include a set of second coupling mechanisms disposed along the adjustable portion 982 (e.g., closer to the first end 986B than the first coupling mechanism 986B). The set of second coupling mechanisms can include, for example, a second coupling mechanism 984A, a third coupling mechanism 984B, and a fourth coupling mechanism 984C (also referred to as a second coupling member, a third coupling member, and a fourth coupling member, respectively). The adjustable portion 982 can be configured such that the second end 986A of the support strap 982 can be looped through a first opening in a first portion of an engagement portion (e.g., the first opening 483 in the first portion 452 of the engagement portion 450) and the first coupling mechanism 986A or the first coupling mechanism 986B can be engaged with any of the coupling mechanism 984A, the coupling mechanism 984B, and the coupling mechanism 984C. Thus, the wearer can adjust the length of the support strap 980 between the engagement portion and the first end 986B based on which of the first coupling mechanism 986A and 986B are engaged with which of the coupling mechanism 984A, the coupling mechanism 984B, and the coupling mechanism 984C. In some embodiments, the first coupling mechanisms 986A and 986B can be male snap connectors and the coupling mechanism 984A, the coupling mechanism 984B, and the coupling mechanism 984C can be female snap connector configured to mate with either of the first coupling mechanism 986A or 986B. In some embodiments, the first coupling mechanisms 986A and 986B can be female snap connectors and the coupling mechanism 984A, the coupling mechanism 984B, and the coupling mechanism 984C can be male snap connector configured to mate with either of the first coupling mechanism 986A or 986B.

The support strap 980 can also include coupling members 945 such that the support strap 980 can be coupled to a pumping panel such as any of the pumping panels described herein via the coupling members 945. The coupling members 945 can be the same or similar in structure and/or function to any of the coupling members described herein such as the coupling members 445 described above. Additionally, as shown in FIG. 21, in some embodiments, one or more edges 997 of the support strap 980 (e.g., all edges except the edge coupled to the back panel) can include fold-over elastic secured to another portion of the support strap 980 via a coverstitch.

In some embodiments, rather than the inner pumping panel being releasably coupleable to the support strap, the inner pumping panel can be releasably coupleable to the outer panel. For example, FIGS. 22-28 illustrate various views and components of a garment 1000 that can be used with a wearable breast pump or wearable milk collection device. Such a wearable breast pumps or milk collection device can be placed in contact with a user's breast and maintained in place by a portion of the garment 1000.

Figure 22:
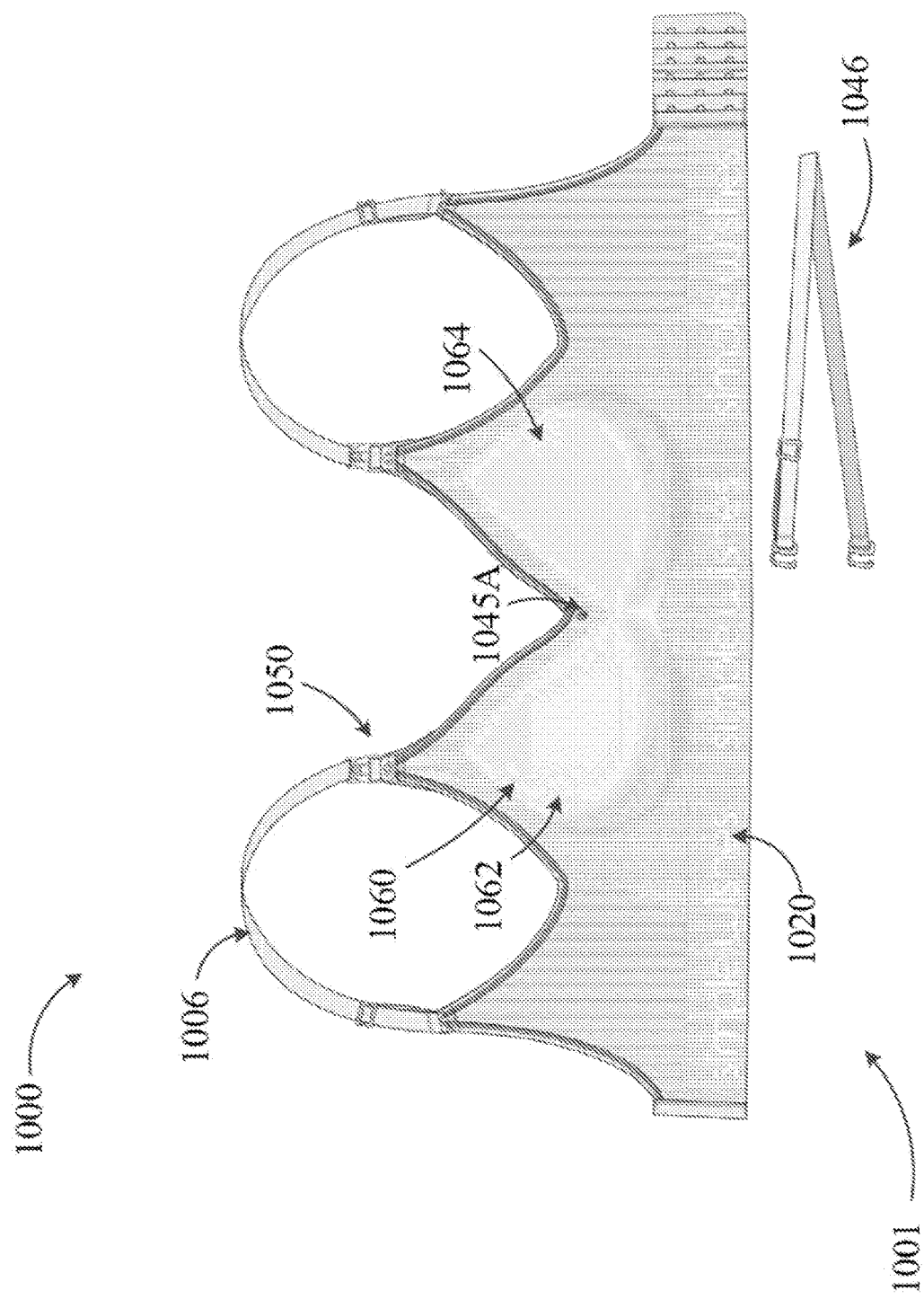
FIG. 22 is a front view of a garment, according to an embodiment.
Figure 23:
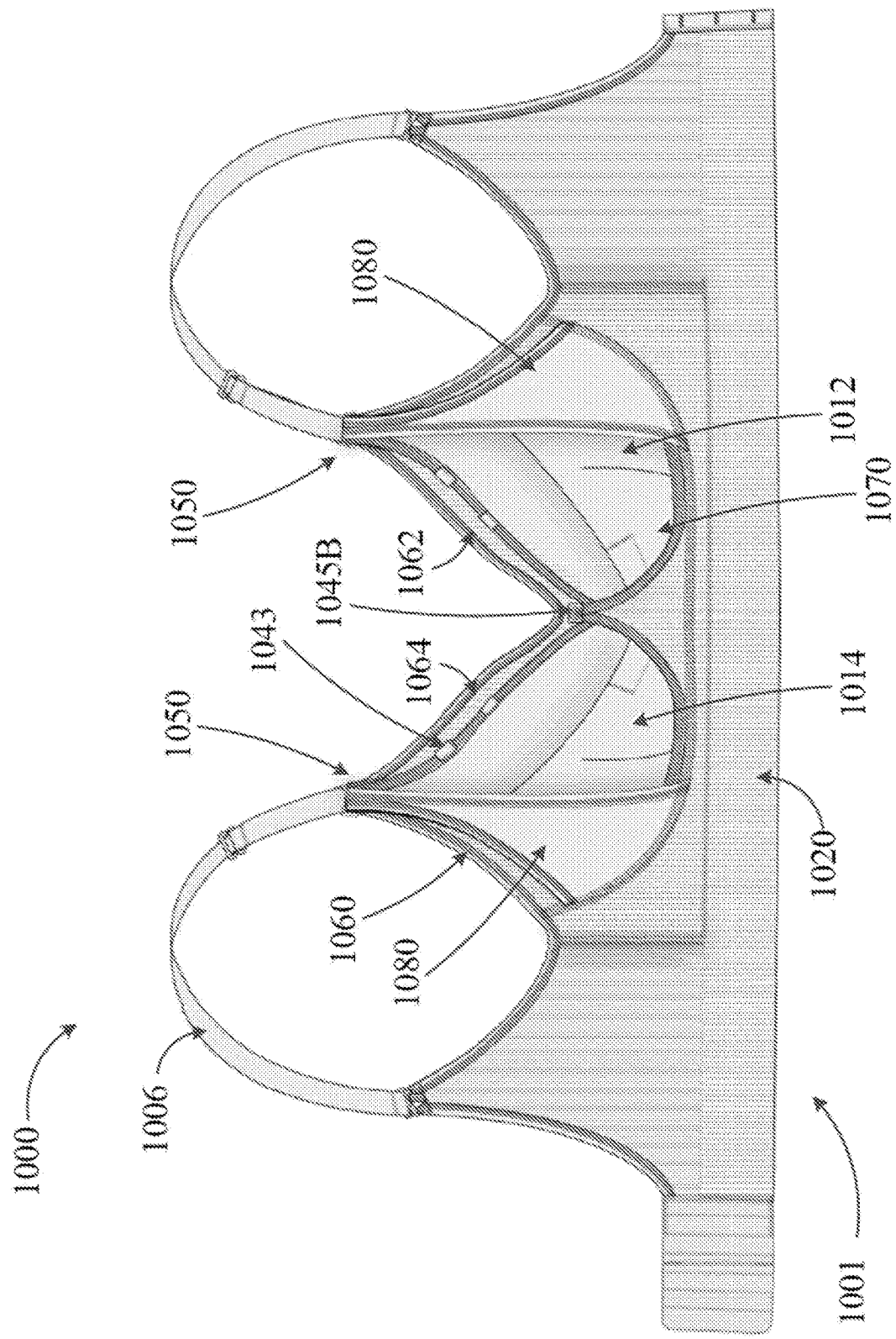
FIG. 23 is a back view of the garment of FIG. 22.
Figure 24:
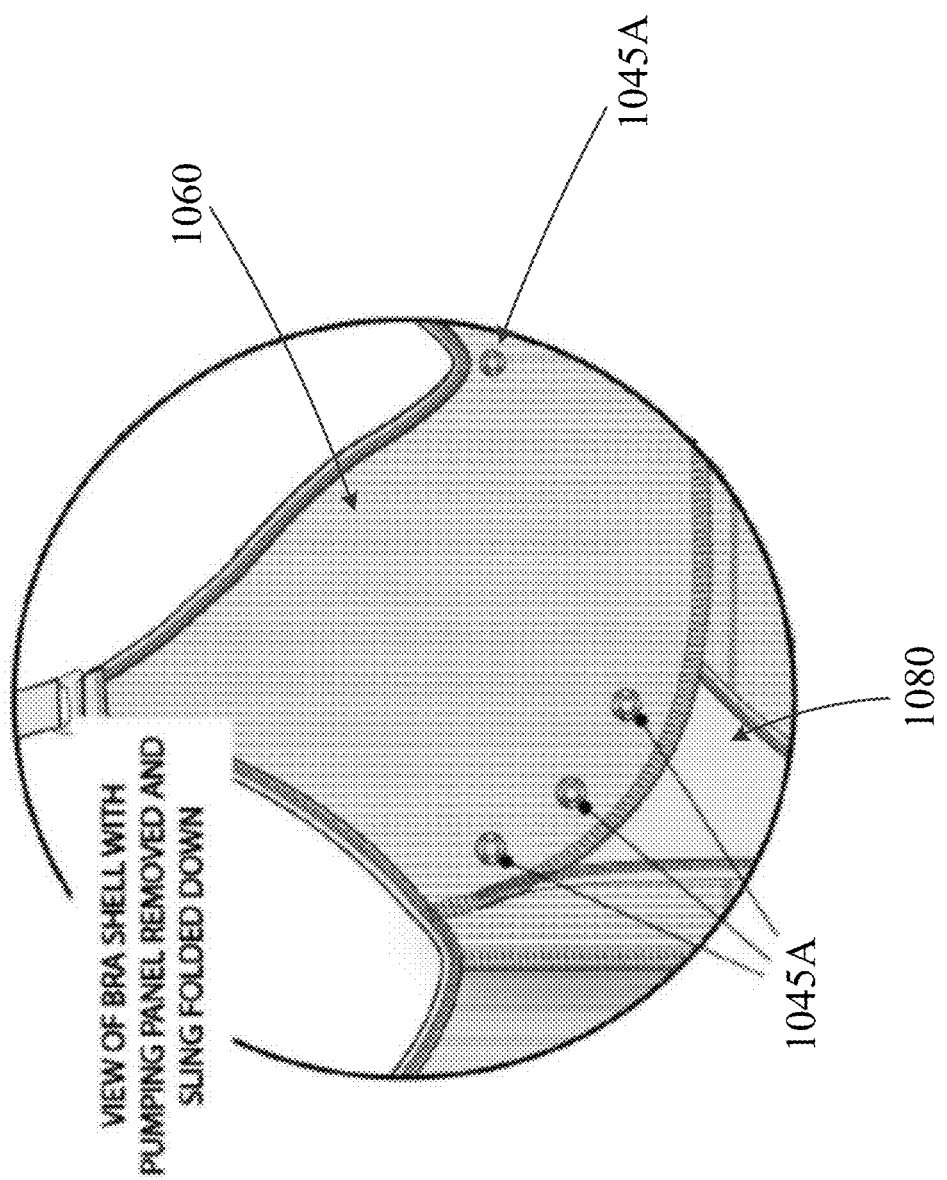
FIG. 24 is a back view of a portion of the garment of FIG. 22 with an optional pumping panel removed and a support strap folded down.
Figure 25:
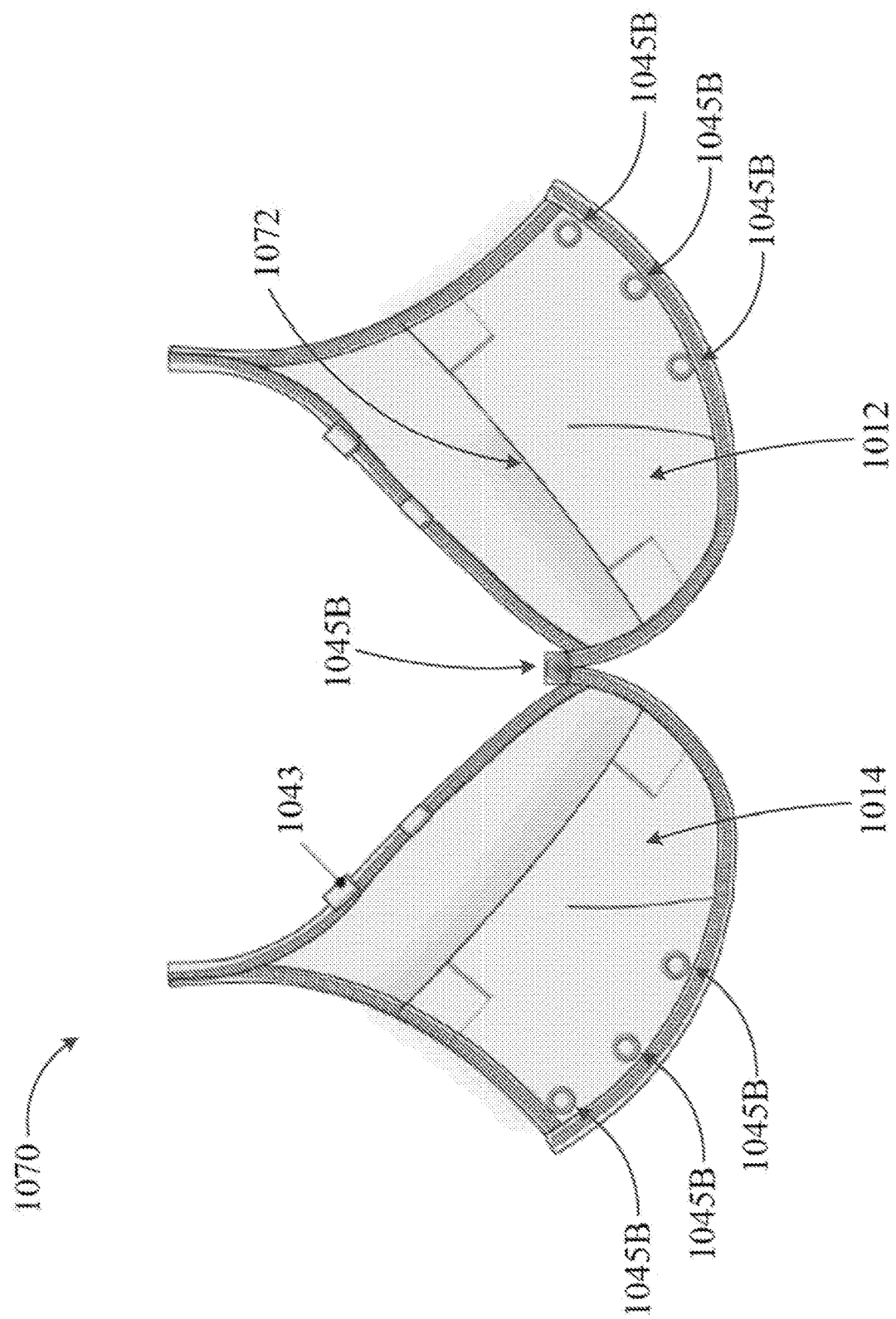
FIG. 25 is a back view of a pumping panel of the garment of FIG. 22.
Figure 26:
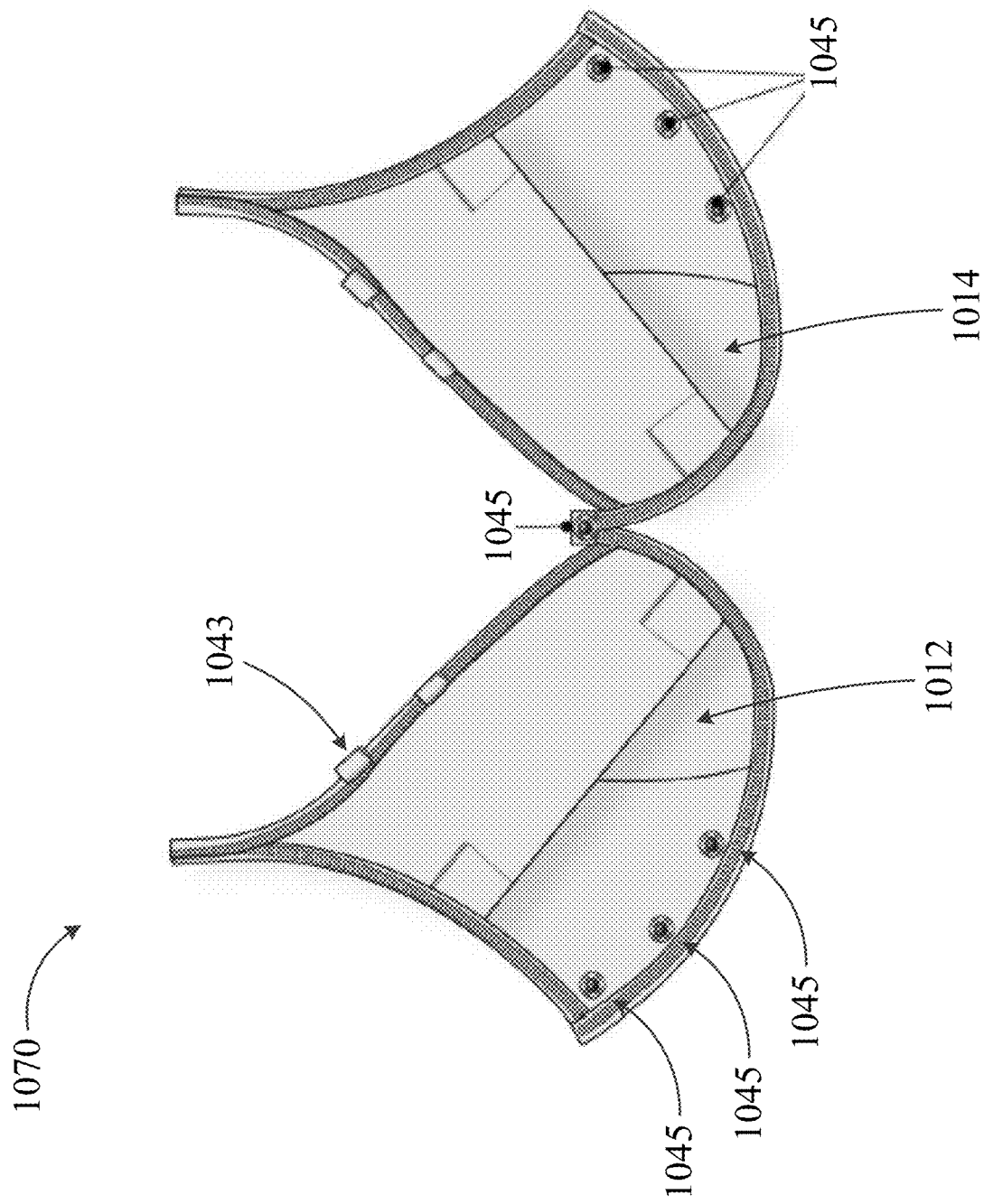
FIG. 26 is a front view of the pumping panel of FIG. 25.

FIG. 22 is a front view of the garment 1000 with an optional center or neck strap 1046 detached. FIG. 23 is a back view of the garment 1000 with an optional inner pumping panel 1070 attached. FIG. 24 is a back view of a portion of the garment 1000 with the optional pumping panel 1070 removed and a support strap 1080 folded down. FIG. 25 is a back view of the pumping panel 1070. FIG. 26 is a front view of the pumping panel 1070. FIGS. 27 and 28 are a front view and a back view of the support strap 1080, respectively. The garment 1000 can include the same or similar components and/or functions as any of the garments described herein. For example, the garment 1000 includes an outer panel 1060, the inner pumping panel 1070 (also referred to as an "inner panel" or a "pumping panel"), a back panel 1020, two support straps 1080 (also referred to as a "sling"), and two shoulder straps 1006. The garment 1000 can also include a center or neck strap 1046 that can be removably coupled to the inner pumping panel 1070. Each shoulder strap 1006 can be coupled to the outer panel 1060, the inner panel 1070, and a support strap 1080 via an engagement mechanism 1050 (also referred to herein as a"clasp"). The engagement mechanism 1050 can be the same or similar as any of the engagement mechanisms described herein, such as the engagement mechanism 250, the engagement mechanism 450, and/or the engagement mechanism 750. The inner panel 1070 can be the same or similar in structure and/or function to any of the inner panels or pumping panels described herein. The outer panel 1060, shoulder straps 1006, and back panel 1020 can be the same or similar in construction and function as, for example, the outer panel 460, support straps 480, 780, 880, and back panel 420, respectively, and therefore, some features and details are not described with reference to this embodiment. For example, the various components can be coupled together in the same manner as described above for previous embodiments. In some embodiments, the various components are coupled together via stitching. In some embodiments, the support straps 1080 can be the same or similar in structure and/or function to any of the support straps described herein, such as the support straps 480, the support straps 880, and/or the support straps 980.

The inner panel 1070 and the outer panel 1060 can each include one or more panels each formed with one or more layers of material. As shown, for example, in FIG. 22, the outer panel 1060 includes a right outer panel 1062 and a left outer panel 1064. As shown, for example, in FIG. 23, the inner panel 1070 includes a right inner panel 1012 and a left inner panel 1014. The right inner panel 1012 and the left inner panel 1014 can be shaped and sized for coverage of a wearer's right breast and left breast, respectively. As shown in FIG. 25, each of the right inner panel 1012 and the left inner panel 1014 can include a first portion and a second portion that are coupled together such that a portion is unattached and can define an opening 1072 between the first portion and the second portion. In some embodiments, the first portion and the second portion can include an overlapping portion which can define the opening 1072. The first portion and the second portion can be separated by, for example, moving the first portion and the second portion away from each other, thereby creating the opening 1072 and providing access to the user's breast. A breast pump can then be inserted through the opening 1072 and the inner pumping panel 1070 can help support the breast pump during milk extraction.

Additionally, as shown in FIG. 23, the inner panel 1070 can include one or more holes 1043 defined in an upper edge of the inner panel 1070. For example, the inner panel 1070 can define the holes 1043 and/or the holes 1043 can be defined by a separate component (e.g., a loop of material) coupled to the inner panel 1070. The center or neck strap 1046 can be attached to the inner panel 1070 via selective releasable engagement with any of the holes 1043.

The support straps 1080 can be coupled on a first end to the back panel 1020 and on a second end to one of the shoulder straps 1006 via the engagement mechanism 1050. In alternative embodiments, the support straps 1080 can be attached to a lower band of the garment 1000 rather than to the back panel 1020. Each of the shoulder straps 1006 can have a first end coupled to a support strap 1080 of the support straps 1080 (via the engagement mechanism 1050) and a second end coupled to the back panel 1020, with for example, sewing/stitching. The outer panel 1060 can be attached to the back panel 1020, for example, along a bottom edge of the outer panel 1060, via, for example, sewing/stitching. The optional inner pumping panel 1070 can be removably coupled to the shoulder straps 1006.

As shown in FIGS. 27 and 28, each support strap 1080 can include an adjustable portion 1082. The adjustable portion 1082 can be the same or similar in structure and/or function to any of the adjustable portion described herein, such as the adjustable portion 482. For example, the adjustable portion 1082 can include a first coupling mechanism 1086 (also referred to as a first coupling member) disposed proximate a second end 1086A of the support strap 1080. The second end 1086A can be an end of the support strap 1080 opposite a first end 1086B. The first end 1086B can be fixedly coupled to the back panel 1020 (e.g., via sewing/stitching). The support strap 1080 can include a first layer 1094 and a second layer 1096 (e.g., the support strap 1080 can be two-ply). Additionally, as shown in FIG. 27, in some embodiments, one or more edges 1097 of the support strap 1080 (e.g., all edges except the edge coupled to the back panel) can include fold-over elastic secured to another portion of the support strap 1080 via a coverstitch. The adjustable portion 1082 can also include a set of second coupling mechanisms disposed along the adjustable portion 1082 (e.g., closer to the first end 1086B than the first coupling mechanism 1086). The set of second coupling mechanisms can include, for example, a second coupling mechanism 1084A, a third coupling mechanism 1084B, and a fourth coupling mechanism 1084C (also referred to as a second coupling member, a third coupling member, and a fourth coupling member, respectively). The adjustable portion 1082 can be configured such that the second end 1086A of the support strap 1082 can be looped through a first opening in a first portion of the engagement portion 1050 and the first coupling mechanism 1086 can be engaged with any of the coupling mechanism 1084A, the coupling mechanism 1084B, and the coupling mechanism 1084C. Thus, the wearer can adjust the length of the support strap 1080 between the engagement portion 1050 and the first end 1086B based on which of the coupling mechanism 1084A, the coupling mechanism 1084B, and the coupling mechanism 1084C the first coupling mechanism 1086 is engaged with. For example, the first coupling mechanism 1086 can be engaged with the coupling mechanism 1084A closest to the first end 1086B in a first configuration in which the support strap 1080 is not being used to support a portion of a breast pump against a breast. When the support strap 1080 is being used to support a portion of a breast pump (e.g., a flange of a shield of a breast pump) against the breast (e.g., by being wrapped fully or partially around a flange and/or a stem of a shield of the breast pump and then being attached to the first portion of the engagement mechanism 1050), the support strap 1080 can be transitioned to a second configuration in which the first coupling mechanism 1086 can be attached to one of the coupling mechanism 1084B or the coupling mechanism 1084C, such that the length of the support strap 1080 between the first portion of the engagement mechanism 1050 and the first end 1086B is longer than in the first configuration and can comfortably maintain the flange of the breast pump against the breast.

In some embodiments, the first coupling mechanism 1086 can be disposed on a length of the support strap 1080 that can be separated from a remainder of the support strap 1080 via, for example, bar tack 1088. Such a length can be, for example, reinforced and/or non-elastic. In some embodiments, the length can have a length L4 of for example, about 6.5 inches. In some embodiments, the length can have a length L4 of, for example, between about 6 inches and about 7 inches. In some embodiments, the length can have a length L4 of, for example, between about 5 inches and about 8 inches.

A base or lower portion of the inner pumping panel 1070 can be removably coupled to the outer panel 1060. For example, the inner pumping panel 1070 can include coupling members 1045B and the outer panel 1060 can include coupling members 1045A. The coupling members 1045B of the inner pumping panel 1070 can be removably coupled to the coupling member 1045A of the outer panel 100. In some embodiments, the coupling members 1045A of the outer panel 1060 and the coupling members 1045B of the inner pumping panel 1070 can be, for example, a female and male snap connector, respectively. In some embodiments, the coupling members 1045A of the outer panel 1060 can be a male snap connector and the coupling members 1045B of the inner pumping panel 1070 can be a female snap connector, and vice versa. In addition, other types of coupling members can alternatively be used such as, for example, hook and loop fasteners such as VELCRO, or buttons, hooks, etc. The coupling members 1045A of the outer panel 100 and the coupling members 1045B of the inner panel 1070 can be attached to the outer panel 1060 and the inner panel 1070, respectively, for example, via sewing or stitching.

In some embodiments, the coupling members 1045A can be disposed on a back side of the outer panel 106 and the coupling members 1045B can be disposed on a front side of the inner pumping panel 1070. In some embodiments, an engagement portion (e.g., a female portion of a snap connector) of each of the coupling members 1045A can be disposed on a back side of the outer panel 106W and an engagement portion (e.g., a male portion of a snap connector) of each of the coupling members 1045B can be disposed on a front side of the inner pumping panel 1070.

The inner pumping panel 1070 can include any suitable number of coupling members 1045B arranged in any suitable arrangement and the outer panel 1060 can include any suitable number of coupling members 1045A arranged in any suitable arrangement complementary to the arrangement of coupling members 1045B of the inner pumping panel 1070. For example, as shown in FIG. 25, the inner pumping panel 1070 can include three coupling members 1045B on each of the right inner panel 1012 and the left inner panel 1014 and one coupling member 1045B in a center region between the right inner panel 1012 and the left inner panel 1014. As shown in FIG. 24, the outer panel 1060 can include three coupling members 1045A on each of the right outer panel 1062 and the left outer panel 1064 and one coupling member 1045A in a center region between the right inner panel 1012 and the left inner panel 1014. The coupling members 1045A of the outer panel 1060 can be arranged on right outer panel 1062 and the left outer panel 1064 such that, when the support straps 1080 associated with each outer panel 1012 and 1014 are coupled to the outer panel 1080 via the engagement mechanism 1050 in the first configuration and the patient is wearing the garment 1000, the respective support strap 1080 is disposed between all of the coupling members 1045A of the right outer panel 1062 or the left outer panel 1064 and the skin of the patient.

In use, the garment 1000 can be worn by a wearer with the inner pumping panel 1070 coupled to the outer panel 1060. If access to a breast of the wearer is desired, such as for breast pumping, the outer panel 1060 (e.g., the right outer panel 1062 and/or the left outer panel 1064) can be detached from the inner pumping panel 1070 (e.g., the right inner panel 1012 and/or the left inner panel 1014) by detaching or uncoupling relative portions of the engagement mechanism 1050 (e.g., as described above with respect to the garment 400) and moving the outer panel 1060 (e.g., folding the outer panel 1060 down) such that the inner panel 1070 is accessible. In some embodiments, some or all of the coupling members 1045A of the outer panel 1060 can remain coupled to the coupling members 1045B of the inner pumping panel 1070. In some embodiments, the coupling members 1045A of the outer panel 1060 can be detached from the coupling members 1045B of the inner pumping panel 1070.

The first portion and the second portion of the inner panel 1070 (e.g., of the right inner panel 1012 and/or the left inner panel 1014) can be separated (e.g., stretched or folded) to create the opening 1072 through which the wearer's breast is accessible and a portion of a breast pump can be inserted. If further access to the breast of the wearer is desired, the inner panel 1070 can be detached from the shoulder straps 1006 by removing/detaching the relative portions of the engagement mechanism 1050 (e.g., as described above with respect to the garment 400) and decoupling any coupling members 1045A remaining coupled to the coupling members 1045B. When desired, the inner panel 1070 and the outer panel 1060 can be reattached to the shoulder strap 1006 by recoupling the relative portions of the engagement mechanism 1050 and recoupling the coupling members 1045A to the coupling members 1045B.

Figure 30:
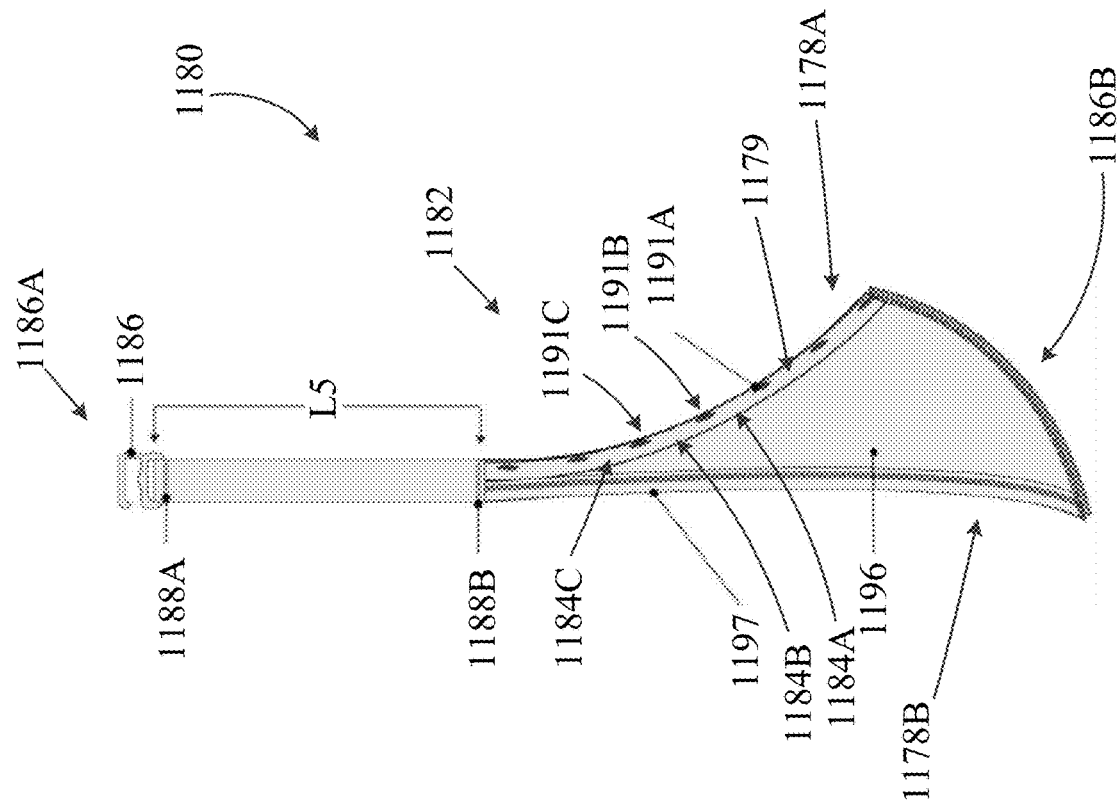
FIG. 30 is a back view of the support strap of FIG. 29.
Figure 29:
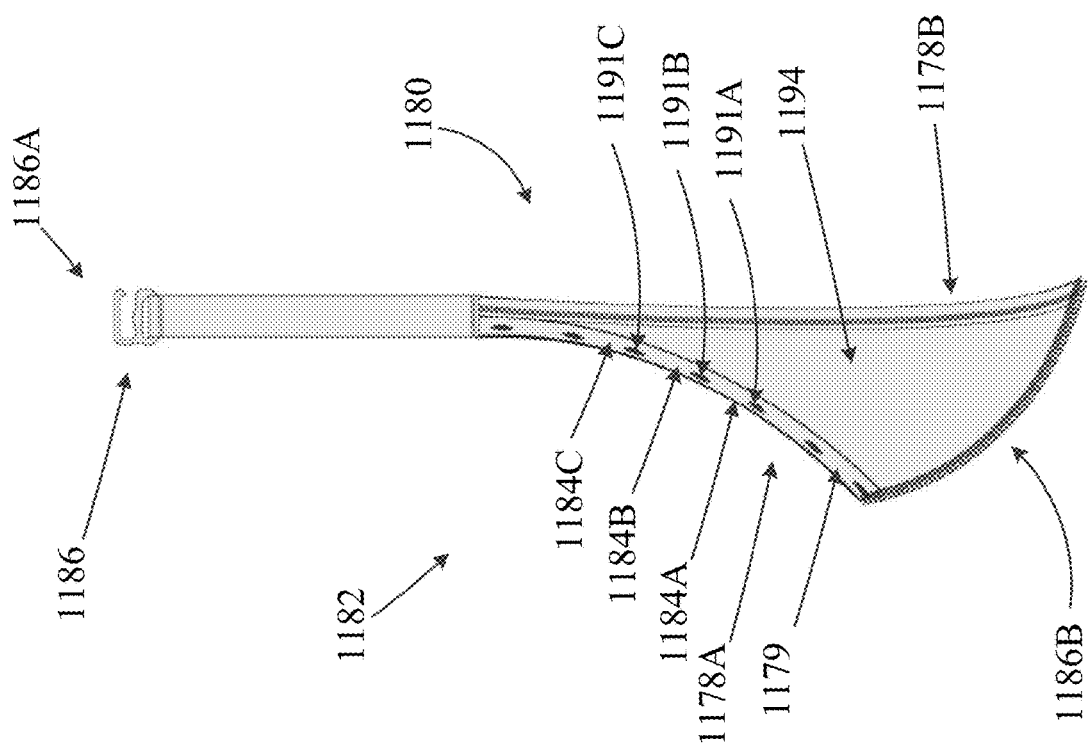
FIG. 29 is a front view of a support strap of a garment, according to an embodiment.

In some embodiments, the first coupling mechanism of a support strap can include a hook and the set of second coupling mechanisms of the support strap can include portions of the support strap disposed adjacent openings defined in the support strap. For example, FIGS. 29 and 30 are a front view and a back view, respectively, of a support strap 1180. The support strap 1180 can be the same or similar in structure and/or function to any of the support straps described herein. For example, the support strap 1180 includes an adjustable portion 1182. Additionally, the support strap 1180 can include a first layer 1194 and a second layer 1196 (e.g., the support strap 1180 can be two-ply). The adjustable portion 1182 can include a first coupling mechanism 1186 disposed proximate a second end 1186A of the support strap 1180. The second end 1186A can be an end of the support strap 1180 opposite a first end 1186B. The first end 1186B can be fixedly coupled to a back panel of a garment that includes the support strap 1180 (e.g., via sewing/stitching). The support strap 1180 can include a first edge 1178A and a second edge 1178B opposite the first edge 1178A. The first edge 1178A and the second edge 1178B can each extend from the first end 1186B to or toward the second end 1186A (e.g., along the entire length of the support strap 1180 or to a location proximate bar tack 1188B).

The first coupling mechanism 1186 can include a hook portion. For example, the first coupling mechanism 1186 can include a swan hook. The adjustable portion 1182 can also include an elongated portion 1179 (also referred to as an elongated strip). The elongated portion 1179 can be disposed along the first edge 1178A. The elongated portion 1179 can at least partially define an elongated interior space. In some embodiments, the elongated portion 1179 can define the elongated interior space in combination with the first layer 1194 of the support strap 1180. In some embodiments, the elongated portion 1179 can define the elongated interior space between two portions of the elongated portion 1179.

The elongated portion 1179 can define a set of openings 1191 such that the interior space can be accessed via an opening of the set of openings 1191. For example, as shown in FIGS. 29 and 30, the elongated portion 1179 can define a first opening 1191A, a second opening 1191B, and a third opening 1191C. In some embodiments, the elongated portion 1179 can include an elongated elastic member coupled to the first layer 1194 and/or the second layer 1196 (e.g., via attaching at least the ends of the elongated elastic member to the first layer 1194 and/or the second layer 1196). In some embodiments, the set of openings 1191 can be defined by the elastic. In some embodiments, the elongated portion 1179 can include a portion of the first layer 1194 and/or the second layer 1196 folded over the first layer 1194 or the second later 1196 to define the interior space. In some embodiments, each opening 1191 extends entirely through the elongated portion 1179 (e.g., each opening 1191 includes an entrance opening on a first or front side of the elongated portion 1179 and an exit opening on a second or back side opposite the first side of the elongated portion 1179) such that a portion of the hook portion of the first coupling mechanism 1186 can extend into each opening 1191 on one side and exit each opening 1191 on the other side. In some embodiments, the elongated portion 1179 defines openings 1191 that provide access to the interior space of the elongated portion 1179 such that a portion of the hook portion is configured to be received into the interior space of the elongated portion 1179 via each opening of the set of openings 1191.

The elongated portion 1179 can include a set of second coupling mechanisms 1184 disposed along the adjustable portion 1182 (e.g., closer to the first end 1186B than the first coupling mechanism 1186). The set of second coupling mechanisms 1184 can include sub-portions of the elongated portion 1179 disposed adjacent the set of openings 1191. For example, the set of second coupling mechanisms can include a coupling mechanism 1184A disposed adjacent the opening 1184A, a coupling mechanism 1184B disposed adjacent the opening 1184B, and a coupling mechanism 1184C disposed adjacent the opening 1184C. Each of the second coupling mechanisms 1184 of the set of second coupling mechanisms 1184 can define a portion of the interior space at least partially defined by the elongated portion 1179. Each of the second coupling mechanisms 1184 can be shaped and size such that the first coupling mechanism 1186 can receive and retain each of the second coupling mechanisms 1184. For example, the hook portion of the first coupling mechanism 1186 can be inserted into an opening of the set of openings 1191 and engage a second coupling mechanism of the set of second coupling mechanisms 1184 adjacent the opening such that the second coupling mechanism is retained by the hook portion. The first coupling mechanism 1186 can be engaged with any of the second coupling mechanisms 1184 and transitioned among various second coupling mechanisms 1184 depending on a desired overall length of the support strap 1180.

In some embodiments, the first coupling mechanism 1186 can be disposed on a length of the support strap 1180 that can be separated from a remainder of the support strap 1180 via, for example, bar tack 1188B. The first coupling mechanism 1186 can be attached to the length of the support strap 1180 via stitching (e.g., bar tack 1188A). Such a length can be, for example, reinforced and/or non-elastic. In some embodiments, the length can have a length L5 of, for example, about 6.5 inches. In some embodiments, the length can have a length L5 of, for example, between about 6 inches and about 7 inches. In some embodiments, the length can have a length L5 of, for example, between about 5 inches and about 8 inches.

Figure 31:
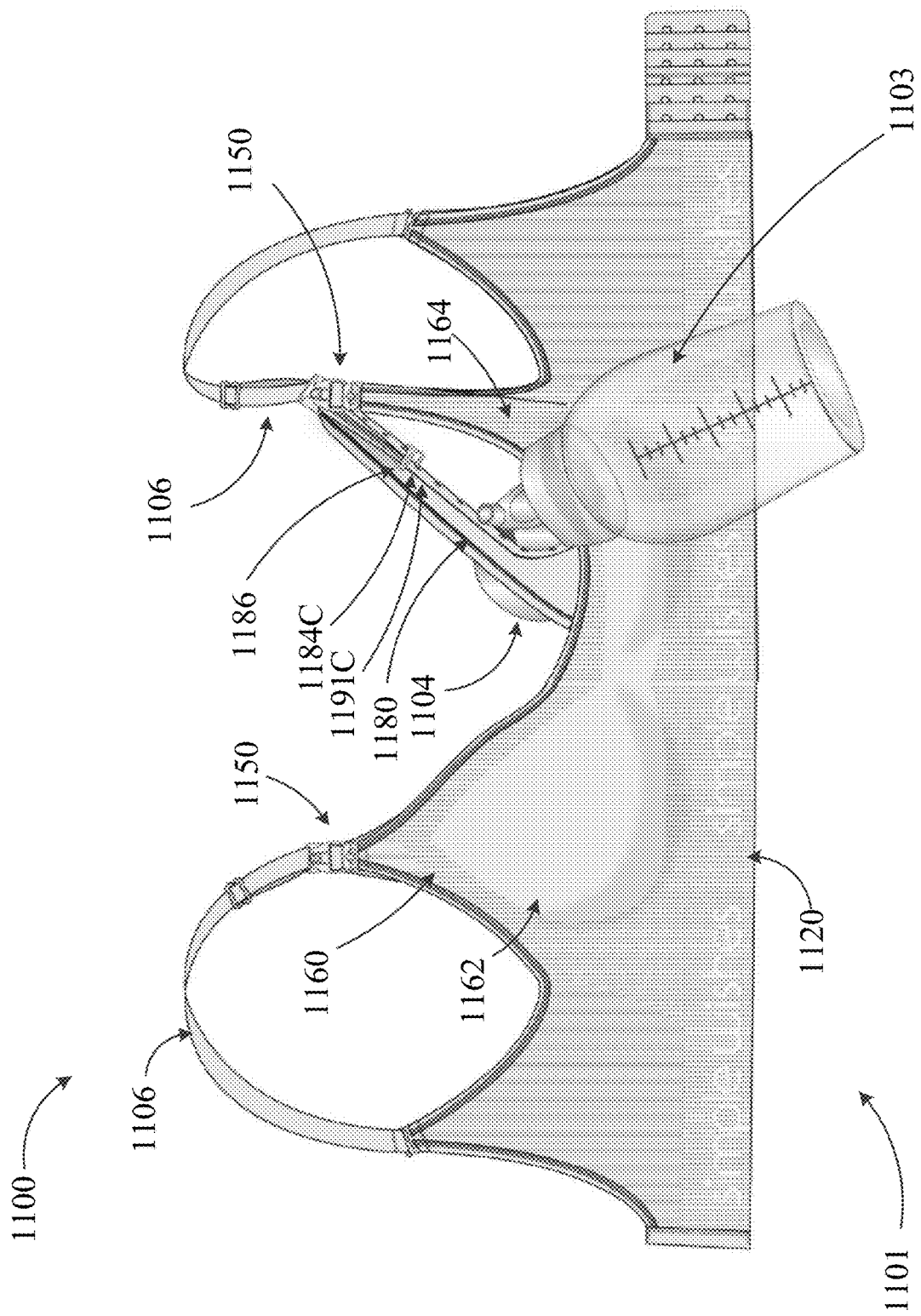
FIG. 31 is a front view of a garment including the support strap of FIG. 29 in a configuration in which the garment is supporting a breast pump, according to an embodiment.
Figure 32:
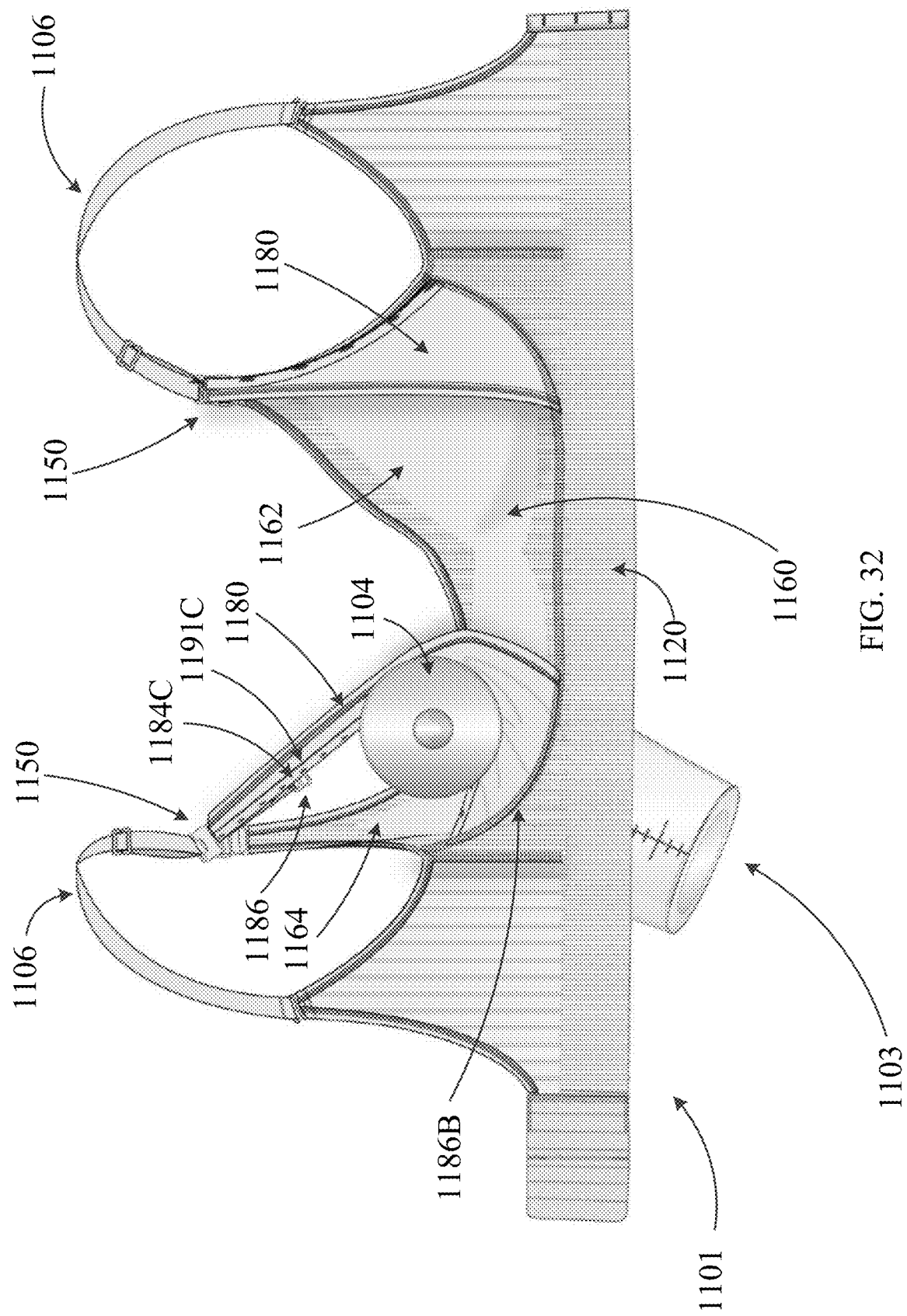
FIG. 32 is a back view of the garment of FIG. 31 the configuration in which the garment is supporting the breast pump.

FIGS. 31 and 32 are a front view and a back view, respectively, of a garment 1100 including two of the support straps 1180 and shown in a configuration in which the garment 1100 is supporting a breast pump 1103. The garment 1100 can be the same or similar in structure and/or function to any of the garments described herein. For example, the garment 1100 includes abase subassembly 1101 including aback panel 1120, an outer panel 1160, two shoulder straps 1106, and two support straps 1180. The outer panel 1160 can have a first portion 1162 and a second portion 1164. The garment 1100 also includes engagement mechanisms 1150 that can be the same or similar in structure and/or function to any of the engagement mechanisms described herein (e.g., the engagement mechanism 450 or the engagement mechanism 750). As shown in FIG. 32, the support strap 1180 can be arranged in a configuration in which the support strap 1180 has a first end 1186B coupled to the back panel 1120, an adjustable portion 1182 coupled to the engagement mechanism 1150, and is disposed around a portion 1104 (e.g., flange and stem) of a breast pump 1103 that is coupled to a wearer's breast to support the breast pump 1103 against the wearer's breast for a pumping operation (e.g., a hands free pumping operation). The outer panel 1160 can also support the breast pump 1103 against the wearer's breast in combination with the support strap 1180. For example, the second portion 1164 can be coupled to the engagement mechanism 1150 and disposed around the portion 1104 (e.g., a different portion of the flange and stem) to support the breast pump 1103 against the wearer's breast for a pumping operation (e.g., a hands free pumping operation). Thus, the breast pump 1103 (e.g., the stem of a breast shield of the breast pump 1103) can be disposed between the support strap 1180 and the portion 1164 of the outer panel 1160 (e.g., in an opening defined between the support strap 1180 and the portion 1164 of the outer panel 1160) during the pumping operation.

As shown in FIGS. 31 and 32, the adjustable portion 1182 can be configured such that the second end 1186A of the support strap 1182 can be looped through a first opening in a first portion of the engagement portion 1150 and the first coupling mechanism 1186 can be inserted through an opening of the set of openings 1191 (e.g., the opening 1191C) and engaged with any of the coupling mechanisms of the set of second coupling mechanisms 1184 (e.g., the coupling mechanism 1184C) to receive the material of the second coupling mechanism within the hook portion of the first coupling mechanism 1186. Thus, the wearer can adjust the overall length of the support strap 1180 between the engagement portion 1150 and the first end 1186B based on which of the openings 1191 and associated coupling mechanisms 1184 the first coupling mechanism 1186 is inserted through and engaged with, respectively. For example, the first coupling mechanism 1186 can be engaged with the coupling mechanism 1184A (e.g., closest to the first end 1186B or closer to the first end 1186B than a coupling mechanism 1184 selected for the second configuration) in a first configuration in which the support strap 1180 is not being used to support a portion of a breast pump against a breast. When the support strap 1180 is being used to support the portion 1104 of the breast pump 1103 (e.g., a flange of a shield of a breast pump) against the breast (e.g., by being wrapped fully or partially around a flange and/or a stem of a shield of the breast pump and then being attached to the first portion of the engagement mechanism 1150), the support strap 1180 can be transitioned to a second configuration in which the first coupling mechanism 1186 can be inserted through the opening 1191B or the opening 1191C and attached to one of the coupling mechanism 1184B or the coupling mechanism 1184C, respectively, such that the length of the support strap 1180 between the first portion of the engagement mechanism 1150 and the first end 186B is longer than in the first configuration and can comfortably maintain the flange of the breast pump against the breast.

In some embodiments, rather than including a first layer 1194 and a second layer 1196, the support strap 1180 can include only a single layer. In some embodiments, rather than including the elongated portion 1179, the first layer 1194 or the second layer 1196 can define the set of openings for receiving the hook portion of the first engagement portion 1186. In some embodiments, any suitable number of openings can be defined and any suitable associated number of second coupling mechanisms can be included in the elongated portion 1179 (e.g., two, three, four, five, six, seven, eight, nine, ten). In some embodiments, rather than the elongated portion 1179 being disposed along an edge of the support strap 1180, the elongated portion 1179 can be disposed in a location on the first layer 1194 or the second layer 1196 that is spaced from an edge of the support strap 1180 (e.g., alone a centerline of the support strap 1180). In some embodiments, rather than the elongated portion 1179 being disposed along the first edge 1178A (e.g., the edge closest to a user's armpit when the user is wearing the garment 1100), the elongated portion 1179 can be disposed along the second edge 1178B (e.g., the edge disposed farther from the user's armpit when the user is wearing the garment 1100). In some embodiments, the elongated portion 1179 can be a first elongated portion, and a second elongated portion can be disposed along the second edge 1178B such that one or more openings can be defined and one or more associated second coupling mechanisms can be included along each of the first edge 1178A and the second edge 1178B.

Although not shown, in some embodiments, the garment 1100 can optionally include an inner panel that can be the same or similar in structure and/or function to any of the inner panels described herein. For example, the outer panel 1160 and/or the support straps 1180 can include coupling members that are the same or similar to any of the coupling members described herein such that the inner panel can be removably attached to the garment 1100 similarly to any of the garments described herein.

In some embodiments, the first coupling mechanism of a support strap can include a hook and the set of second coupling mechanisms of the support strap can include tabs or loops shaped and sized to receive and retain the hook. For example FIGS. 33 and 34 are a front view and a back view, respectively, of a support strap 1280. The support strap 1280 can be the same or similar in structure and/or function to any of the support straps described herein. For example, the support strap 1280 includes an adjustable portion 1282. Additionally, the support strap 1280 can include a first layer 1294 and a second layer 1296 (e.g., the support strap 1280 can be two-ply). The adjustable portion 1282 can include a first coupling mechanism 1286 disposed proximate a second end 1286A of the support strap 1280. The second end 1286A can be an end of the support strap 1280 opposite a first end 1286B. The first end 1286B can be fixedly coupled to a back panel of a garment that includes the support strap 1280 (e.g., via sewing/stitching). The support strap 1280 can include a first edge 1278A and a second edge 1278B opposite the first edge 1278A. The first edge 1278A and the second edge 1278B can each extend from the first end 1286B to or toward the second end 1286A (e.g., along the entire length of the support strap 1280 or to a location proximate bar tack 1288B). The second edge 1278B can have a clean finish (e.g., the first layer 1294 and the second layer 1296 can be sewn or attached along the second edge 1278B using adhesive, or the first layer 1294 and the second layer 1296 can be formed of a continuous material folded along the second edge 1278B).

The first coupling mechanism 1286 can include a hook portion. For example, the first coupling mechanism 1286 can include a swan hook. The adjustable portion 1282 can also include an elongated portion 1279 (also referred to as an elongated strip). The elongated portion 1279 can be disposed along the first edge 1278A (e.g., attached via adhesive or sewing). For example, as shown in FIG. 33, the elongated portion 1279 can be coupled to the first edge 1278A via stitching 1293. The elongated portion 1279 can include, for example, one or more laser cut pieces of material (e.g., fabric). The elongated portion 1279 can include a set of second coupling mechanisms 1284. The set of second coupling mechanisms 1284 are disposed along the adjustable portion 1282 closer to the first end 1286B than the first coupling mechanism 1286. The set of second coupling mechanisms 1284 can include sub-portions of the elongated portion 1279. Each of the second coupling mechanisms 1284 of the set of second coupling mechanisms 1284 can include a loop or tab shaped and sized to receive and retain the hook portion of the first coupling mechanism 1286. As an example, the set of second coupling mechanisms 1284 can include a coupling mechanism 1284A, a coupling mechanism 1284B, and a coupling mechanism 1284C. The hook portion of the first coupling mechanism 1286 can be inserted into an opening defined at least in part by a second coupling mechanism 1284 and engage the second coupling mechanism such that the second coupling mechanism is retained by the hook portion. The first coupling mechanism 1286 can be engaged with any of the second coupling mechanisms 1284 and transitioned among various second coupling mechanisms 1284 depending on a desired overall length of the support strap 1280.

In some embodiments, the elongated portion 1279 can include a first layer 1292A and a second layer 1292B. The first layer 1292A and the second layer 1292B can be coupled to each other at various locations along the length of each layer to define the second coupling mechanisms 1284 (e.g., the loops or tabs). For example, the first layer 1292A and the second layer 1292B can be coupled together using bar tack (e.g., see bar tack 1288C). Each of the second coupling mechanisms 1284 can be defined between a first bar tack and a second bar tack such that each second coupling 1284 mechanism defines an opening therethrough configured to receive the hook portion of the first coupling mechanism 1286. In some embodiments, the first layer 1292A of the elongated portion 1279 (shown in FIG. 33) can be coupled (e.g., sewn via stitching 1293 or otherwise attached) to the first layer 1294 and/or the second layer 1296, and a portion of the second layer 1292B of the elongated portion 1279 that forms the second coupling mechanisms 1284 (shown in FIG. 34) can be attached to the first layer 1292A via segments of the bar tack 1288C. Thus, the portions of the first layer 1292A and the second layer 1292B between each adjacent pair of bar tack 1288C define the openings through which each of the second coupling mechanisms 1284 can be accessible via the back side of the support strap 1280 such that the hook portion of the first coupling mechanism 1286 can be inserted through a first side of a second coupling mechanism and a portion of the hook portion can exit the second side opposite the first side and engage with a portion of the second coupling mechanism.

Although not shown, in some embodiments, rather than the openings through each of the second coupling mechanisms 1284 being accessible on the back side of the support strap 1280 as shown in FIG. 34 such that the first coupling mechanism 1286 can be coupled to the back side of the support strap 1280, the openings through each of the second coupling mechanisms 1284 can be accessible on the front side of the support strap 1280 such that the first coupling mechanism 1286 can be coupled to the front side of the support strap 1280. For example, rather than the first layer 1292A being coupled to the first edge 1278A via the stitching 1293, the second layer 1292B can be coupled to the first edge 1278A via the stitching 1293. Thus, each of the second coupling mechanisms 1286 can define an opening from a first end through a second end through which a portion of the first engagement mechanism 1286 can pass on the front side of the support strap 1280.

In some embodiments, the first coupling mechanism 1286 can be disposed on a length of the support strap 1280 that can be separated from a remainder of the support strap 1280 via, for example, bar tack 1288B. The first coupling mechanism 1286 can be attached to the length of the support strap 1280 via stitching (e.g., bar tack 1288A). Such a length can be, for example, reinforced and/or non-elastic. In some embodiments, the length can have a length L6 of, for example, about 6.5 inches. In some embodiments, the length can have a length L6 of, for example, between about 6 inches and about 7 inches. In some embodiments, the length can have a length L6 of, for example, between about 5 inches and about 8 inches.

Figure 35:
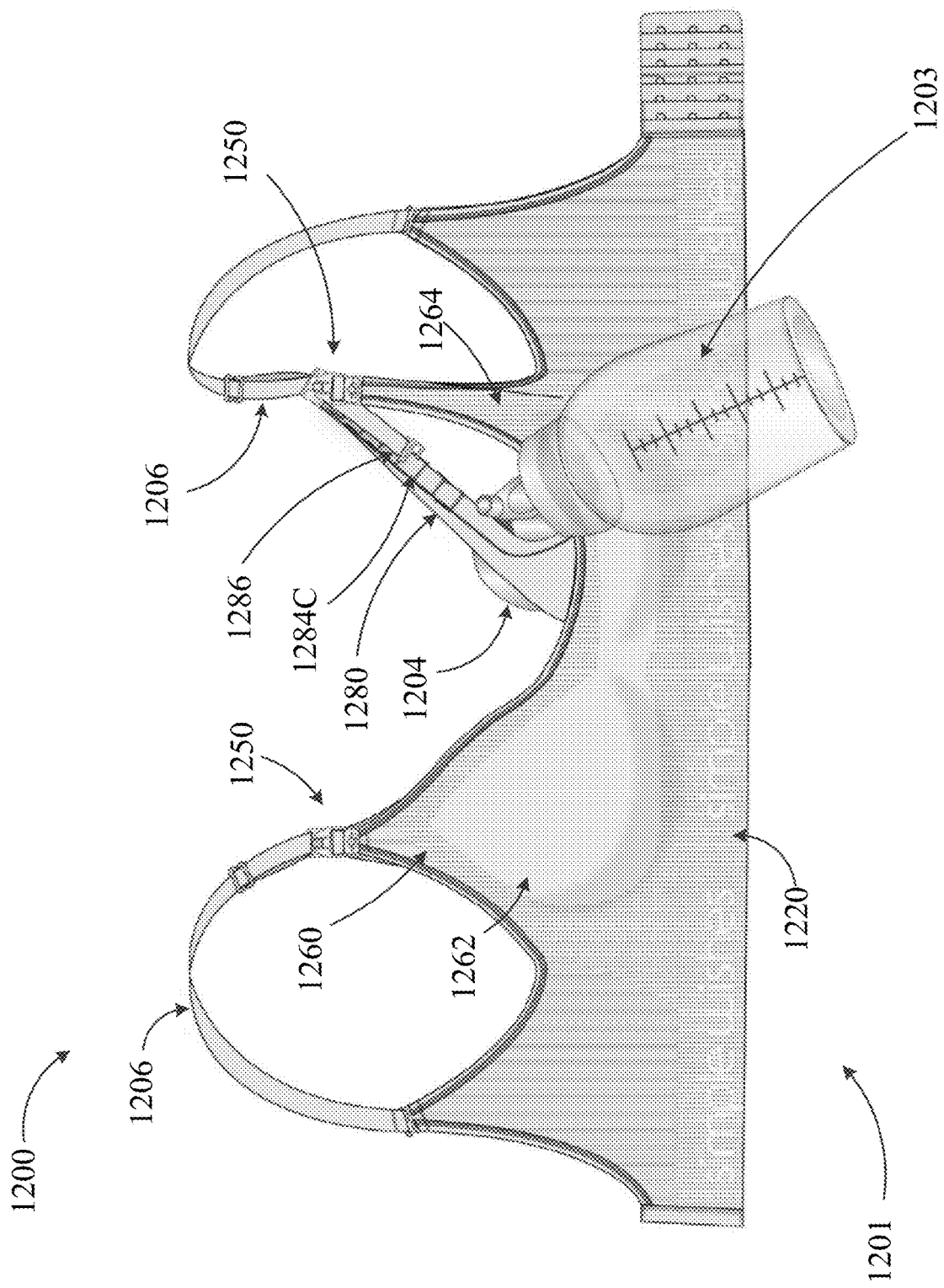
FIG. 35 is a front view of a garment including the support strap of FIG. 33 in a configuration in which the garment is supporting a breast pump, according to an embodiment.
Figure 36:
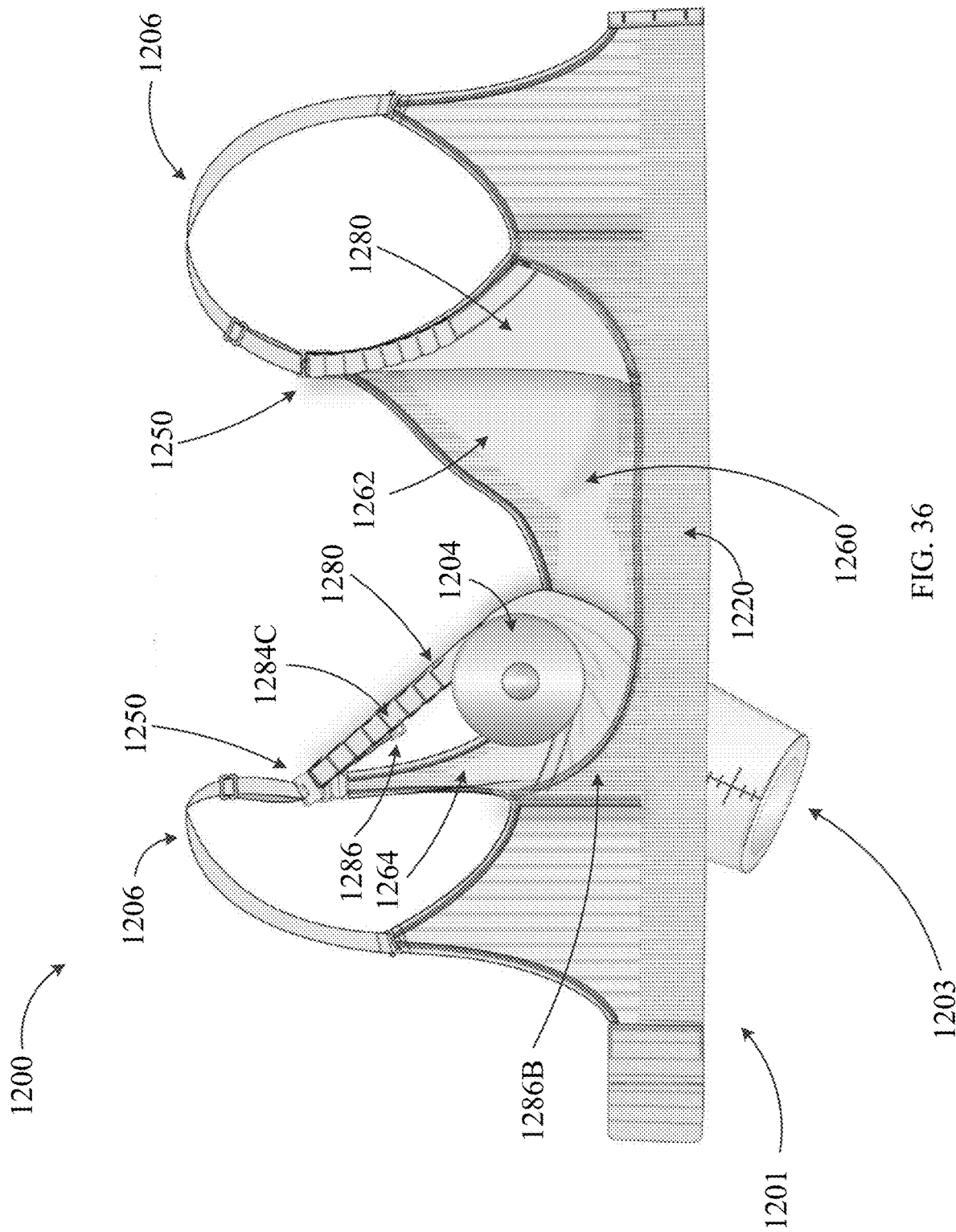
FIG. 36 is a back view of the garment of FIG. 35 in the configuration in which the garment is supporting the breast pump.

FIGS. 35 and 36 are a front view and a back view, respectively, of a garment 1200 include two of the support straps 1280 and shown in a configuration in which the garment 1200 is supporting a breast pump 1203. The garment 1200 can be the same or similar in structure and/or function to any of the garments described herein. For example, the garment 1200 includes a base subassembly 1201 including a back panel 1220, an outer panel 1260, two shoulder straps 1206, and two support straps 1280. The outer panel 1260 can have a first portion 1262 and a second portion 1264. The garment 1200 also includes engagement mechanisms 1250 that can be the same or similar in structure and/or function to any of the engagement mechanisms described herein (e.g., the engagement mechanism 450 or the engagement mechanism 750). As shown in FIG. 36, the support strap 1280 can be arranged in a configuration in which the support strap 1280 has a first end 1286B coupled to the back panel 1220, an adjustable portion 1282 coupled to the engagement mechanism 1250, and is disposed around a portion 1204 (e.g., flange and stem) of a breast pump 1203 that is coupled to a wearer's breast to support the breast pump 1203 against the wearer's breast for a pumping operation (e.g., a hands free pumping operation). The outer panel 1260 can also support the breast pump 1203 against the wearer's breast in combination with the support strap 1280. For example, the second portion 1264 can be coupled to the engagement mechanism 1250 and disposed around the portion 1204 (e.g., a different portion of the flange and stem) to support the breast pump 1203 against the wearer's breast for a pumping operation (e.g., a hands free pumping operation). Thus, the breast pump 1203 (e.g., the stem of a breast shield of the breast pump 1203) can be disposed between the support strap 1280 and the portion 1264 of the outer panel 1260 (e.g., in an opening defined between the support strap 1280 and the portion 1264 of the outer panel 1260) during the pumping operation.

As shown in FIGS. 35 and 36, the adjustable portion 1282 can be configured such that the second end 1286A of the support strap 1282 can be looped through a first opening in a first portion of the engagement portion 1250 and the first coupling mechanism 1286 can be inserted through an opening of any of the coupling mechanisms of the set of second coupling mechanisms 1284 (e.g., the coupling mechanism 1284C) to receive a portion of a loop of the second coupling mechanism within the hook portion of the first coupling mechanism 1286. Thus, the wearer can adjust the overall length of the support strap 1280 between the engagement portion 1250 and the first end 1286B based on which of the second coupling mechanisms 1286 the first coupling mechanism 1286 is inserted through and engaged with. For example, the first coupling mechanism 1286 can be engaged with the coupling mechanism 1284A (e.g., closest to the first end 1286B or closer to the first end 1286B than a coupling mechanism 1284 selected for the second configuration) in a first configuration in which the support strap 1280 is not being used to support a portion of a breast pump against a breast. When the support strap 1280 is being used to support the portion 1204 of the breast pump 1203 (e.g., a flange of a shield of a breast pump) against the breast (e.g., by being wrapped fully or partially around a flange and/or a stem of a shield of the breast pump and then being attached to the first portion of the engagement mechanism 1250), the support strap 1280 can be transitioned to a second configuration in which the first coupling mechanism 1286 can be inserted through the opening of one of the coupling mechanism 1284B or the coupling mechanism 1284C, respectively, such that the length of the support strap 1280 between the first portion of the engagement mechanism 1250 and the first end 1286B is longer than in the first configuration and can comfortably maintain the flange of the breast pump against the breast.

In some embodiments, rather than including a first layer 1294 and a second layer 1296, the support strap 1280 can include only a single layer. In some embodiments, the second coupling mechanisms 1284 can be disposed on both the front side and the back side of the support strap. In some embodiments, any suitable associated number of second coupling mechanisms 1284 can be included in the elongated portion 1279 (e.g., two, three, four, five, six, seven, eight, nine, ten). In some embodiments, rather than the second coupling mechanisms 1284 being disposed along an edge of the support strap 1280, the second coupling mechanisms 1284 can be disposed in a location on the first layer 1294 or the second layer 1296 that is spaced from an edge of the support strap 1280 (e.g., along a centerline of the support strap 1280). In some embodiments, rather than the second coupling mechanisms 1284 being disposed along the first edge 1278A (e.g., the edge closest to a user's armpit when the user is wearing the garment 1200), the second coupling mechanisms 1284 can be disposed alternatively or additionally along the second edge 1278B (e.g., the edge disposed farther from the user's armpit when the user is wearing the garment 1200).

Although not shown, in some embodiments, the garment 1200 can optionally include an inner panel that can be the same or similar in structure and/or function to any of the inner panels described herein. For example, the outer panel 1260 and/or the support straps 1280 can include coupling members (e.g., snap portions) that are the same or similar to any of the coupling members described herein such that the inner panel can be removably attached to the garment 1200 similarly to any of the garments described herein (e.g., via corresponding snap portions).

Figure 37:
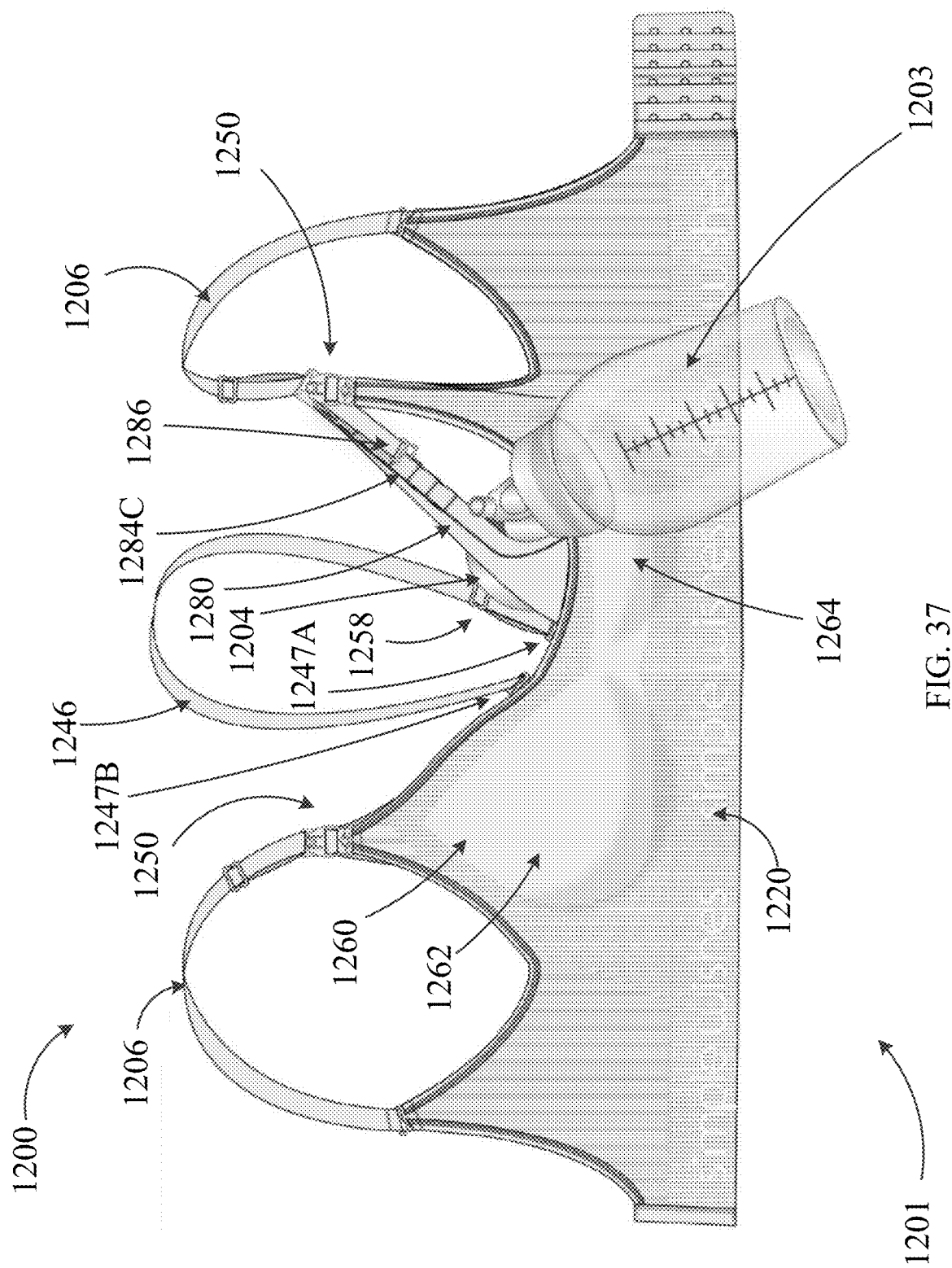
FIG. 37 is a front view of a garment in a configuration in which the garment is supporting a breast pump and a neck strap of the garment is coupled to an outer panel of the garment, according to an embodiment.
Figure 38A:
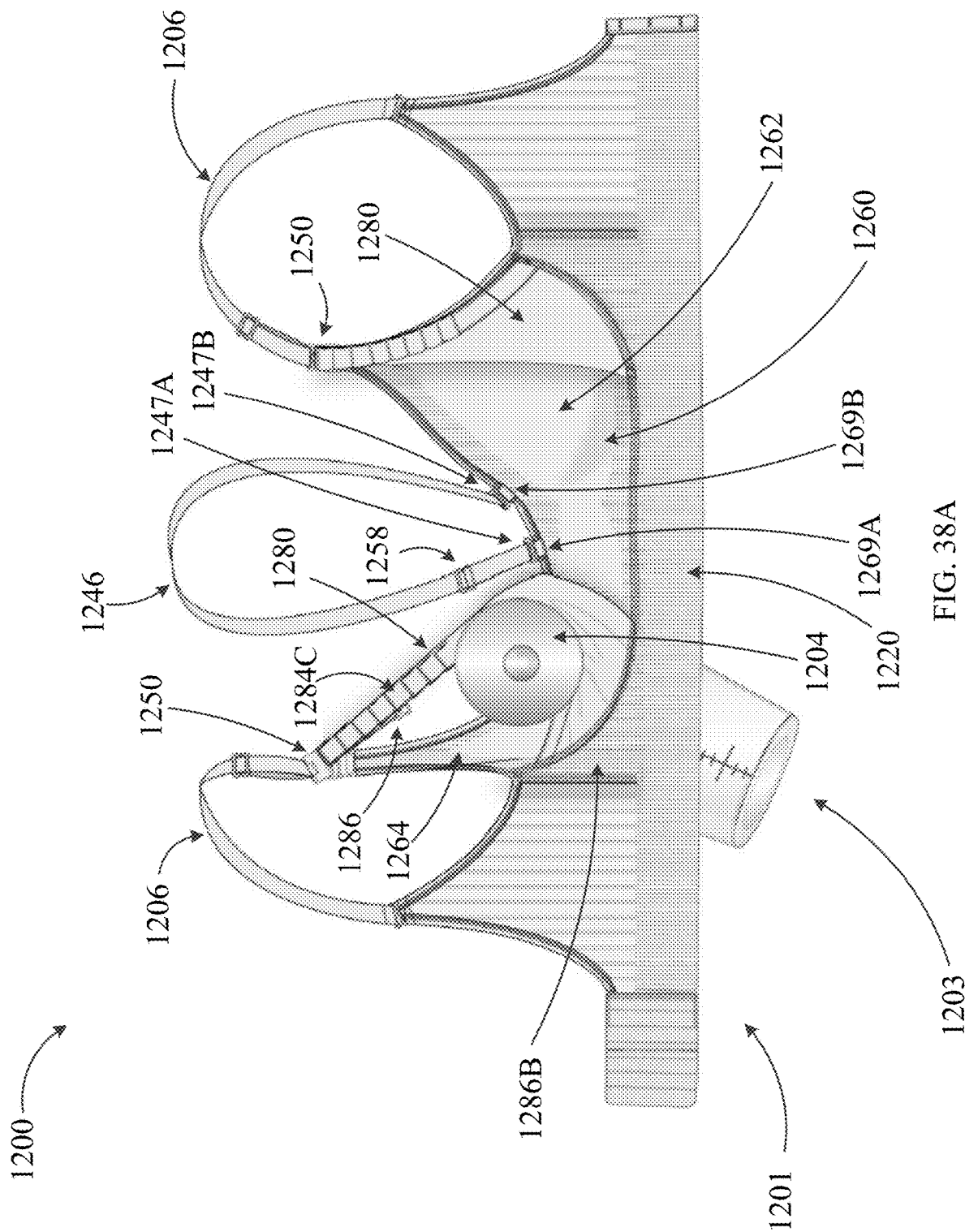
FIG. 38A is a back view of the garment of FIG. 37 in the configuration in which the garment is supporting the breast pump and the neck strap of the garment is coupled to the outer panel.

In some embodiments, any of the garments herein, such as the garment 1200, can include a removeable neck strap (also referred to as a center strap or a halter strap). For example, FIGS. 37 and 38A are a front view and a back view, respectively, of the garment 1200 shown in a configuration in which the garment 1200 is supporting the breast pump 1203 and a neck strap 1246 of the garment 1200 is coupled to the outer panel 1260. The neck strap 1246 can be attached to the outer panel 1260 before or after the breast pump 1203 has been disposed between the outer panel 1260 and the support strap 1280. The neck strap 1246 can support a center portion of the outer panel 1260 such that the outer panel 1260 supports the breast pump 1203 at a height that is properly aligned with the wearer's breast and such that a flange of the breast shield is properly sealed against the wearer's breast during a pumping operation. In embodiments in which an inner panel, such as any of the inner panels described herein, is optionally included in the garment for a pumping procedure, the neck strap 1246 can optionally be used to support the inner panel rather than the outer panel 1260.

The neck strap 1246 can include a first coupling member 1247A on a first end of the neck strap 1246 and a second coupling member 1247B on a second end of the neck strap 1246. The outer panel 1260 can include a first loop portion 1269A and a second loop portion 1269B. In some embodiments, the first loop portion 1269A and the second loop portion 1269B can be coupled to an upper edge of the first portion 1262 and the second portion 1264 of the outer panel 1260, respectively. In some embodiments, the first loop portion 1269A and the second loop portion 1269B can be disposed near a center of the top edge of the outer panel 1260. For example, the first loop portion 1269A can be disposed closer to a center of the outer panel 1260 than a portion of the outer panel 1260 and/or a portion of the support strap 1280 (e.g. the left support strap in FIG. 38A) contacting the portion 1204 of the breast pump 1203 when the garment 1200 is supporting the breast pump 1203 in contact with a left breast of a wearer. The second loop portion 1269B can be disposed closer to a center of the outer panel 1260 than a portion of the outer panel 1260 and/or a portion of the support strap 1280 (e.g. the right support strap in FIG. 38A) contacting the portion 1204 of the breast pump 1203 when the garment is supporting the breast pump 1203 in contact with a right breast of a wearer. In some embodiments, the first loop portion 1269A and the second loop portion 1269B can be disposed along the upper edge of the outer panel 1260, for example, less than 5 inches apart, less than 4 inches apart, less than 3 inches apart, less than 2 inches apart, or less than 1 inch apart.

The first loop portion 1269A and the second loop portion 1269B can each be configured to removably engage with at least one of the first coupling member 1247A and the second coupling member 1247B such that the neck strap 1246 is wrapped around the neck of the wearer of the garment 1200 and can support the outer panel 1260 during a pumping operation (e.g., a hands free pumping operation) in combination with one or both of the shoulder straps 1206. For example, as shown in FIG. 38A, the first coupling member 1247A can be releasably engaged with the first loop portion 1269A and the second coupling member 1247B can be releasably engaged with the second loop portion 1269B. The first coupling member 1247A and the second coupling member 1247B can each include or be formed as any suitable coupling mechanism. For example, in some embodiments, each of the first coupling member 1247A and the second coupling member 1247B can include a hook portion that can be partially pushed through and secured to the first loop portion 1269A or the second loop portion 1269B. For example, as shown in FIG. 38A, each of the first coupling member 1247A and the second coupling member 1247B can be formed as a swan hook.

The overall length of the neck strap 1246 can be adjustable. For example, a length of the neck strap 1246 between the first coupling member 1247A and the second coupling member 1247B can be adjusted. The neck strap 1246 can include a strap portion having a first end and a second end. The first end can be coupled to a slider component 1258 (also referred to as a "slider") and the second end can be coupled to the second coupling member 1247B. The strap portion can form a loop through the first coupling member 1247A and extend through a portion of the slider 1258 such that the slider can be translated along the strap portion to adjust the size of the loop extending through the first coupling member 1247A. As the size of the loop increases, the length of the neck strap 1246 between the first coupling member 1247A and the second coupling member 1247B decreases. As the size of the loop decreases, the length of the neck strap 1246 between the first coupling member 1247A and the second coupling member 1247B increases. In some embodiments, rather than the first end of the strap portion being coupled to the slider 1258 and the second end being coupled to the second coupling member 1247B, the second end of the strap portion can be coupled to the slider 1258 and the first end can be coupled to the first coupling member 1247A. In some embodiments, both of the first end and the second end of the strap portion can be coupled to sliders such that the strap portion can be looped through both the first coupling member 1247A and the second coupling member 1247B such that each end can be separately adjusted.

In some embodiments, rather than each of the first coupling member 1247A and the second coupling member 1247B including a hook portion and the outer panel 1260 including the first loop portion 1269A and the second loop portion 1269B, the first coupling member 1247A and the second coupling member 1247B can be formed in any shape configured to mate with a receiving shape of the outer panel 1260 such that the neck portion 1246 can support the outer panel 1260 (e.g., corresponding snap portions, corresponding hook and loop fastener portions, and/or corresponding loop and button portions).

In some embodiments, rather than including the first loop portion 1269A and the second loop portion 1269B, the garment 1200 can include only one loop portion that is configured to simultaneously engage with the first coupling member 1247A and the second coupling member 1247B (e.g., configured to simultaneously receive two hook portions of two swan hooks). The one loop portion can be disposed, for example, in a center portion of the outer panel 1260 near or adjacent to an upper edge of the outer panel 1260.

In some embodiments, rather than including a first loop portion or a second loop portion, the outer panel 1260 can include one or more holes defined in an upper edge of the outer panel 1260. For example, the outer panel 1260 can define the holes and/or the holes can be defined by a separate elongated component coupled to the outer panel 1260. At least some of the holes can be disposed in a center of the outer panel 1260 similarly as described above with respect to the first loop portion 1269A and/or the second loop portion 1269B. The neck strap 1246 can be attached to the outer panel 1260 via selective releasable engagement between the first coupling member 1247A and the second coupling member 1247B with one or more holes and one or more portions of material adjacent to the one or more holes.

In some embodiments, rather than disposing the support strap 1280 partially around the portion 1204 (e.g., a stem or neck of a shield) of the breast pump 1203 as shown in FIGS. 37 and 38A, the support strap 1280 can be wrapped fully around the flange and/or stem of the shield of the breast pump. For example, FIG. 38B shows a back view of the garment 1200 shown in a configuration in which the garment 1200 is supporting the breast pump 1203. The flange of the breast shield of the breast pump 1203 is not shown for visibility of the support strap 1280 surrounding the stem portion 1204 of the breast shield of the breast pump 1203. As shown, the support strap 1280 is arranged to surround the stem portion 1204 with a complete turn of the support strap 1280.

Figure 39:
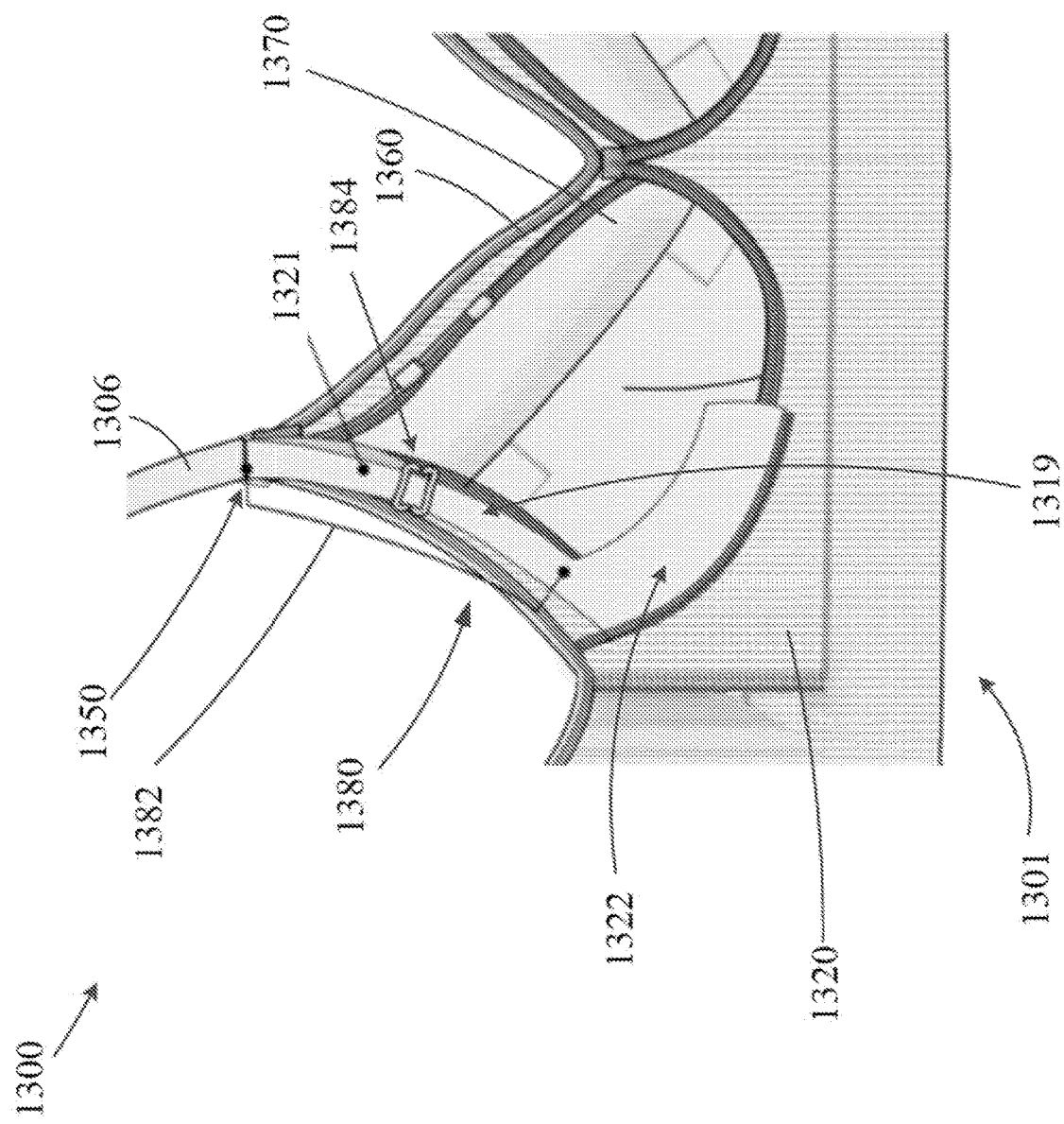
FIG. 39 is a back view of a portion of a garment, according to an embodiment.

In some embodiments, a support strap can include a slider component that is configured to be translated along a strap portion of the support strap to adjust the overall length of the support strap. For example, FIG. 39 is a back view of a portion of a garment 1300. The garment 1300 can be the same or similar in structure and/or function to any of the garments described herein. For example, the garment 1300 includes a base subassembly 1301 that can be the same or similar in structure and/or function to any of the base subassemblies described herein. For example, the base subassembly 1301 can include a back panel 1320, an outer panel 1360, a shoulder strap 1306, and a support strap 1380. The garment 1300 also includes an optional removeable inner panel 1370 that can be the same or similar in structure and/or function to any of the inner panels described herein. Additionally, the garment 1300 includes an engagement mechanism 1350 that can be the same or similar in structure and/or function to any of the engagement mechanisms described herein (e.g., the engagement mechanism 450 or the engagement mechanism 750).

The support strap 1380 can include an adjustable portion 1382 and a base portion 1322. The adjustable portion 1382 includes a coupling mechanism 1384 and a strap portion 1319. The strap portion 1319 includes at least a portion having a constant width along which the coupling mechanism 1384 can be slid. For example, as shown in FIG. 39, the strap portion 1219 can have a constant width from the first end to the second end of the strap portion 1319. The coupling mechanism 1384 can include, for example, a slider component or buckle. A first end of the strap portion 1319 can be coupled to the base portion 1322 and a second end of the strap portion 1319 can be coupled to the coupling mechanism 1384. The strap portion 1319 includes a loop portion 1321 that extends between a portion of the strap portion 1319 that is threaded through the coupling mechanism 1384 and the second end of the strap portion 1319 that is securely coupled to the coupling mechanism 1384. The coupling mechanism 1384 can secure (e.g., via friction) the portion of the strap portion 1319 that is threaded through the coupling mechanism 1384 such that the size of the loop portion 1321 is maintained by the coupling mechanism 1384 unless a wearer translates the coupling mechanism 1384 along the strap portion 1319 (e.g., by pulling or pushing the coupling mechanism 1384 relative to the strap portion 1319).

The loop portion 1321 is threaded through an opening of the engagement mechanism 1350. For example, the loop portion 1321 can be looped through an opening of a first portion of an engagement mechanism that is the same as or similar in structure and/or function to the first portion 452 of the engagement mechanism 450 described above with reference to FIGS. 7-10 and/or the first portion 752 of the engagement mechanism 750 described above with reference to FIGS. 15-17 (e.g., opening 783 and/or opening 483). The coupling mechanism 1384 can be translated along the strap portion 1319 to adjust the size of the loop portion 1321 and the overall length of the strap portion 1319 between the base portion 1322 and the engagement mechanism 1350 (and between the portion of the back panel 1320 to which the support strap 1380 is attached and the engagement mechanism 1350). For example, the coupling mechanism 1384 can be moved away from the engagement mechanism 1350 (or the portion of the engagement mechanism 1350 through which the loop portion 1321 is secured) such that the size of the loop portion 1321 increases. As the size of the loop portion 1321 increases, the length of the portion of the strap portion 1319 between the coupling member 1384 and the engagement mechanism 1350 decreases such that the overall length of the support strap 1380 decreases. The coupling mechanism 1384 can be moved toward the engagement mechanism 1350 (or the portion of the engagement mechanism 1350 through which the loop portion 1321 is secured) such that the size of the loop portion 1321 decreases. As the size of the loop portion 1321 decreases, the length of the portion of the strap portion 1319 between the coupling member 1384 and the engagement mechanism 1350 increases such that the overall length of the support strap 1380 increases.

Thus, the wearer can adjust the overall length of the support strap 1380 between the engagement portion 1350 and the portion of the base panel 1320 to which the support strap 1380 (e.g., the base portion 1322) is attached by sliding the coupling mechanism 1384 along the strap portion 1319. For example, the coupling mechanism 1384 can be engaged with the support strap 1380 in a first location in a first configuration in which the support strap 1380 is not being used to support a portion of a breast pump against a breast. When the support strap 1380 is being used to support a portion of the breast pump (e.g., a flange of a shield of a breast pump) against the breast (e.g., by pulling the support strap 1380 toward a center of the garment, pressing the flange of the shield against the user's breast, and wrapping the support strap 1380 partially or fully around a flange and/or a stem of a shield of the breast pump), the support strap 1380 can be transitioned to a second configuration in which the coupling mechanism 1384 is engaged with the support strap 1380 in a second location farther from the base portion 1322 than the first location of the first configuration. The support strap 1384 has a longer overall length in the second configuration than in the first configuration and can wrap around the flange and/or stem of a shield of the breast pump to comfortably maintain the flange of the breast pump against the breast.

As shown in FIG. 39, in some embodiments, the base portion 1322 can be arched and can have at least a portion having a constant width. The strap portion 1319 of the adjustable portion 1382 can be coupled to the base portion 1322 at a first end of the base portion 1322, and the base portion 1322 can be attached (e.g., via sewing and/or adhesive) to the base panel 1320 along a bottom edge of the base portion 1322 from the first end to a second end of the base portion 1322. In some embodiments, the base portion 1322 can have any suitable shape. For example, in some embodiments, the base portion 1322 can be crescent shaped. In some embodiments, the base portion 1322 can have a shape that tapers from the first end to the second end such that the width of the base portion 1322 near the next end is smaller than the width of the base portion 1322 at the first end to which the strap portion 1319 is coupled. In some embodiments, the base portion 1322 has a substantially triangular shape. In some embodiments, the base portion 1322 and the strap portion 1319 are unitary or monolithically formed. In some embodiments, the base portion 1322 and the strap portion 1319 are coupled to one another via, for example, stitching or adhesive. In some embodiments, the strap portion 1319 can be coupled to the base portion 1322 at a location between the first end and the second end of the base portion 1322. In some embodiments, the support strap 1380 does not include a base portion 1322, and the strap portion 1319 can be coupled directly to the base panel 1320 (e.g., via stitching and/or adhesive).

Figure 40:
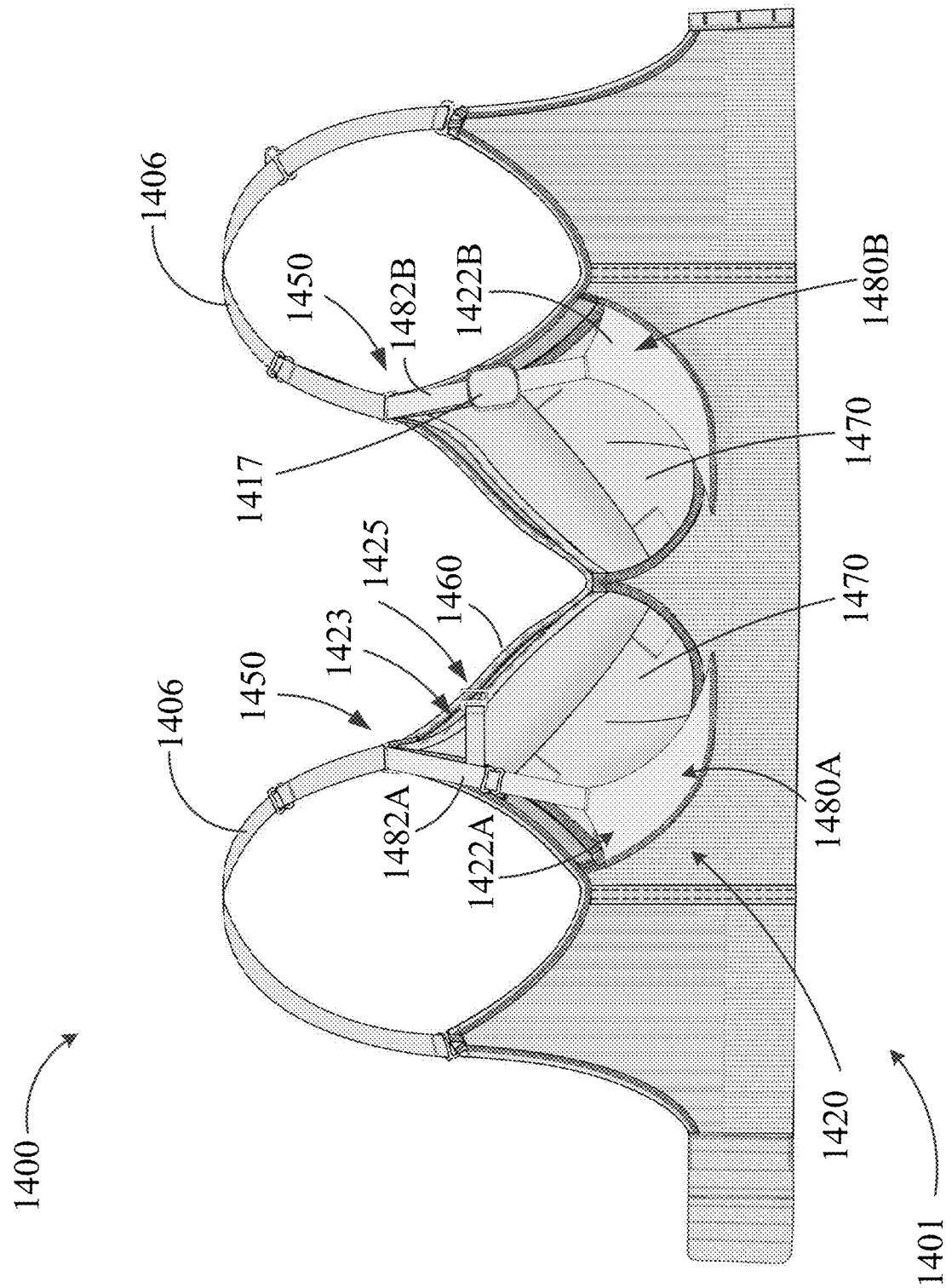
FIG. 40 is a back view of a garment, according to an embodiment.

In some embodiments, a garment, such as any of the garments described herein, can include a snare component coupled to a first support strap that is configured to maintain the first support strap and/or a second support strap in a pump-supporting configuration. For example, FIG. 40 is a back view of a garment 1400. The garment 1400 can be the same or similar in structure and/or function to any of the garments described herein. For example, the garment 1400 includes a base subassembly 1401 including a back panel 1420, an outer panel 1460, two shoulder straps 1406, a first support strap 1480A, and a second support strap 1480B. The garment 1400 also includes an optional removeable inner panel 1470 that can be the same or similar in structure and/or function to any of the inner panels described herein. The garment 1400 also includes a pair of engagement mechanisms 1450 that can be the same or similar in structure and/or function to any of the engagement mechanisms described herein (e.g., the engagement mechanism 450 or the engagement mechanism 750).

The first support strap 1480A and the second support strap 1480B can be the same or similar in structure and/or function to the support strap 1380 described above with respect to FIG. 39. For example, the first support strap 1480A includes an adjustable portion 1482A and a base portion 1422A and the second support strap 1480B includes an adjustable portion 1482B and a base portion 1422B. The adjustable portion 1482A can include a coupling mechanism 1484A and a strap portion 1419A that are the same or similar in structure and/or function to the coupling mechanism 1384 and strap portion 1319 described above with respect to the garment 1300.

Figure 41:
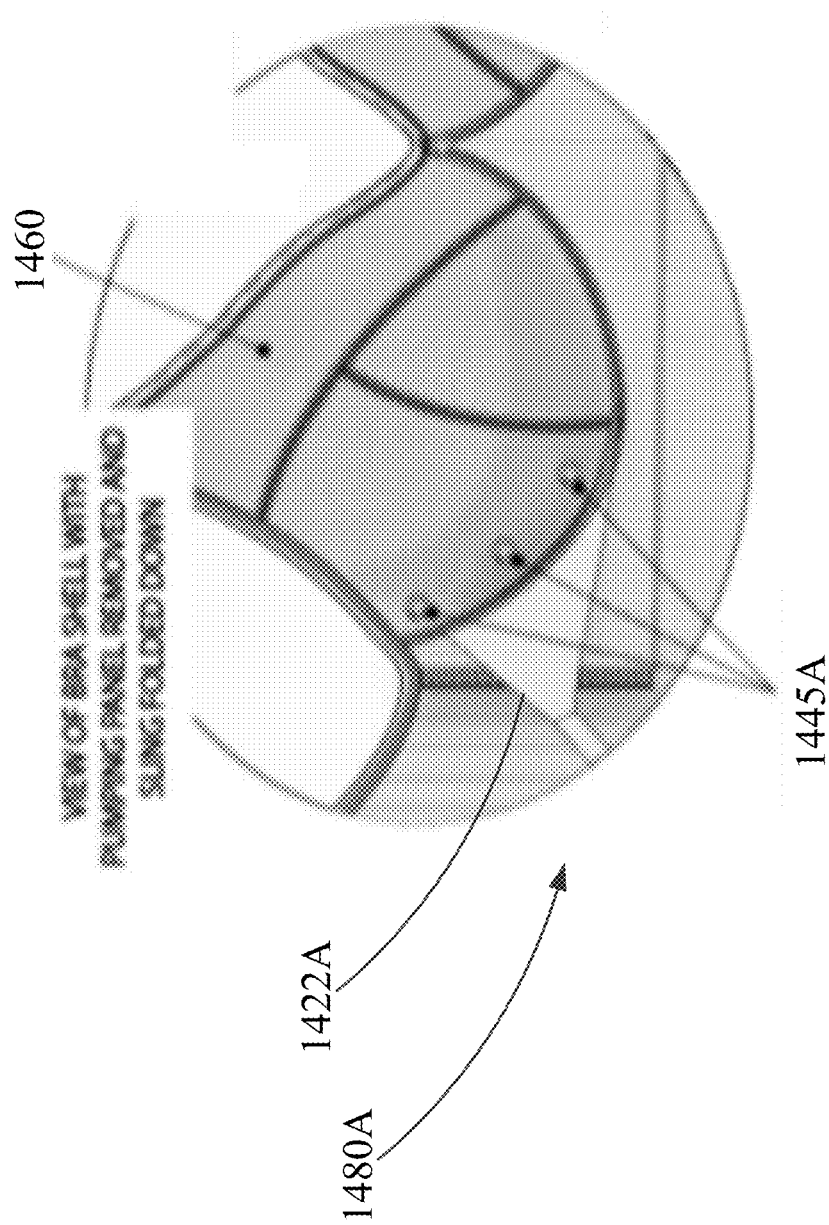
FIG. 41 is a back view of a portion of the garment of FIG. 40.

The inner panel 1470 can be removed from the base subassembly 1401. For example, as shown in FIG. 41, which shows a portion of the garment 1400 with the inner panel 1470 removed and the support strap 1480 folded down, the outer panel 1460 can include a number of coupling members (e.g., coupling members 1445A) configured to be coupled to complementary coupling members on the inner panel 1470. The coupling members 1445A can be disposed on a portion of the outer panel 1460 that is covered by the base portion 1422A of the support strap 1480A when the garment 1400 is in a first configuration in which the support strap 1480A is not being used to support a portion of a breast pump against a breast and the outer panel 1460 is in a configuration covering the breast.

Figure 42:
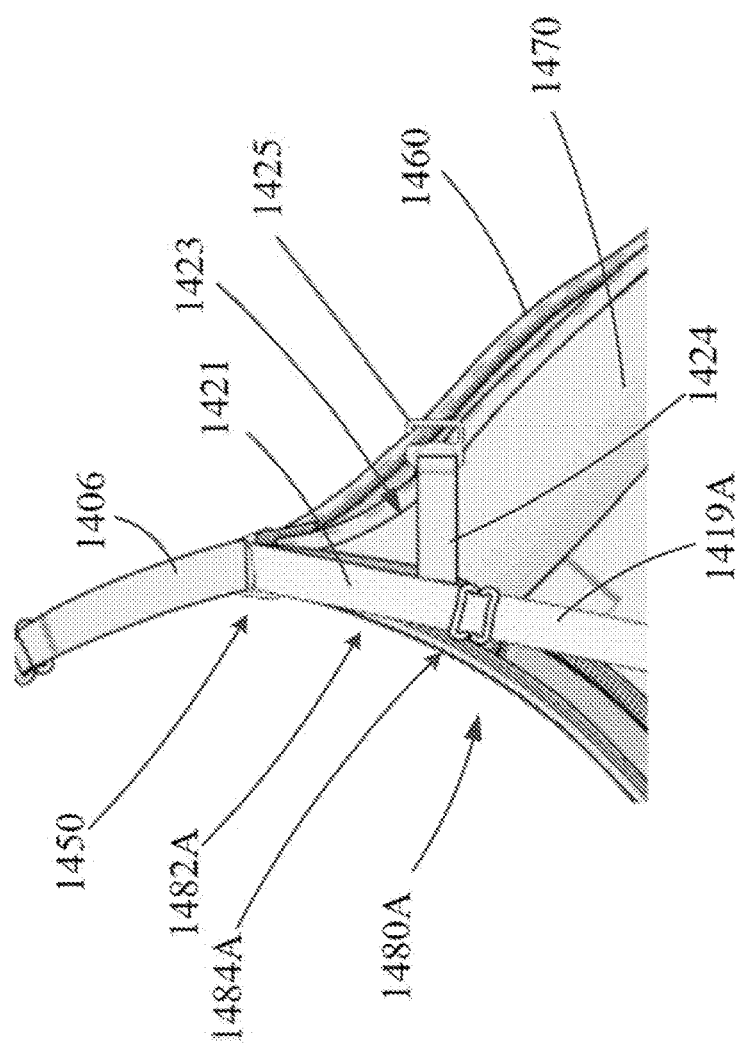
FIG. 42 is a back view of a portion of the garment of FIG. 40 including a snare component, according to an embodiment.

As shown in FIG. 42, which shows a portion of a back view of the garment 1400, the garment 1400 can include a snare component 1423. The snare component 1423 can include a coupling mechanism 1425 and a strap portion 1424. The strap portion 1424 can include a first end coupled to the first support strap 1480A and a second end coupled to the coupling mechanism 1425. In some embodiments, the strap portion 1424 can be elastic. In some embodiments, the strap portion 1424 can be inelastic. The coupling mechanism 1425 can include a hook portion. For example, the coupling mechanism 1425 can include a swan hook. The strap portion 1424 of the snare component 1423 can be wrapped around the second support strap 1480B and the coupling mechanism 1425 of the snare component 1423 can be coupled to a portion of the strap portion 1424 such that the snare component 1423 forms a loop around the second support strap 1480B.

Figure 43:
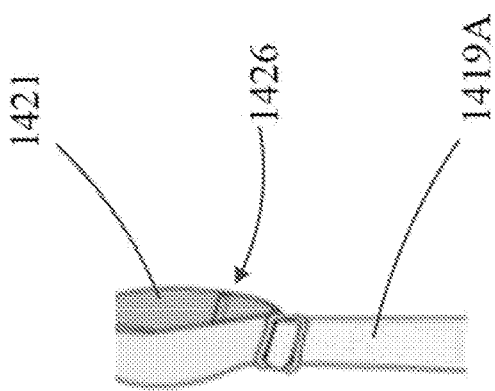
FIG. 43 is a perspective view of a portion of a support strap of the garment of FIG. 42.

As shown in FIG. 42, the snare component 1423 can be coupled to the first support strap 1480A. In some embodiments, the snare component 1423 can be coupled to a loop portion 1421 of the support strap 1480A. For example, the first end of the strap portion 1419A that is secured to the coupling mechanism 1484A can be secured to a securement bar of the coupling mechanism 1484A by looping the first end around the securement bar and securing the strap portion 1419A onto itself via a seam 1426 (e.g., using stitching and/or adhesive). The first end of the strap portion 1424 of the snare component 1423 can be sewn to the seam 1426. For example, the first end of the strap portion 1424 of the snare component 1423 can be sewn to an internal portion of the loop portion 1421 (shown, for example, in FIG. 43) using stitching disposed perpendicular to the seam 1426.

In some embodiments, rather than being coupled to the seam 1426 on an internal side of the loop portion 1421, the snare component 1423 can be coupled to any suitable portion of the first support strap 1480A. For example, in some embodiments, the first end of the strap portion 1424 of the snare component 1423 can be securely coupled to (e.g., via stitching) the non-loop portion of the adjustable portion 1482A (e.g., below the coupling mechanism 1484A). In some embodiments, the first end of the strap portion 1424 of the snare component 1423 can be securely coupled to (e.g., via stitching) an outer surface of the loop portion 1421 (e.g., near or adjacent to the coupling mechanism 1484A). In some embodiments, rather than the snare component 1423 being coupled to the first support strap 1480A which is shown as being on the left side of the garment 1400 in the back view, the snare component 1423 can be coupled to the second support strap 1480B and configured to wrap around the first support strap 1480A to form a loop capturing the first support strap 1480A. In some embodiments, alternatively or in addition to the snare component 1423 being configured to form a loop such that the coupling mechanism 1425 attaches to the strap portion 1424 of the snare component 1423, the coupling mechanism 1425 can be configured to be coupled directly to a strap portion of the adjustable portion 1482B of the second support strap 1482B to secure the first support strap 1480A to the second support strap 1480B.

Figure 44:
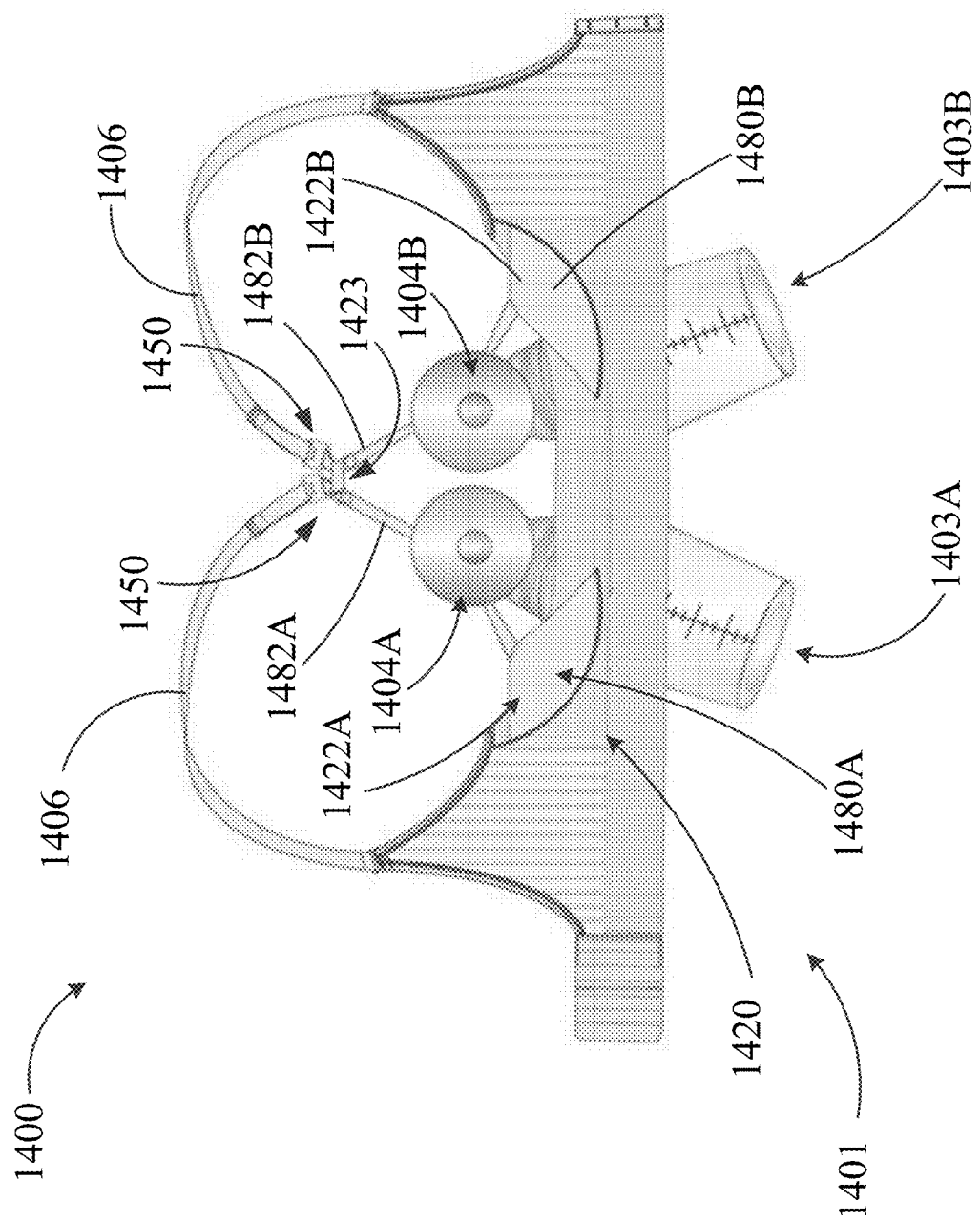
FIG. 44 is a back view of the garment of FIG. 42 shown in a configuration in which the garment is supporting a first breast pump and a second breast pump.

FIG. 44 is a back view of the garment 1400 shown in a configuration in which the garment 1400 is supporting a first breast pump 1403A and a second breast pump 1403B. As shown in FIG. 44, the first support strap 1480A can be arranged in a configuration in which the first support strap 1480A is disposed around a portion 1404A (e.g., flange and stem) of the first breast pump 1403A that is coupled to a wearer's left breast to support the breast pump 1403A against the wearer's left breast for a pumping operation (e.g., a hands free pumping operation). The first support strap 1480A can be partially wrapped around the portion 1404A or fully wrapped around the portion 1404A including any suitable number of turns (e.g., half a turn, 1 turn, 1.5 turns). The second support strap 1480B can be arranged in a configuration in which the second support strap 1480B is disposed around a portion 1404B (e.g., flange and stem) of the second breast pump 1403B that is coupled to a wearer's right breast to support the breast pump 1403A against the wearer's right breast for the pumping operation. The second support strap 1480B can be partially wrapped around the portion 1404B or fully wrapped around the portion 1404B including any suitable number of turns (e.g., half a turn, 1 turn, 1.5 turns). The strap portion 1424 of the snare component 1423 is wrapped around the second support strap 1480B and the coupling mechanism 1425 of the snare component 1423 is coupled to a portion of the strap portion 1424 such that the snare component 1423 forms a loop around the second support strap 1480B. Thus, as shown, the snare component 1423 pulls the first support strap 1480A and the second support strap 1480B towards each other (and the first and second shoulder straps 1406 towards each other) such that the snare component 1423 can be centered over a wearer's chest during the pumping operation. In some embodiments, such as an embodiment in which only one breast pump is being used for a pumping operation, the snare component 1423 can pull the first support strap 1480A and the second support strap 1480B toward each other and the snare component 1423 can be center, left of center, or right of center in such a configuration.

As shown in FIG. 40, the garment 1400 can also include an adjustable pad 1417 on the second support strap 1480B to improve the comfort of the wearer of the garment 1400. The adjustable pad 1417 can define a through-hole configured to receive the strap portion 1419A such that the adjustable pad 1417 can be translated along the strap portion 1419A and maintained in a position relative along the strap portion 1419A via friction. For example, the adjustable pad 1417 can be configured to be slid along the second support strap 1480B and disposed such that a portion of the adjustable pad 1417 can be disposed between a coupling mechanism (e.g., a slider component) of the adjustable portion 1482B and the wearer's skin. For example, to adjust a length of the adjustable portion 1482B, the adjustable pad 1417 can be slid away from the coupling mechanism to expose the coupling mechanism. The coupling mechanism can then be adjusted to a new location along the strap portion 1419A similarly as described with respect to the coupling mechanism 1384 of FIG. 39 above. The adjustable pad 1417 can be translated to the new location of the coupling mechanism. Although the adjustable pad 1417 is shown on only the second support strap 1480B, in some embodiments, the garment 1400 can include two adjustable pads 1417, with an adjustable pad 1417 included on each of the first support strap 1480A and the second support strap 1480B.

In some embodiments, a garment can include a support strap having a first portion configured to couple a shoulder strap of the garment to a first portion of a back panel of the garment (e.g., adjacent a bottom of a cup portion of an inner layer) and a second portion configured to couple the shoulder strap to a center portion of the back panel. For example, FIG. 45 is a back view of a garment 1500. The garment 1500 can be the same or similar in structure and/or function to any of the garments described herein. For example, the garment 1500 includes a base subassembly 1501 including a back panel 1520, an outer panel 1560, two shoulder straps 1506, a first support strap 1580A, and a second support strap 1580B. The garment 1500 also includes a first engagement mechanism 1550A and a second engagement mechanism 1550B that each can be similar in structure and/or function to any of the engagement mechanisms described herein (e.g., the engagement mechanism 450 or the engagement mechanism 750). The engagement mechanism 1550A can include a first portion 1552A and the engagement mechanism 1550B can include a first portion 1552B that can each be the same or similar in structure and/or function to the first portion 452 of the engagement mechanism 450 described above with reference to FIGS. 7-10 and/or the first portion 752 of the engagement mechanism 750 described above with reference to FIGS. 15-17. The engagement mechanism 1550A can include a third portion (not shown) coupled to the outer panel 1560 and the engagement mechanism 1550B can include a third portion (not shown) coupled to the outer panel 1560. Each of the third portion of the engagement mechanism 1550A and the third portion of the engagement mechanism 1550A can be the same or similar in structure and/or function to the third portion 456 of the engagement mechanism 450 described above with reference to FIGS. 7-10 and/or the third portion 756 of the engagement mechanism 750 described above with reference to FIGS. 15-17.

The first support strap 1580A includes a first portion 1530 and a second portion 1527. The first portion 1530 includes an adjustable portion 1582 and a base portion 1522. The first portion 1530 extends between a portion of the back panel 1520 coupled to a bottom portion of the outer panel 1560 and the first portion 1552A of the engagement mechanism 1550A. The second portion 1527 can extend between a center portion 1528 of the back panel 1520 (e.g., a portion disposed between two cup portions (e.g., a right outer panel and a left outer panel) of the outer panel 1660) and the first portion 1552A of the engagement mechanism 1550A. The second portion 1527 can have a first end secured to the first portion 1552A of the engagement mechanism 1550A (e.g., via looping the first end through an opening in the first portion 1552A and stitching the first end to the strap portion of the second portion 1527). The second portion 1527 can have a second end secured to the center portion 1528 (e.g., via stitching). The second portion 1527 can have the same length in both the first and second configuration of the first portion 1530 of the first support strap 1580A. For example, the length of the second portion 1527 can be non-adjustable (e.g., fixed) and/or inelastic. The second support strap 1580B can be the same or similar in structure and/or function to the first support strap 1580A.

The first portion 1530 can be similar in structure and/or function to the first support strap 1480A and the support strap 1380 described above. For example, the adjustable portion 1582 can include a coupling mechanism 1584 that can be the same or similar in structure and/or function to the coupling mechanism 1484A or the coupling mechanism 1384. The coupling mechanism 1584 can include, for example, a slider component or buckle. The adjustable portion 1582 includes a strap portion 1519 that includes at least a portion having a constant width along which the coupling mechanism 1584 can be slid. The strap portion 1519 can have a constant width from the first end to the second end of the strap portion 1519. The first portion 1530 can include a connecting component 1529 that couples the adjustable portion 1582 to the base portion 1522. The connecting component 1529 can define an opening and can have any suitable shape (e.g., a ring shape).

The first end of the strap portion 1519 can be secured to the first portion 1552A of the engagement mechanism 1550A (e.g., via looping the first end through an opening in the first portion 1552A and stitching the first end to the strap portion 1519) and the second end of the strap portion 1519 can be coupled to the coupling mechanism 1584. The first end of the strap portion 1519 can be secured through the same opening of the first portion 1552A as the second portion 1527. The strap portion 1519 includes a loop portion 1521 that extends between a portion of the strap portion 1519 that is threaded through the coupling mechanism 1584 and the second end of the strap portion 1519 that is securely coupled to the coupling mechanism 1584. The coupling mechanism 1584 can secure (e.g., via friction) the portion of the strap portion 1519 that is threaded through the coupling mechanism 1584 such that the size of the loop portion 1521 is maintained by the coupling mechanism 1584 unless a wearer translates the coupling mechanism 1584 along the strap portion 1519 (e.g., by pulling or pushing the coupling mechanism 1584 relative to the strap portion 1519).

The loop portion 1521 is threaded through the opening of the connecting component 1529. The coupling mechanism 1584 can be translated along the strap portion 1519 to adjust the size of the loop portion 1521 and the overall length of the strap portion 1519 between the base portion 1522 and the engagement mechanism 1550 (and between the portion of the back panel 1520 to which the support strap 1580 is attached and the engagement mechanism 1550). For example, the coupling mechanism 1584 can be moved away from the connecting component 1529 such that the size of the loop portion 1521 increases. As the size of the loop portion 1521 increases, the length of the portion of the strap portion 1519 between the coupling member 1584 and the connecting component 1529 decreases such that the overall length of the support strap 1580A decreases. The coupling mechanism 1584 can be moved toward the connecting component 1529 such that the size of the loop portion 1521 decreases. As the size of the loop portion 1521 decreases, the length of the portion of the strap portion 1519 between the coupling member 1584 and the connecting component 1529 increases such that the overall length of the support strap 1580 increases.

Thus, the wearer can adjust the overall length of the support strap 1580A between the engagement portion 1550 and the portion of the base panel 1520 to which the support strap 1580 (e.g., the base portion 1522) is attached by sliding the coupling mechanism 1584 along the strap portion 1519. For example, the coupling mechanism 1584 can be engaged with the support strap 1580 in a first location in a first configuration in which the support strap 1580A is not being used to support a portion of a breast pump against a breast. The outer panel 1560 can be configured to be folded down relative to the first support strap 1580A and/or the second support strap 1580A to expose a breast or breasts of the wearer of the garment 1500 by decoupling the third portion of the engagement mechanism 1550A from the first portion 1552A and/or by decoupling the third portion of the engagement mechanism 1550B from the first portion 1552B. When the support strap 1580A is being used to support a portion of the breast pump (e.g., a flange of a shield of a breast pump) against the breast (e.g., by pulling the support strap 1580A toward a center of the garment, pressing the flange of the shield against the user's breast, and wrapping or partially wrapping the support strap 1580A around a flange and/or a stem of a shield of the breast pump), the support strap 1580A can be transitioned to a second configuration in which the coupling mechanism 1584 is engaged with the support strap 1580A in a second location closer to the base portion 1522 than the first location of the first configuration. The first portion 1530 of the support strap 1584 has a longer overall length in the second configuration than in the first configuration and can wrap around the flange and/or stem of a shield of the breast pump to comfortably maintain the flange of the breast pump against the breast. In the second configuration, the first portion 1530 and the second portion 1527 can both be disposed on the side of the flange and/or stem of the shield of the breast pump that is closer to the center portion 1528 rather than a side opposite the center portion 1528 and closer to a wearer's armpit. In some embodiments, the support strap 1580A can optionally not include the second portion 1527 of the support strap 1580A.

Figure 46:
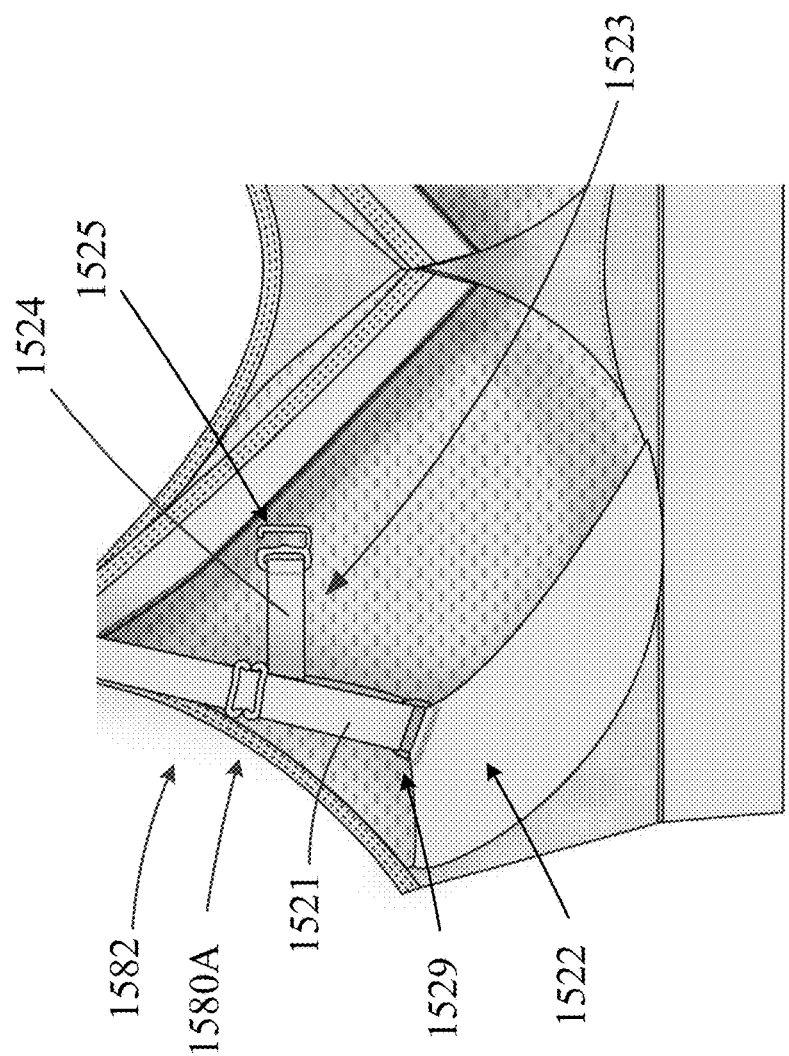
FIG. 46 is a back view of a portion of the garment of FIG. 45 including a snare component, according to an embodiment.

As shown in FIG. 46, which is a back view of a portion of the garment 1500, in some embodiments, the garment 1500 can include a snare component 1523. The snare component 1523 can be the same or similar in structure and/or function to the snare component 1423 described above with respect to the garment 1400. For example, the snare component 1523 can include a coupling mechanism 1525 and a strap portion 1524. The strap portion 1524 can include a first end coupled to the first support strap 1580A and a second end coupled to the coupling mechanism 1525. In some embodiments, the strap portion 1524 can be elastic. In some embodiments, the strap portion 1524 can be inelastic. The coupling mechanism 1525 can include a hook portion. For example, the coupling mechanism 1525 can include a swan hook. The strap portion 1524 of the snare component 1523 can be wrapped around the second support strap 1580B and the coupling mechanism 1525 of the snare component 1523 can be coupled to a portion of the strap portion 1524 such that the snare component 1523 forms a loop around the second support strap 1580B.

Figure 47:
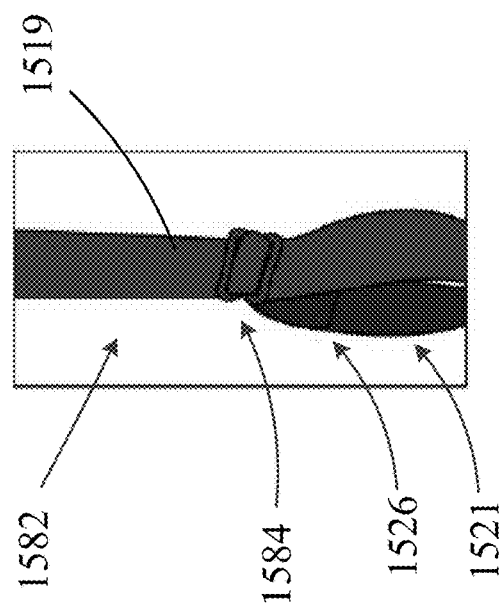
FIG. 47 is a perspective view of a portion of a support strap of the garment of FIG. 46.

As shown in FIG. 46, the snare component 1523 can be coupled to a loop portion 1521 of the support strap 1580A. For example, the first end of the strap portion 1519 that is secured to the coupling mechanism 1584 can be secured to a securement bar of the coupling mechanism 1584 by looping the first end around the securement bar and securing the strap portion 1519 onto itself via a seam 1526 (e.g., using stitching and/or adhesive). The first end of the strap portion 1524 of the snare component 1523 can be sewn to the seam 1526. For example, the first end of the strap portion 1524 of the snare component 1523 can be sewn to an internal portion of the loop portion 1521 (shown, for example, in FIG. 47) using stitching disposed perpendicular to the seam 1526.

Figure 48:
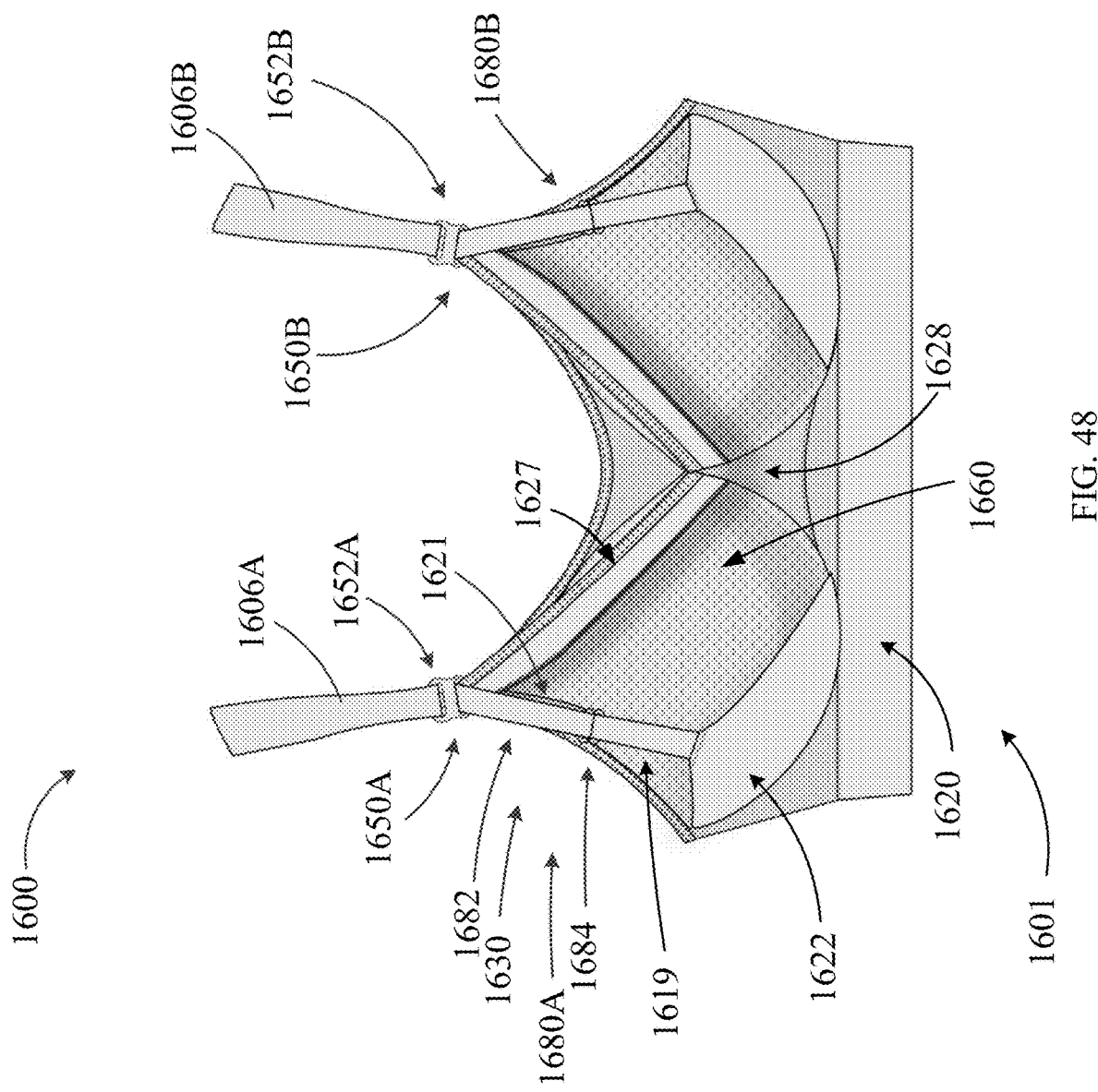
FIG. 48 is a back view of a garment, according to an embodiment.

FIG. 48 is a back view of a garment 1600. The garment 1600 can be the same or similar in structure and/or function to any of the garments described herein. For example, the garment 1600 includes a base subassembly 1601 including a back panel 1620, an outer panel 1660, a first shoulder strap 1606A, a second shoulder strap 1606B, a first support strap 1680A, and a second support strap 1680B. The garment 1600 also includes a first engagement mechanism 1650A and a second engagement mechanism 1650B that each can be similar in structure and/or function to any of the engagement mechanisms described herein (e.g., the engagement mechanism 450 or the engagement mechanism 750). The engagement mechanism 1650A can include a first portion 1652A and the engagement mechanism 1650B can include a first portion 1652B that can each be the same or similar in structure and/or function to the first portion 452 of the engagement mechanism 450 described above with reference to FIGS. 7-10 and/or the first portion 752 of the engagement mechanism 750 described above with reference to FIGS. 15-17. The engagement mechanism 1650A can include a third portion (not shown) coupled to the outer panel 1660 and the engagement mechanism 1650B can include a third portion (not shown) coupled to the outer panel 1660. Each of the third portion of the engagement mechanism 1650A and the third portion of the engagement mechanism 1650A can be the same or similar in structure and/or function to the third portion 456 of the engagement mechanism 450 described above with reference to FIGS. 7-10 and/or the third portion 756 of the engagement mechanism 750 described above with reference to FIGS. 15-17.

Figure 49:
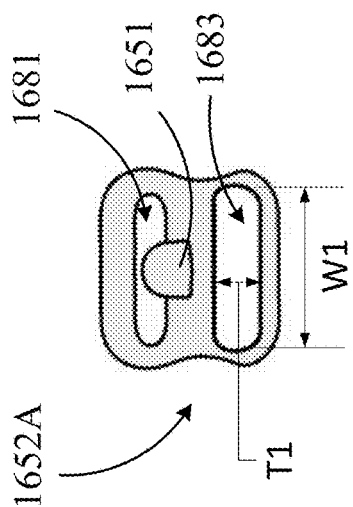
FIG. 49 is a front view of a first portion of an engagement mechanism of the garment of FIG. 48, according to an embodiment.

As shown in FIG. 49, which is a front view of the first portion 1652A of the engagement mechanism 1650A, the first portion 1652A can include an extension portion 1651, and can define a first opening 1681 and a second opening 1683. As shown in FIG. 49, the second opening 1683 can be on an opposite side of the extension portion 1651 than the first opening 1681. The extension portion 1651 can be formed as a hook that forms a slot similar to slot 451A or slot 751A described above with respect to the first portion 452 or the first portion 752, respectively. The first shoulder strap 1606A can be secured to the first portion 1652A of the engagement mechanism 1650A via looping an end of the shoulder first strap 1606A through the opening 1681 in the first portion 1652A and stitching the end to a portion of the shoulder strap 1606. The first portion 1652B of the engagement mechanism 1650B can be the same or similar in structure and/or function to the first portion 1652A of the engagement mechanism 1650A.

The first support strap 1680A includes a first portion 1630 and a second portion 1627. The first portion 1630 includes an adjustable portion 1682 and a base portion 1622. The first portion 1630 extends between a portion of the back panel 1620 coupled to a bottom portion of the outer panel 1660 and the first portion 1652A of the engagement mechanism 1650A. The second portion 1627 can extend from a center portion 1628 of the back panel 1620 (e.g., a portion disposed between two cup portions of the outer panel 1660) to the first portion 1652A of the engagement mechanism 1650A. The second portion 1627 can have a first end secured to the first portion 1652A of the engagement mechanism 1650A (e.g., via looping the first end through the opening 1683 in the first portion 1652A and stitching the first end to the strap portion of the second portion 1627). The second portion 1627 can have a second end secured to the center portion 1628 (e.g., via stitching). The second portion 1627 can have the same length in both the first and second configuration of the first portion 1630 of the first support strap 1680A. For example, the length of the second portion 1627 can be non-adjustable (e.g., fixed) and/or inelastic. The second support strap 1680B can be the same or similar in structure and/or function to the first support strap 1680A.

The first portion 1630 can be similar in structure and/or function to the first support strap 1480A and the support strap 1380 described above. For example, the adjustable portion 1682 can include a coupling mechanism 1684 that can be the same or similar in structure and/or function to the coupling mechanism 1484A or the coupling mechanism 1384. The coupling mechanism 1684 can include, for example, a slider component or buckle. The adjustable portion 1682 includes a strap portion 1619 that includes at least a portion having a constant width along which the coupling mechanism 1684 can be slid. The strap portion 1619 can have a constant width from the first end to the second end of the strap portion 1619.

The first end of the strap portion 1619 is coupled to the base portion 1622 (e.g. via stitching) and the second end of the strap portion 1619 can be coupled to the coupling mechanism 1684. The strap portion 1619 includes a loop portion 1621 that extends between a portion of the strap portion 1619 that is threaded through the coupling mechanism 1684 and the second end of the strap portion 1619 that is securely coupled to the coupling mechanism 1684. The coupling mechanism 1684 can secure (e.g., via friction) the portion of the strap portion 1619 that is threaded through the coupling mechanism 1684 such that the size of the loop portion 1621 is maintained by the coupling mechanism 1684 unless a wearer translates the coupling mechanism 1684 along the strap portion 1619 (e.g., by pulling or pushing the coupling mechanism 1684 relative to the strap portion 1619).

The loop portion 1621 is threaded through the second opening 1683 of the first portion 1652A of the engagement mechanism 1650A. The coupling mechanism 1684 can be translated along the strap portion 1619 to adjust the size of the loop portion 1621 and the overall length of the strap portion 1619 between the base portion 1622 and the engagement mechanism 1650A (and between the portion of the back panel 1620 to which the support strap 1680A is attached and the engagement mechanism 1650A). For example, the coupling mechanism 1684 can be moved away from the first portion 1652A of the engagement mechanism 1650A such that the size of the loop portion 1621 increases. As the size of the loop portion 1621 increases, the length of the portion of the strap portion 1619 between the coupling member 1684 and the first portion 1652A of the engagement mechanism 1650A decreases such that the overall length of the support strap 1680A decreases. The coupling mechanism 1684 can be moved toward the first portion 1652A of the engagement mechanism 1650A such that the size of the loop portion 1621 decreases. As the size of the loop portion 1621 decreases, the length of the portion of the strap portion 1619 between the coupling member 1684 and the first portion 1652A of the engagement mechanism 1650A increases such that the overall length of the support strap 1680 increases.

The second opening 1683 can have a thickness T1 that can be sufficiently wide to simultaneously allow the second portion 1627 to be secured within the second opening 1683 and for the loop portion 1621 to be disposed within the second opening 1683 and slidable through the second opening 1683 (e.g., during adjustment of the size of the loop portion 1621). The loop portion 1621 can be disposed around the portion of the second portion 1627 disposed within the second opening 1683. The portion of the loop portion 1621 within the second opening 1683 can be stacked on the portion of the second portion 1627 within the second opening 1683 such that the overall width of the stacked portions can be substantially equal to the width of the portion of the loop portion 1621 within the second opening 1683 or the greater of the width of the portion of the loop portion 1621 within the second opening 1683 and the portion of the second portion 1627 within the second opening 1683.

In some embodiments, the thickness T1 can be 8 mm. In some embodiments, the thickness T1 can be 5 mm, 6 mm, 7 mm, 9 mm. 10, mm, 11 mm, or any suitable width in between. Additionally, the second opening 1683 can have any suitable width W1. The width W1 can be, for example, substantially similar to the width of the strap portion 1619 and/or the second portion 1627. In some embodiments, for example, the width W1 can be 16 mm. In some embodiments, the width W1 can be 13 mm, 14 mm, 15 mm, 17 mm, 18 mm, 19 mm, or any suitable length in between. In some embodiments, the width W1 can be substantially double the thickness T1. In some embodiments, the width W1 can be substantially equal to or greater than the sum of the thicknesses of the strap portion 1619 and the second portion 1627.

The wearer can adjust the overall length of the support strap 1680A between the engagement portion 1650 and the portion of the base panel 1620 to which the support strap 1680A (e.g., the base portion 1622) is attached by sliding the coupling mechanism 1684 along the strap portion 1619. For example, the coupling mechanism 1684 can be engaged with the support strap 1680A in a first location in a first configuration in which the support strap 1680A is not being used to support a portion of a breast pump against a breast. The outer panel 1660 can be configured to be folded down relative to the first support strap 1680A and/or the second support strap 1680A to expose a breast or breasts of the wearer of the garment 1600 by decoupling the third portion of the engagement mechanism 1650A from the first portion 1652A and/or by decoupling the third portion of the engagement mechanism 1650B from the first portion 1652B. When the support strap 1680A is being used to support a portion of the breast pump (e.g., a flange of a shield of a breast pump) against the breast (e.g., by pulling the support strap 1680A toward a center of the garment, pressing the flange of the shield against the user's breast, and wrapping or partially wrapping the support strap 1680A around a flange and/or a stem of a shield of the breast pump), the support strap 1680A can be transitioned to a second configuration in which the coupling mechanism 1684 is engaged with the support strap 1680A in a second location farther from the base portion 1622 than the first location of the first configuration. The first portion 1630 of the support strap 1684 has a longer overall length in the second configuration than in the first configuration and can wrap around the flange and/or stem of a shield of the breast pump to comfortably maintain the flange of the breast pump against the breast. In the second configuration, the first portion 1630 and the second portion 1627 can both be disposed on the side of the flange and/or stem of the shield of the breast pump that is closer to the center portion 1628 rather than a side opposite the center portion 1628 and closer to a wearer's armpit. In some embodiments, the support strap 1680A can optionally not include the second portion 1627 of the support strap 1680A.

Figure 50:
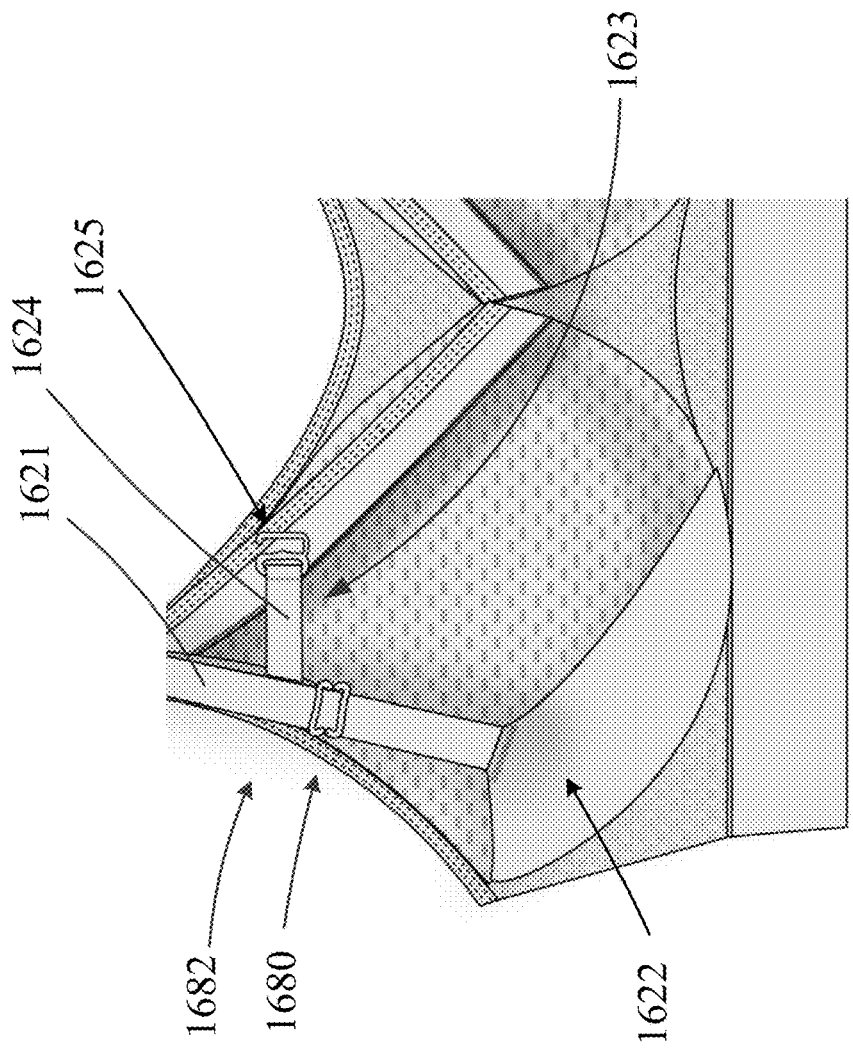
FIG. 50 is a back view of a portion of the garment of FIG. 45 including a snare component, according to an embodiment.

As shown in FIG. 50, which is a back view of a portion of the garment 1600, in some embodiments, the garment 1600 can include a snare component 1623. The snare component 1623 can be the same or similar in structure and/or function to the snare component 1423 described above with respect to the garment 1400. For example, the snare component 1623 can include a coupling mechanism 1625 and a strap portion 1624. The strap portion 1624 can include a first end coupled to the first support strap 1680A and a second end coupled to the coupling mechanism 1625. In some embodiments, the strap portion 1624 can be elastic. In some embodiments, the strap portion 1624 can be inelastic. The coupling mechanism 1625 can include a hook portion. For example, the coupling mechanism 1625 can include a swan hook. The strap portion 1624 of the snare component 1623 can be wrapped around the second support strap 1680B and the coupling mechanism 1625 of the snare component 1623 can be coupled to a portion of the strap portion 1624 such that the snare component 1623 forms a loop around the second support strap 1680B.

Figure 51:
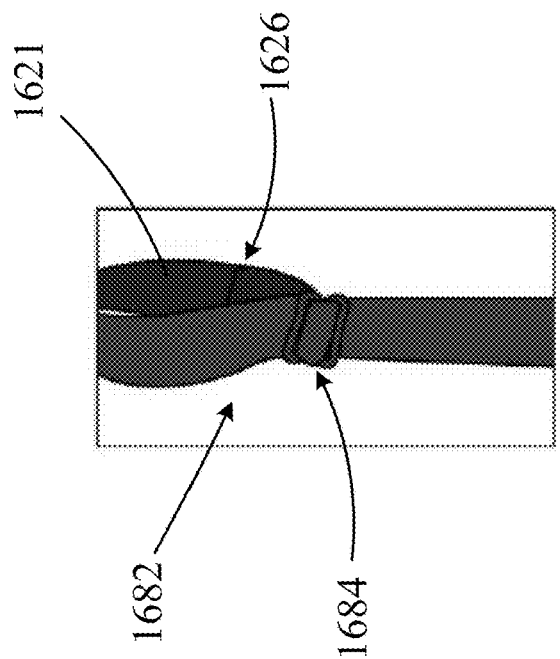
FIG. 51 is a perspective view of a portion of a support strap of the garment of FIG. 50.

As shown in FIG. 51, the snare component 1623 can be coupled to a loop portion 1621 of the support strap 1680A. For example, the second end of the strap portion 1619 that is secured to the coupling mechanism 1684 can be secured to a securement bar of the coupling mechanism 1684 by looping the second end around the securement bar and securing the strap portion 1619 onto itself via a seam 1626 (e.g., using stitching and/or adhesive). The first end of the strap portion 1624 of the snare component 1623 can be sewn to the seam 1626. For example, the first end of the strap portion 1624 of the snare component 1623 can be sewn to an internal portion of the loop portion 1621 (shown, for example, in FIG. 51) using stitching disposed perpendicular to the seam 1626.

In some embodiments, a neck strap of a garment can be attached to a base panel of the garment in a storage configuration prior to and/or after being coupled to an outer panel or pumping panel of the garment for support. For example, FIGS. 52 and 53 are a front view of a neck strap 1746 and a garment 1700 including the neck strap 1746 in a storage configuration, respectively. The neck strap 1746 can be the same or similar in structure and/or function to any of the neck straps described herein. For example, the neck strap 1746 can include a first coupling member 1747A on a first end of the neck strap 1746 and a second coupling member 1747B on a second end of the neck strap 1746.

The garment 1700 can be the same or similar in structure and/or function to any of the garments described herein. For example, the garment 1700 includes a base subassembly 1701 including a back panel 1720, an outer panel 1760, a first shoulder strap (not shown), a second shoulder strap (not shown), a first support strap 1780A, and a second support strap 1780B. The garment 170 (can optionally include an inner or pumping panel (not shown) that can be removeable and can be the same or similar in structure and/or function to any of the inner panels described herein. The garment 1700 also includes a first engagement mechanism 1750A and a second engagement mechanism 1750B. The first engagement mechanism 1750A and the second engagement mechanism 1750B can each be any suitable engagement mechanism (e.g., a two part engagement mechanism a three part engagement mechanism, etc.). In some embodiments, the first engagement mechanism 1750A and the second engagement mechanism 1750B can be similar in structure and/or function to any of the engagement mechanisms described herein (e.g., the engagement mechanism 450 or the engagement mechanism 750).

As shown in FIG. 53, the garment 1700 can include a first loop portion 1709A, a second loop portion 1709B, and a third loop portion 1711. The first loop portion 1709A, the second loop portion 1709B, and the third loop portion 1711 can each be coupled to the front surface of the base panel 1720. As shown in FIG. 53, the third loop portion 1711 can be elongated such that the third loop portion 1711 is longer and/or wider than the first loop portion 1709A and/or the second loop portion 1709B. The first loop portion 1709A and the second loop portion 1709B can each define an opening or throughholes having an axis disposed in a direction perpendicular to the opening or throughhole defined by the third loop portion 1711. The first loop portion 1709A can be configured to engage with the first coupling member 1747A of the neck strap 1746 by receiving a hook portion of the first coupling member 1747A within the loop of the first loop portion 1709A. The second loop portion 1709B can be configured to engage with the second coupling member 1747B of the neck strap 1746 by receiving a hook portion of the second coupling member 1747B within the loop of the second loop portion 1709B. The third loop portion 1711 can be configured to receive a portion of the strap of the neck strap 1746 extending between the first coupling member 1747A and the second coupling member 1747B such that the neck strap 1746 is supported and maintained in place on a front surface of the garment 1700. The third loop portion 1711 can be disposed in a location that is centered relative to cup portions of the garment 1700. In some embodiments, the third loop portion 1711 can be optional and not included.

In use, to attached the neck strap 1746 to the front surface of the base panel 1720 in a first storage configuration, the first coupling member 1747A can be coupled to the first loop portion 1709A, the second coupling member 1747B can be passed through the third loop portion 1711 and coupled to the second loop portion 1709B. To use the neck strap 1746 to support the outer panel 1760 or an inner panel attached to the garment 1700 in a second support configuration, the neck strap 1746 can be decoupled from the first loop portion 1709A, the second loop portion 1709B, and the third loop portion 1711.

In some embodiments, rather than attaching a neck strap to a front surface of a garment in a storage configuration as shown in FIG. 53, a neck strap can be coupled to a back surface of the garment. For example, FIGS. 54 and 55 are a front view of a neck strap 1846 and a back view of a garment 1800 including the neck strap 1846 in a storage configuration, respectively. The neck strap 1846 can be the same or similar in structure and/or function to any of the neck straps described herein, such as the neck strap 1746. For example, the neck strap 1846 can include a first coupling member 1847A on a first end of the neck strap 1846 and a second coupling member 1847B on a second end of the neck strap 1846.

The garment 1800 can be the same or similar in structure and/or function to any of the garments described herein. For example, the garment 1800 includes a base subassembly 1801 including a back panel 1820, an outer panel 1860, a first shoulder strap 1806A, a second shoulder strap 1806B, a first support strap 1880A, and a second support strap 1880B. The garment 1800 can optionally include an inner or pumping panel (not shown) that can be removeable and can be the same or similar in structure and/or function to any of the inner panels described herein. The garment 1800 also includes a first engagement mechanism 1850A and a second engagement mechanism 1850B. The first engagement mechanism 1850A and the second engagement mechanism 1850B can each be any suitable engagement mechanism (e.g., a two part engagement mechanism, a three part engagement mechanism, etc.). In some embodiments, the first engagement mechanism 1850A and the second engagement mechanism 1850B can be similar in structure and/or function to any of the engagement mechanisms described herein (e.g., the engagement mechanism 450 or the engagement mechanism 750).

As shown in FIG. 53, the garment 1800 can include a first loop portion 1809A, a second loop portion 1809B, and a third loop portion 1811. The first loop portion 1809A, the second loop portion 1809B, and the third loop portion 1811 can each be coupled to the back surface of the base panel 1820. As shown in FIG. 53, the third loop portion 1811 can be elongated such that the third loop portion 1811 is longer and/or wider than the first loop portion 1809A and/or the second loop portion 1809B. The first loop portion 1809A and the second loop portion 1809B can each define an opening or throughholes having an axis disposed in a direction perpendicular to the opening or throughhole defined by the third loop portion 1811. The first loop portion 1809A can be configured to engage with the first coupling member 1847A of the neck strap 1846 by receiving a hook portion of the first coupling member 1847A within the loop of the first loop portion 1809A. The second loop portion 1809B can be configured to engage with the second coupling member 1847B of the neck strap 1846 by receiving a hook portion of the second coupling member 1847B within the loop of the second loop portion 1809B. The third loop portion 1811 can be configured to receive a portion of the strap of the neck strap 1846 extending between the first coupling member 1847A and the second coupling member 1847B such that the neck strap 1846 is supported and maintained in place on a front surface of the garment 1800. The third loop portion 1811 can be disposed in a location that is centered relative to cup portions of the garment 1800. In some embodiments, the third loop portion 1811 can be optional and not included.

In use, to attached the neck strap 1846 to the back surface of the base panel 1820 in a first storage configuration, the first coupling member 1847A can be coupled to the first loop portion 1809A, the second coupling member 1847B can be passed through the third loop portion 1811 and coupled to the second loop portion 1809B. To use the neck strap 1846 to support the outer panel 1860 or an inner panel attached to the garment 1800 in a second support configuration, the neck strap 1846 can be decoupled from the first loop portion 1809A, the second loop portion 1809B, and the third loop portion 1811.

Figure 56:
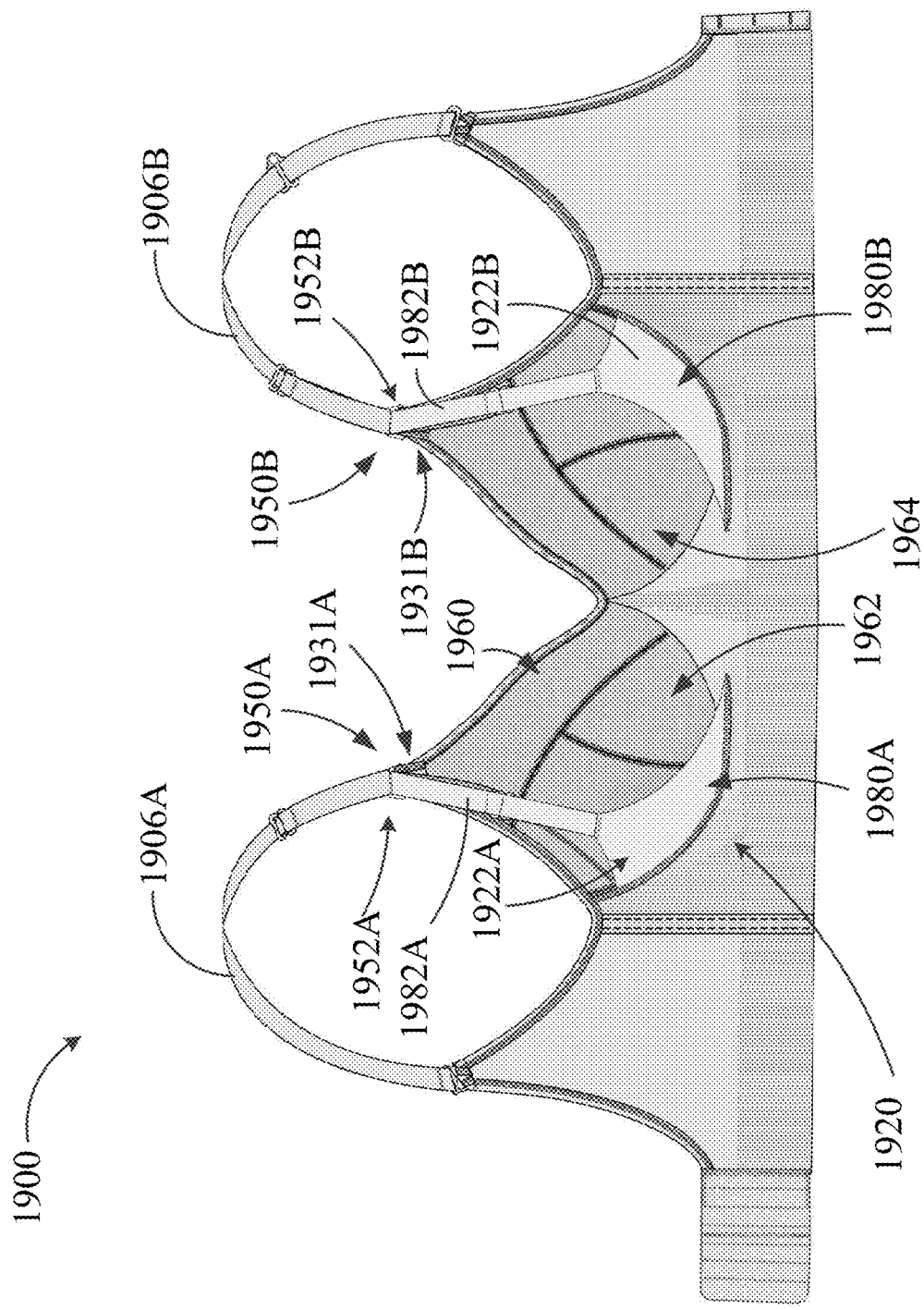
FIG. 56 is a back view of a garment, according to an embodiment.

In some embodiments, an outer panel of a garment can include a pair of loop portions, each configured to be disposed at or near an apex of a cup of the outer panel and to be releasably coupled with a coupling member of a neck strap. FIG. 56 is a back view of a garment 1900 in a first configuration in which the garment 190 is not supporting a breast pump for a pumping operation. The garment 1900 can be the same or similar in structure and/or function to any of the garments described herein. For example, the garment 1900 includes a base subassembly 1901 including a back panel 1920, an outer panel 1960, a first shoulder strap 1906A, a second shoulder strap 1906B, a first support strap 1980A, and a second support strap 1980B. The garment 1900 can optionally include an inner or pumping panel (not shown) that can be removeable and can be the same or similar in structure and/or function to any of the inner panels described herein. The garment 1900 also includes a first engagement mechanism 1950A and a second engagement mechanism 1950B. The first engagement mechanism 1950A and the second engagement mechanism 1950B can each be any suitable engagement mechanism (e.g., a two part engagement mechanism, a three part engagement mechanism, etc.). In some embodiments, the first engagement mechanism 1950A and the second engagement mechanism 1950B can be similar in structure and/or function to any of the engagement mechanisms described herein (e.g., the engagement mechanism 450 or the engagement mechanism 750). The first engagement mechanism 1950A can include a first portion 1952A and the second engagement mechanism 1950B can include a first portion 1952B that can each be the same or similar in structure and/or function to the first portion 452 of the engagement mechanism 450 described above with reference to FIGS. 7-10 and/or the first portion 752 of the engagement mechanism 750 described above with reference to FIGS. 15-17.

The first support strap 1980A and the second support strap 1980B can be the same or similar in structure and/or function to any of the support straps described herein. For example, the first support strap 1980A includes an adjustable portion 1982A and a base portion 1922A. The second support strap 1980B includes an adjustable portion 1982B and a base portion 1922B. The adjustable portion 1982A is coupled to the first portion 1952A of the engagement mechanism 1952A and the adjustable portion 1982B is coupled to the first portion 1952B of the engagement mechanism 1952B.

The outer panel 1960 includes a left outer panel 1962 and a right outer panel 1964 (each also referred to herein as a "cup portion"). The left outer panel 1962 includes a loop portion 1931A and the right outer panel includes a loop portion 1931B. The loop portion 1931A can be disposed at an apex of the left outer panel 1962 and the loop portion 1931B can be disposed at an apex of the right outer panel 1964. For example, the first loop portion 1931A can be disposed behind or slightly underneath a portion of the left outer panel 1962 that is attached to a second portion 1956A (shown in FIG. 58A) of the first engagement mechanism 1950A that can be the same or similar in structure and/or function to any of the second or third portions of the engagement mechanisms described herein that can be configured to be releasably coupled with the first portion 1952A (e.g., the third portion 456 or the third portion 756). The second loop portion 1931B can be disposed behind or slightly underneath a portion of the right outer panel 1964 that is attached to a second portion 1956B (shown in FIG. 58A) of the second engagement mechanism 1950B that can be the same or similar in structure and/or function to any of the second or third portions of the engagement mechanisms described herein that can be configured to be releasably coupled with the first portion 1952B (e.g., the third portion 456 or the third portion 756).

Figure 57:
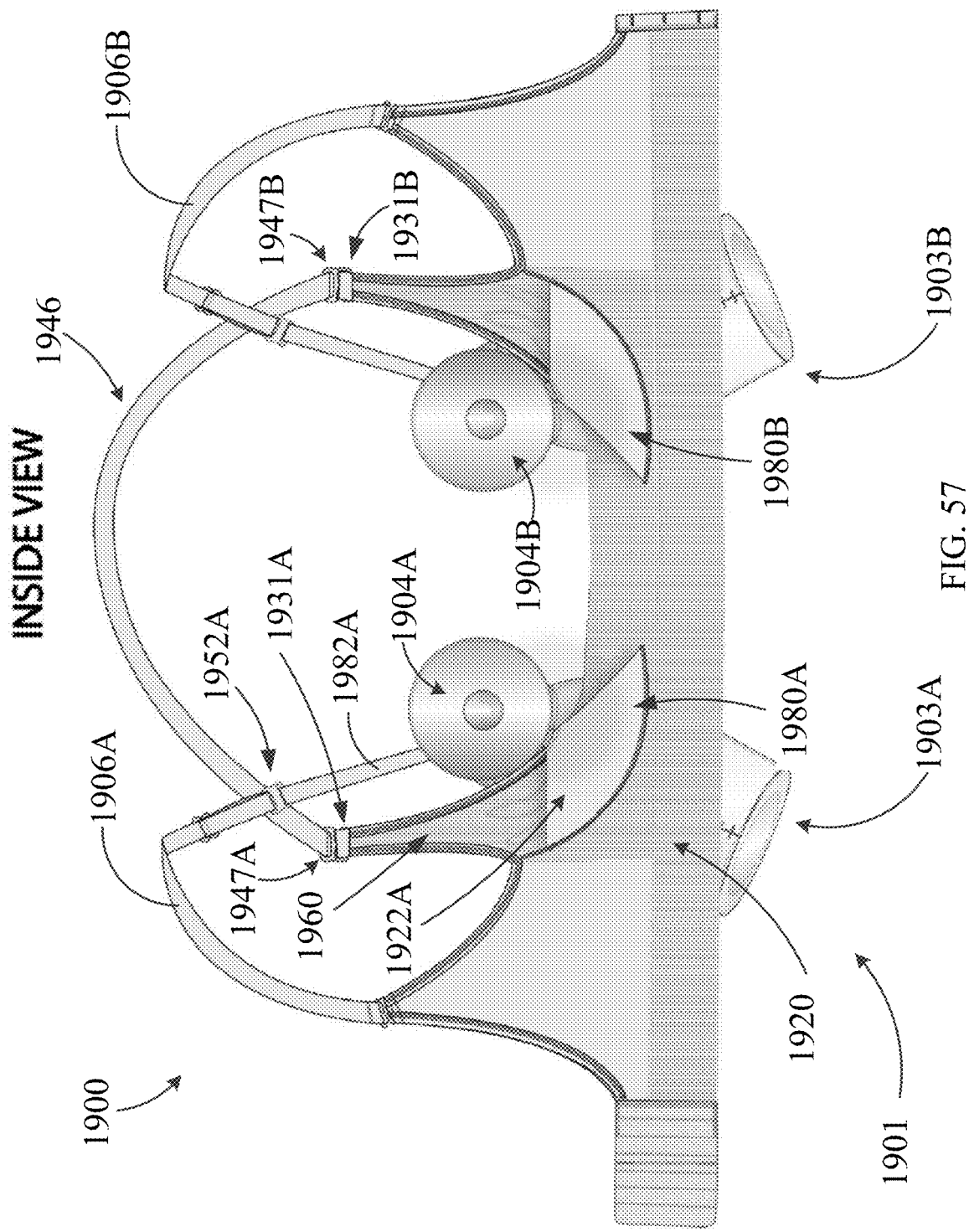
FIG. 57 is a back view of the garment of FIG. 56 in a configuration in which the garment includes a neck strap and is supporting a first breast pump and a second breast pump.

FIGS. 57 and 58A are a back view and a front view, respectively, of the garment 1900 shown in a second configuration in which the garment 1900 is supporting a first breast pump 1903A and a second breast pump 1903B. To transition the garment 1900 from the first configuration shown in FIG. 56 in which the garment 1900 is not supporting a breast pump to the second configuration, the second portion 1956A can be uncoupled from the first portion 1952A of the first engagement mechanism 1950A and the second portion 1956B can be uncoupled from the first portion 1952B of the second engagement mechanism 1950B such that the upper portions of the outer panel 1960 (e.g., the apex of each of the left outer panel 1962 and the right outer panel 1964) are freely moveable relative to the first portion 1952A and the second portion 1952B.

The first adjustable portion 1982A can be adjusted such that the length of the first support strap 1980A is increased. The second adjustable portion 1982B can be adjusted such that the length of the second support strap 1980B is increased. The first support strap 1980A can be wrapped partially or fully around a portion 1904A of the breast pump 1903A (e.g., a flange of a shield of a breast pump). For example, the first support strap 1980A can be wrapped a full turn around the portion 1904A as shown in FIG. 58A, similarly as shown with respect to the support strap 1280 shown above with respect to FIG. 38B. Alternatively, the first support strap 1980A can wrapped only partially around the portion 1904A (similarly to the support strap 1280 shown in FIG. 36). The second support strap 1980B can be wrapped partially or fully around a portion 1204B of the breast pump 1203B (e.g., a flange of a shield of a breast pump). For example, the second support strap 1980B can be wrapped a full turn around the portion 1904B as shown in FIG. 58A, similarly as shown with respect to the support strap 1280 shown above with respect to FIG. 38B. Alternatively, the second support strap 1980B can be wrapped only partially around the portion 1904B (similarly to the support strap 1280 shown in FIG. 36).

A neck strap 1946 of the garment 1900, which can be the same or similar in structure and/or function to any of the neck straps described herein, can be coupled to the first loop portion 1931A and the second loop portion 1931B and can be disposed partially behind the wearer's neck. For example, the neck strap 1946 can include a first coupling member 1947A and a second coupling member 1947B. The first coupling member 1947A can include a hook portion (e.g., a swan hook) that is configured to be pushed into the first loop portion 1931A. The second coupling member 1947B can include a hook portion (e.g., a swan hook) that is configured to be pushed into the second loop portion 1931B. In some embodiments, the neck strap 1946 can have an adjustable length such that the height of the apex of the left panel portion 1962 and the height of the apex of the right panel portion 1964 can be adjusted by adjusting the length of the neck strap 1946.

In the second configuration of the garment 1900, the first support strap 1980A and the left outer panel 1962 can maintain the portion 1904A of the breast pump 1903A against the breast of the wearer such that the flange of the breast pump 1903B is sealed properly against the breast of the user. In some embodiments, the portion 1904A can be disposed between the first support strap 1980A and the left outer panel 1962 such that the first support strap 1980A and the left outer panel 1962 collectively support the breast pump 1903A against the wearer's left breast for a hands-free pumping procedure.

The second support strap 1980B and the right outer panel 1964 can maintain the portion 1904B of the breast pump 1903B against the breast of the wearer such that the flange of the breast pump 1903B is sealed properly against the breast of the user. In some embodiments, the portion 1904B can be disposed between the second support strap 1980B and the right outer panel 1964 such that the second support strap 1980B and the right outer panel 1964 collectively support the breast pump 1903B against the wearer's right breast for a pumping procedure.

Although FIGS. 57 and 58A show the garment 1900 supporting two breast pumps simultaneously, in some embodiments, the wearer can use the garment 1900 to support only one breast pump at a time. For example, the garment 1900 can be used to support only the first breast pump 1903A, and the second support strap 1980B can remain in a first configuration in which the adjustable portion 1982B is shorter than in a pumping configuration in which the second support strap 1980B is used to support the breast pump 1903B.

Figure 58B:
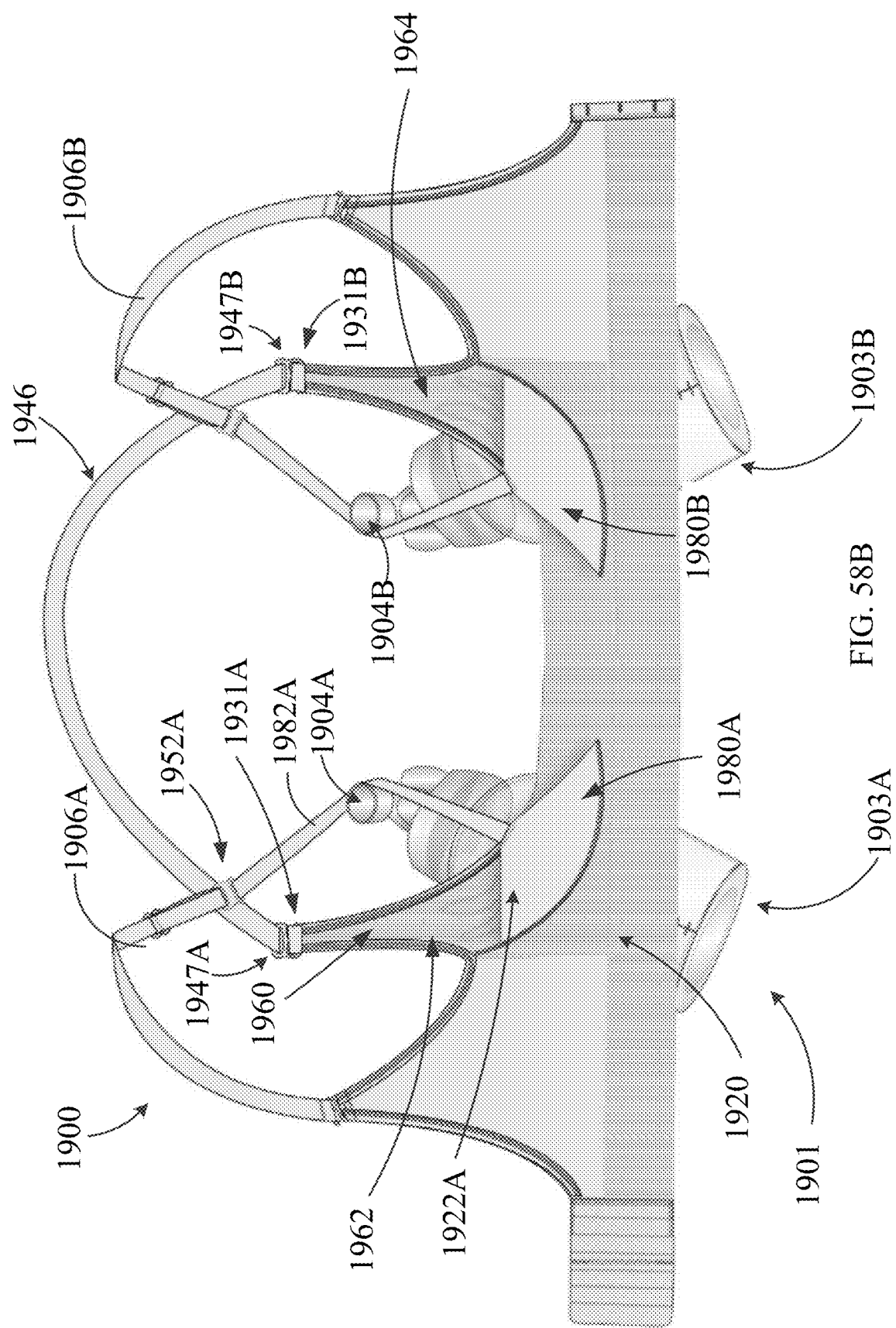
FIG. 58B is a back view of the garment of FIG. 56 shown without the flange of the breast shield in an alternative support strap configuration.

As referenced above, in some embodiments, rather than disposing the first support strap 1980A and the second support strap 1980B such that each are wrapped a full turn around the portions 1904A and the 1904B, respectively, the first support strap 1980A and/or the second support strap 1980B can be wrapped only partially (e.g., a partial turn) around the portion 1904A (e.g., a stem or neck of the shield of breast pump 1903A) and 1904B (e.g., a stem or neck of the shield of breast pump 1903B). For example, FIG. 58B shows a back view of the garment 1900 shown in a configuration in which the garment 1900 is supporting the breast pump 1903A and the breast pump 1903B, with the flange of the breast shield of the breast pump 1903A and the flange of the breast shield of the breast pump 1903B not shown for visibility of the support strap 1980A relative to the stem portion 1904A of the breast shield of the breast pump 1903A and visibility of the support strap 1980B relative to the stem portion 1904B of the breast shield of the breast pump 1903B. As shown, the first support strap 1980A is arranged against an inner portion of the stem portion 1904A to only partially surround the stem portion 1904A. The second support strap 1980B is arranged against an inner portion of the stem portion 1904B to only partially surround the stem portion 1904B.

In some embodiments, rather than or in addition to each of a left outer panel and a right outer panel of an outer panel including a loop portion (e.g., loop portions 1931A and 1931B), an inner or pumping panel of a garment, such as any of the pumping panels (e.g., pumping panel 470) and garments described herein, can include a first loop portion and a second loop portion. The first loop portion can be the same or similar in structure and/or function to the first loop portion 1931A and the second loop portion can be the same or similar in structure and/or function to the second loop portion 1931B. The first loop portion can be disposed at an apex of a left panel of the pumping panel and the second loop portion can be disposed at an apex of a right panel of the pumping panel. The pumping panel can include coupling mechanisms, such as at least one snap portion disposed at a bottom of each of the right panel and the left panel (e.g., between a right opening and a base panel and between a left opening and a base panel), that are each configured to mate with an associated mating snap portion on an outer panel and/or a support strap of the garment. A neck strap, such as any of the neck straps described herein (e.g., the neck strap 1946) can be coupled to the first loop portion and the second loop portion of the pumping panel via a first coupling member and a second coupling member, respectively, (e.g., swan hooks) of the neck strap to support the pumping panel when the pumping panel is coupled to a base subassembly of the garment via the coupling mechanisms and a breast pump is disposed in at least one of the openings defined in the pumping panel.

In some embodiments, a neck strap, such as any of the neck straps described herein, can be transitioned between a first configuration in which the neck strap supports at least one breast pump (e.g., via an outer panel or an inner or pumping panel) and a second configuration in which the neck strap can be worn by the wearer as a bracelet (e.g., in between pumping procedures).

For example, FIG. 59 is a top view of a neck strap 2046. The neck strap 2046 can be the same or similar in structure and/or function to any of the neck straps described herein. For example, the neck strap 2046 can include a first coupling member 2047A on a first end of the neck strap 2046 and a second coupling member 2047B on a second end of the neck strap 2046. The first coupling member 2047A and the second coupling member 2047B can each be formed as swan hooks. The neck strap 2046 can also include a first strap portion 2035, a second strap portion 2036, and an adjustable strap portion 2038 coupling the first strap portion 2035 to the second strap portion 2036. The adjustable strap portion 2038 includes a strap having a first end coupled to the second strap portion 2036 and a first end coupled to a slider 2058. The adjustable strap portion 2038 can be coupled to the first strap portion 2035 via a ring 2034. For example, the strap of the adjustable strap portion 2038 can have a loop portion looped through the ring 2034. The slider 2058 can secure (e.g., via friction) a portion of the strap that is threaded through the slider 2058 such that the size of the loop portion is maintained by the slider 2058 unless a wearer translates the slider 2058 along the strap (e.g., by pulling or pushing the slider 2058 relative to the strap). The adjustable strap portion 2038 can also include a neck pad 2033. The neck pad 2033 can be secured to a portion of the strap of the adjustable strap portion 2038 (e.g., via the strap being threaded through a portion of the neck pad 2033) and can optionally be slidable along the strap.

The first strap portion 2035 and the second strap portion 2036 each include a set of elongated parallel straps (e.g., spaghetti straps). As shown in FIG. 59, the first strap portion 2035 includes multiple parallel straps (e.g., three straps) coupled to and extending between the first coupling member 2047A and the ring 2034. The second strap portion 2036 includes a number of parallel straps (e.g., three straps) coupled to and extending between the adjustable strap portion 2038 and the second coupling member 2047B.

The neck strap 2046 can be configured in a first configuration to be coupled to any of the garments described herein to support at least one breast pump. For example, the first coupling member 2047A and the second coupling member 2047B can be coupled to loops or engaged with portions adjacent openings of an outer panel or an inner panel of any of the garments described herein. For example, the first coupling member 2047A can be coupled to the first loop portion 1269A and the second coupling member 2047B can be coupled to the second loop portion 1269B of the outer panel 1260 described above with respect to the garment 1200 in place of the neck strap 1246. As another example, the first coupling member 2047A can be coupled to the first loop portion 1931A and the second coupling member 2047B can be coupled to the second loop portion 1931B of the outer panel 1960 described above with respect to the garment 1900 in place of the neck strap 1946. Additionally, the neck strap 2046 can be wrapped around a wrist of a wearer in a second configuration (e.g., as a bracelet) any suitable number of times (e.g., 1 turn, 2 turns, 3 turns, or any suitable number of partial turns therebetween). In some embodiments, the first coupling member 2047A and the second coupling member 2047B can each be coupled to one of the first strap portion 2035 and/or the second strap portion 2036 to secure the neck strap 2046 in the second configuration. In some embodiments, the first coupling member 2047A can be coupled to the second coupling member 2047B (e.g., by engaging the swan hook portions with each other).

In some embodiments, rather than the first strap portion and the second strap portion of a neck strap each including a set of elongated parallel straps, the first strap portion and the second strap portion can include braids. For example, FIG. 60 is a top view of a neck strap 2146. The neck strap 2146 can be the same or similar in structure and/or function to the neck strap 2046. For example, the neck strap 2146 can include a first coupling member 2147A, a second coupling member 2147B, a first strap portion 2135, a second strap portion 2136, and an adjustable strap portion 2138. The first coupling member 2147A, the second coupling member 2147B, the first strap portion 2135, the second strap portion 2136, and the adjustable strap portion 2138 can be the same or similar in structure and/or function to the first coupling member 2047A, the second coupling member 2047B, the first strap portion 2035, the second strap portion 2036, and the adjustable strap portion 2038 described above with respect to the neck strap 2046. For example, the adjustable strap portion 2138 includes a strap having a first end coupled to the second strap portion 2136 and a first end coupled to a slider 2158. The adjustable strap portion 2138 can be coupled to the first strap portion 2135 via a ring 2134. The adjustable strap portion 2138 can also include a neck pad 2133. The slider 2158, the ring 2134, and the neck pad 2133 can be the same or similar in structure and/or function to the slider 2058, the ring 2034, and the neck pad 2033 described above with respect to the adjustable strap portion 2038.

The first strap portion 2135 and the second strap portion 2136 each include a braid. As shown in FIG. 60, the first strap portion 2135 includes multiple elongated straps (e.g., three straps) forming a braid between the first coupling member 2147A and the ring 2134. The second strap portion 2136 includes a multiple elongated straps (e.g., three straps) forming a braid between the adjustable strap portion 2138 and the second coupling member 2147B.

In some embodiments, the first strap portion and the second strap portion of a neck strap can each include a series of link portions. For example, FIG. 61 is a top view of a neck strap 2246. The neck strap 2246 can be the same or similar in structure and/or function to the neck strap 2046. For example, the neck strap 2246 can include a first coupling member 2247A, a second coupling member 2247B, a first strap portion 2235, a second strap portion 2236, and an adjustable strap portion 2238. The first coupling member 2247A, the second coupling member 2247B, the first strap portion 2235, the second strap portion 2236, and the adjustable strap portion 2238 can be the same or similar in structure and/or function to the first coupling member 2047A, the second coupling member 2047B, the first strap portion 2035, the second strap portion 2036, and the adjustable strap portion 2038 described above with respect to the neck strap 2046. For example, the adjustable strap portion 2238 includes a strap having a first end coupled to the second strap portion 2236 and a first end coupled to a slider 2258. The adjustable strap portion 2238 can be coupled to the first strap portion 2235 via a ring 2234. The adjustable strap portion 2238 can also include a neck pad 2233. The slider 2258, the ring 2234, and the neck pad 2233 can be the same or similar in structure and/or function to the slider 2058, the ring 2034, and the neck pad 2033 described above with respect to the adjustable strap portion 2038.

The first strap portion 2235 and the second strap portion 2236 each include a series of link portions. As shown in FIG. 61, the first strap portion 2235 includes a sequence of link portions forming a chain between the first coupling member 2247A and the ring 2234. The second strap portion 2236 includes a sequence of link portions forming a chain between the adjustable strap portion 2238 and the second coupling member 2247B.

Figure 62:
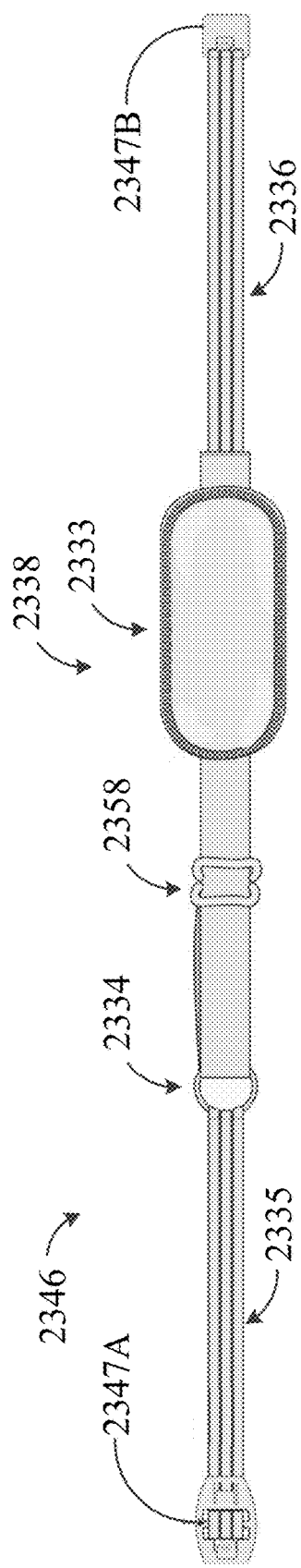
FIG. 62 is a top view of a neck strap, according to an embodiment.

In some embodiments, rather than the first coupling member and the second coupling member including swan hooks, the first coupling member and the second coupling member can be configured to engage with complementary portions of any of the engagement mechanisms described herein. For example, FIG. 62 is a top view of a neck strap 2346. The neck strap 2346 can be the same or similar in structure and/or function to the neck strap 2046. For example, the neck strap 2346 can include a first coupling member 2347A, a second coupling member 2347B, a first strap portion 2335, a second strap portion 2336, and an adjustable strap portion 2338. The first strap portion 2335, the second strap portion 2336, and the adjustable strap portion 2338 can be the same or similar in structure and/or function to the first strap portion 2035, the second strap portion 2036, and the adjustable strap portion 2038 described above with respect to the neck strap 2046. For example, the adjustable strap portion 2338 includes a strap having a first end coupled to the second strap portion 2336 and a first end coupled to a slider 2358. The adjustable strap portion 2338 can be coupled to the first strap portion 2335 via a ring 2334. The adjustable strap portion 2338 can also include a neck pad 2333. The slider 2358, the ring 2334, and the neck pad 2333 can be the same or similar in structure and/or function to the slider 2058, the ring 2034, and the neck pad 2033 described above with respect to the adjustable strap portion 2038.

The first coupling member 2347A can be the same or similar in structure and/or function to the second portion 454 of the engagement mechanism 450 described above or to the second portion 754 of the engagement mechanism 750 described above. For example, the first coupling member 2347A can include an opening, a tab portion, and a securement portion configured to mate with an extension portion. Additionally, the first coupling member 2347A can include a securement bar to which the first strap portion 2335 can be secured. The second coupling member 2347B can be the same or similar in structure and/or function to the first portion 452 of the engagement mechanism 450 described above or to the first portion 752 of the engagement mechanism 750 described above. For example, the second coupling member 2347B can include an extension portion that is hook-shaped and defines a slot. Additionally, the second coupling member 2347B can include a securement bar to which the second strap portion 2336 can be secured. Thus, the first coupling member 2347A and the second coupling member 2347B can be releasably engaged with any of the second or third portions of the engagement mechanisms described herein, such as the third portion 456 or the third portion 756. Thus, the neck strap 2346 can be coupled to any of the outer portions of garments described herein by coupling the first coupling member 2347A to a second or third portion of a first engagement mechanism of a garment and by coupling the second coupling member 2347B to a second or third portion of a second engagement mechanism of the garment such that the neck strap 2346 supports the outer panel and/or the inner panel of the garment. In some embodiments, the first coupling member 2347A and/or second coupling member 2347B can be identical to the second portion 454 of the engagement mechanism 450 and the first portion 452 of the engagement mechanism 450, respectively, such that fewer distinct types of clasp portions are needed for construction of a garment including at least one engagement mechanism such as the engagement mechanism 450 and the neck strap 2346. In some embodiments, the first coupling member 2347A and/or second coupling member 2347B can be identical to the second portion 754 of the engagement mechanism 750 and the first portion 752 of the engagement mechanism 750, respectively, such that fewer distinct types of clasp portions are needed for construction of a garment including at least one engagement mechanism such as the engagement mechanism 750 and the neck strap 2346.

Additionally, the first coupling member 2347A can be engaged with the second coupling member 2347B (e.g., via inserting a hook-shaped extension portion of the second coupling member 2347B through an opening of the first coupling member 2347A and engaging the extension portion with a securement portion and tab portion of the first coupling member 2347A). Thus, the neck strap 1246 can be worn as a bracelet by wrapping the neck strap 1246 any suitable number of turns (e.g., one, two, three, four) around a wrist of the wearer and coupling the first coupling member 2347A to the second coupling member 2346B when the neck strap 2346 is not needed to support an outer panel for a pumping procedure.

In some embodiments, as shown in FIG. 62, the second coupling member 2347B can be the same as the first portion 452 of the engagement mechanism 450 described above except that the second coupling member 2347B optionally does not define the opening 483. In some embodiments, the locations of the first coupling member 2347A and the second coupling member 2347B can be switched such that the first coupling member 2347A is coupled to the second portion 2336 and the second coupling member 2347B is coupled to the first portion 2335.

Figure 63:
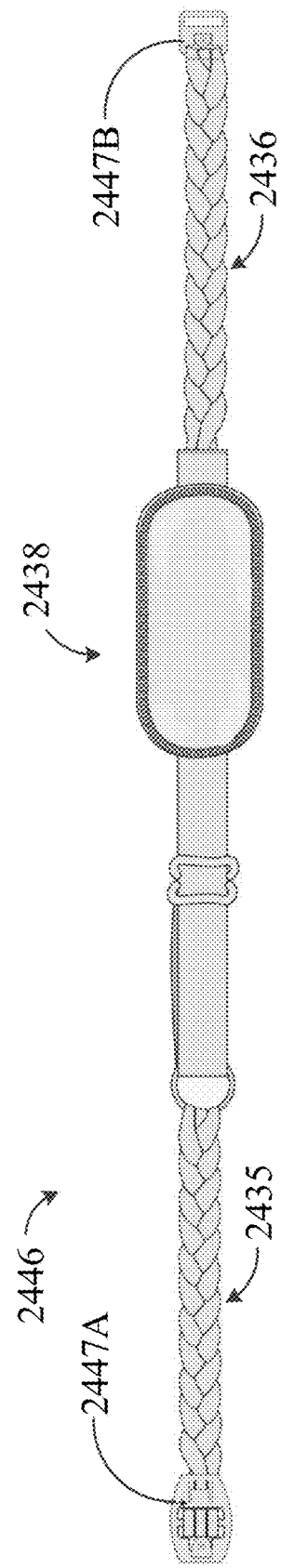
FIG. 63 is a top view of a neck strap, according to an embodiment.

FIG. 63 is a top view of a neck strap 2446. The neck strap 2446 can be the same or similar in structure and/or function to any of the neck straps described herein, such as the neck strap 2346. For example, the neck strap 2446 can include a first coupling member 2447A, a second coupling member 2447B, a first strap portion 2435, a second strap portion 2436, and an adjustable strap portion 2438. The first coupling member 2447A and the second coupling member 2447B can be the same or similar in structure and/or function to the first coupling member 2347A and the second coupling member 2347B described above with respect to neck strap 2346. The first strap portion 2435, the second strap portion 2436, and the adjustable strap portion 2438 can be the same or similar in structure and/or function to the first strap portion 2135, the second strap portion 2136, and the adjustable strap portion 2138 described above with respect to the neck strap 2146. For example, the first strap portion 2135 and the second strap portion 2135 can each include a braid.

Figure 64:
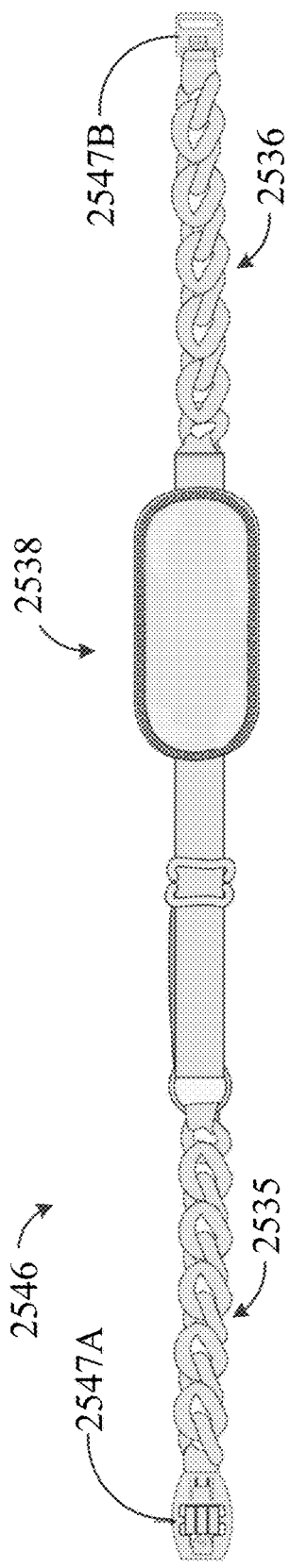
FIG. 64 is a top view of a neck strap, according to an embodiment.

FIG. 64 is a top view of a neck strap 2546. The neck strap 2546 can be the same or similar in structure and/or function to any of the neck straps described herein, such as the neck strap 2346. For example, the neck strap 2546 can include a first coupling member 2547A, a second coupling member 2547B, a first strap portion 2535, a second strap portion 2536, and an adjustable strap portion 2538. The first coupling member 2547A and the second coupling member 2547B can be the same or similar in structure and/or function to the first coupling member 2347A and the second coupling member 2347B described above with respect to neck strap 2346. The first strap portion 2535, the second strap portion 2536, and the adjustable strap portion 2538 can be the same or similar in structure and/or function to the first strap portion 2235, the second strap portion 2236, and the adjustable strap portion 2238 described above with respect to the neck strap 2246. For example, the first strap portion 2535 and the second strap portion 2535 can each include a chain of link portions.

Figure 65:
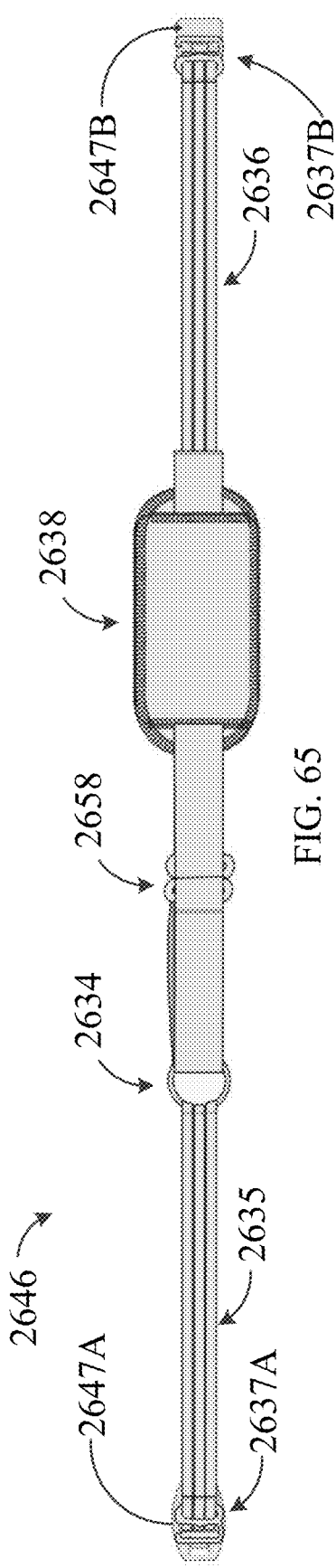
FIG. 65 is a top view of a neck strap, according to an embodiment.

In some embodiments, a neck strap can include both a coupling member that is configured to engage with complementary portions of any of the engagement mechanisms described herein and a swan hook coupling member on or near each end of the neck strap. For example, FIG. 65 is a top view of a neck strap 2646. The neck strap 2646 can be the same or similar in structure and/or function to any of the neck straps described herein, such as the neck strap 2346. For example, the neck strap 2646 can include a first coupling member 2647A, a second coupling member 2647B, a first strap portion 2635, a second strap portion 2636, and an adjustable strap portion 2638. The first coupling member 2647A and the second coupling member 2647B can be the same or similar in structure and/or function to the first coupling member 2347A and the second coupling member 2347B described above with respect to the neck strap 2346. The first strap portion 2635, the second strap portion 2636, and the adjustable strap portion 2638 can be the same or similar in structure and/or function to the first strap portion 2035, the second strap portion 2036, and the adjustable strap portion 2038 described above with respect to the neck strap 2046, to the first strap portion 2135, the second strap portion 2136, and the adjustable strap portion 2138 described above with respect to the neck strap 2146, and/or to the first strap portion 2235, the second strap portion 2236, and the adjustable strap portion 2238 described above with respect to the neck strap 2246.

The neck strap 2646 also includes a first swan hook coupling member 2637A and a second swan hook coupling member 2637B. The first swan hook coupling member 2637A can be coupled to the first strap portion 2635 and the second swan hook coupling member 2637B can be coupled to the second strap portion 2636. In some embodiments, the first swan hook coupling member 2637A and the second swan hook coupling member 2637B can be slidable along the first strap portion 2635 and the second swan hook coupling member 2637B, respectively. The first swan hook coupling member 2637A and the second swan hook coupling member 2637B can each be configured to releasably couple to loops of or to be engaged with portions adjacent openings of an outer panel or an inner panel of any of the garments described herein. Thus, the neck strap 2646 can be coupled to either a portion of a first engagement mechanism and a portion of a second engagement mechanism via the first coupling member 2647A and the second coupling member 2647B, or the first swan hook coupling member 2637A and the second swan hook coupling member 2637B of the neck strap 2646 can be coupled to a loop coupled to or through an opening defined in an inner panel or an outer panel of a garment such as any of the garments described herein.

Figure 66:
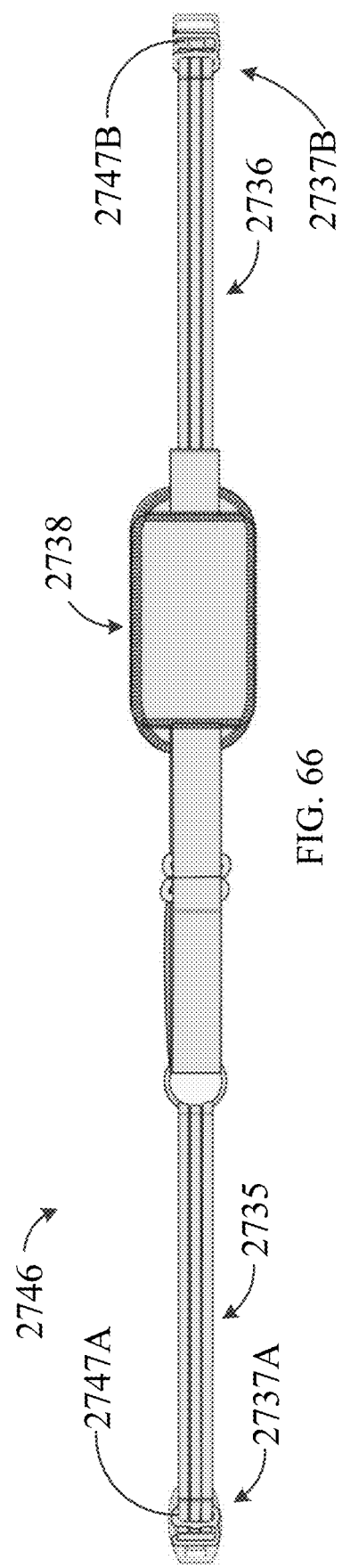
FIG. 66 is a top view of a neck strap, according to an embodiment.

FIG. 66 is a top view of a neck strap 2746. The neck strap 2746 can be the same or similar in structure and/or function to any of the neck straps described herein, such as the neck strap 2646. For example, the neck strap 2746 can include a first coupling member 2747A, a second coupling member 2747B, a first strap portion 2735, a second strap portion 2736, and an adjustable strap portion 2738. The first coupling member 2747A and the second coupling member 2747B can be the same or similar in structure and/or function to the first coupling member 2647A and the second coupling member 2647B described above with respect to the neck strap 2646, except that the second coupling member 2747B can optionally include an opening the same as or similar to the opening 483 of the first portion 452. The first strap portion 2735, the second strap portion 2736, and the adjustable strap portion 2738 can be the same or similar in structure and/or function to the first strap portion 2635, the second strap portion 2636, and the adjustable strap portion 2638 described above with respect to the neck strap 2646. The neck strap 2746 also includes a first swan hook coupling member 2737A and a second swan hook coupling member 2737B, which can be the same or similar in structure and/or function to the first swan hook coupling member 2637A and/or the second swan hook coupling member 2637B, respectively.

Figure 67:
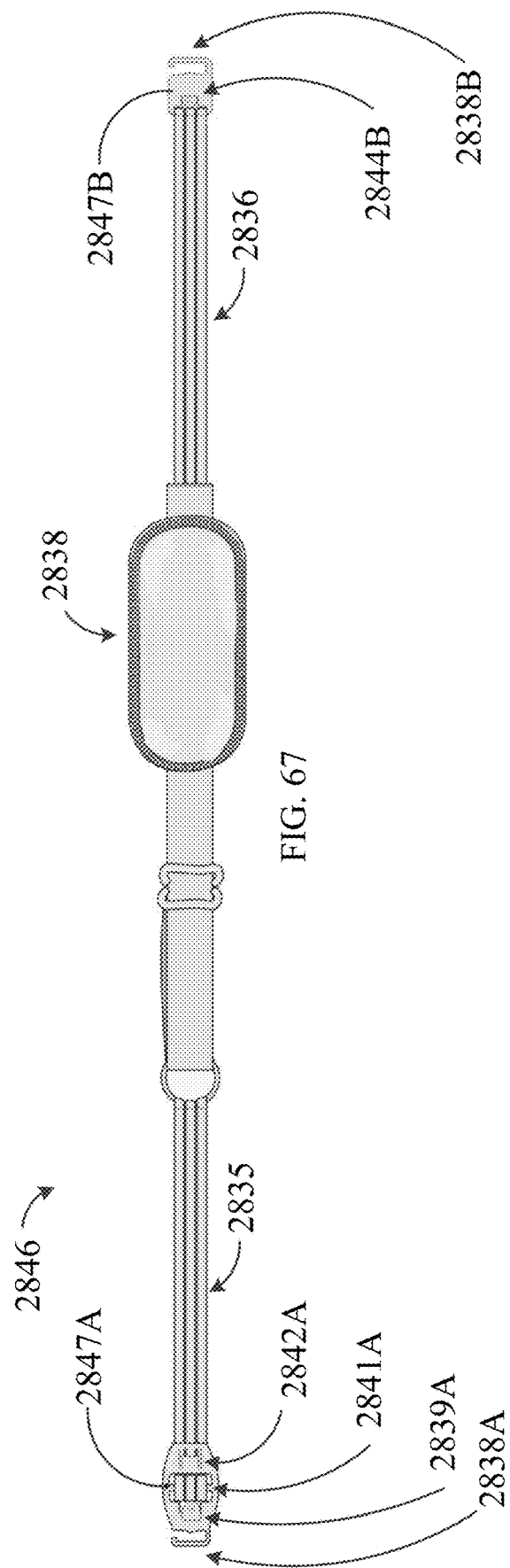
FIG. 67 is a top view of a neck strap, according to an embodiment.

In some embodiments, the first coupling member and the second coupling member can include both features of the engagement mechanisms described herein and swan hooks. FIG. 67 shows a top view of a neck strap 2846. The neck strap 2846 can be the same or similar in structure and/or function to any of the neck straps described herein, such as the neck strap 2646. For example, the neck strap 2846 can include a first coupling member 2847A, a second coupling member 2847B, a first strap portion 2835, a second strap portion 2836, and an adjustable strap portion 2838. The first strap portion 2835, the second strap portion 2836, and the adjustable strap portion 2838 can be the same or similar in structure and/or function to the first strap portion 2635, the second strap portion 2636, and the adjustable strap portion 2638 described above with respect to the neck strap 2646. The first coupling member 2847A and the second coupling member 2847B can include the same features as the first coupling member 2647A and the second coupling member 2647B described above. For example, as shown in FIG. 67, the first coupling member 2847A includes an engagement portion 2839A, a securement bar 2841A, and a tab portion 2842A. The engagement portion 2839A can be the same or similar in structure and/or function to the extension portion 485 of the engagement mechanism 450 described above. The securement bar 2841A can be the same or similar in structure and/or function to the securement bar 498 of the engagement mechanism 450 described above. The tab portion 2842A can be the same or similar in structure and/or function to the tab portion 453 of the engagement mechanism 450 described above. The second coupling member 2847B includes an extension portion 2844B that can be the same or similar in structure and/or function to the extension portion 451 of the engagement mechanism 450 described above.

Additionally, the first coupling member 2847A can include a first swan hook 2838A extending from an end of the first coupling member 2847A and the second coupling member 2847B can include a second swan hook 2838B extending from an end of the second coupling member 2847A. The first swan hook 2838A can be molded onto the end of the first coupling member 2847A such that the first swan hook 2838A and the first coupling member 2847A are formed as one piece. The second swan hook 2838B can be molded onto the end of the second coupling member 2847B such that the second swan hook 2838B and the second coupling member 2847B are formed as one piece.

Figure 68:
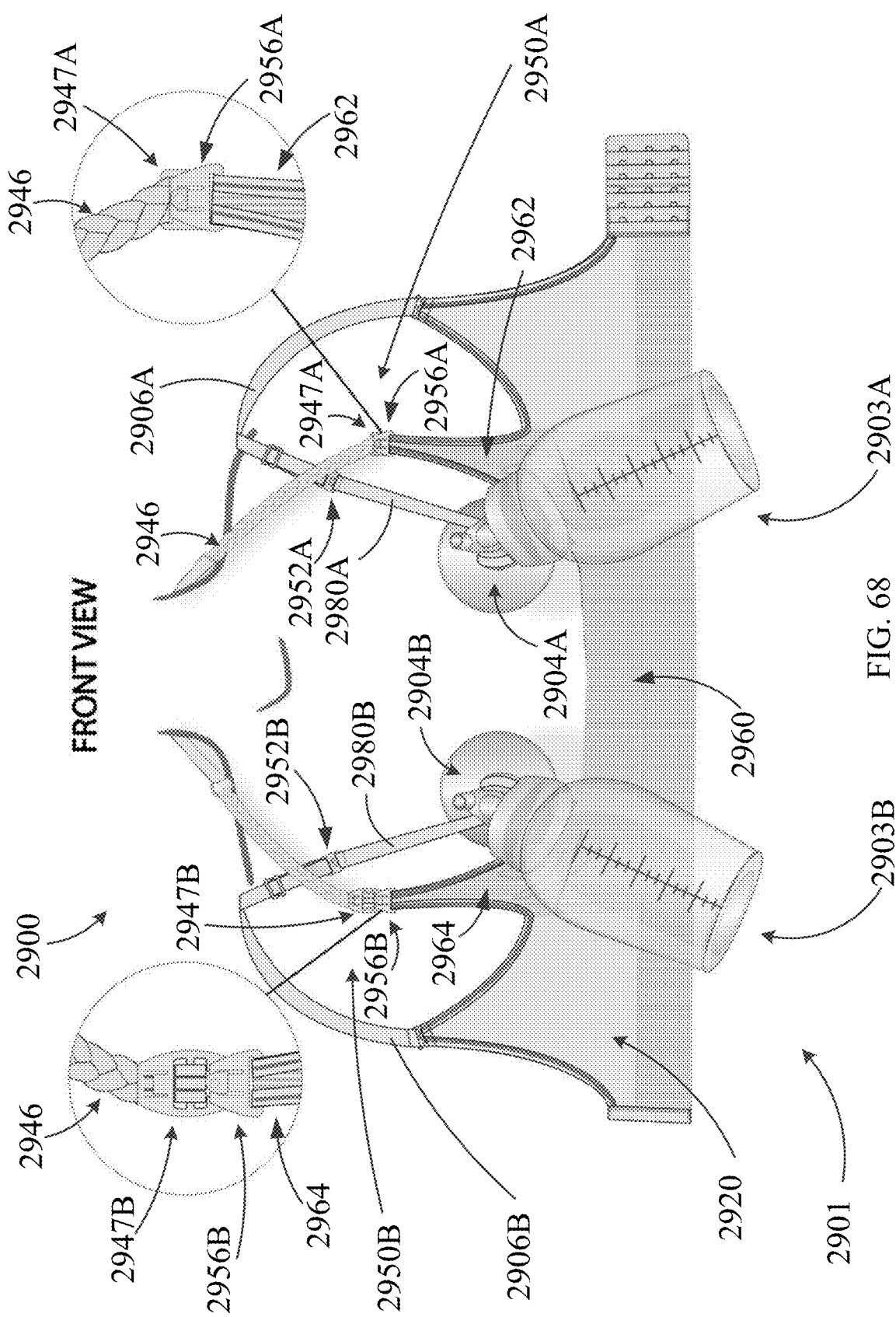
FIG. 68 is a front view of a garment in a configuration in which the garment is supporting a first breast pump and a second breast pump.
Figure 69:
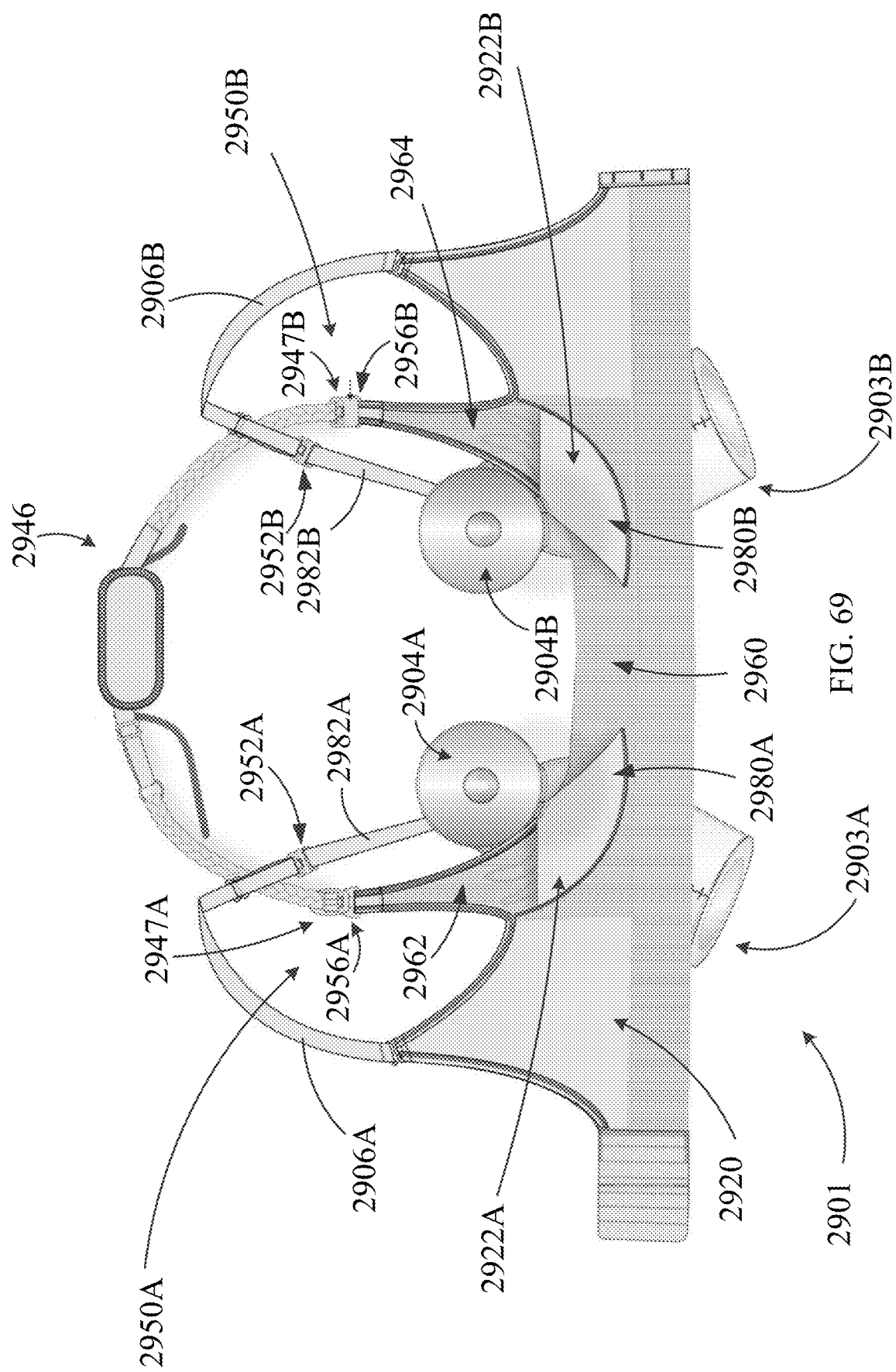
FIG. 69 is a back view of the garment of FIG. 68 in the configuration in which the garment is supporting the first breast pump and the second breast pump.

FIGS. 68 and 69 are a front view and a back view, respectively, of a garment 2900 shown in a second configuration in which the garment 2900 is supporting a first breast pump 2903A and a second breast pump 2903B. The garment 2900 can be the same or similar in structure and/or function to any of the garments described herein. For example, the garment 2900 includes a base subassembly 2901 including a back panel 2920, an outer panel 2960, a first shoulder strap 2906A, a second shoulder strap 2906B, a first support strap 2980A, and a second support strap 2980B. The garment 2900 can optionally include an inner or pumping panel (not shown) that can be removeable and can be the same or similar in structure and/or function to any of the inner panels described herein. The garment 2900 also includes a first engagement mechanism 2950A and a second engagement mechanism 2950B. The first engagement mechanism 2950A and the second engagement mechanism 2950B can each be any suitable engagement mechanism (e.g., a two part engagement mechanism, a three part engagement mechanism, etc.). In some embodiments, the first engagement mechanism 2950A and the second engagement mechanism 2950B can be similar in structure and/or function to any of the engagement mechanisms described herein (e.g., the engagement mechanism 450 or the engagement mechanism 750). The first engagement mechanism 2950A can include a first portion 2952A and the second engagement mechanism 2950B can include a first portion 2952B that can each be the same or similar in structure and/or function to the first portion 452 of the engagement mechanism 450 described above with reference to FIGS. 7-10 and/or the first portion 752 of the engagement mechanism 750 described above with reference to FIGS. 15-17. The first engagement mechanism 2950A can include a second portion 2956A and the second engagement mechanism 2950B can include a second portion 2956B that can each be the same or similar in structure and/or function to the third portion 456 of the engagement mechanism 450 described above with reference to FIGS. 7-10 and/or the third portion 756 of the engagement mechanism 750 described above with reference to FIGS. 15-17. In embodiments including an inner or pumping panel, the first engagement mechanism 2950A and the second engagement mechanism 2950B and/or the inner or pumping panel can include another portion that may be the same or similar in structure and/or function to the second portion 454 of the second portion 754 described above.

The first support strap 2980A and the second support strap 2980B can be the same or similar in structure and/or function to any of the support straps described herein. For example, the first support strap 2980A includes an adjustable portion 2982A and a base portion 2922A. The second support strap 2980B includes an adjustable portion 2982B and a base portion 2922B. The adjustable portion 2982A is coupled to the first portion 2952A of the engagement mechanism 2952A and the adjustable portion 2982B is coupled to the first portion 2952B of the engagement mechanism 2952B.

As shown in FIG. 68, the garment 2900 includes a neck strap 2946. The neck strap 2946 can be the same or similar in structure and/or function to any of the neck straps described herein, such as the neck strap 2446 shown and described with respect to FIG. 63. For example, the neck strap 2946 includes a first coupling member 2947A and a second coupling member 2947B, which can be the same or similar in structure and/or function to the first coupling member 2447A and the second coupling member 2447B described above. As shown in FIGS. 68 and 69, the first coupling member 2947A can be configured to engage with the second portion 2956A of the first engagement mechanism 2950A and the second coupling member 2947B can be configured to engage with the second portion 2956B of the second engagement mechanism 2950B.

The outer panel 2960 includes a left outer panel 2962 and a right outer panel 2964 (each also referred to herein as a "cup portion"). The left outer panel 2962 is attached to the second portion 2956A of the first engagement mechanism 2950A (e.g., at an apex of the left outer panel 2962) and the right outer panel 2964 is attached to the second portion 2956B of the second engagement mechanism 2950B (e.g., at an apex of the right outer panel 2964).

In a first configuration, the neck strap 2946 can be separate from the base subassembly 2901. For example, the neck strap 2946 can be stored in a bag or worn as a bracelet (e.g., via coupling the first coupling member 2947A to the second coupling member 2947B). In the first configuration, the first portion 2952A is coupled to the second portion 2956A of the first engagement mechanism 2950A and the second portion 2952B is coupled to the second portion 2956B of the second engagement mechanism 2950B. Thus, the first shoulder strap 2906A supports the left outer panel 2962 and the first support strap 2980A and the second shoulder strap 2906B supports the right outer panel 2964 and the second support strap 2980B.

To transition the garment 2900 from a first configuration in which the garment 2900 is not supporting a breast pump to the second configuration in which the garment 2900 is supporting a first breast pump 2903A and a second breast pump 2903B, the second portion 2956A can be uncoupled from the first portion 2952A of the first engagement mechanism 2950A and the second portion 2956B can be uncoupled from the first portion 2952B of the second engagement mechanism 2950B such that the outer panel 2960 can be folded down or moved out of the way relative to the first support strap 2980A and the second support strap 2980B.

The first support strap 2980A and the second support strap 2980B can be adjusted in length as needed to support the first breast pump 2903A and the second breast pump 2903B, respectively. For example, the first adjustable portion 2982A can be adjusted such that the length of the first support strap 2980A is increased and/or the second adjustable portion 2982B can be adjusted such that the length of the second support strap 2980B is increased. The first support strap 2980A can be wrapped partially or fully around a portion 2904A of the breast pump 2903A (e.g., a flange of a shield of a breast pump). For example, the first support strap 2980A can be wrapped a full turn around the portion 2904A as shown in FIG. 68 and then the portion 2904A can be place against the left breast of the wearer. Alternatively, the first support strap 2980A can wrapped only partially around the portion 2904A (similarly to the support strap 1280 shown in FIG. 36) by pulling a portion of the first support strap 2980A toward a center of the user's chest, placing the portion 2904A of the first breast pump 2903A against the left breast of the wearer, and then placing the portion of the first support strap 2980A against the portion 2904A to support the first breast pump 2903A. The second support strap 2980B can be wrapped partially or fully around a portion 2904B of the breast pump 2903B (e.g., a flange of a shield of a breast pump). For example, the second support strap 2980B can be wrapped a full turn around the portion 2204B as shown in FIG. 68 and then the portion 2904B can be place against the right breast of the wearer. Alternatively, the second support strap 2980B can be wrapped only partially around the portion 2904B (similarly to the support strap 1280 shown in FIG. 36) by pulling a portion of the second support strap 2980B toward a center of the user's chest, placing the portion 2904B of the second breast pump 2903B against the right breast of the wearer, and then placing the portion of the second support strap 2980B against the portion 2904B to support the second breast pump 2903B.

The second portion 2956A of the first engagement mechanism 2950A can be coupled to the first coupling member 2947A of the neck strap 2946 and the second portion 2956B of the second engagement mechanism 2950B can be coupled to the second coupling member 2947B of the neck strap 2946 such that the neck strap 2946 supports the left outer panel 2962 and the right outer panel 2964. A portion of the neck strap 2946 can be arranged to be disposed behind the neck of the wearer before or after coupling the first coupling member 2947A and/or the second coupling member 2947B to the second portion 2956A and the second portion 2956B, respectively. Additionally, the length of the neck strap 2946 (e.g., the length between the first coupling member 2947A and the second coupling member 2947B) can be adjusted before or after coupling the first coupling member 2947A and/or the second coupling member 2947B to the second portion 2956A and the second portion 2956B, respectively.

In the second configuration of the garment 2900, the first support strap 2980A and the left outer panel 2962 can maintain the portion 2904A of the breast pump 2903A against the breast of the wearer such that the flange of the breast pump 2903B is sealed properly against the breast of the user. In some embodiments, the portion 2904A can be disposed between the first support strap 2980A and the left outer panel 2962 such that the first support strap 1980A and the left outer panel 1962 collectively support the breast pump 1903A against the wearer's left breast for a hands free pumping procedure.

The second support strap 2980B and the right outer panel 2964 can maintain the portion 2904B of the breast pump 2903B against the breast of the wearer such that the flange of the breast pump 2903B is sealed properly against the breast of the user. In some embodiments, the portion 2904B can be disposed between the second support strap 2980B and the right outer panel 2964 such that the second support strap 2980B and the right outer panel 2964 collectively support the breast pump 2903B against the wearer's right breast for a hands-free pumping procedure.

Although FIGS. 68 and 69 show the garment 2900 supporting two breast pumps simultaneously, in some embodiments, the wearer can use the garment 2900 to support only one breast pump at a time. For example, the garment 2900 can be used to support only the first breast pump 2903A, and the second support strap 2980B can remain in a first configuration in which the adjustable portion 2982B is shorter than in a pumping configuration in which the second support strap 2980B is used to support the second breast pump 2903B.

Figure 70:
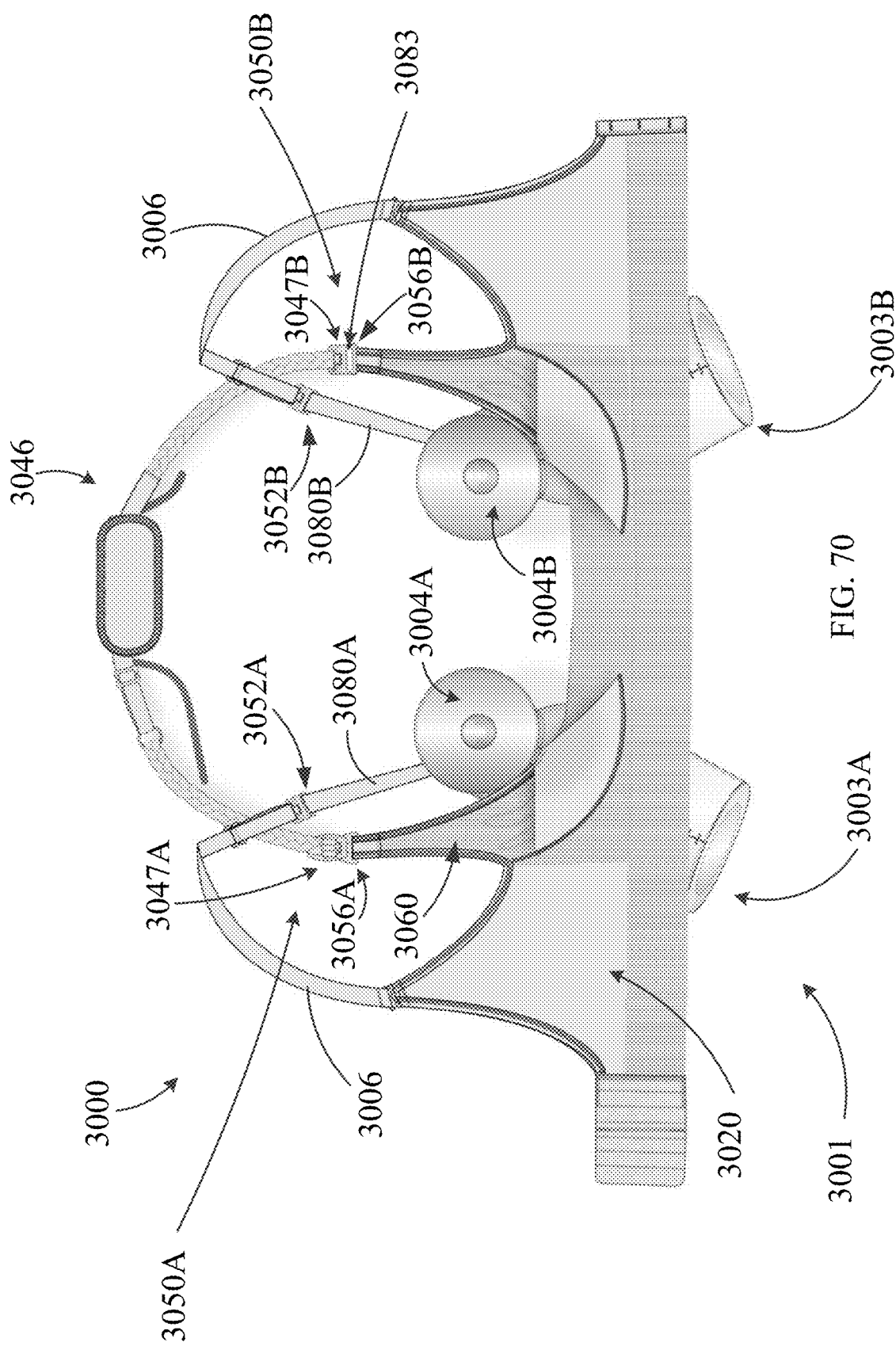
FIG. 70 is a back view of a garment in a configuration in which the garment is supporting a first breast pump and a second breast pump.

Similarly as described above with respect to FIGS. 62 and 63, in some embodiments, as shown in FIG. 69, the second coupling member 2947B can be the same as the first portion 452 of the engagement mechanism 450 described above except that the second coupling member 2947B optionally does not define an opening such as the opening 483. In some embodiments, the second coupling member can be identical to the first portion 452 of the engagement mechanism 450 or the first portion 752 of the engagement mechanism 450 described above such that fewer distinct types of clasp portions are needed for construction of the garment. For example, FIG. 70 is a back view of a garment 3000 shown in a second configuration in which the garment 3000 is supporting a first breast pump 3003A and a second breast pump 3003B. The garment 3000 can be the same or similar in structure and/or function to any of the garments described herein. For example, the garment 300 includes a base subassembly 3001 including a back panel 3020, an outer panel 3060, a first shoulder strap 3006A, a second shoulder strap 3006B, a first support strap 3080A, and a second support strap 3080B. The garment 3000 can optionally include an inner or pumping panel (not shown) that can be removeable and can be the same or similar in structure and/or function to any of the inner panels described herein. The garment 3000 also includes a first engagement mechanism 3050A and a second engagement mechanism 3050B. The first engagement mechanism 3050A and the second engagement mechanism 3050B can each be any suitable engagement mechanism (e.g., a two part engagement mechanism, a three part engagement mechanism, etc.). In some embodiments, the first engagement mechanism 3050A and the second engagement mechanism 3050B can be similar in structure and/or function to any of the engagement mechanisms described herein (e.g., the first engagement mechanism 2950A and/or the second engagement mechanism 2950B). The engagement mechanism 3050A can include a first portion 3052A and the engagement mechanism 3050B can include a first portion 3052B that can each be the same or similar in structure and/or function to the first portion 2952A and/or the first portion 2952B described above with respect to the garment 290. The engagement mechanism 3050A can include a second portion 3056A and the engagement mechanism 3050B can include a second portion 3056B that can each be the same or similar in structure and/or function to the second portion 2956A and/or the second portion 2956B described above with respect to the garment 2900.

The garment 3000 includes a neck strap 3046. The neck strap 3046 can be the same or similar in structure and/or function to any of the neck straps described herein, such as the neck strap 2946 shown and described with respect to the garment 2900. For example, the neck strap 3046 includes a first coupling member 3047A and a second coupling member 3047B, which can be the same or similar in structure and/or function to the first coupling member 2947A and the second coupling member 2947B described above. As shown in FIG. 70, the first coupling member 3047A can be configured to engage with the second portion 3056A of the first engagement mechanism 3050A and the second coupling member 3047B can be configured to engage with the second portion 3056B of the second engagement mechanism 3050B. As also shown in FIG. 70, the second coupling member 3047B can define an opening 3083 such that the second coupling member 3047B is identical to the first portion 3052B of the engagement mechanism 3050B, thereby requiring fewer distinctly shaped parts to be needed to manufacture the garment 3000 (e.g., fewer distinct molds may be needed to manufacture the individual components for each garment 3000).

Figure 72:
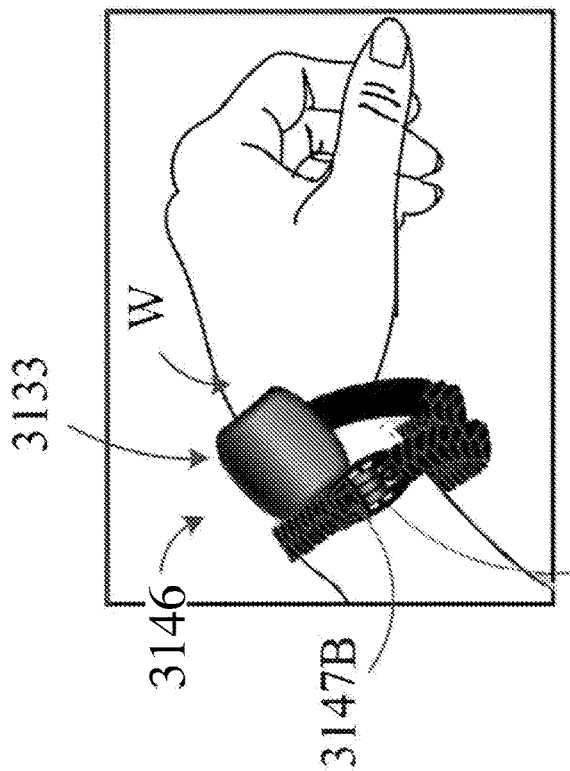
FIGS. 71 and 72 are perspective views of a neck strap worn as a bracelet on a wrist of a wearer, according to an embodiment.
Figure 71:
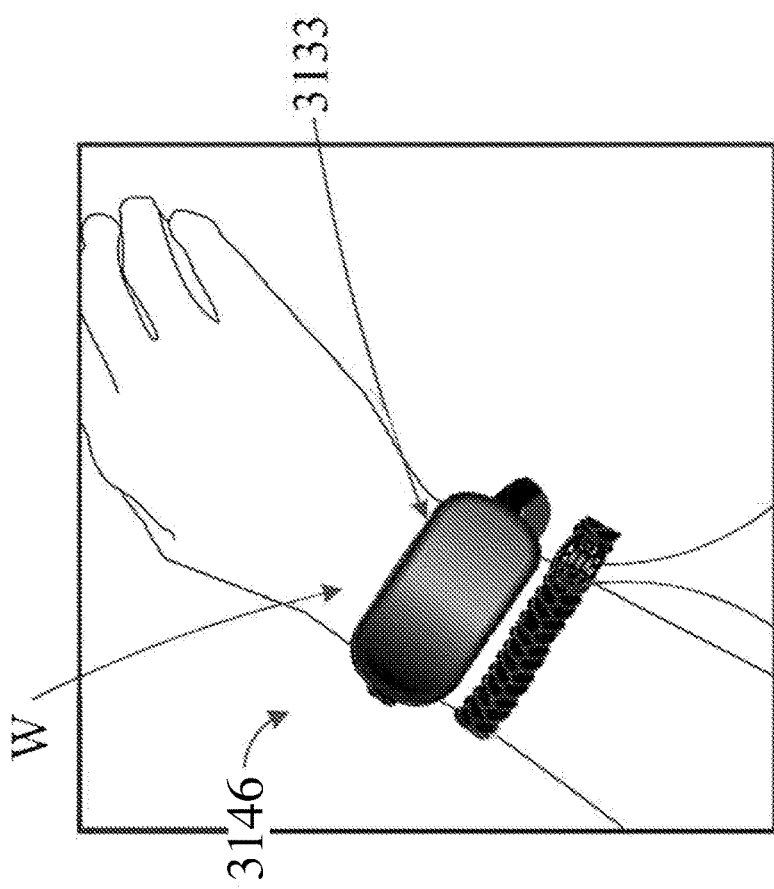

FIGS. 71 and 72 each show a neck strap 3146 worn in a bracelet configuration around a wrist of a user. The neck strap 3146 can be the same or similar in structure and/or function to any of the neck straps described herein, such as the neck strap 2446 shown in FIG. 63. For example, the neck strap 3146 includes a first coupling member 3147A, a second coupling member 3147B, and a neck pad 2333. The neck strap 3146 is shown wrapped around the user's wrist W with two turns and the first coupling member 3147A coupled to the second coupling member 3147B. The neck strap 3146 can be adjusted in length (e.g., as described with respect to the other neck straps herein) prior to wearing the neck strap 3146 as a bracelet such that the neck strap 3146 is secured and comfortable around the wrist W. For example, after wearing the neck strap 3146 in conjunction with a pumping procedure, the neck strap 3146 can be shortened in length, wrapped around the wrist W, and the first coupling member 3147A can be coupled to the second coupling member 3147B. To transition the neck strap 3146 to a pumping configuration to support a pumping panel or an outer panel of a garment as described herein, the first coupling member 3147A can be decoupled from the second coupling member 3147B, the neck strap 3146 can be adjusted if needed, and the first coupling member 3147A and the second coupling member 3147B can be coupled to complementary components of the garment.

Figure 73:
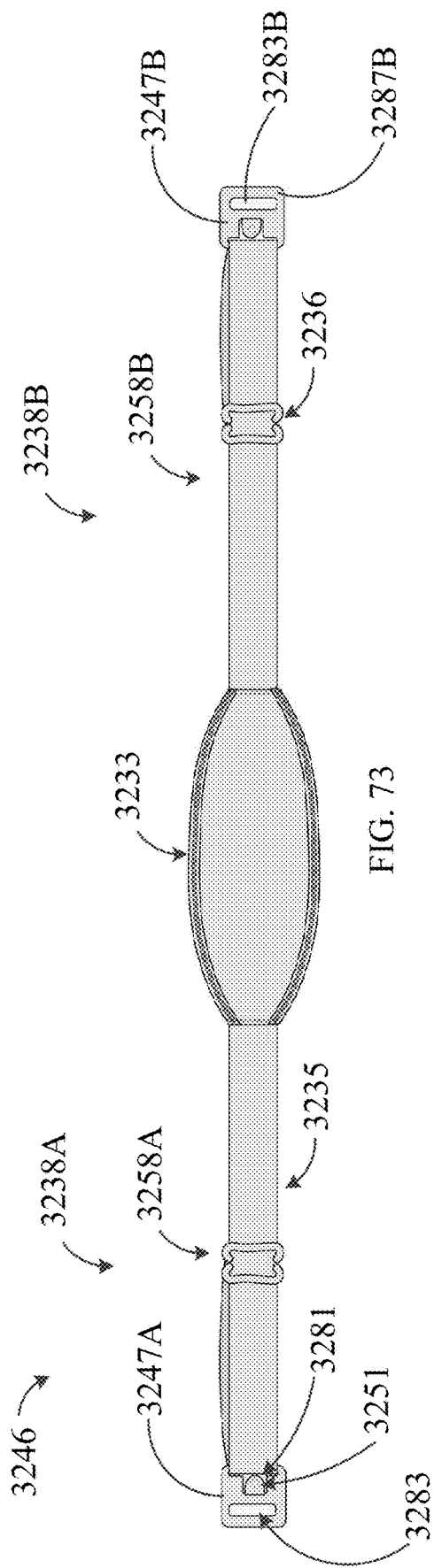
FIG. 73 is a top view of a neck strap, according to an embodiment.

FIG. 73 is a top view of a neck strap 3246. The neck strap 3246 can be the same or similar in structure and/or function any of the neck straps described herein. For example, the neck strap 3246 can include a first coupling member 3247A and a second coupling member 3247B. The neck strap 3246 includes a first adjustable strap portion 3238A, a second adjustable strap portion 3238B, and a neck pad 3233. The first coupling member 3247A is coupled to the neck pad 3233 via the first adjustable strap portion 3238A and the second coupling member 3247B is coupled to the neck pad 3233 via the second adjustable strap portion 3238B.

Each of the first adjustable strap portion 3238A and the second adjustable strap portion 3238B can be the same or similar in structure and/or function to the adjustable strap portion 2358 described above with respect to FIG. 62. For example, the first adjustable strap portion 3238A includes a strap 3235 and a slider 3258A. The strap 3235 has a first end coupled to the neck pad 3233 and a second end coupled to the slider 3258A. The slider 3258A is configured to maintain a position of the second end of the strap 3235 relative to a portion of the strap 3235 that is threaded through the slider 3258A such that a portion of the strap 3235 forms a loop extending through a first opening 3281 of the first coupling member 3247A. The second adjustable strap portion 3258B can be the same or similar in structure and/or function to the first adjustable strap portion 3258A. For example, the second adjustable strap portion 3258B includes a strap 3236 and a slider 3258B. The strap 3236 has a first end coupled to the neck pad 3233 and a second end coupled to the slider 3258B. The slider 3258B is configured to maintain a position of the second end of the strap 3236 relative to a portion of the strap 3236 that is threaded through the slider 3258B such that a portion of the strap 3236 forms a loop extending through an opening of the second coupling member 3247B.

In some embodiments, although not shown, the neck strap 3246 can include one strap portion that couples the first coupling member 3247A to the second coupling member 3247B and has one or two adjustable portions (e.g., a slider coupled to one or both ends). The neck pad 3233 can be slidable along the strap or secured to the strap. In some embodiments, the neck pad 3233 can be optional or not included.

The first coupling member 3247A and the second coupling member 3247B can be the same or similar in structure and/or function to the first portion 452 of the engagement mechanism 450 described above or to the first portion 752 of the engagement mechanism 750 described above. For example, the first coupling member 3247A can include the first opening 3281, an extension portion 3251, and a second opening 3283. The extension portion 3251 can be hook-shaped and define a slot. The second coupling member 3247B can be the same or similar in structure and/or function to the first coupling member 3247A. Both the first coupling member 3247A and the second coupling member 3247B can be releasably engageable with a portion of an engagement mechanism coupled to an outer panel of a garment. For example, both the first coupling member 3247A and the second coupling member 3247B can be releasably engageable with a portion of an engagement mechanism that is the same or similar in structure and/or function to the third portion 456 of the engagement mechanism 450 (e.g., the extension portion 3251 can be received by the opening 487 and the securement bar 487A can be received by the slot defined by the extension portion 3251). Thus, the first coupling member 3247A can be coupled to a portion of an engagement mechanism associated with (e.g., coupled to) a left outer panel and the second coupling member 3247B can be coupled to a portion of an engagement mechanism associated with (e.g., coupled to) a right outer panel (e.g., similarly as shown in FIG. 70 and described above with reference to the first coupling member 3047A and the second coupling member 3047B of the neck strap 3046) such that the neck strap 3246 forms a loop. When the loop formed by the neck strap 3246 is disposed around a wearer's neck, the neck strap 3246 can be used to support at least a portion of an outer panel of the garment (e.g., to support at least a portion of one or two breast pumps). In some embodiments, the first coupling member 3247A can be coupled to the second coupling member 3247A such that the neck strap 3246 can be worn as a bracelet as described with respect to FIGS. 71 and 72. For example, the extension portion 3251 of the first coupling member 3247A can be received by the opening 3283B of the second coupling member 3247B such that a securement bar 3283B of the second coupling member 3247B is received by the slot defined by the extension portion 3251.

In some embodiments, a neck strap can include a first coupling member configured to be engaged with a second coupling member and configured to be coupled to a portion of any of the engagement mechanisms described herein. For example, a first coupling member can be configured to be engaged with a complementary engagement mechanism portion, and a second coupling member can be configured to be engaged with the first coupling member such that the neck strap forms a loop and can support the engagement mechanism portion when the loop surrounds a wearer's neck. In some embodiments, the engagement mechanism portion can be coupled to a first portion of an outer panel (e.g., a left portion or a right portion) and the neck strap can support the first portion of the outer panel to collectively support a breast pump in conjunction with a support strap to pump milk from a first breast as described herein. Simultaneously, a baby can nurse from a second breast of the wearer without the second breast being obstructed by the neck strap or outer panel of the garment.

Figure 74:
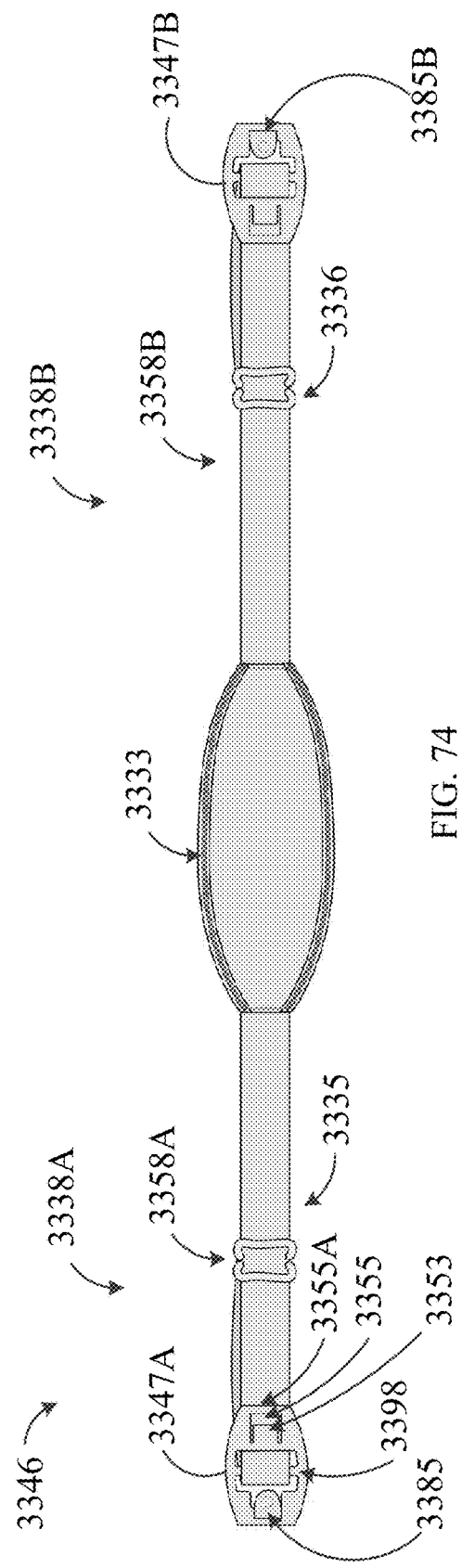
FIG. 74 is a top view of a neck strap, according to an embodiment.

FIG. 74 is a top view of a neck strap 3346. The neck strap 3346 can be the same or similar in structure and/or function any of the neck straps described herein, such as the neck strap 3246. For example, the neck strap 3346 can include a first coupling member 3347A and a second coupling member 3347B. The neck strap 3346 includes a first adjustable strap portion 3338A, a second adjustable strap portion 3338B, and a neck pad 3333. The first coupling member 3347A is coupled to the neck pad 3333 via the first adjustable strap portion 3338A and the second coupling member 3347B is coupled to the neck pad 3333 via the second adjustable strap portion 3338B.

Each of the first adjustable strap portion 3338A and the second adjustable strap portion 3338B can be the same or similar in structure and/or function to the adjustable strap portion 2358 described above with respect to FIG. 62. For example, the first adjustable strap portion 3338A includes a strap 3335 and a slider 3358A. The strap 3335 has a first end coupled to the neck pad 3333 and a second end coupled to the slider 3358A. The slider 3358A is configured to maintain a position of the second end of the strap 3335 relative to a portion of the strap 3335 that is threaded through the slider 3358A such that a portion of the strap 3335 forms a loop extending around a securement bar 3398 of the first coupling member 3347A. The second adjustable strap portion 3358B can be the same or similar in structure and/or function to the first adjustable strap portion 3358A. For example, the second adjustable strap portion 3358B includes a strap 3336 and a slider 3358B. The strap 3336 has a first end coupled to the neck pad 3333 and a second end coupled to the slider 3358B. The slider 3358B is configured to maintain a position of the second end of the strap 3336 relative to a portion of the strap 3336 that is threaded through the slider 3358B such that a portion of the strap 3336 forms a loop extending around a securement bar of the second coupling member 3347B.

The first coupling member 3347A and the second coupling member 3347B can be the same or similar in structure and/or function to the second portion 454 of the engagement mechanism 450 described above or to the second portion 754 of the engagement mechanism 750 described above. For example, the first coupling member 3347A can include an extension portion 3385, the securement bar 3398, and a tab portion 3353. The extension portion can be hook-shaped and define a slot. The second coupling member 3347B can be the same or similar in structure and/or function to the first coupling member 3347A. The first coupling member 3347A can be releasably engageable with a portion of an engagement mechanism coupled to an outer panel of a garment. For example, the first coupling member 3347A can be releasably engageable with a portion of an engagement mechanism that is the same or similar in structure and/or function to the third portion 456 of the engagement mechanism 450 (e.g., the extension portion 3385 can be received by the opening 487 and the securement bar 487A can be received by the slot defined by the extension portion 3385). The second coupling member 3347B can be releasably engageable with the first coupling member 3347B such that the extension portion of the second coupling member 3347B can be received by an opening 3353 of the first coupling member 3347A and the tab portion 3353 of the first coupling member 3347A snaps into locking engagement with the extension portion of the second coupling member 3347B. Thus, the first coupling member 3347A can be coupled to the portion of the engagement mechanism and the second coupling member 3347B can be coupled to the first coupling member 3347A such that the neck strap 3346 forms a loop. When the loop formed by the neck strap 3346 is disposed around a wearer's neck, the neck strap 3346 can be used to support at least a portion of an outer panel of the garment (e.g., to support at least a portion of a breast pump). In some embodiments, the first coupling member 3247A can be coupled to the portion of the engagement mechanism before or after coupling the second coupling member 3247A to the first coupling member 3247A.

Figure 75:
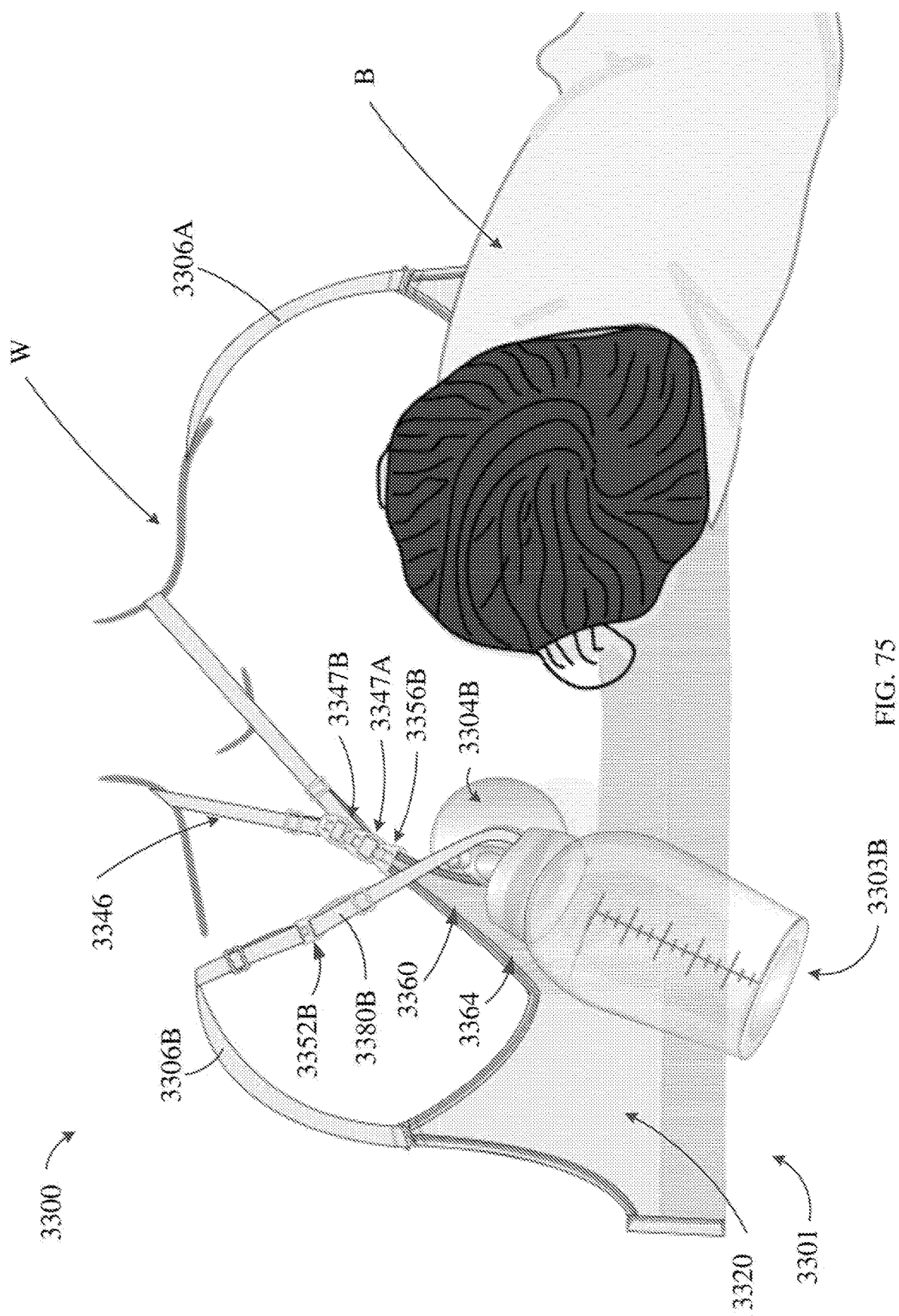
FIG. 75 is a front view of a garment including the neck strap of FIG. 74, according to an embodiment.

FIG. 75 is a front view of a garment 3300 in a configuration in which the garment 3300 is supporting a breast pump 3303B and the wearer W of the garment 330 can nurse a baby B simultaneously with pumping milk into the breast pump 3303B. The garment 3300 can be the same or similar in structure and/or function to any of the garments described herein, such as, for example, the garment 2900. For example, the garment 3300 includes a base subassembly 3301 including a back panel 3320, an outer panel 3360, a first shoulder strap 3306A, a second shoulder strap 3306B, a first support strap 3380A, and a second support strap (not shown). The garment 3300 also includes a first engagement mechanism including a first portion 3352B and a second portion 3356B. The garment 3300 can also include a second engagement mechanism (not shown). The first engagement mechanism and the second engagement mechanism can each be any suitable engagement mechanism (e.g., a two part engagement mechanism, a three part engagement mechanism, etc.). In some embodiments, the first engagement mechanism and the second engagement mechanism can be similar in structure and/or function to any of the engagement mechanisms described herein (e.g., the engagement mechanism 450 or the engagement mechanism 750). For example, the first portion 3352B and can be the same or similar in structure and/or function to the first portion 452 of the engagement mechanism 450 described above with reference to FIGS. 7-10 and/or the first portion 752 of the engagement mechanism 750 described above with reference to FIGS. 15-17. The second portion 3356B can be the same or similar in structure and/or function to the third portion 456 of the engagement mechanism 450 described above with reference to FIGS. 7-10 and/or the third portion 756 of the engagement mechanism 750 described above with reference to FIGS. 15-17.

As shown in FIG. 75, the outer panel 3360 includes a second panel portion 3364 (also referred to as a right outer panel) coupled to the second portion 3356B. The first coupling member 3347A is engaged with the second portion 3364 and the second coupling member 3347B is engaged with the first coupling member 3347A. For example, an extension portion 3385 of the first coupling member 3347A is received in an opening of the second portion 3356B and retaining a securement bar of the second portion 3356B in the slot defined by the extension portion 3385, and an extension portion 3385B of the second coupling member 3347B is received in an opening 3355 of the first coupling member 3347A and retaining a securement bar 3355A of the first coupling member 3347A in a slot defined by the extension portion 3385B. In some embodiments, one or both of the first coupling member 3347A and the second coupling member 3347B can be configured to engage with the second portion 3364 the same or similarly to the engagement between the second portion 454 and the third portion 456 described above with reference to FIGS. 7-10. In some embodiments, one or both of the first coupling member 3347A and the second coupling member 3347B can be configured to engage with each other the same or similarly to the engagement between the second portion 454 and the third portion 456 described above with reference to FIGS. 7-10. Thus, the second portion 3364 can supportively contact a portion 3304B of the breast pump 3303B and the support strap 3380B can supportively contact another portion 3304B of the breast pump 3303B such that the breast pump 3303B is supported between the support strap 3380B and the second panel portion 3364 and supported against the breast of the wearer for a pumping procedure while the baby B nurses from the other breast (e.g., after a first portion of the outer panel has been folded and/or pulled away from the other breast). In some embodiments, the first coupling member 3347A and the second coupling member 3347B can be interchangeable such that either can be coupled directly to the second portion 3356B or indirectly coupled to the second portion 3356B via the other.

In embodiments in which the garment 3300 includes an inner or pumping panel, the first engagement mechanism and the second engagement mechanism and/or the inner or pumping panel can include another portion that may be the same or similar in structure and/or function to the second portion 454 or the second portion 754 described above. The neck strap 3346 can be configured to support the inner or pumping panel by coupling the first coupling member 3347A to the portion of the first engagement mechanism or the second engagement mechanism coupled to the inner or pumping panel.

Although the first coupling member 3347A and the second coupling member 3347B are shown and described as being similar to or the same as the second portion 454 of the second portion 754 described above, in some embodiments any suitable type of complementary coupling member(s) having a first mating feature and a second complementary mating feature can be used in place of the first coupling member 3347A and/or the second coupling member 3347B and/or any suitable complementary coupling member having a complementary mating feature to a mating feature of the first coupling member 3347A can be used in place of the second portion 3356B. For example, the complementary coupling members can include hook and loop fasteners such as VELCRO, buttons, hooks, etc.

Figure 76:
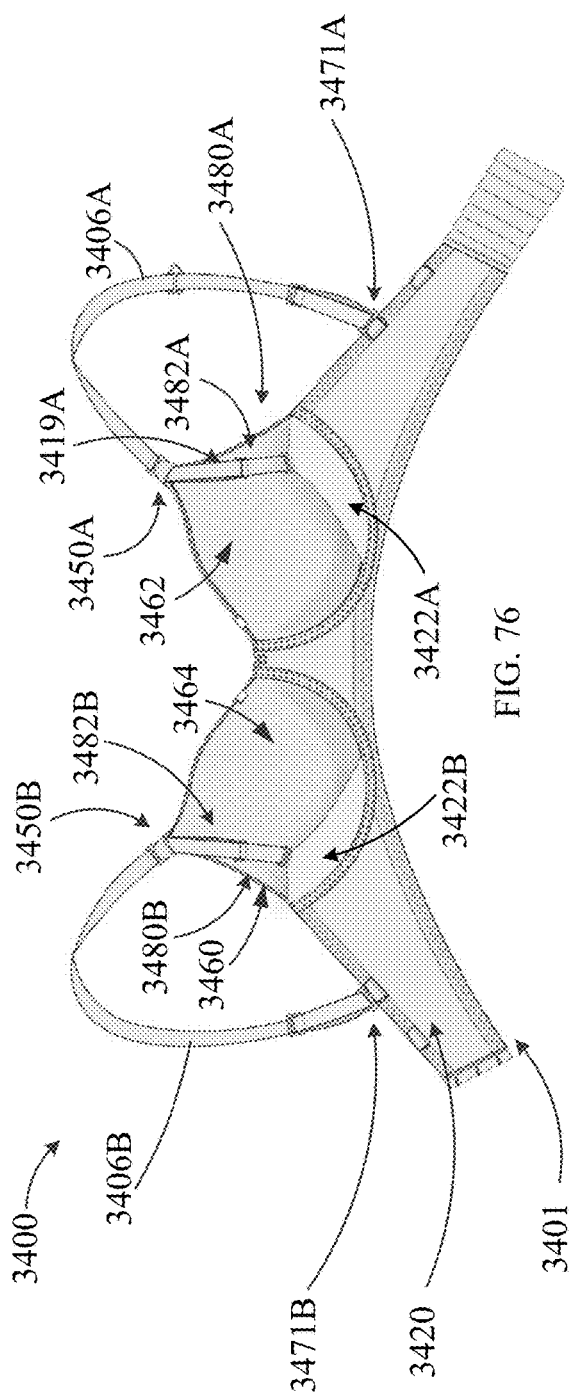
FIG. 76 is a back view of a garment, according to an embodiment.

In some embodiments, a support strap can be removable from and/or replaceable with respect to the remainder of the garment such that the garment can be worn without the support strap (e.g., when the wearer is no longer regularly pumping and/or nursing and/or if the support strap has stretched out and needs to be replaced). Additionally and/or alternatively, in some embodiments, shoulder straps can be replaced with shoulder straps configured to support an outer panel of the garment without using the same engagement mechanism as used to support the support strap. For example, FIG. 76 is a back view of a garment 340. The garment 3400 can be the same or similar in structure and/or function to any of the garments described herein. For example, the garment 3400 includes a base subassembly 3401 including a back panel 3420, an outer panel 3460, a first shoulder strap 3406A, a second shoulder strap 3406B, a first support strap 3480A, and a second support strap 3480B. The garment 3400 includes a first engagement mechanism 3450A and a second engagement mechanism 3450B that each can be similar in structure and/or function to any of the engagement mechanisms described herein (e.g., the engagement mechanism 450 or the engagement mechanism 750). The engagement mechanism 3450A can include a first portion 3452A (shown in FIG. 77) that can each be the same or similar in structure and/or function to the first portion 452 of the engagement mechanism 450 described above with reference to FIGS. 7-10 and/or the first portion 752 of the engagement mechanism 750 described above with reference to FIGS. 15-17. The engagement mechanism 3450A can include a second portion 3456A (shown in FIG. 78) coupled to the outer panel 3460 that can be the same or similar in structure and/or function to the third portion 456 of the engagement mechanism 450 described above with reference to FIGS. 7-10 and/or the third portion 756 of the engagement mechanism 750 described above with reference to FIGS. 15-17. The second engagement mechanism 3450B can be the same or similar in structure and/or function to the first engagement mechanism 3450A.

Figure 77:
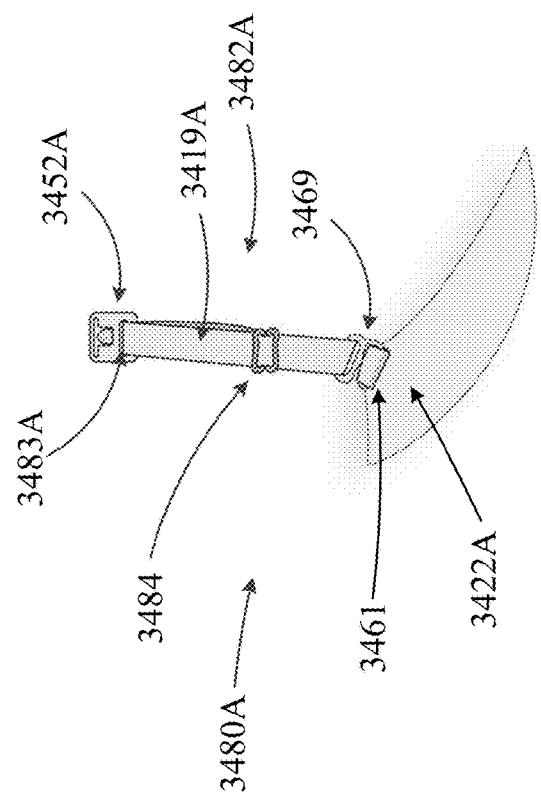
FIG. 77 is a front view of a portion of the garment of FIG. 76, according to an embodiment.

The first support strap 3480A includes an adjustable portion 3482A and a base portion 3422A. The second support strap 3480B can be the same or similar in structure and/or function to the first support strap 3480A. FIG. 77 is a front view of the first support strap 3480A in a configuration in which the adjustable portion 3482A is threaded through an opening 3483A of the first portion 3452A of the engagement mechanism 3450A and is coupled to the base portion 3422A. The adjustable portion 3482A includes a strap portion 3419A, a slider 3484, and a swan hook 3469.

Figure 79:
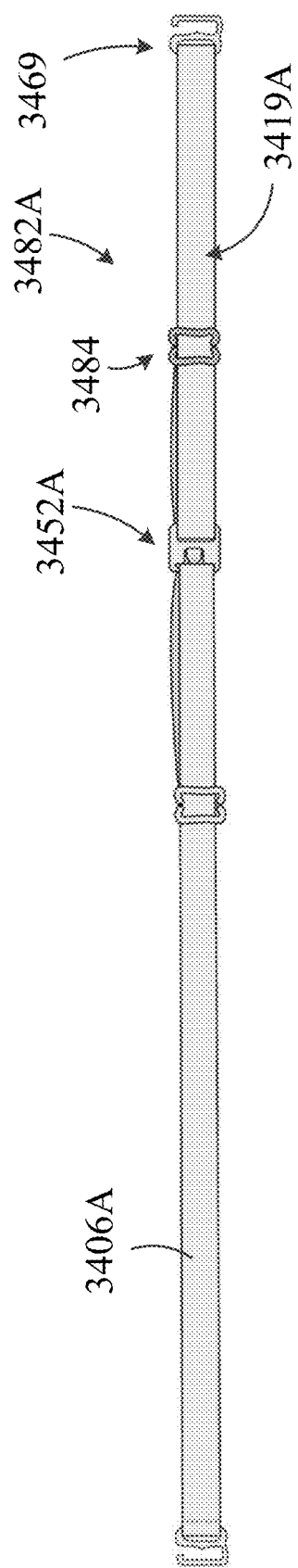
FIG. 79 is a top view of a portion of the garment of FIG. 76.

FIG. 79 is a top view of the first adjustable portion 3482A coupled to the first shoulder strap 3406A via the first portion 3452A of the engagement mechanism 3450A. A first end of the strap portion 3419A is coupled to the swan hook 3469. A second end of the strap portion 3419A can be coupled to the slider 3484 such that the strap portion 3419A forms a loop. The slider 3484 can be translated along the strap portion 3419A to change an overall length of the adjustable portion 3482A (e.g., to transition from a first non-pumping configuration to a second pumping configuration as described herein with respect to other support straps).

As shown in FIG. 77, the first base portion 3422A includes a loop portion 3461 (also referred to as a loop connector) configured to receive the swan hook 3469. Although the swan hook 3469 is shown and described as a swan hook, in some embodiments any suitable type of coupling member can be used in place of the swan hook 3469 and any suitable complementary coupling member can be used in place of the loop portion 3461. For example, the complementary coupling members can include hook and loop fasteners such as VELCRO, buttons, hooks, etc. Additionally, rather than including the slider 3484, the first adjustable portion 3482A and/or the second adjustable portion 3482B can include features of any of the adjustable support straps described herein such that the overall length of the support straps 3480A and 3480B can be adjusted as described with respect to any of the embodiments described herein.

Figure 78:
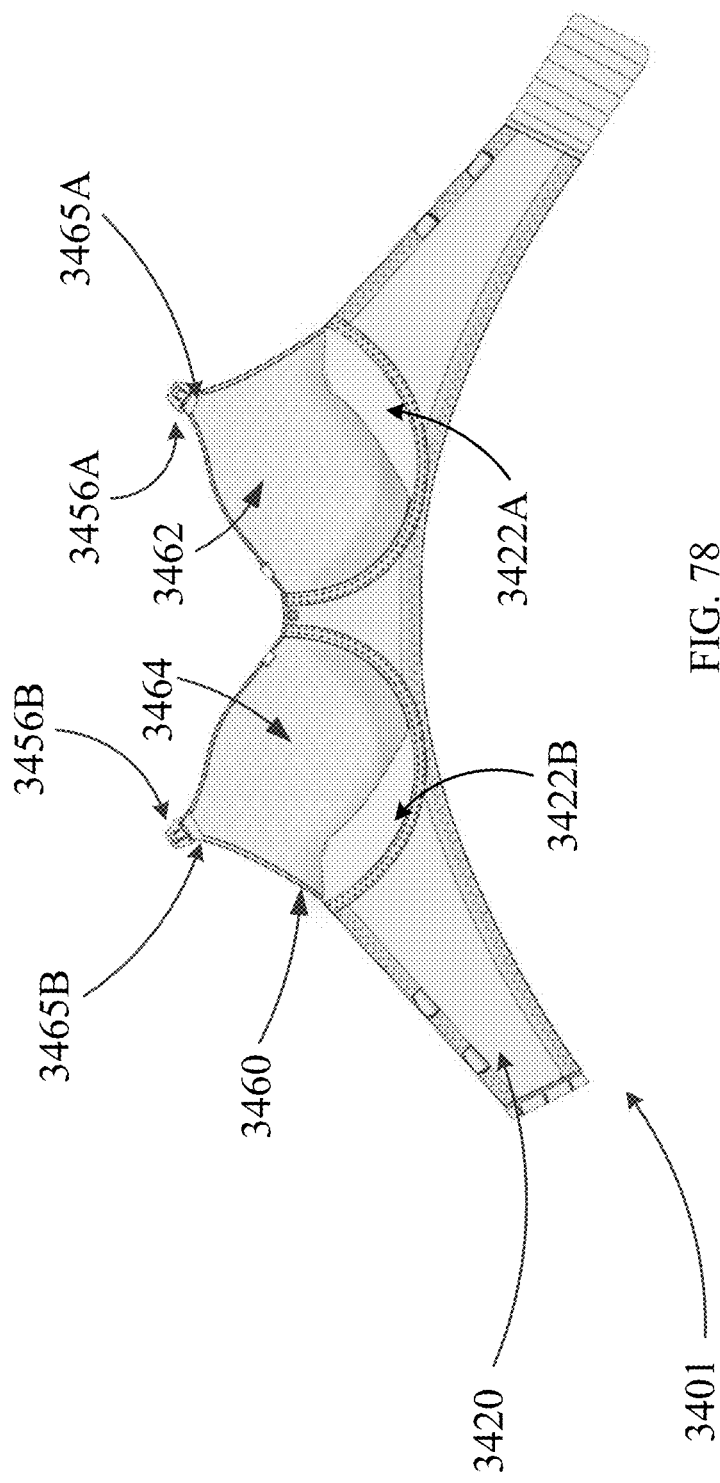
FIG. 78 is a back view of a portion of the garment of FIG. 76.

In some embodiments, a wearer may want to remove the first adjustable portion 3482A and the first portion 3452A of the first engagement portion 3452A so that the garment 3400 can be worn as a non-nursing bra. For example, FIG. 78 is a back view of a portion of the garment 3400 with the first adjustable portion 3482A decoupled from the second portion 3456A and the first base portion 3422A and the second adjustable portion 3482B decoupled from the second portion 3456B and the second base portion 3422B, respectively. Additionally, the first shoulder strap 3406A and the second shoulder strap 3406B are decoupled from the back panel 3420 and the outer panel 3460. In some embodiments, the garment 3400 can be transitioned from the configuration shown in FIG. 76 to the configuration shown in FIG. 78 by decoupling a coupling member 3471A (e.g., a swan hook) disposed on an end of the first shoulder strap 3406A from the base panel 3420 (e.g., from a loop or opening included or defined by the base panel 3420 such as loop portion 3473A), decoupling the swan hook 3469 from the base portion 3422A, and decoupling the first portion 3452A from the second portion 3456A (if needed). Thus, in some embodiments, the first shoulder strap 3406A and the first adjustable portion 3482A can be removed and maintained in the configuration shown in FIG. 79. The second shoulder strap 3406B and the second adjustable portion 3482B can be decoupled similarly (e.g., via decoupling the coupling member 3471B (e.g., a swan hook) from the base panel 3420 and decoupling the adjustable portion 3482B from the base portion 3422B).

Figure 80:
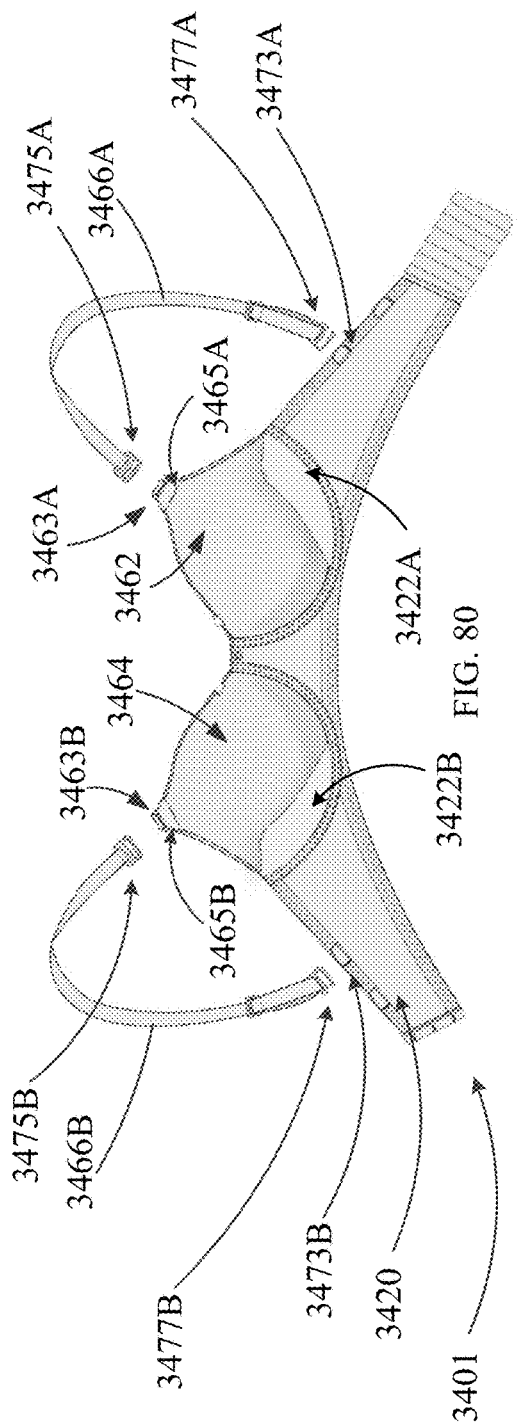
FIG. 80 is a back view of the garment of FIG. 76 in a configuration prior to new strap portions being attached, according to an embodiment.

As shown in FIG. 78, after removal of the first shoulder strap 3406A, the first adjustable portion 3482A, the second shoulder strap 3406B, and the second adjustable portion 3482B, the second portion 3465A and the second portion 3456A and the second portion 3456B remain coupled to the first portion 3462 and the second portion 3464 of the outer panel 3460, respectively. The first portion 3462 can include a first concealment pocket 3465A near the apex of the first portion 3462 and the second portion 3464 can include a second concealment pocket 3465B near the apex of the second portion 3464. As shown in FIG. 80, the second portion 3456A can be configured to be rotated into a space defined by the first concealment pocket 3465A and the second portion 3456B can be configured to be rotated in a space defined by the second concealment pocket 3465B such that the second portion 3456A and the second portion 3456B are each secured relative to the first portion 3462 and the second portion 3464, respectively. In some embodiments, the space defined by the first concealment pocket 3465A can be defined by the first concealment pocket 3465A and an inner surface of the right outer panel 3462. In some embodiments, the space defined by the first concealment pocket 3465A can be closed along on a bottom edge of the first concealment pocket 3465A. In some embodiments, the space defined by the first concealment pocket 3465A for receiving a portion of the second portion 3456A and securing the second portion 3465A can be defined entirely by the first concealment pocket 3465A (e.g., the first concealment pocket can include an inner portion and an outer portion and the second portion 3456A can be tucked between the inner portion and the outer portion). In some embodiments, the first concealment pocket 3465A can include or be formed as a strap (e.g., an elastic strap) extending from a first edge of the right outer panel 3462 to a second edge of the right outer panel 3462 and the space defined by the first concealment pocket 3465A can be open along a bottom edge of the first concealment pocket 3465A. The strap can be configured to secure the second portion 3456A between the strap and an inner surface of the right outer panel 3462. The second concealment pocket 3465B can be the same or similar in structure and/or function to the first concealment pocket 3465A.

Figure 81:
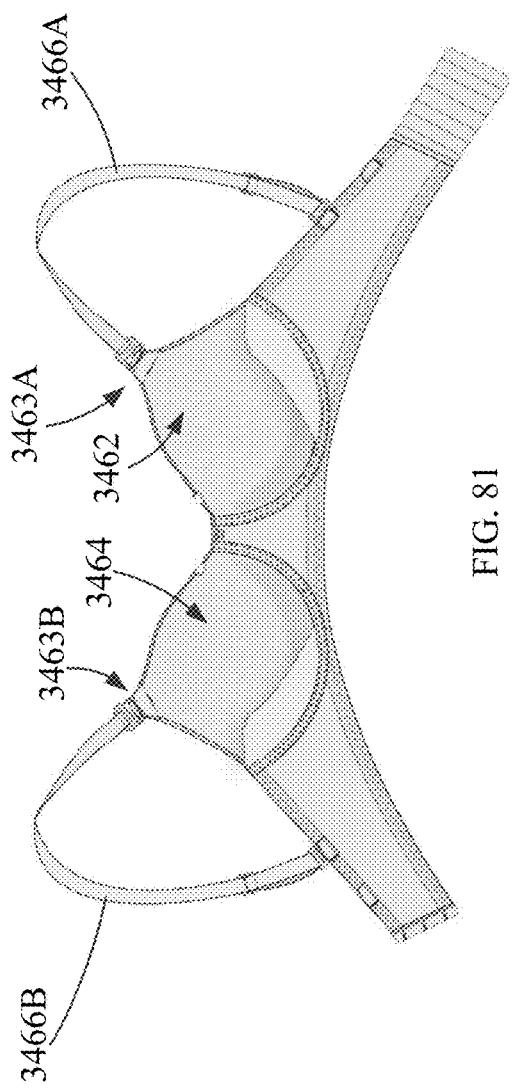
FIG. 81 is a back view of the garment of FIG. 80 with the new strap portions attached.

As shown in FIG. 80, which shows the second portion 3456A and the second portion 3456B tucked into the first concealment pocket 3465A and the second concealment pocket 3465B, respectively, the first portion 3462 can include a first loop portion 3463A (also referred to as a loop connector) at an apex of the first portion 3462. The second portion 3464 can include a second loop portion 3463B (also referred to as a loop connector) at an apex of the second portion 3464. As shown in FIGS. 80 and 81, a shoulder strap 3466A having coupling members (e.g., swan hooks) at both ends can be coupled to the first loop portion 3463A via a first coupling member 3475A and can be coupled to a loop portion 3473A (also referred to as a loop connector) of the base panel 3420 via a second coupling member 3477A on an opposite end of the shoulder strap 3466A from the first coupling member 3475A. A shoulder strap 3466B having coupling members (e.g., swan hooks) at both ends can be coupled to the second loop portion 3463B via a first coupling member 3475B and can be coupled to a loop portion 3473B (also referred to as a loop connector) of the base panel 3420 via a second coupling member 3477B on an opposite end of the shoulder strap 3466B from the first coupling member 3475B. Thus, the garment 3400 can be worn by the wearer in the configuration shown in FIG. 81 when pumping access and pumping support of a breast pump is not needed.

If the wearer desires to convert the garment 3400 back to a pumping and/or nursing configuration, the wearer can detach the first shoulder strap 3466A and the second shoulder strap 3466B via detaching the first coupling member 3475A, the second coupling member 3477A, the first coupling member 3475B, and the second coupling member 3475B from the outer panel 3460 and the base panel 3420. The second portion 3456A and the second portion 3456B can be rotated out of the respective concealment pockets 3465A and 3465B. The first shoulder strap 3406A and the first adjustable portion 3482A (or alternative similar or identical components) and the second shoulder strap 3406B and the second adjustable portion 3482B (or alternative similar or identical components) can be recoupled to the base subassembly of the garment 3400. For example, the coupling member 3471A of the first shoulder strap 3406A can be coupled to the loop portion 3473A of the base panel 3420 and the swan hook 3469 can be coupled to the base portion 3422A (e.g., threaded through the loop portion 3461 of the base portion 3422A). The first portion 3452A of the engagement mechanism 3450A can be coupled to the second portion 3456A such that the apex of the right outer panel 3462 is secured to the first shoulder strap 3406A. The second shoulder strap 3406B and the second adjustable portion 3482B can be recoupled similarly (e.g., via recoupling the coupling member 3471B (e.g., a swan hook) to the loop portion 3473B of the base panel 3420, recoupling the adjustable portion 3482B to the base portion 3422B, and coupling the first portion 3452A to the second portion 3456A).

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination and/or sub-combination, except mutually exclusive combinations. The embodiments described herein can include various combinations and/or sub-combinations of the functions, components and/or features of the different embodiments described.

The invention claimed is:

1. A garment, comprising:
a back panel;
a shoulder strap having a first end and a second end, the first end coupled to the back panel; and
a support strap having a first end coupled to the back panel, the support strap coupled to the second end of the shoulder strap via an engagement mechanism, the support strap configured to be transitioned between a first configuration and a second configuration, the support strap having a first length between the first end of the support strap and the engagement mechanism in the first configuration, the support strap having a second length greater than the first length between the first end of the support strap and the engagement mechanism in the second configuration such that the support strap can be disposed in supportive contact with a portion of a breast pump disposed against a breast of the wearer to hold the breast pump against the breast of the wearer.

2. The garment of claim 1, wherein the support strap is coupled to the shoulder strap via a first portion of the engagement mechanism, the garment further comprising:
an outer panel coupled to the back panel, the outer panel removably coupleable to the first portion of the engagement mechanism via a second portion of the engagement mechanism.

3. The garment of claim 1, wherein the support strap includes a loop portion and a coupling mechanism, the support strap having a second end coupled to the coupling mechanism, the coupling mechanism slidable along a strap portion of the support strap to adjust the size of the loop portion such that the support strap transitions from the first configuration to the second configuration.

4. The garment of claim 1, wherein the support strap includes a first coupling member, a second coupling member, and a third coupling member, the first coupling member disposed closer to a second end of the support strap than the second coupling member and the third coupling member, the first coupling member configured to be coupled to the second coupling member such that the support strap includes a loop portion having a first size in the first configuration, the first coupling member configured to be couple to the third coupling member such that the support strap forms a loop portion having a second size in the second configuration.

5. The garment of claim 1, wherein the support strap includes a swan hook disposed at a second end of the support strap, the swan hook configured to be engaged with a first opening defined along an edge of the support strap to form a loop portion having a first size in the first configuration, the swan hook configured to be engaged with a second opening defined along an edge of the support strap to form a loop portion having a second size in the second configuration.

6. The garment of claim 1, wherein the support strap includes a base portion and an elongated portion, the elongated portion having a constant width.

7. The garment of claim 4, wherein the support strap can include a first layer and a second layer, the first coupling member, the second coupling member, and the third coupling member being disposed on the first layer, the second layer configured to be disposed between the second coupling member and the wearer in the first configuration of the support strap.

8. The garment of claim 2, wherein outer panel includes at least one coupling member configured to be reversibly coupled to at least one complementary coupling member of an inner panel, the at least one coupling member of the outer panel disposed on an inner surface of the outer panel such that the support strap is disposed between the at least one coupling member of the outer panel and the wearer in the first configuration of the support strap.

9. The garment of claim 2, wherein the portion of the breast pump is a first portion of the breast pump, and further comprising:
a neck strap, the neck strap including a first coupling member and a second coupling member, the first coupling member and the second coupling member configured to be coupled to the outer panel such that the neck strap maintains the outer panel in supportive contact with a second portion of the breast pump.

10. The garment of claim 9, wherein the support strap is a first support strap, the shoulder strap is a first shoulder strap, and the engagement mechanism is a first engagement mechanism, further comprising:
a second support strap, a second shoulder strap, and a second engagement mechanism, the second shoulder strap having a first end and a second end, the first end coupled to the back panel, the second support strap coupled to a second end of the second shoulder strap via a first portion of the second engagement mechanism,
the outer panel including a left outer panel and a right outer panel, the left outer panel configured to be releasably coupled to the first portion of the first engagement mechanism via the second portion of the first engagement mechanism, the right outer panel configured to be releasably coupled to the first portion of the second engagement mechanism via the second portion of the second engagement mechanism,
the first coupling member of the neck strap configured to be reversibly engaged with the second portion of the first engagement mechanism and the second coupling member of the neck strap configured to be reversibly engaged with the second portion of the second engagement mechanism in a configuration in which the neck strap is coupled to the outer panel such that the neck strap maintains the outer panel in supportive contact with the second portion of the breast pump.

11. The garment of claim 1, wherein the support strap is a first support strap, the shoulder strap is a first shoulder strap, the engagement mechanism is a first engagement mechanism the breast pump is a first breast pump, and the breast is a first breast, further comprising:
a second support strap, a second shoulder strap, and a second engagement mechanism, the second shoulder strap having a first end and a second end, the first end coupled to the back panel, the second support strap coupled to a second end of the second shoulder strap via a first portion of the second engagement mechanism, the second support strap configured to be transitioned between a first configuration and a second configuration, the second support strap having a first length between the first end of the second support strap and the second engagement mechanism in the first configuration, the support strap having a second length greater than the first length between the first end of the second support strap and the second engagement mechanism in the second configuration such that the second support strap can be disposed in supportive contact with a portion of a second breast pump disposed against a second breast of the wearer to hold the second breast pump against the second breast of the wearer simultaneously to the first support strap holding the first breast pump against the first breast of the wearer in the second configuration of the first support strap.

12. The garment of claim 1, wherein the support strap is a first portion of the support strap and the first portion of the support strap is coupled to the second end of the shoulder strap via a first portion of the engagement mechanism, further comprising:
a second portion of the support strap, the second portion having a first end secured to the first portion of the engagement mechanism, the second portion having a second end secured to a center portion of the back panel, the first portion of the support strap including an adjustable loop portion having a portion that slidably extends through an opening of the first portion of the engagement mechanism.

13. The garment of claim 2, wherein the portion of the breast pump is a first portion of the breast pump, and further comprising:
a neck strap, the neck strap including a first coupling member and a second coupling member, the second coupling member configured to be coupled to the first coupling member such that the neck strap forms a loop, the first coupling member configured to be engaged with the second portion of the engagement mechanism such that the neck strap maintains the outer panel in supportive contact with a second portion of the breast pump.

14. The garment of claim 3, wherein the loop portion is a first loop portion, the support strap including a base portion and an adjustable portion, the base portion including a second loop portion, the adjustable portion having a first end removably coupled to the second loop portion via a second swan hook, the adjustable portion configured to be uncoupled from the base portion via decoupling the second swan hook from the second loop portion.

15. The garment of claim 2, wherein the outer panel includes a concealment pocket disposed near an apex of the outer panel, the second portion of the engagement mechanism configured to be rotated from a first configuration in which the second portion is disposed outside of the concealment pocket to a second configuration in which the second portion is retained within the concealment pocket.

16. A method, comprising:
decoupling a bottom portion of an engagement mechanism from a top portion of the engagement mechanism, the bottom portion secured to an outer panel, the top portion secured to a shoulder strap and coupled to a support strap;
adjusting a length of the support strap between a base of the support strap and the top portion of the engagement mechanism from a first length to a second length greater than the first length;
disposing a breast pump against a breast of the wearer such that the breast pump can be operated for a pumping procedure; and
arranging the support strap relative to the breast pump such that breast pump is maintained against the breast by the support strap.

17. The method of claim 16, wherein adjusting the length of the support strap from the first length to the second length includes sliding a coupling mechanism along a strap portion of the support strap such that a loop portion extending through an opening of the top portion of the engagement mechanism decreases in size.

18. The method of claim 16, wherein adjusting the length of the support strap from the first length to the second length includes decoupling a first coupling mechanism disposed at a first end of the support strap from a complementary second coupling mechanism disposed along the support strap and coupling the first coupling mechanism to a complementary third coupling mechanism disposed along the support strap such that a loop portion of the support strap extending through an opening of the top portion of the engagement mechanism decreases in size.

19. The method of claim 16, further comprising:
arranging the outer panel relative to the breast pump such that the breast pump is disposed between the outer panel and the support strap and the outer panel and the support strap collectively maintain the breast pump against the breast of the wearer; and
coupling the bottom portion of the engagement mechanism to the top portion of the engagement mechanism such that the shoulder strap maintains the outer panel against a portion of the breast pump.

20. The method of claim 16, further comprising:
arranging the outer panel relative to the breast pump such that the breast pump is disposed between the outer panel and the support strap and the outer panel and the support strap collectively maintain the breast pump against the breast of the wearer; and
coupling a first coupling member of a neck strap to the outer panel such that the neck strap maintains the outer panel against a portion of the breast pump.

21. The method of claim 20, wherein the coupling the first coupling member of the neck strap to the outer panel includes engaging a hook portion of the first coupling member with a loop portion of the outer panel.

22. The method of claim 20, wherein the coupling the first coupling member of the neck strap to the outer panel includes engaging the first coupling member with the bottom portion of the engagement mechanism coupled to the outer panel.

23. The method of claim 20, wherein the outer panel is a left outer panel, further comprising:
coupling a second coupling member of the neck strap to a right outer panel.

24. The method of claim 16, wherein the arranging the support strap relative to the breast pump includes wrapping the support strap fully around a portion of the breast pump.

25. The method of claim 16, wherein the arranging the support strap relative to the breast pump includes pulling a portion of the support strap laterally inwardly toward a center of the chest of the wearer prior to disposing the breast pump against a breast of the wearer.

26. The method of claim 22, further comprising:
coupling a second coupling member of the neck strap to the first coupling member such that the neck strap forms a loop around a neck of the wearer.

27. A method, comprising:
decoupling a first end of a first shoulder strap from a back panel of a garment, a second end of the first shoulder strap coupled to a first portion of an engagement mechanism, the garment including an outer panel including a second portion of the engagement mechanism, the second portion configured to be releasably coupled to the first portion of the engagement mechanism;
decoupling a first end of an adjustable portion of a support strap from a base portion of the support strap, the base portion of the support strap coupled to the back panel of the garment, a second end of the adjustable portion coupled to the first portion of the engagement mechanism;
coupling a first end of a second shoulder strap to the back panel of the garment; and
coupling a second end of the second shoulder strap to the outer panel.

28. The method of claim 27, wherein the decoupling the first end of the first shoulder strap from the back panel of the garment includes decoupling a first swan hook disposed on the first end of the first shoulder strap from a loop portion of the back panel, and coupling the first end of the second shoulder strap to the back panel of the garment includes coupling a second swan hook disposed on the first end of the second shoulder strap to the loop portion of the back panel.

29. The method of claim 27, wherein decoupling the first end of the adjustable portion of the support strap from the base portion includes decoupling a first swan hook disposed on the first end of the adjustable portion from a loop portion of the base portion of the support strap.

30. The method of claim 27, further comprising: rotating the second portion of the engagement mechanism from a first configuration in which the second portion of the engagement mechanism is disposed outside of a concealment pocket of the outer panel to a second configuration in which the second portion of the engagement mechanism is disposed inside of the concealment pocket of the outer panel.

* * * * *